US008987453B2

(12) United States Patent
Schrimpf et al.

(10) Patent No.: US 8,987,453 B2
(45) Date of Patent: Mar. 24, 2015

(54) AZAADAMANTANE DERIVATIVES AND METHODS OF USE

(71) Applicant: AbbVie Inc., North Chicago, IL (US)

(72) Inventors: Michael R. Schrimpf, Grayslake, IL (US); Diana L. Nersesian, Gurnee, IL (US); Kevin B. Sippy, Antioch, IL (US); Jianguo Ji, Libertyville, IL (US); Tao Li, Grayslake, IL (US); Marc Scanio, Lindenhurst, IL (US); Lei Shi, Gurnee, IL (US); Chih-Hung Lee, Vernon Hills, IL (US); William H. Bunnelle, Mundelein, IL (US); Geoff G. Z. Zhang, Libertyville, IL (US); Paul J. Brackemeyer, Sterling, IL (US); Shuang Chen, Gurnee, IL (US); Rodger F. Henry, Wildwood, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/653,192

(22) Filed: Oct. 16, 2012

(65) Prior Publication Data

US 2013/0096132 A1 Apr. 18, 2013

Related U.S. Application Data

(62) Division of application No. 11/935,157, filed on Nov. 5, 2007, now Pat. No. 8,314,119.

(60) Provisional application No. 60/856,992, filed on Nov. 6, 2006, provisional application No. 60/908,143, filed on Mar. 26, 2007.

(51) Int. Cl.
*C07D 471/18* (2006.01)
*A61K 45/06* (2006.01)
*A61K 31/444* (2006.01)
*C07D 471/08* (2006.01)
*C07F 5/02* (2006.01)
*A61K 31/439* (2006.01)
*A61K 31/496* (2006.01)
*A61K 31/497* (2006.01)
*A61K 31/501* (2006.01)
*A61K 31/506* (2006.01)

(52) U.S. Cl.
CPC ............ *C07D 471/18* (2013.01); *C07D 471/08* (2013.01); *C07F 5/022* (2013.01); *A61K 31/439* (2013.01); *A61K 31/444* (2013.01); *A61K 31/496* (2013.01); *A61K 31/497* (2013.01); *A61K 31/501* (2013.01); *A61K 31/506* (2013.01); *A61K 45/06* (2013.01)
USPC .............................. 546/97; 514/294; 544/238

(58) Field of Classification Search
USPC ........................................... 546/97; 514/294
See application file for complete search history.

(56) References Cited

U.S. PATENT DOCUMENTS

| 4,578,382 | A | 3/1986 | Jarreau et al. |
| 4,816,453 | A | 3/1989 | Watts |
| 4,950,759 | A | 8/1990 | Van Wijngaarden et al. |
| 4,985,424 | A | 1/1991 | Van Wijngaarden et al. |
| 5,260,303 | A | 11/1993 | Becker et al. |
| 5,280,028 | A | 1/1994 | Flynn et al. |
| 5,385,912 | A | 1/1995 | Neuenschwander et al. |
| 5,399,562 | A | 3/1995 | Becker et al. |
| 5,434,151 | A | 7/1995 | Cai et al. |
| 5,591,749 | A | 1/1997 | Becker et al. |
| 5,604,239 | A | 2/1997 | Becker et al. |
| 5,643,917 | A | 7/1997 | Flynn et al. |
| 5,723,472 | A | 3/1998 | Miyazawa et al. |
| 5,840,903 | A | 11/1998 | Flynn et al. |
| 5,852,037 | A | 12/1998 | Bodick et al. |
| 5,952,339 | A | 9/1999 | Bencherif et al. |
| 5,986,100 | A | 11/1999 | Crooks et al. |
| 6,057,446 | A | 5/2000 | Crooks et al. |
| 6,093,724 | A | 7/2000 | Grewal et al. |
| 6,251,916 | B1 | 6/2001 | Grewal et al. |
| 6,277,870 | B1 | 8/2001 | Gurley et al. |
| 6,323,194 | B1 | 11/2001 | Grewal et al. |
| 6,417,359 | B1 | 7/2002 | Crooks et al. |
| 6,423,842 | B1 | 7/2002 | Grewal et al. |
| 6,555,550 | B1 | 4/2003 | Grewal et al. |
| 6,627,648 | B1 | 9/2003 | Dull et al. |
| 6,861,443 | B2 | 3/2005 | Gurley et al. |
| 6,890,922 | B2 | 5/2005 | Niewohner et al. |

(Continued)

FOREIGN PATENT DOCUMENTS

| CA | 2736871 A1 | 3/2010 |
| EP | 0088484 A1 | 9/1983 |

(Continued)

OTHER PUBLICATIONS

Adams C.E. et al., "Development of the a7 nicotinic cholinergic receptor in rat hippocampal formation," Developmental Brain Research, 2002, vol. 139 (2), pp. 175-187.
Adler L.E., et al., "Schizophrenia, Sensory Gating, and Nicotinic Receptors," Schizophrenia Bulletin, 1998, vol. 24 (2), pp. 189-202.
Banker G.S. et al., Modern Pharmaceutics, 3rd Edition, Marcel Dekker, 1996, pp. 596.
Becker D.P., et al., "A Short Synthesis of 1-Azaadamantan-4-One and the 4r and 4s Isomers of 4-Amino-1-Azaadamantane," Synthesis, 1992, vol. 11, pp. 1080-1082.

(Continued)

*Primary Examiner* — Rita Desai
(74) *Attorney, Agent, or Firm* — Lisa V. Mueller; Michael Best & Friedrich LLP

(57) ABSTRACT

The invention relates to compounds that are azaadamantane derivatives, particularly ether- or amine-substituted azaadamantane derivatives and salts and prodrugs thereof, compositions comprising such compounds, methods of using such compounds and compositions, processes for preparing such compounds, and intermediates obtained during such processes.

6 Claims, 15 Drawing Sheets

(56) References Cited

U.S. PATENT DOCUMENTS

| | | |
|---|---|---|
| 7,018,797 B2 | 3/2006 | Reitz et al. |
| 7,067,261 B2 | 6/2006 | Bencherif et al. |
| 7,112,593 B2 | 9/2006 | Okada et al. |
| 7,122,540 B2 | 10/2006 | Niewohner et al. |
| 7,135,454 B2 | 11/2006 | Chimienti et al. |
| 7,253,196 B2 | 8/2007 | Henriksson et al. |
| 7,652,010 B2 | 1/2010 | Peters et al. |
| 7,691,808 B2 | 4/2010 | Chimienti et al. |
| 7,696,206 B2 | 4/2010 | Niewohner et al. |
| 7,704,997 B1 | 4/2010 | Carroll et al. |
| 7,704,999 B2 | 4/2010 | Niewohner et al. |
| 7,718,677 B2 | 5/2010 | Quik et al. |
| 7,723,367 B2 | 5/2010 | Carroll et al. |
| 7,732,163 B2 | 6/2010 | O'Brien et al. |
| 7,763,725 B2 | 7/2010 | Poitout et al. |
| 7,807,700 B2 | 10/2010 | Henriksson et al. |
| 7,981,906 B2 | 7/2011 | Dull et al. |
| 8,217,067 B2 | 7/2012 | Carroll et al. |
| 2004/0185468 A1 | 9/2004 | Leonard et al. |
| 2004/0209886 A1 | 10/2004 | Salvati et al. |
| 2005/0043347 A1 | 2/2005 | Betschmann et al. |
| 2005/0065178 A1 | 3/2005 | Basha et al. |
| 2005/0101602 A1 | 5/2005 | Basha et al. |
| 2006/0052374 A1 | 3/2006 | Carroll et al. |
| 2008/0153806 A1 | 6/2008 | Peters et al. |
| 2009/0093403 A1 | 4/2009 | Zhang et al. |
| 2009/0099038 A1 | 4/2009 | Deisseroth et al. |
| 2009/0118326 A1 | 5/2009 | Jiang et al. |
| 2009/0148525 A1 | 6/2009 | Cowen |
| 2009/0239901 A1 | 9/2009 | Bencherif |
| 2009/0291976 A1 | 11/2009 | Ferchmin et al. |
| 2009/0306075 A1 | 12/2009 | McCoull et al. |
| 2009/0312372 A1 | 12/2009 | McCoull et al. |
| 2010/0029723 A1 | 2/2010 | Quik et al. |
| 2010/0047795 A1 | 2/2010 | Leonard et al. |
| 2010/0105658 A1 | 4/2010 | Nagashima et al. |
| 2010/0130420 A1 | 5/2010 | Sternson et al. |
| 2010/0144538 A1 | 6/2010 | Belouchi et al. |
| 2010/0152108 A1 | 6/2010 | Hung et al. |
| 2010/0158895 A1 | 6/2010 | Quik et al. |
| 2010/0159004 A1 | 6/2010 | Quik et al. |
| 2010/0166735 A1 | 7/2010 | Quik et al. |
| 2010/0196463 A1 | 8/2010 | Quik et al. |
| 2010/0197740 A1 | 8/2010 | Wang et al. |
| 2010/0234349 A1 | 9/2010 | Olsen et al. |
| 2011/0034475 A1 | 2/2011 | Feuerbach et al. |
| 2011/0059947 A1 | 3/2011 | Bencherif et al. |
| 2011/0077276 A1 | 3/2011 | Quik et al. |
| 2011/0097324 A1 | 4/2011 | Liu |
| 2011/0098312 A1 | 4/2011 | Bencherif et al. |
| 2011/0124678 A1 | 5/2011 | Bencherif et al. |
| 2011/0136791 A1 | 6/2011 | Bergis et al. |

FOREIGN PATENT DOCUMENTS

| | | |
|---|---|---|
| EP | 227215 A1 | 7/1987 |
| EP | 76755 B1 | 1/1988 |
| EP | 645391 A2 | 3/1995 |
| EP | 709381 A1 | 5/1996 |
| EP | 774256 A1 | 5/1997 |
| EP | 1977746 A1 | 10/2008 |
| EP | 2255848 A2 | 12/2010 |
| EP | 2322166 A1 | 5/2011 |
| EP | 2322167 A1 | 5/2011 |
| EP | 2322168 A1 | 5/2011 |
| JP | 2005232071 A | 9/2005 |
| WO | 9215579 A1 | 9/1992 |
| WO | 9215593 A1 | 9/1992 |
| WO | 9400454 A1 | 1/1994 |
| WO | 9402482 A1 | 2/1994 |
| WO | 9720819 A1 | 6/1997 |
| WO | 9827983 A1 | 7/1998 |
| WO | 9920757 A2 | 4/1999 |
| WO | 9924433 A1 | 5/1999 |
| WO | 9951601 A1 | 10/1999 |
| WO | 9951602 A1 | 10/1999 |
| WO | 9956745 A1 | 11/1999 |
| WO | 9962505 A2 | 12/1999 |
| WO | 0011001 A1 | 3/2000 |
| WO | 0071520 A2 | 11/2000 |
| WO | 0140261 A1 | 6/2001 |
| WO | 0202564 A1 | 1/2002 |
| WO | 0250045 A1 | 6/2002 |
| WO | 02076973 A1 | 10/2002 |
| WO | 03044020 A1 | 5/2003 |
| WO | 03094831 A2 | 11/2003 |
| WO | 2004009577 A1 | 1/2004 |
| WO | 2004016608 A1 | 2/2004 |
| WO | 2004091646 A2 | 10/2004 |
| WO | 2005020921 A2 | 3/2005 |
| WO | 2005028477 A1 | 3/2005 |
| WO | 2005047303 A2 | 5/2005 |
| WO | 2005116002 A2 | 12/2005 |
| WO | 2005123732 A1 | 12/2005 |
| WO | 2006005608 A1 | 1/2006 |
| WO | 2006010811 A1 | 2/2006 |
| WO | 2006012395 A2 | 2/2006 |
| WO | 2006026469 A2 | 3/2006 |
| WO | 2006040352 A1 | 4/2006 |
| WO | 2006045716 A1 | 5/2006 |
| WO | 2007024391 A2 | 3/2007 |
| WO | 2007065892 A1 | 6/2007 |
| WO | 2008002594 A2 | 1/2008 |
| WO | 2008020131 A1 | 2/2008 |
| WO | 2008028903 A2 | 3/2008 |
| WO | 2008051599 A2 | 5/2008 |
| WO | 2008053194 A2 | 5/2008 |
| WO | 2008058096 A2 | 5/2008 |
| WO | 2008096870 A1 | 8/2008 |
| WO | 2008112177 A2 | 9/2008 |
| WO | 2008118742 A1 | 10/2008 |
| WO | 2008122049 A2 | 10/2008 |
| WO | 2009017454 A1 | 2/2009 |
| WO | 2009018505 A1 | 2/2009 |
| WO | 2009018511 A2 | 2/2009 |
| WO | 2009058120 A1 | 5/2009 |
| WO | 2009066735 A1 | 5/2009 |
| WO | 2009071326 A2 | 6/2009 |
| WO | 2009102962 A2 | 8/2009 |
| WO | 2009140201 A1 | 11/2009 |
| WO | 2009149562 A1 | 12/2009 |
| WO | 2010030887 A1 | 3/2010 |
| WO | 2010042799 A2 | 4/2010 |
| WO | 2010056622 A1 | 5/2010 |
| WO | 2010088400 A1 | 8/2010 |
| WO | 2011014817 A1 | 2/2011 |
| WO | 2011022467 A2 | 2/2011 |
| WO | 2011044537 A2 | 4/2011 |
| WO | 2011058582 A1 | 5/2011 |
| WO | 2012040404 A1 | 3/2012 |
| WO | 2012041476 A1 | 4/2012 |
| WO | 2012059932 A1 | 5/2012 |

OTHER PUBLICATIONS

Bitner R., et al., Soc. Neuroscience, Abstract 325.6 (2006).

Bunnelle W.H., et al., "Design of Ligands for the Nicotinic Acetylcholine Receptors: The Quest for Selectivity," Current Topics in Medicinal Chemistry, 2004, vol. 4 (3), pp. 299-334.

Bunnelle W.H., et al., "Neuronal Nicotinic Acetylcholine Receptor Ligands as Potential Analgesics," Expert Opinion on Therapeutic Patents, 2003, vol. 13 (7), pp. 1003-1021.

Burger., "Principles and Practice" in: Medicinal Chemistry and Drug Discovery, 5th Edition, Wolff M.E., ed., John Wiley and Sons, 1994, pp. 975-977.

Cordero-Erausquin M., et al., "Tonic Nicotinic Modulation of Serotoninergic Transmission in the Spinal Cord," Proceedings of the National Academy of Sciences, 2001, vol. 98 (5), pp. 2803-2807.

Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.

(56) References Cited

OTHER PUBLICATIONS

Eliel, E. L. et al., "Stereochemistry of Organic Compounds," 1994, John Wiley & Sons, Inc. New York. Table of Contents.

Falk L., et al., "Higher Expression of .Alpha.7 Nicotinic Acetylcholine Receptors in Human Fetal Compared to Adult Brain," Developmental Brian Research, 2003, vol. 142 (2), pp. 151-160.

Final Office Action mailed Oct. 25, 2011 for U.S. Appl. No. 11/935,157, filed Nov. 5, 2007.

Flynn D.L., et al., "New Aza(NOR)Adamantanes are Agonists at the Newly Identified Serotonin 5-Ht4 Receptor and Antagonists at the 5-HT3 Receptor," Bioorganic & Medicinal Chemistry Letters, 1992, vol. 2 (12), pp. 1613-1618.

Friedman J.I., et al., "A Double Blind Placebo Controlled Trial of Donepezil Adjunctive Treatment to Risperidone for the Cognitive Impairment of Schizophrenia," Biological Psychiatry, 2002, vol. 51, pp. 349-357.

Furniss B.S., et al., Vogel's Textbook of Practical Organic Chemistry, 5th Edition, Longman Scientific & Technical, 1989, Table of Contents.

Greene T.W., et al., "Protection for the Amino group," Protective Groups in Organic Synthesis, 1999, Third Edition, pp. 494-653.

Heeschen C., et al., "A Novel Angiogenic Pathway Mediated by Non-Neuronal Nicotinic Acetycholine Reeports," Journal of Clinical Investigation, 2002, vol. 110 (4), pp. 527-536.

Heeschen C., et al., "Nicotine Stimulates Angiogenesis and Promotes Tumor Growth and Athersclerosis," Nature Medicine, 2001, vol. 7 (7), pp. 833-839.

Higuchi T., et al., eds., Pro-drugs as Novels Delivery Systems, vol. 14, ACS Symposium Series, 1975, Table of Contents.

International Preliminary Report on Patentability and Written Opinion for Application No. PCT/US2007/083687, mailed on May 12, 2009, 8 pages.

International Search Report for Application No. PCT/US2007/083687, mailed on May 26, 2008, 3 pages.

Iriepa I., et al., "Synthesis and Structure Study of a Series of Amides Derived from 4alpha-and 4beta-Amino-1-Azaadamantanes as Potential 5-HT3 Receptor Antagonists," Journal of Molecular Structure, 1999, vol. 509, pp. 105-114.

Jacobi J., et al., "Nicotine Accelerates Angiogenesis and would Healing in Genetically Diabetic Mice," American Journal of Pathology, 2002, vol. 161 (1), pp. 97-104.

Jonnala R.R., et al., "Relationship between the Increased Cell Surface .alpha.7 nicotinic Receptor Expression and Neuroprotection Induced by Several Nicotinic Receptor Agonists," Journal of Neuroscience Research, 2001, vol. 66 (4), pp. 565-572.

Kihara T., et al., "Alpha.7 Nicotinic Receptor Transduces Signals to Phosphatidylinositol 3-kinase to Block A .beta.-amyloid-induced Neurotoxicity," Journal of Biological Chemistry, 2001, vol. 276 (17), pp. 13541-13546.

Leonard S., et al., "Smoking and Schizophrenia: Abnormal Nicotinic Receptor Expression," European Journal of Pharmacology, 2000, vol. 393 (1-3), pp. 237-242.

Levin E.D., "Nicotinic Receptor Subtypes and Cognitive Function," Journal of Neurobiology, 2002, vol. 53 (4), pp. 633-640.

Liu Q.S., et al., "Beta-Amyloid Peptide Blocks the Response of Alpha.7-Containing Nicotinic Receptors on Hippocampal Neurons," Proceedings of the National Academy of Sciences, 2001, vol. 98 (8), pp. 4734-4739.

Non-Final Office Action mailed Mar. 14, 2011 for U.S. Appl. No. 11/935,157, filed Nov. 5, 2007.

Notice of Allowance mailed May 1, 2012 for U.S. Appl. No. 11/935,157, filed Nov. 5, 2007.

Notice of Allowance mailed Sep. 4, 2012 for U.S. Appl. No. 11/935,157, filed Nov. 5, 2007.

Pabreza L.A., et al., "[.sup.3H]Cytisine Binding to Nicotinic Cholinergic Receptors in Brain," Molecular Pharmacology, 1990, vol. 39, pp. 9-12.

Paterson D., et al., "Neuronal Nicotinic Receptors in the Human Brain," Progress in Neurobiology, 2000, vol. 61 (1), pp. 75-111.

Poste G. et al., "Lipid Vesicles as Carriers for Introducing Biologically Active Materials into Cells," Methods in Cell Biology, 1976, vol. 14, pp. 33-71.

Radek R., et al., "Alpha4beta2 Nicotinic Receptor Stimulation Contributes to the effects of Nicotine in the DBA/2 mouse model of Sensory Gating," Psychopharmacology, 2006, vol. 187 (1), pp. 47-55.

Roche E.B., ed., Bioreversible Carries in Drug Design Theory and Application, Pergamon Press, 1987, Table of Contents.

Rowley M., et al., "Current and Novel Approaches to the Drug Treatment of Schizophrenia," Journal of Medicinal Chemistry, 2001, vol. 44 (4), pp. 477-501.

Sawa A., et al., "Schizophrenia: Neural Mechanisms for Novel Therapies," Molecular Medicine, 2003, vol. 9 (1-2), pp. 3-9.

Schildan A., et al., ""Synthesis and Evaluation of Tritium Labelled 10-methylgalanthamine Iodide: A Novel Compound to Examine the Mechanism of Interaction of Galantamine Derivatives with the Nicotinic Acetylcholine Receptors,"" Journal of Labelled Compounds and Radiopharmaceuticals, 2003, vol. 46 (12), pp. 1117-1125.

Shimohama S.,et al., "Nicotinic Alpha 7 Receptors Protect Against Glutamate Neurotoxicity and Neuronal Ischemic Damage," Brain Research, 1998, vol. 779 (1-2), pp. 359-363.

Son J.H., et al., "Evidence Suggesting that the Mouse Sperm Acrosome Reaction Initiated by the Zona Pellucida Involves an .Alpha.7 Nicotinic Acetylcholine Receptor," Biology of Reproduction, 2003, vol. 68 (4), pp. 1348-1353.

Stevens K.E., et al., "Selective A7-Nicotinic Agonists Normalize Inhibition of Auditory Response in Dba Mice," Psychopharmacology, 1998, vol. 136 (4), pp. 320-327.

Stotter P.L., et al., "Quinuclidine Boranes as Intermediates in Formation and Isolation of Functionalized Quinuclidine Systems," Heterocycles, 1987, vol. 25, pp. 251-258.

Tsuneki H. et al., "Mouse Muscle Denervation Increases Expression of an A7 Nicotinic Receptor with Unusual Pharmacology," Journal of Physiology, 2003, vol. 547 (1), pp. 169-179.

Vachal P., et al., "General Facile Synthesis of 2,5-Diarylheteropentalenes," Tetrahedron Letters, 2004, vol. 45, pp. 7157-7161.

Wang H., et al., "Nicotinic Acetylcholine Receptor Alpha7 Subunit is an Essential Regulator of Inflammation," Nature, 2003, vol. 421 (6921), pp. 384-388.

Wilens T.E., et al., "A Pilot Controlled Clinical Trial of ABT-418, a Cholinergic Agonist, in the Treatment of Adults with Attention Deficit Hyperactivity Disorder," American Journal of Psychiatry, 1999, vol. 156 (12), pp. 1931-1937.

Yasuda T., et al., "Synthesis, Solid Structure, and Optical Properties of New Thiophene-Based Alternating Conjugated Copolymers Containing 4-Alky-1,2,4-Triazole or 1,2,3-Thiadiazole Unit as the Partner Unit," Macromolecules, 2005, vol. 38, pp. 1500-1503.

Zubets V., et al., "Synthesis and Mass Spectrometric study of 2-Aminoand 2-Chloro-5-Aryl-1,3,4-Thiadiazoles," Khimiya Geterotsiklichesskikh Soedininii, 1986, vol. 10, pp. 1416-1419.

Costa Rican Opposition for Application No. 2013-0169 by Asociacion de la Industria Farmaceutica Nacional, filed Sep. 20, 2013 (with English Translation).

Greene T.W., et al., in: Protective Groups in Organic Synthesis, 3rd Edition, John Wiley and Sons, Inc., 1999, Preface, Table of Contents, Abbreviations.

International Search Report for Application No. PCT/US2011/052668, mailed on Oct. 26, 2011, 3 pages.

Prescott D.M., "Methods in Cell Biology", Academic Press, 1976, Table of Contents.

Wolff, Mandred E. "Burger's Medicinal Chemistry and Drug Discovery," Principles and Practice, 1995, 975-977, 5th Ed,vol. 1, John Wiley & Sons.

Non-Final Office Action mailed Mar. 31, 2014 for U.S. Appl. No. 13/238,239, filed Sep. 21, 2011.

Shekunov, B.Y. et al., "Crystallization processes in pharmaceutical technology and drug delivery design," J. Crystal Growth (2000) 211(1-4):122-136.

US 8,987,453 B2

AZAADAMANTANE DERIVATIVES AND METHODS OF USE

CROSS-REFERENCE OF RELATED APPLICATIONS

This application is a divisional application of U.S. patent application Ser. No. 11/935,157, filed Nov. 5, 2007, now U.S. Pat. No. 8,314,119, issued Nov. 20, 2012, which claims the benefit of U.S. Provisional Patent Application Ser. No. 60/856,992, filed Nov. 6, 2006, and U.S. Provisional Patent Application Ser. No. 60/908,143, filed Mar. 26, 2007, each application of which is herein incorporated by reference in its entirety.

BACKGROUND OF THE INVENTION

1. Technical Field

The invention relates to azaadamantane derivatives, and more particularly ether- or amine-substituted azaadamantane derivatives, compositions comprising such compounds, methods of preventing or treating conditions and disorders using such compounds and compositions, processes for preparing such compounds, and intermediates obtained during such processes.

2. Description of Related Technology

Nicotinic acetylcholine receptors (nAChRs) are widely distributed throughout the central (CNS) and peripheral (PNS) nervous systems. Such receptors play an important role in regulating CNS function, particularly by modulating release of a wide range of neurotransmitters, including, but not necessarily limited to, acetylcholine, norepinephrine, dopamine, serotonin, and GABA. Consequently, nicotinic receptors mediate a very wide range of physiological effects, and have been targeted for therapeutic treatment of disorders relating to cognitive function, learning and memory, neurodegeneration, pain, inflammation, psychosis, sensory gating, mood, and emotion, among other conditions.

Many subtypes of the nAChR exist in the CNS and periphery. Each subtype has a different effect on regulating the overall physiological function. Typically, nAChRs are ion channels that are constructed from a pentameric assembly of subunit proteins. At least 12 subunit proteins, $\alpha 2$-$\alpha 10$ and $\beta 2$-$\beta 4$, have been identified in neuronal tissue. These subunits provide for a great variety of homomeric and heteromeric combinations that account for the diverse receptor subtypes. For example, the predominant receptor that is responsible for high affinity binding of nicotine in brain tissue has composition $(\alpha 4)_2(\beta 2)_3$ (the $\alpha 4\beta 2$ subtype), while another major population of receptors is comprised of homomeric $(\alpha 7)_5$ (the $\alpha 7$ subtype) receptors.

Certain compounds, like the plant alkaloid nicotine, interact with all subtypes of the nAChRs, accounting for the profound physiological effects of this compound. While nicotine has been demonstrated to have many beneficial properties, not all of the effects mediated by nicotine are desirable. For example, nicotine exerts gastrointestinal and cardiovascular side effects that interfere at therapeutic doses, and its addictive nature and acute toxicity are well-known. Ligands that are selective for interaction with only certain subtypes of the nAChR offer potential for achieving beneficial therapeutic effects with an improved margin for safety.

The $\alpha 7$ and $\alpha 4\beta 2$ nAChRs have been shown to play a significant role in enhancing cognitive function, including aspects of learning, memory and attention (Levin, E. D., J. Neurobiol. 53: 633-640, 2002). For example, $\alpha 7$ nAChRs have been linked to conditions and disorders related to attention deficit disorder, attention deficit hyperactivity disorder (ADHD), schizophrenia, Alzheimer's disease (AD), mild cognitive impairment, senile dementia, dementia associated with Lewy bodies, dementia associated with Down's syndrome, AIDS dementia, and Pick's disease, as well as inflammation. The $\alpha 4\beta 2$ receptor subtype is implicated in attention, cognition, epilepsy, and pain control (Paterson and Norberg, *Progress in Neurobiology* 61 75-111, 2000) as well as smoking cessation or nicotine withdrawal syndrome.

The activity at both $\alpha 7$ and $\alpha 4\beta 2$ nAChRs can be modified or regulated by the administration of subtype selective nAChR ligands. The ligands can exhibit antagonist, agonist, or partial agonist properties. Compounds that function as allosteric modulators are also known.

Although compounds that nonselectively demonstrate activity at a range of nicotinic receptor subtypes including the $\alpha 4\beta 2$ and $\alpha 7$ nAChRs are known, it would be beneficial to provide compounds that interact selectively with $\alpha 7$-containing neuronal nAChRs, $\alpha 4\beta 2$ nAChRs, or both $\alpha 7$ and $\alpha 4\beta 2$ nAChRs compared to other subtypes.

BRIEF DESCRIPTION OF THE DRAWINGS

FIGS. 5, 7, 9, and 11 were determined from the single cell crystal data of their respective compounds.

SUMMARY OF THE INVENTION

Figure 1:
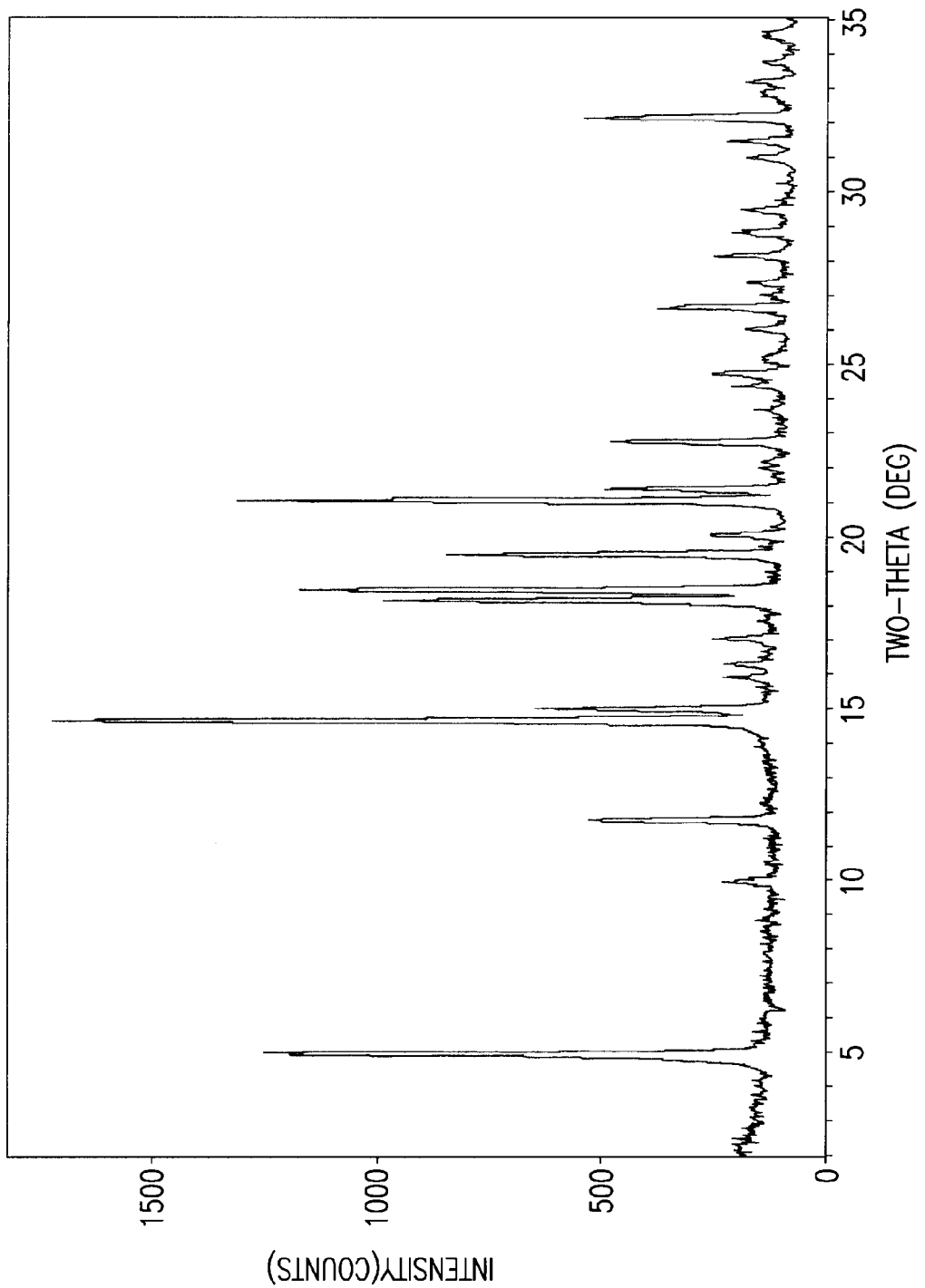
FIG. 1 is a powder X-ray diffraction pattern of an anhydrous L-bitartrate of (4s)-4-(5-phenyl-1,3,4-thiadiazol-2-yloxy)-1-azatricyclo[3.3.1.1$^{3,7}$]decane.

The invention is directed to azaadamantane derivatives, compositions comprising such compounds, processes for preparing such compounds, and intermediates obtained during such processes. More particularly, the invention relates to ether- or amine-substituted azaadamantane compounds and related methods and processes thereof.

One aspect of the invention relates to a compound of formula (I)

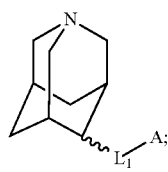

(I)

or a pharmaceutically acceptable salt or prodrug thereof, wherein $L_1$ is —O— or —NR$_a$—;
A is —Ar$_1$, —Ar$_2$-L$_2$-Ar$_3$ or —Ar$_4$-L$_3$-Ar$_5$;
Ar$_1$ is aryl or heteroaryl;
Ar$_2$ is aryl or monocyclic heteroaryl;
Ar$_3$ is aryl or heteroaryl;
Ar$_4$ is a bicyclic heteroaryl;
Ar$_5$ is aryl or heteroaryl;
$L_2$ is a bond, —O—, —NR$_a$—, —C(O)NR$_a$—, or CH$_2$—;
$L_3$ is a bond, —O—, —NR$_a$— or CH$_2$—; and
$R_a$ is hydrogen or alkyl.

Another aspect of the invention relates to pharmaceutical compositions comprising compounds of the invention. Such compositions can be administered in accordance with a method of the invention, typically as part of a therapeutic regimen for treatment or prevention of conditions and disorders related to nAChR activity, and more particularly α7 nAChR activity, α4β2 nAChR activity, or both α7 nAChR activity and α4β2 nAChR activity.

Yet another aspect of the invention relates to a method of modulating both α7 and α4β2 nAChR activity. The method is useful for treating, preventing or both treating and preventing conditions and disorders related to both α7 and α4β2 nAChR activity, particularly in mammals.

A further aspect of the invention relates to a method of selectively modulating nAChR activity, for example α7 nAChR activity. The method is useful for treating, preventing or both treating and preventing conditions and disorders related to α7 nAChR activity in mammals. A method of selectively modulating α4β2 nAChR activity also is contemplated.

Such methods are useful for conditions and disorders related to attention deficit disorder, attention deficit hyperactivity disorder (ADHD), Alzheimer's disease (AD), schizophrenia, mild cognitive impairment, age-associated memory impairment (AAMI), senile dementia, AIDS dementia, Pick's disease, dementia associated with Lewy bodies, dementia associated with Down's syndrome, schizophrenia, smoking cessation, nicotinic withdrawal syndrome, amyotrophic lateral sclerosis, Huntington's disease, diminished CNS function associated with traumatic brain injury, acute pain, post-surgical pain, chronic pain, inflammatory pain, neuropathic pain, infertility, lack of circulation, need for new blood vessel growth associated with wound healing, more particularly circulation around a vascular occlusion, need for new blood vessel growth associated with vascularization of skin grafts, ischemia, inflammation, sepsis, wound healing, and other complications associated with diabetes, among other systemic and neuroimmunomodulatory activities.

The invention also relates to particular salts of certain compounds of the invention as well as compositions comprising and processes for preparing such compounds and salts.

The compounds, including salts thereof, compositions comprising the compounds, methods for using the compounds, and processes for preparing the compounds, as well as intermediates obtained in such processes, are further described herein.

DETAILED DESCRIPTION OF THE INVENTION

Definition of Terms

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of from 2 to 10 carbon atoms containing at least one double bond. Representative examples of alkenylene include, but are not limited to, —CH═CH—, —CH═CH$_2$CH$_2$—, and —CH═C(CH$_3$)CH$_2$—.

The term "alkenyloxy" as used herein, means an alkenyl group, as defined herein, appended to the parent molecular moiety through an oxygen atom. Representative examples of alkenyloxy include, but are not limited to, allyloxy, 2-butenyloxy and 3-butenyloxy.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkoxyalkyl" as used herein, means an alkoxyalkoxy group, as defined herein, appended to the parent molecular moiety through an alkyl group, as defined herein. Representative examples of alkoxyalkoxyalkyl include, but are not limited to, tert-butoxymethoxymethyl, ethoxymethoxymethyl, (2-methoxyethoxy)methyl, and 2-(2-methoxyethoxy)ethyl.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkoxysulfonyl" as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched chain hydrocarbon of from 1 to 10 carbon atoms. Representative examples of alkylene include, but are not limited to, —$CH_2$—, —$CH(CH_3)$—, —$C(CH_3)_2$—, —$CH_2CH_2$—, —$CH_2CH_2CH_2$—, —$CH_2CH_2CH_2CH_2$—, and —$CH_2CH(CH_3)CH_2$—.

The term "alkylsulfinyl" as used herein, means an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfinylalkyl" as used herein, means an alkylsulfinyl group, as defined herein, appended to the parent molecular moiety through an alkyl group, as defined herein. Representative examples of alkylsulfinylalkyl include, but are not limited to, methylsulfinylmethyl and ethylsulfinylmethyl.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylalkyl" as used herein, means an alkylsulfonyl group, as defined herein, appended to the parent molecular moiety through an alkyl group, as defined herein. Representative examples of alkylsulfonylalkyl include, but are not limited to, methylsulfonylmethyl and ethylsulfonylmethyl.

The term "alkylthio" as used herein, means an alkyl group, as defined herein, appended to the parent molecular moiety through a sulfur atom. Representative examples of alkylthio include, but are not limited to, methylthio, ethylthio, tert-butylthio, and hexylthio.

The term "alkylthioalkyl" as used herein, means an alkylthio group, as defined herein, appended to the parent molecular moiety through an alkyl group, as defined herein. Representative examples of alkylthioalkyl include, but are not limited to, methylthiomethyl and 2-(ethylthio)ethyl.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "alkynylene" means a divalent group derived from a straight or branched chain hydrocarbon of from 2 to 10 carbon atoms containing at least one triple bond. Representative examples of alkynylene include, but are not limited to, —C≡C—, —$CH_2$C≡C—, —$CH(CH_3)CH_2$C≡C—, —C≡$CCH_2$—, and —C≡$CCH(CH_3)CH_2$—.

The term "alkynyloxy" as used herein, means an alkynyl group, as defined herein, appended to the parent molecular moiety through an oxygen atom. Representative examples of alkynyloxy include, but are not limited to, 2-propynyloxy and 2-butynyloxy.

The term "aryl," as used herein, means phenyl, a bicyclic aryl or a tricyclic aryl. The bicyclic aryl is naphthyl, a phenyl fused to a cycloalkyl, or a phenyl fused to a cycloalkenyl. Representative examples of the bicyclic aryl include, but are not limited to, dihydroindenyl, indenyl, naphthyl, dihydronaphthalenyl, and tetrahydronaphthalenyl. The tricyclic aryl is anthracene or phenanthrene, or a bicyclic aryl fused to a cycloalkyl, or a bicyclic aryl fused to a cycloalkenyl, or a bicyclic aryl fused to a phenyl. Representative examples of tricyclic aryl ring include, but are not limited to, azulenyl, dihydroanthracenyl, fluorenyl, and tetrahydrophenanthrenyl.

The aryl groups of this invention can be substituted with 1, 2, 3, 4 or 5 substituents independently selected from alkenyl, alkoxy, alkoxyalkoxy, alkoxyalkoxyalkyl, alkoxyalkyl, alkoxycarbonyl, alkoxycarbonylalkyl, alkyl, alkylcarbonyl, alkylcarbonylalkyl, alkylcarbonyloxy, alkylsulfinyl, alkylsulfinylalkyl, alkylsulfonyl, alkylsulfonylalkyl, alkylthio, alkylthioalkyl, alkynyl, carboxy, carboxyalkyl, cyano, cyanoalkyl, formyl, formylalkyl, halogen, haloalkyl, hydroxy, hydroxyalkyl, mercapto, nitro, —$NZ_1Z_2$, and ($NZ_3Z_4$)carbonyl.

The term "arylalkoxy" as used herein, means an aryl group, as defined herein, appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkoxycarbonyl" as used herein, means an arylalkoxy group, as defined herein, appended to the parent molecular moiety through a carbonyl group, as defined herein. Representative examples of arylalkoxycarbonyl include, but are not limited to, benzyloxycarbonyl and naphth-2-ylmethoxycarbonyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylalkylthio" as used herein, means an arylalkyl group, as defined herein, appended to the parent molecular moiety through a sulfur atom. Representative examples of arylalkylthio include, but are not limited to, 2-phenylethylthio, 3-naphth-2-ylpropylthio, and 5-phenylpentylthio.

The term "arylcarbonyl" as used herein, means an aryl group, as defined herein, appended to the parent molecular moiety through a carbonyl group, as defined herein. Representative examples of arylcarbonyl include, but are not limited to, benzoyl and naphthoyl.

The term "aryloxy" as used herein, means an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "aryloxyalkyl" as used herein, means an aryloxy group, as defined herein, appended to the parent molecular moiety through an alkyl group, as defined herein. Representative examples of aryloxyalkyl include, but are not limited to, 2-phenoxyethyl, 3-naphth-2-yloxypropyl and 3-bromophenoxymethyl.

The term "arylthio" as used herein, means an aryl group, as defined herein, appended to the parent molecular moiety through a sulfur atom. Representative examples of arylthio include, but are not limited to, phenylthio and 2-naphthylthio.

The term "arylthioalkyl" as used herein, means an arylthio group, as defined herein, appended to the parent molecular moiety through an alkyl group, as defined herein. Representative examples of arylthioalkyl include, but are not limited to, phenylthiomethyl, 2-naphth-2-ylthioethyl, and 5-phenylthiomethyl.

The term "azido" as used herein, means a —$N_3$ group.

The term "carbonyl" as used herein, means a —C(O)— group.

The term "carboxy" as used herein, means a —$CO_2H$ group.

The term "carboxyalkyl" as used herein, means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkenyl" as used herein, means a cyclic hydrocarbon containing from 3 to 8 carbons and containing at least one carbon-carbon double bond formed by the removal of two hydrogens. Representative examples of cycloalkenyl include, but are not limited to, 2-cyclohexen-1-yl, 3-cyclohexen-1-yl, 2,4-cyclohexadien-1-yl and 3-cyclopenten-1-yl.

The term "cycloalkyl" as used herein, means a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two adjacent or non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[$3.3.1.0^{3,7}$]nonane and tricyclo[$3.3.1.1^{3,7}$]decane (adamantane).

The cycloalkyl groups of the invention are optionally substituted with 1, 2, 3, 4 or 5 substituents selected from the group consisting of alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkylthioalkyl, alkynyl, carboxy, cyano, formyl, haloalkoxy, haloalkyl, halogen, hydroxy, hydroxyalkyl, mercapto, oxo, —$NZ_1Z_2$, and ($NZ_3Z_4$)carbonyl.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "cycloalkylcarbonyl" as used herein, means cycloalkyl group, as defined herein, appended to the parent molecular moiety through a carbonyl group, as defined herein. Representative examples of cycloalkylcarbonyl include, but are not limited to, cyclopropylcarbonyl, 2-cyclobutylcarbonyl, and cyclohexylcarbonyl.

The term "cycloalkyloxy" as used herein, means cycloalkyl group, as defined herein, appended to the parent molecular moiety through an oxygen atom, as defined herein. Representative examples of cycloalkyloxy include, but are not limited to, cyclopropyloxy, cyclobutyloxy, cyclopentyloxy, cyclohexyloxy, cycloheptyloxy, and cyclooctyloxy.

The term "cycloalkylthio" as used herein, means cycloalkyl group, as defined herein, appended to the parent molecular moiety through a sulfur atom, as defined herein. Representative examples of cycloalkylthio include, but are not limited to, cyclopropylthio, cyclobutylthio, cyclopentylthio, cyclohexylthio, cycloheptylthio, and cyclooctylthio.

The term "ethylenedioxy" as used herein, means a —$O(CH_2)_2O$— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The term "formyl" as used herein, means a —C(O)H group.

The term "formylalkyl" as used herein, means a formyl group, as defined herein, appended to the parent molecular moiety through an alkyl group, as defined herein. Representative examples of formylalkyl include, but are not limited to, formylmethyl and 2-formylethyl.

The term "halo" or "halogen" as used herein, means —Cl, —Br, —I or —F.

The term "haloalkoxy" as used herein, means at least one halogen, as defined herein, appended to the parent molecular moiety through an alkoxy group, as define herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic heteroaryl. The monocyclic heteroaryl is a 5 or 6 membered ring that contains at least one heteroatom selected from the group consisting of nitrogen, oxygen and sulfur. The 5 membered ring contains two double bonds and the 6 membered ring contains three double bonds. The 5 or 6 membered heteroaryl is connected to the parent molecular moiety through any carbon atom or any substitutable nitrogen atom contained within the heteroaryl, provided that proper valance is maintained. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The bicyclic heteroaryl is connected to the parent molecular moiety through any carbon atom or any substitutable nitrogen atom contained within the bicyclic heteroaryl, provided that proper valance is maintained. Representative examples of bicyclic heteroaryl include, but are not limited to, azaindolyl, benzimidazolyl, benzofuranyl, benzoxadiazolyl, benzoisoxazole, benzoisothiazole, benzooxazole, 1,3-benzothiazolyl, benzothienyl(or benzothiophenyl), cinnolinyl, furopyridine, indolyl, indazolyl, indolinonyl, isobenzofuran, isoindolyl, isoquinolinyl, naphthyridinyl, oxadiazolyl, oxazolopyridine, quinolinyl, quinoxalinyl, thiadiazolyl and thienopyridinyl, The heteroaryl groups of the invention are optionally substituted with 1, 2, 3 or 4 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, nitro, —$NZ_1Z_2$ and ($NZ_3Z_4$)carbonyl. Heteroaryl groups of the invention that are substituted with a hydroxy group may be present as tautomers. The heteroaryl groups of the invention encompasses all tautomers including non-aromatic tautomers. In addition, the nitrogen heteroatoms can be optionally quaternized or oxidized to the N-oxide.

The term "heteroarylalkoxy" as used herein, means a heteroaryl group, as defined herein, appended to the parent molecular moiety through an alkoxy group, as defined herein. Representative examples of heteroarylalkoxy include, but are not limited to, fur-3-ylmethoxy, 1H-imidazol-2-ylmethoxy, 1H-imidazol-4-ylmethoxy, 1-(pyridin-4-yl)ethoxy, pyridin-3-ylmethoxy, 6-chloropyridin-3-ylmethoxy, pyridin-4-ylmethoxy, (6-(trifluoromethyl)pyridin-3-yl)methoxy, (6-(cyano)pyridin-3-yl)methoxy, (2-(cyano)pyridin-4-yl)methoxy, (5-(cyano)pyridin-2-yl)methoxy, (2-(chloro)pyridin-4-yl)methoxy, pyrimidin-5-ylmethoxy, 2-(pyrimidin-2-yl)propoxy, thien-2-ylmethoxy, and thien-3-ylmethoxy.

The term "heteroarylalkyl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, and thien-3-ylmethyl.

The term "heteroarylalkylcarbonyl" as used herein, means a heteroarylalkyl, as defined herein, appended to the parent molecular moiety through a carbonyl group, as defined herein.

The term "heteroarylalkylthio" as used herein, means a heteroarylalkyl group, as defined herein, appended to the parent molecular moiety through a sulfur atom. Representative examples of heteroarylalkylthio include, but are not limited to, fur-3-ylmethylthio, 1H-imidazol-2-ylmethylthio, 1H-imidazol-4-ylmethylthio, pyridin-3-ylmethylthio, 6-chloropyridin-3-ylmethylthio, pyridin-4-ylmethylthio, (6-(trifluoromethyl)pyridin-3-yl)methylthio, (6-(cyano)pyridin-3-yl)methylthio, (2-(cyano)pyridin-4-yl)methylthio, (5-(cyano)pyridin-2-yl)methylthio, (2-(chloro)pyridin-4-yl)methylthio, pyrimidin-5-ylmethylthio, 2-(pyrimidin-2-yl)propylthio, thien-2-ylmethylthio, and thien-3-ylmethylthio.

The term "heteroarylcarbonyl" as used herein, means a heteroaryl group, as defined herein, appended to the parent molecular moiety through a carbonyl group, as defined herein. Representative examples of heteroarylcarbonyl include, but are not limited to, fur-3-ylcarbonyl, 1H-imidazol-2-ylcarbonyl, 1H-imidazol-4-ylcarbonyl, pyridin-3-ylcarbonyl, 6-chloropyridin-3-ylcarbonyl, pyridin-4-ylcarbonyl, (6-(trifluoromethyl)pyridin-3-yl)carbonyl, (6-(cyano)pyridin-3-yl)carbonyl, (2-(cyano)pyridin-4-yl)carbonyl, (5-(cyano)pyridin-2-yl)carbonyl, (2-(chloro)pyridin-4-yl)carbonyl, pyrimidin-5-ylcarbonyl, pyrimidin-2-ylcarbonyl, thien-2-ylcarbonyl, and thien-3-ylcarbonyl.

The term "heteroaryloxy" as used herein, means a heteroaryl group, as defined herein, appended to the parent molecular moiety through an oxygen atom. Representative examples of heteroaryloxy include, but are not limited to, fur-3-yloxy, 1H-imidazol-2-yloxy, 1H-imidazol-4-yloxy, pyridin-3-yloxy, 6-chloropyridin-3-yloxy, pyridin-4-yloxy, (6-(trifluoromethyl)pyridin-3-yl)oxy, (6-(cyano)pyridin-3-yl)oxy, (2-(cyano)pyridin-4-yl)oxy, (5-(cyano)pyridin-2-yl)oxy, (2-(chloro)pyridin-4-yl)oxy, pyrimidin-5-yloxy, pyrimidin-2-yloxy, thien-2-yloxy, and thien-3-yloxy.

The term "heteroaryloxyalkyl" as used herein, means a heteroaryloxy group, as defined herein, appended to the parent molecular moiety through an alkyl group, as defined herein. Representative examples of heteroaryloxyalkyl include, but are not limited to, pyridin-3-yloxymethyl and 2-quinolin-3-yloxyethyl.

The term "heteroarylthio" as used herein, means a heteroaryl group, as defined herein, appended to the parent molecular moiety through a sulfur atom. Representative examples of heteroarylthio include, but are not limited to, pyridin-3-ylthio and quinolin-3-ylthio.

The term "heteroarylthioalkyl" as used herein, means a heteroarylthio group, as defined herein, appended to the parent molecular moiety through an alkyl group, as defined herein. Representative examples of heteroarylthioalkyl include, but are not limited to, pyridin-3-ylthiomethyl, and 2-quinolin-3-ylthioethyl.

The term "heterocycle" or "heterocyclic" as used herein, means a monocyclic heterocycle, a bicyclic heterocycle or a tricyclic heterocycle. The monocyclic heterocycle is a 3, 4, 5, 6 or 7 membered ring containing at least one heteroatom independently selected from the group consisting of O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a 5 or 6 membered monocyclic heterocycle fused to a phenyl group, or a 5 or 6 membered monocyclic heterocycle fused to a cycloalkyl, or a 5 or 6 membered monocyclic heterocycle fused to a cycloalkenyl, or a 5 or 6 membered monocyclic heterocycle fused to a monocyclic heterocycle. The bicyclic heterocycle is connected to the parent molecular moiety through any carbon atom or any nitrogen atom contained within the bicyclic heterocycle. Representative examples of bicyclic heterocycle include, but are not limited to, 1,3-benzodioxolyl, 1,3-benzodithiolyl, 2,3-dihydro-1,4-benzodioxinyl, benzodioxolyl, 2,3-dihydro-1-benzofuranyl, 2,3-dihydro-1-benzothienyl, chromenyl and 1,2,3,4-tetrahydroquinolinyl. The tricyclic heterocycle is a bicyclic heterocycle fused to a phenyl, or a bicyclic heterocycle fused to a cycloalkyl, or a bicyclic heterocycle fused to a cycloalkenyl, or a bicyclic heterocycle fused to a monocyclic heterocycle. The tricyclic heterocycle is connected to the parent molecular moiety through any carbon atom or any nitrogen atom contained within the tricyclic heterocycle. Representative examples of tricyclic heterocycle include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl.

The heterocycles of this invention are optionally substituted with 1, 2, 3 or 4 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, oxo, —$NZ_1Z_2$ and ($NZ_3Z_4$)carbonyl.

The term "heterocyclealkoxy" as used herein, means a heterocycle group, as defined herein, appended to the parent molecular moiety through an alkoxy group, as defined herein. Representative examples of heterocyclealkoxy include, but are not limited to, 2-pyridin-3-ylethoxy, 3-quinolin-3-ylpropoxy, and 5-pyridin-4-ylpentyloxy.

The term "heterocyclealkyl" as used herein, means a heterocycle, as defined herein, appended to the parent molecular moiety through an alkyl group, as defined herein. Representative examples of heterocyclealkyl include, but are not limited to, piperidin-4-ylmethyl, piperazin-1-ylmethyl, 3-methyl-1-pyrrolidin-1-ylbutyl, (1R)-3-methyl-1-pyrrolidin-1-ylbutyl, (1S)-3-methyl-1-pyrrolidin-1-ylbutyl.

The term "heterocyclealkylcarbonyl" as used herein, means a heterocyclealkyl, as defined herein, appended to the parent molecular moiety through a carbonyl group, as defined herein. Representative examples of heterocyclealkylcarbonyl include, but are not limited to, piperidin-4-ylmethylcarbonyl, piperazin-1-ylmethylcarbonyl, 3-methyl-1-pyrrolidin-1-ylbutylcarbonyl, (1R)-3-methyl-1-pyrrolidin-1-ylbutylcarbonyl, (1S)-3-methyl-1-pyrrolidin-1-ylbutylcarbonyl.

The term "heterocyclealkylthio" as used herein, means a heterocyclealkyl group, as defined herein, appended to the parent molecular moiety through a sulfur atom. Representative examples of heterocyclealkylthio include, but are not limited to, 2-pyridin-3-ylethylthio, 3-quinolin-3-ylpropythio, and 5-pyridin-4-ylpentylthio.

The term "heterocyclecarbonyl" as used herein, means a heterocycle, as defined herein, appended to the parent molecular moiety through a carbonyl group, as defined herein.

The term "heterocyclecarbonylalkyl" as used herein, means a heterocyclecarbonyl, as defined herein, appended to the parent molecular moiety through an alkyl group, as defined herein.

The term "heterocycleoxy" as used herein, means a heterocycle group, as defined herein, appended to the parent molecular moiety through an oxygen atom. Representative examples of heterocycleoxy include, but are not limited to, pyridin-3-yloxy and quinolin-3-yloxy.

The term "heterocycleoxyalkyl" as used herein, means a heterocycleoxy group, as defined herein, appended to the parent molecular moiety through an alkyl group, as defined herein. Representative examples of heterocycleoxyalkyl include, but are not limited to, pyridin-3-yloxymethyl and 2-quinolin-3-yloxyethyl.

The term "heterocyclethio" as used herein, means a heterocycle group, as defined herein, appended to the parent molecular moiety through a sulfur atom. Representative examples of heterocyclethio include, but are not limited to, pyridin-3-ylthio and quinolin-3-ylthio.

The term "heterocyclethioalkyl" as used herein, means a heterocyclethio group, as defined herein, appended to the parent molecular moiety through an alkyl group, as defined herein. Representative examples of heterocyclethioalkyl include, but are not limited to, pyridin-3-ylthiomethyl, and 2-quinolin-3-ylthioethyl.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "hydroxy-protecting group" or "O-protecting group" means a substituent which protects hydroxy groups against undesirable reactions during synthetic procedures. Examples of hydroxy-protecting groups include, but are not limited to, substituted methyl ethers, for example, methoxymethyl, benzyloxymethyl, 2-methoxyethoxymethyl, 2-(trimethylsilyl)-ethoxymethyl, benzyl, and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates. Commonly used hydroxy-protecting groups are disclosed in T. W. Greene and P. G. M. Wuts, Protective Groups in Organic Synthesis, 3rd edition, John Wiley & Sons, New York (1999).

The term "lower alkenyl" as used herein, is a subset of alkenyl, as defined herein, and means an alkenyl group containing from 2 to 4 carbon atoms. Examples of lower alkenyl are ethenyl, propenyl, and butenyl.

The term "lower alkoxy" as used herein, is a subset of alkoxy, as defined herein, and means a lower alkyl group, as defined herein, appended to the parent molecular moiety through an oxygen atom, as defined herein. Representative examples of lower alkoxy include, but are not limited to, methoxy, ethoxy, propoxy, 2-propoxy, butoxy, and tert-butoxy.

The term "lower alkyl" as used herein, is a subset of alkyl as defined herein and means a straight or branched chain hydrocarbon group containing from 1 to 4 carbon atoms. Examples of lower alkyl are methyl, ethyl, n-propyl, isopropyl, n-butyl, iso-butyl, sec-butyl, and tert-butyl.

The term "lower alkylthio" as used herein, is a subset of alkylthio, means a lower alkyl group, as defined herein, appended to the parent molecular moiety through a sulfur atom. Representative examples of lower alkylthio include, but are not limited to, methylthio, ethylthio, and tert-butylthio.

The term "lower alkynyl" as used herein, is a subset of alkynyl, as defined herein, and means an alkynyl group containing from 2 to 4 carbon atoms. Examples of lower alkynyl are ethynyl, propynyl, and butynyl.

The term "lower haloalkoxy" as used herein, is a subset of haloalkoxy, as defined herein, and means a straight or branched chain haloalkoxy group containing from 1 to 4 carbon atoms. Representative examples of lower haloalkoxy include, but are not limited to, trifluoromethoxy, trichloromethoxy, dichloromethoxy, fluoromethoxy, and pentafluoroethoxy.

The term "lower haloalkyl" as used herein, is a subset of haloalkyl, as defined herein, and means a straight or branched chain haloalkyl group containing from 1 to 4 carbon atoms. Representative examples of lower haloalkyl include, but are not limited to, trifluoromethyl, trichloromethyl, dichloromethyl, fluoromethyl, and pentafluoroethyl.

The term "mercapto" as used herein, means a —SH group.

The term "mercaptoalkyl" as used herein, means a mercapto group, as defined herein, appended to the parent molecular moiety through an alkyl group, as defined herein. Representative examples of mercaptoalkyl include, but are not limited to, 2-mercaptoethyl and 3-mercaptopropyl.

The term "methylenedioxy" as used herein, means a —OCH$_2$O— group wherein the oxygen atoms of the methylenedioxy are attached to the parent molecular moiety through two adjacent carbon atoms.

The term "nitrogen protecting group" as used herein, means those groups intended to protect an amino group against undesirable reactions during synthetic procedures. Preferred nitrogen protecting groups are acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl (trityl).

The term "nitro" as used herein, means a —NO$_2$ group.

The term "NZ$_1$Z$_2$" as used herein, means two groups, Z$_1$ and Z$_2$, which are appended to the parent molecular moiety through a nitrogen atom. Z$_1$ and Z$_2$ are each independently selected from the group consisting of hydrogen, alkyl, alkylcarbonyl, alkoxycarbonyl, aryl, arylalkyl, formyl and (NZ$_5$Z$_6$)carbonyl. In certain instances within the invention, Z$_1$ and Z$_2$ taken together with the nitrogen atom to which they are attached form a heterocyclic ring. Representative examples of NZ$_1$Z$_2$ include, but are not limited to, amino, methylamino, acetylamino, acetylmethylamino, phenylamino, benzylamino, azetidinyl, pyrrolidinyl and piperidinyl.

The term "NZ$_3$Z$_4$" as used herein, means two groups, Z$_3$ and Z$_4$, which are appended to the parent molecular moiety through a nitrogen atom. Z$_3$ and Z$_4$ are each independently selected from the group consisting of hydrogen, alkyl, aryl and arylalkyl. Representative examples of NZ$_3$Z$_4$ include, but are not limited to, amino, methylamino, phenylamino and benzylamino The term "NZ$_5$Z$_6$" as used herein, means two groups, Z$_5$ and Z$_6$, which are appended to the parent molecular moiety through a nitrogen atom. Z$_5$ and Z$_6$ are each independently selected from the group consisting of hydrogen, alkyl, aryl and arylalkyl. Representative examples of NZ$_5$Z$_6$ include, but are not limited to, amino, methylamino, phenylamino and benzylamino The term "(NZ$_3$Z$_4$)carbonyl" as used herein, means a NZ$_3$Z$_4$ group, as defined herein, appended to the parent molecular moiety through a carbonyl group, as defined herein. Representative examples of (NZ$_3$Z$_4$)carbonyl include, but are not limited to, aminocarbonyl, (methylamino)carbonyl, (dimethylamino)carbonyl, and (ethylmethylamino)carbonyl.

The term "oxo" as used herein, means a =O moiety.

The term "sulfinyl" as used herein, means a —S(O)— group.

The term "sulfonyl" as used herein, means a —SO$_2$— group.

The term "tautomer" as used herein means a proton shift from one atom of a compound to another atom of the same compound wherein two or more structurally distinct compounds are in equilibrium with each other.

Although typically it may be recognized that an asterisk is used to indicate that the exact subunit composition of a receptor is uncertain, for example α3β4* indicates a receptor that contains the α3 and β4 proteins in combination with other subunits, the term α7 as used herein is intended to include receptors wherein the exact subunit composition is both certain and uncertain. For example, as used herein α7 includes homomeric (α7)$_5$ receptors and α7* receptors, which denote a nAChR containing at least one α7 subunit.

COMPOUNDS OF THE INVENTION

Compounds of the invention can have the formula (I) as described in the Summary of the Invention.

Within the scope of the invention, the compounds of the invention have the formula

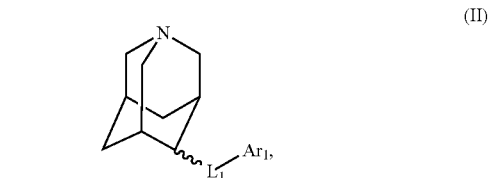

(II)

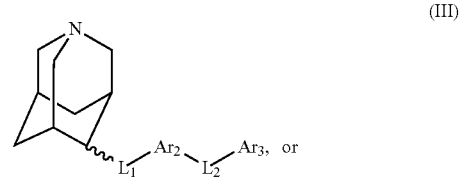

(III)

-continued (IV)

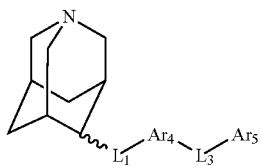

wherein $L_1$, $Ar_1$, $Ar_2$, $L_2$, $L_3$, $Ar_3$, $Ar_4$ and $Ar_5$ are defined in formula (I).

In one embodiment, the compounds of the invention can have the formula (II) wherein $L_1$ and $Ar_1$ are as previously defined for formula (I). In compounds of formula (II), $Ar_1$ can more particularly be selected from a group having the structure

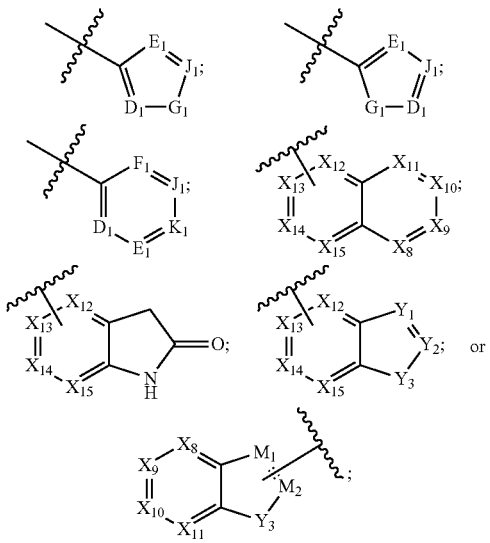

wherein $D_1$, $E_1$, $F_1$, $J_1$, $K_1$, and $X_8$-$X_{11}$ are each independently —$CR_1$ or N; $X_{12}$-$X_{15}$, $M_1$ and $M_2$ are each independently $CR_1$, N, or C; $G_1$ is —O—, $NR_{1a}$, or —S—; $Y_1$ is —$CR_1$ or N; $Y_2$ is —$CR_1$ or N; $Y_3$ is NH, —O—, or —S—; $R_1$ is hydrogen, alkyl, alkoxy, alkoxycarbonyl, cyano, halo, nitro, —$NR_bR_c$, haloalkyl, or —$C(O)NR_bR_c$; $R_{1a}$ is hydrogen or alkyl; $R_b$ and $R_c$ are each independently hydrogen, alkyl, alkoxycarbonyl or alkylcarbonyl. In a group represented by $Ar_1$, preferably no more than two of $D_1$, $E_1$, $F_1$, $J_1$, and $K_1$ are N. In a group represented by $Ar_1$, preferably no more than two in the groups $X_{12}$-$X_{15}$ or $X_8$-$X_{11}$ are N. In a group represented by $Ar_1$, one of $X_{12}$-$X_{15}$ is C. In a group represented by $Ar_1$, $M_1$ or $M_2$ is C. Preferably, $Ar_1$ is imidazolyl, isoxazolyl, furyl, oxazolyl, phenyl, pyridinyl, pyrimidinyl, pyridazinyl, pyrazinyl, thiophenyl, 1,3-thiazolyl, 1,3,4-thiadiazolyl, 1,3,4-oxadiazolyl, benzoxazolyl, or 1,3-benzothiazolyl. Preferred $Ar_1$ groups are pyridazinyl, pyridinyl, 1,3-thiazolyl, 1,3,4-thiadiazolyl, 1,3,4-oxadiazolyl, benzoxazol-2-yl or 1,3-benzothiazol-2-yl. In a particular embodiment, $L_1$ is —O— and $Ar_1$ is as described herein for formula (I) or any of the particular or preferred embodiments. In another particular embodiment, $L_1$ is $NR_a$— and $Ar_1$ is as described herein for formula (I) or any of the particular or preferred embodiments.

In another embodiment, compounds of the invention can have the formula (III), wherein $L_1$, $Ar_2$, $L_2$, and $Ar_3$ are as previously described for compounds of formula (I). In compounds of formula (III), $Ar_2$ can more particularly be selected from a group having the structure

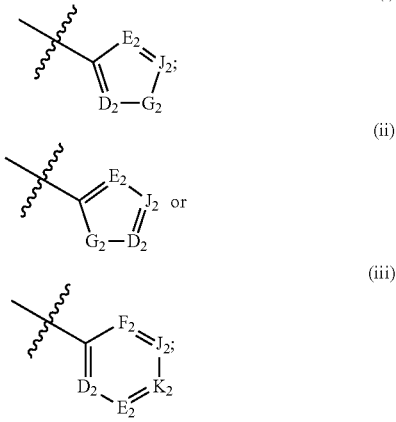

wherein $D_2$, $E_2$, $F_2$, $J_2$, and $K_2$ are each independently —$CT_2$ or —N; $G_2$ is —O—, —$NR_{2a}$, or —S—; in each group of (i), (ii), and (iii) above, one substituent represented by $T_2$, or $R_{2a}$ wherein $R_{2a}$ is $T_2$, is $L_2$-$Ar_3$ and the other substituents represented by $T_2$ are hydrogen, alkyl, alkoxy, alkoxycarbonyl, cyano, halo, nitro, or —$NR_bR_c$; $R_{2a}$ is hydrogen, alkyl, or $T_2$; and $R_b$ and $R_c$, are each independently hydrogen, alkyl, alkoxycarbonyl, or alkylcarbonyl. $Ar_3$ can more particularly be selected from a group of the structure

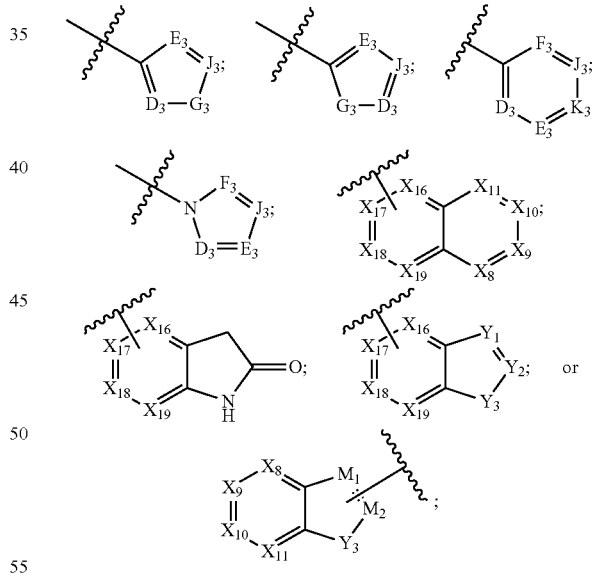

wherein $D_3$, $E_3$, $F_3$, $J_3$, $K_3$, and $X_8$, $X_9$, $X_{10}$, and $X_{11}$ are each independently —$CR_3$ or N; $X_{16}$, $X_{17}$, $X_{18}$, $X_{19}$, $M_1$, and $M_2$ are each independently —$CR_3$, N, or C; $G_3$ is —O—, —$NR_{3a}$, or —S—; $Y_1$ and $Y_2$ are —$CR_3$ or N; $Y_3$ is NH, —O—, or S—; $R_3$ is hydrogen, alkyl, alkoxy, alkoxyalkyl, alkoxycarbonyl, alkylcarbonyl, cyano, halo, haloalkoxy, haloalkyl, hydroxy, nitro, $R_eR_fN$—, or aryl; $R_{3a}$ is hydrogen, alkyl, alkylcarbonyl, trityl, or aryl, wherein aryl is preferably phenyl; $R_e$ and $R_f$ are each independently hydrogen, alkyl, alkoxycarbonyl or alkylcarbonyl, or $R_e$ and $R_f$ are each taken together with the nitrogen atom to which they are attached form a heterocyclic ring. The preferred aryl group for $R_3$ is phenyl optionally substituted with halo, alkyl or cyano. The preferred heterocyclic ring wherein $R_e$ and $R_f$ are each taken together to form a ring is pyrrolidinyl, piperidinyl or piperazinyl. In a group represented by $Ar_3$, preferably no more than two of $D_3$, $E_3$, $F_3$, $J_3$, and $K_3$ are N. In a group represented by $Ar_3$, preferably no more than two in the groups $X_{16}$-$X_{19}$ or $X_8$-$X_{11}$ are N. In a group represented by $Ar_3$, one of $X_{16}$, $X_{17}$, $X_{18}$, or $X_{19}$ is C. In a group represented by $Ar_3$, $M_1$ or $M_2$ is C. One particular embodiment relates to compounds of formula (III) wherein $L_1$ is —O— or —$NR_{1a}$ and $L_2$ is —O—. Compounds of formula (III) wherein $L_1$ is —O— or —$NR_{1a}$ and $L_2$ is a bond also are contemplated. Preferably, $L_1$ is —O—; and $L_2$ is a bond in compounds of formula (III) wherein $Ar_2$ and $Ar_3$ are as previously described for compounds of formula (I) or particular or preferred embodiments as previously described. In one particular embodiment, the invention relates to compounds of formula (III) wherein $L_1$ is —O— or —$NR_a$; $Ar_2$ is phenyl or a heteroaryl ring; $L_2$ is a bond, —O—, —$NR_a$—, —$CH_2$—, or —$C(O)NR_a$—; and $Ar_3$ is an aryl or heteroaryl ring, preferentially phenyl, pyrazinyl or pyridyl.

In another embodiment, compounds of the invention can have the formula (IV), wherein $L_1$, $Ar_4$, $L_3$, and $Ar_5$ are as defined for compounds of formula (I). Preferably, in compounds of formula (IV), $Ar_4$-$L_3$-$Ar_5$ group is a group selected from

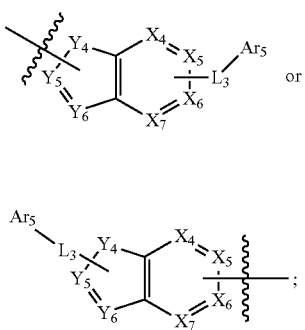

wherein $Y_4$ is —$NR_{4a}$—, —O— or S—; $Y_5$ and $Y_6$ are N—, —$CR_4$— or C, provided that one of $Y_5$ or $Y_6$ is C; $R_4$ is hydrogen, alkyl, alkoxy, alkoxyalkyl, alkoxycarbonyl, alkylcarbonyl, cyano, halo, haloalkoxy, haloalkyl, hydroxy, nitro, oxo, or $R_eR_fN$—; $R_{4a}$ is hydrogen or alkyl; $R_e$ and $R_f$ are each independently hydrogen, alkyl, alkoxycarbonyl, or alkylcarbonyl, or $R_e$ and $R_f$ are each taken together with the nitrogen atom to which they are attached form a heterocyclic ring, wherein the heterocyclic ring is preferably pyrrolidinyl, piperidinyl or piperazinyl; $X_4$ is N—, —$CR_{X4}$—, or C, $X_5$ is N—, $CR_{X5}$—, or C, $X_6$ is N—, $CR_{X6}$—, or C, and $X_7$ is N—, $CR_{X7}$—, or C, provided that only one of $X_4$, $X_5$, $X_6$ or $X_7$ may be N—, only one is C, and the remaining must be other than N—, and $R_{X4}$, $R_{X5}$, $R_{X6}$ and $R_{X7}$ are each independently hydrogen or alkyl. Preferably $Ar_4$ is 1,3-benzothiazol-2-yl.

Suitable and preferred groups for $Ar_5$ in compounds of formula (IV) are as defined for $Ar_1$ for compounds of formula (II) or $Ar_3$ for compounds of formula (III).

In addition, the invention also contemplates compounds of formula (VI) or compounds of formula (VII)

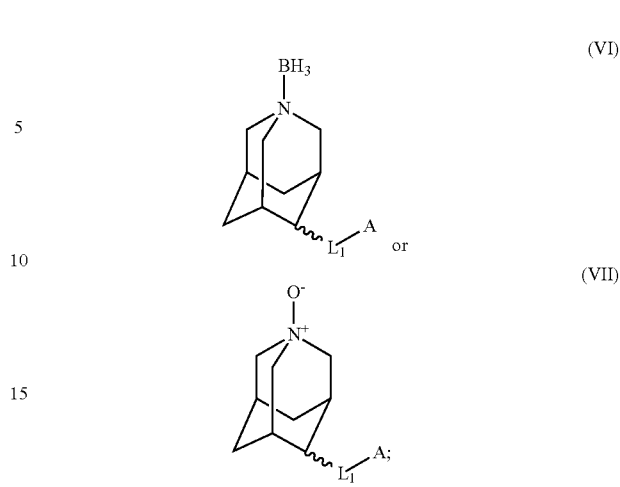

or a pharmaceutically acceptable salt or prodrug thereof, wherein $L_1$ is —O— or —$NR_a$—; A is —$Ar_1$, —$Ar_2$-$L_2$-$Ar_3$ or —$Ar_4$-$L_3$-$Ar_5$; $Ar_1$ is aryl or heteroaryl; $Ar_2$ is aryl or heteroaryl; $Ar_3$ is aryl or heteroaryl; $Ar_4$ is a bicyclic heteroaryl; $Ar_5$ is aryl or heteroaryl; $L_2$ is a bond, —O—, —$NR_a$—, —$CH_2$—, or —$C(O)NR_a$—; $L_3$ is a bond, —O—, —$NR_a$— or CH—; and $R_a$ is hydrogen or alkyl.

Furthermore, compound of formula (VI) or of formula (VII), are useful as prodrugs of compounds of formula (I).

Specific embodiments contemplated as part of the invention include, but are not limited to compounds of formula (I), or salts or prodrugs thereof, for example:

(4s)-4-(6-chloropyridazin-3-yloxy)-1-azatricyclo[3.3.1.1$^{3,7}$]decane;

(4r)-4-(6-chloropyridazin-3-yloxy)-1-azatricyclo[3.3.1.1$^{3,7}$]decane;

(4s)-4-(6-phenylpyridazin-3-yloxy)-1-azatricyclo[3.3.1.1$^{3,7}$]decane;

(4r)-4-(6-phenylpyridazin-3-yloxy)-1-azatricyclo[3.3.1.1$^{3,7}$]decane;

(4s)-4-[6-(1H-indol-5-yl)pyridazin-3-yloxy]-1-azatricyclo[3.3.1.1$^{3,7}$]decane;

(4r)-4-[6-(1H-indol-5-yl)pyridazin-3-yloxy]-1-azatricyclo[3.3.1.1$^{3,7}$]decane;

(4s)-4-[6-(1-benzothien-5-yl)pyridazin-3-yloxy]-1-azatricyclo[3.3.1.1$^{3,7}$]decane;

(4r)-4-[6-(1-benzothien-5-yl)pyridazin-3-yloxy]-1-azatricyclo[3.3.1.1$^{3,7}$]decane;

(4r)-4-(5-bromopyridin-2-yloxy)-1-azatricyclo[3.3.1.1$^{3,7}$]decane;

(4s)-4-(5-phenylpyridin-2-yloxy)-1-azatricyclo[3.3.1.1$^{3,7}$]decane;

(4r)-4-(5-phenylpyridin-2-yloxy)-1-azatricyclo[3.3.1.1$^{3,7}$]decane;

(4s)-4-[5-(1H-indol-5-yl)pyridin-2-yloxy]-1-azatricyclo[3.3.1.1$^{3,7}$]decane;

(4r)-4-[5-(1H-indol-5-yl)pyridin-2-yloxy]-1-azatricyclo[3.3.1.1$^{3,7}$]decane;

(4r)-4-[5-(benzothien-5-yl)pyridin-2-yloxy]-1-azatricyclo[3.3.1.1$^{3,7}$]decane;

(4s)-4-(6-chloropyridin-3-yloxy)-1-azatricyclo[3.3.1.1$^{3,7}$]decane;

(4s)-4-(6-nitropyridin-3-yloxy)-1-azatricyclo[3.3.1.1$^{3,7}$]decane;

(4s)-4-(6-aminopyridin-3-yloxy)-1-azatricyclo[3.3.1.1$^{3,7}$]decane;

(4r)-4-(6-nitropyridin-3-yloxy)-1-azatricyclo[3.3.1.1$^{3,7}$]decane;
(4r)-4-(6-aminopyridin-3-yloxy)-1-azatricyclo[3.3.1.1$^{3,7}$]decane;
(4s)-4-(5-bromothiazol-2-yloxy)-1-azatricyclo[3.3.1.1$^{3,7}$]decane;
(4s)-4-(thiazol-2-yloxy)-1-azatricyclo[3.3.1.1$^{3,7}$]decane;
(4s)-4-(5-phenylthiazol-2-yloxy)-1-azatricyclo[3.3.1.1$^{3,7}$]decane;
(4s)-4-[5-(4-methoxyphenyl)-thiazol-2-yloxy]-1-azatricyclo[3.3.1.1$^{3,7}$]decane;
(4s)-4-[5-(3-chlorophenyl)-thiazol-2-yloxy]-1-azatricyclo[3.3.1.1$^{3,7}$]decane;
(4s)-4-[5-(3-chloro-4-methoxyphenyl)-thiazol-2-yloxy]-1-azatricyclo[3.3.1.1$^{3,7}$]decane;
(4s)-4-[5-(4-fluorophenyl)-thiazol-2-yloxy]-1-azatricyclo[3.3.1.1$^{3,7}$]decane;
(4s)-4-[5-(3,5-difluorophenyl)-thiazol-2-yloxy]-1-azatricyclo[3.3.1.1$^{3,7}$]decane;
(4s)-4-[5-(1H-indol-5-yl)-thiazol-2-yloxy]-1-azatricyclo[3.3.1.1$^{3,7}$]decane;
(4s)-4-[5-(1H-indol-5-yl)-thiazol-2-yloxy]-1-azatricyclo[3.3.1.1$^{3,7}$]decane-1-oxide; 5-[2-(1-azatricyclo[3.3.1.1$^{3,7}$]decan-(4s)-yloxy)thiazol-5-yl]-indolin-2-one;
5-[2-(1-azatricyclo[3.3.1.1$^{3,7}$]decan-1-oxide-(4s)-yloxy)thiazol-5-yl]-indolin-2-one;
(4s)-4-[5-(2-trifluoromethyl-1H-indol-5-yl)-thiazol-2-yloxy]-1-azatricyclo[3.3.1.1$^{3,7}$]decane;
(4s)-4-[5-(1H-indol-4-yl)-thiazol-2-yloxy]-1-azatricyclo[3.3.1.1$^{3,7}$]decane;
(4s)-4-[5-(1H-indol-6-yl)-thiazol-2-yloxy]-1-azatricyclo[3.3.1.1$^{3,7}$]decane;
(4s)-4-[5-(1H-indol-3-yl)-thiazol-2-yloxy]-1-azatricyclo[3.3.1.1$^{3,7}$]decane;
(4s)-4-[5-(pyridin-4-yl)-thiazol-2-yloxy]-1-azatricyclo[3.3.1.1$^{3,7}$]decane;
(4s)-4-[5-(furan-2-yl)-thiazol-2-yloxy]-1-azatricyclo[3.3.1.1$^{3,7}$]decane;
(4s)-4-[5-(furan-3-yl)-thiazol-2-yloxy]-1-azatricyclo[3.3.1.1$^{3,7}$]decane;
(4s)-4-[5-(thien-3-yl)-thiazol-2-yloxy]-1-azatricyclo[3.3.1.1$^{3,7}$]decane;
(4s)-4-[5-(pyrazol-4-yl)-thiazol-2-yloxy]-1-azatricyclo[3.3.1.1$^{3,7}$]decane;
(4s)-4-(5-bromo-1,3,4-thiadiazol-2-yloxy)-1-azatricyclo[3.3.1.1$^{3,7}$]decane;
(4s)-4-(1,3,4-thiadiazol-2-yloxy)-1-azatricyclo[3.3.1.1$^{3,7}$]decane;
(4s)-4-(5-phenyl-1,3,4-thiadiazol-2-yloxy)-1-azatricyclo[3.3.1.1$^{3,7}$]decane;
(4s)-4-(5-phenyl-1,3,4-thiadiazol-2-yloxy)-1-azatricyclo[3.3.1.1$^{3,7}$]decane-1-oxide;
(4r)-4-(5-phenyl-1,3,4-thiadiazol-2-yloxy)-1-azatricyclo[3.3.1.1$^{3,7}$]decane;
(4s)-4-[5-(4-fluorophenyl)-1,3,4-thiadiazol-2-yloxy]-1-azatricyclo[3.3.1.1$^{3,7}$]decane;
(4r)-4-[5-(4-fluorophenyl)-1,3,4-thiadiazol-2-yloxy]-1-azatricyclo[3.3.1.1$^{3,7}$]decane;
(4s)-4-[5-(3-fluorophenyl)-1,3,4-thiadiazol-2-yloxy]-1-azatricyclo[3.3.1.1$^{3,7}$]decane;
(4r)-4-[5-(3-fluorophenyl)-1,3,4-thiadiazol-2-yloxy]-1-azatricyclo[3.3.1.1$^{3,7}$]decane;
(4s)-4-[5-(1H-indol-5-yl)-1,3,4-thiadiazol-2-yloxy]-1-azatricyclo[3.3.1.1$^{3,7}$]decane;
(4s)-4-[5-(1H-indol-6-yl)-1,3,4-thiadiazol-2-yloxy]-1-azatricyclo[3.3.1.1$^{3,7}$]decane;
(4s)-4-[5-(1H-indol-4-yl)-1,3,4-thiadiazol-2-yloxy]-1-azatricyclo[3.3.1.1$^{3,7}$]decane;
(4s)-4-[5-(benzothien-5-yl)-1,3,4-thiadiazol-2-yloxy]-1-azatricyclo[3.3.1.1$^{3,7}$]decane;
(4s)-4-[5-(pyrazol-4-yl)-1,3,4-thiadiazol-2-yloxy]-1-azatricyclo[3.3.1.1$^{3,7}$]decane;
(4s)-4-(5-phenoxy-1,3,4-thiadiazol-2-yloxy)-1-azatricyclo[3.3.1.1$^{3,7}$]decane;
(4s)-4-(5-tert-butyl-1,3,4-thiadiazol-2-yloxy)-1-azatricyclo[3.3.1.1$^{3,7}$]decane;
(4r)-4-(5-tert-butyl-1,3,4-thiadiazol-2-yloxy)-1-azatricyclo[3.3.1.1$^{3,7}$]decane;
(4s)-4-(5-phenyl-1,3,4-oxadiazol-2-yloxy)-1-azatricyclo[3.3.1.1$^{3,7}$]decane;
(4r)-4-(5-phenyl-1,3,4-oxadiazol-2-yloxy)-1-azatricyclo[3.3.1.1$^{3,7}$]decane;
(4s)-4-(benzothiazol-2-yloxy)-1-azatricyclo[3.3.1.1$^{3,7}$]decane;
(4r)-4-(benzothiazol-2-yloxy)-1-azatricyclo[3.3.1.1$^{3,7}$]decane;
(4s)-4-(6-chlorobenzothiazol-2-yloxy)-1-azatricyclo[3.3.1.1$^{3,7}$]decane;
(4r)-4-(6-chlorobenzothiazol-2-yloxy)-1-azatricyclo[3.3.1.1$^{3,7}$]decane;
(4s)-4-(benzoxazol-2-yloxy)-1-azatricyclo[3.3.1.1$^{3,7}$]decane;
(4s)-N-(6-chloropyridin-3-yl)-1-azatricyclo[3.3.1.1$^{3,7}$]decan-4-amine;
(4r)-N-(6-chloropyridin-3-yl)-1-azatricyclo[3.3.1.1$^{3,7}$]decan-4-amine;
(4s)-N-(6-phenylpyridin-3-yl)-1-azatricyclo[3.3.1.1$^{3,7}$]decan-4-amine;
(4s)-N-[6-(indol-5-yl)-pyridin-3-yl]-1-azatricyclo[3.3.1.1$^{3,7}$]decan-4-amine;
(4s)-N-(5-bromopyridin-3-yl)-1-azatricyclo[3.3.1.1$^{3,7}$]decan-4-amine;
(4s)-N-[5-(indol-5-yl)-pyridin-3-yl]-1-azatricyclo[3.3.1.1$^{3,7}$]decan-4-amine;
(4s)-N-[5-(indol-6-yl)-pyridin-3-yl]-1-azatricyclo[3.3.1.1$^{3,7}$]decan-4-amine;
(4s)-N-[5-(indol-4-yl)-pyridin-3-yl]-1-azatricyclo[3.3.1.1$^{3,7}$]decan-4-amine;
(4s)-N-[5-(3-methylphenyl)-pyridin-3-yl]-1-azatricyclo[3.3.1.1$^{3,7}$]decan-4-amine;
(4s)-N-[5-(3-chlorophenyl)-pyridin-3-yl]-1-azatricyclo[3.3.1.1$^{3,7}$]decan-4-amine;
(4s)-4 N-[5-(3-chlorophenylphen-3-yl)-pyridin-3-yl]-1-azatricyclo[3.3.1.1$^{3,7}$]decan-4-amine;
(4s)-4-(pyridin-3-yloxy)-1-azatricyclo[3.3.1.1$^{3,7}$]decane;
(4s)-4-[(1-oxidopyridin-3-yl)oxy]-1-azatricyclo[3.3.1.1$^{3,7}$]decane;
(4r)-4-(pyridin-3-yloxy)-1-azatricyclo[3.3.1.1$^{3,7}$]decane;
(4s)-4-[(2-chloropyridin-3-yl)oxy]-1-azatricyclo[3.3.1.1$^{3,7}$]decane;
(4s)-4-[(2-bromopyridin-3-yl)oxy]-1-azatricyclo[3.3.1.1$^{3,7}$]decane;
(4s)-4-[(4-chloropyridin-3-yl)oxy]-1-azatricyclo[3.3.1.1$^{3,7}$]decane;
(4s)-4-[(4-methylpyridin-3-yl)oxy]-1-azatricyclo[3.3.1.1$^{3,7}$]decane;
(4s)-4-{[4-(trifluoromethyl)pyridin-3-yl]oxy}-1-azatricyclo[3.3.1.1$^{3,7}$]decane;
(4s)-4-[(5-fluoropyridin-3-yl)oxy]-1-azatricyclo[3.3.1.1$^{3,7}$]decane;
(4s)-4-[(5-chloropyridin-3-yl)oxy]-1-azatricyclo[3.3.1.1$^{3,7}$]decane;

(4s)-4-[(5-bromopyridin-3-yl)oxy]-1-azatricyclo[3.3.1.1³,⁷]decane;
(4s)-4-[(5-iodopyridin-3-yl)oxy]-1-azatricyclo[3.3.1.1³,⁷]decane;
5-[(4s)-1-azatricyclo[3.3.1.1³,⁷]dec-4-yloxy]nicotinamide;
(4s)-4-{[5-(1H-pyrazol-4-yl)pyridin-3-yl]oxy}-1-azatricyclo[3.3.1.1³,⁷]decane;
(4s)-4-{[5-(1-methyl-1H-pyrazol-4-yl)pyridin-3-yl]oxy}-1-azatricyclo[3.3.1.1³,⁷]decane;
(4s)-4-{[5-(1H-pyrazol-1-yl)pyridin-3-yl]oxy}-1-azatricyclo[3.3.1.1³,⁷]decane;
(4s)-4-{[5-(4-chlorophenyl)pyridin-3-yl]oxy}-1-azatricyclo[3.3.1.1³,⁷]decane;
(4s)-4-(3,4'-bipyridin-5-yloxy)-1-azatricyclo[3.3.1.1³,⁷]decane;
(4s)-4-[(5-pyrimidin-5-ylpyridin-3-yl)oxy]-1-azatricyclo[3.3.1.1³,⁷]decane;
(4r)-4-[(6-chloropyridin-3-yl)oxy]-1-azatricyclo[3.3.1.1³,⁷]decane;
(4s)-4-[(6-bromopyridin-3-yl)oxy]-1-azatricyclo[3.3.1.1³,⁷]decane;
5-[(4s)-1-azatricyclo[3.3.1.1³,⁷]dec-4-yloxy]pyridine-2-carbonitrile;
(4s)-4-[(5-thien-2-ylpyridin-2-yl)oxy]-1-azatricyclo[3.3.1.1³,⁷]decane;
(4s)-4-{[6-(1H-indol-5-yl)pyridin-3-yl]oxy}-1-azatricyclo[3.3.1.1³,⁷]decane;
(4r)-4-{[6-(1H-indol-5-yl)pyridin-3-yl]oxy}-1-azatricyclo[3.3.1.1³,⁷]decane;
(4s)-4-{[6-(1H-indol-6-yl)pyridin-3-yl]oxy}-1-azatricyclo[3.3.1.1³,⁷]decane;
(4r)-4-{[6-(1H-indol-6-yl)pyridin-3-yl]oxy}-1-azatricyclo[3.3.1.1³,⁷]decane;
5-{5-[(4s)-1-azatricyclo[3.3.1.1³,⁷]dec-4-yloxy]pyridin-2-yl}-1,3-dihydro-2H-indol-2-one;
(4r)-4-{[6-(1-benzofuran-5-yl)pyridin-3-yl]oxy}-1-azatricyclo[3.3.1.1³,⁷]decane;
(4s)-4-[(5,6-dibromopyridin-3-yl)oxy]-1-azatricyclo[3.3.1.1³,⁷]decane;
(4s)-4-(pyridin-2-yloxy)-1-azatricyclo[3.3.1.1³,⁷]decane;
(4s)-4-[(5-fluoropyridin-2-yl)oxy]-1-azatricyclo[3.3.1.1³,⁷]decane;
(4s)-4-[(5-bromopyridin-2-yl)oxy]-1-azatricyclo[3.3.1.1³,⁷]decane;
(4s)-4-[(4-bromopyridin-2-yl)oxy]-1-azatricyclo[3.3.1.1³,⁷]decane;
(4s)-4-(3,3'-bipyridin-6-yloxy)-1-azatricyclo[3.3.1.1³,⁷]decane;
(4s)-4-(3,4'-bipyridin-6-yloxy)-1-azatricyclo[3.3.1.1³,⁷]decane;
(4r)-4-(3,4'-bipyridin-6-yloxy)-1-azatricyclo[3.3.1.1³,⁷]decane;
(4s)-4-[(5-pyrimidin-5-ylpyridin-2-yl)oxy]-1-azatricyclo[3.3.1.1³,⁷]decane;
(4s)-4-{[5-(1H-pyrazol-4-yl)pyridin-2-yl]oxy}-1-azatricyclo[3.3.1.1³,⁷]decane;
6-[(4s)-1-azatricyclo[3.3.1.1³,⁷]dec-4-yloxy]-N-pyridin-4-ylpyridine-2-carboxamide;
(4s)-4-[(2-chloropyridin-4-yl)oxy]-1-azatricyclo[3.3.1.1³,⁷]decane;
(4s)-4-[(6-methylpyridazin-3-yl)oxy]-1-azatricyclo[3.3.1.1³,⁷]decane;
(4s)-4-(pyrimidin-2-yloxy)-1-azatricyclo[3.3.1.1³,⁷]decane;
(4s)-4-[(5-bromopyrimidin-2-yl)oxy]-1-azatricyclo[3.3.1.1³,⁷]decane;
(4s)-4-(pyrimidin-5-yloxy)-1-azatricyclo[3.3.1.1³,⁷]decane;
(4s)-4-(pyrimidin-4-yloxy)-1-azatricyclo[3.3.1.1³,⁷]decane;
(4s)-4-[(6-chloropyrimidin-4-yl)oxy]-1-azatricyclo[3.3.1.1³,⁷]decane;
(4s)-4-{[6-(1-trityl-1H-pyrazol-4-yl)pyrimidin-4-yl]oxy}-1-azatricyclo[3.3.1.1³,⁷]decane;
(4s)-4-{[6-(1H-pyrazol-4-yl)pyrimidin-4-yl]oxy}-1-azatricyclo[3.3.1.1³,⁷]decane;
(4s)-4-[(6-pyridin-4-ylpyrimidin-4-yl)oxy]-1-azatricyclo[3.3.1.1³,⁷]decane;
(4s)-4-(pyrazin-2-yloxy)-1-azatricyclo[3.3.1.1³,⁷]decane;
4-[(6-methylpyrazin-2-yl)oxy]-1-azatricyclo[3.3.1.1³,⁷]decane;
(4r)-4-[(6-phenylpyrazin-2-yl)oxy]-1-azatricyclo[3.3.1.1³,⁷]decane;
(4r)-4-(1,3-thiazol-2-yloxy)-1-azatricyclo[3.3.1.1³,⁷]decane;
(4r)-4-[(5-bromo-1,3-thiazol-2-yl)oxy]-1-azatricyclo[3.3.1.1³,⁷]decane;
(4s)-4-({5-[4-(trifluoromethoxy)phenyl]-1,3-thiazol-2-yl}oxy)-1-azatricyclo[3.3.1.1³,⁷]decane;
(4s)-4-{[5-(4-chlorophenyl)-1,3-thiazol-2-yl]oxy}-1-azatricyclo[3.3.1.1³,⁷]decane;
4-{2-[(4s)-1-azatricyclo[3.3.1.1³,⁷]dec-4-yloxy]-1,3-thiazol-5-yl}aniline;
(4s)-4-[(5-pyridin-3-yl-1,3-thiazol-2-yl)oxy]-1-azatricyclo[3.3.1.1³,⁷]decane;
(4r)-4-[(5-pyridin-3-yl-1,3-thiazol-2-yl)oxy]-1-azatricyclo[3.3.1.1³,⁷]decane;
(4s)-4-[(5-pyrimidin-5-yl-1,3-thiazol-2-yl)oxy]-1-azatricyclo[3.3.1.1³,⁷]decane;
(4s)-4-{[5-(2-methoxypyrimidin-5-yl)-1,3-thiazol-2-yl]oxy}-1-azatricyclo[3.3.1.1³,⁷]decane;
(4s)-4-{[5-(2-pyrrolidin-1-ylpyrimidin-5-yl)-1,3-thiazol-2-yl]oxy}-1-azatricyclo[3.3.1.1³,⁷]decane;
(4s)-4-{[5-(6-piperazin-1-ylpyridin-3-yl)-1,3-thiazol-2-yl]oxy}-1-azatricyclo[3.3.1.1³,⁷]decane;
(4s)-4-{[5-(1H-pyrazol-1-yl)-1,3-thiazol-2-yl]oxy}-1-azatricyclo[3.3.1.1³,⁷]decane;
(4s)-4-{[5-(1-trityl-1H-pyrazol-4-yl)-1,3-thiazol-2-yl]oxy}-1-azatricyclo[3.3.1.1³,⁷]decane;
(4s)-4-{[5-(1-propyl-1H-pyrazol-4-yl)-1,3-thiazol-2-yl]oxy}-1-azatricyclo[3.3.1.1³,⁷]decane;
(4s)-4-{[5-(1-isobutyl-1H-pyrazol-4-yl)-1,3-thiazol-2-yl]oxy}-1-azatricyclo[3.3.1.1³,⁷]decane;
(4s)-4-{[5-(1-acetyl-1H-pyrazol-4-yl)-1,3-thiazol-2-yl]oxy}-1-azatricyclo[3.3.1.1³,⁷]decane;
(4s)-4-{[5-(5-methyl-1-phenyl-1H-pyrazol-4-yl)-1,3-thiazol-2-yl]oxy}-1-azatricyclo[3.3.1.1³,⁷]decane;
(4s)-4-[(5-isoxazol-4-yl-1,3-thiazol-2-yl)oxy]-1-azatricyclo[3.3.1.1³,⁷]decane;
(4s)-4-[(4-bromo-1,3-thiazol-2-yl)oxy]-1-azatricyclo[3.3.1.1³,⁷]decane;
(4r)-4-[(4-bromo-1,3-thiazol-2-yl)oxy]-1-azatricyclo[3.3.1.1³,⁷]decane;
(4s)-4-[(4-chloro-1,3-thiazol-2-yl)oxy]-1-azatricyclo[3.3.1.1³,⁷]decane;
(4s)-4-{[4-(1H-pyrazol-4-yl)-1,3-thiazol-2-yl]oxy}-1-azatricyclo[3.3.1.1³,⁷]decane;
(4s)-4-[(4-phenyl-1,3-thiazol-2-yl)oxy]-1-azatricyclo[3.3.1.1³,⁷]decane;
(4s)-4-[(4-pyridin-4-yl-1,3-thiazol-2-yl)oxy]-1-azatricyclo[3.3.1.1³,⁷]decane;
(4s)-4-[(4-pyridin-3-yl-1,3-thiazol-2-yl)oxy]-1-azatricyclo[3.3.1.1³,⁷]decane;
2-[(4s)-1-azatricyclo[3.3.1.1³,⁷]dec-4-yloxy]-N-pyridin-4-yl-1,3-thiazole-4-carboxamide;
2-[(4s)-1-azatricyclo[3.3.1.1³,⁷]dec-4-yloxy]-N-(4-chlorophenyl)-1,3-oxazole-4-carboxamide;

2-[(4s)-1-azatricyclo[3.3.1.1³,⁷]dec-4-yloxy]-N-phenyl-1,3-oxazole-4-carboxamide;

(4s)-4-{[5-(3-bromophenyl)-1,3,4-thiadiazol-2-yl]oxy}-1-azatricyclo[3.3.1.1³,⁷]decane;

(4s)-4-{5-[1-azatricyclo[3.3.1.1³,⁷]dec-4-yloxy]-1,3,4-thiadiazol-2-yl}phenol;

(4s)-N-pyridin-3-yl-1-azatricyclo[3.3.1.1³,⁷]decan-4-amine;

(4s)-N-(5-bromo-6-chloropyridin-3-yl)-1-azatricyclo[3.3.1.1³,⁷]decan-4-amine;

(4s)-N-[6-(1H-indol-6-yl)pyridin-3-yl]-1-azatricyclo[3.3.1.1³,⁷]decan-4-amine;

(4s)-N-[6-(1H-indol-3-yl)pyridin-3-yl]-1-azatricyclo[3.3.1.1³,⁷]decan-4-amine;

(4s)-4-[5-(1H-indol-5-yl)pyridin-3-yloxy]-1-azatricyclo[3.3.1.1³,⁷]decane;

(4s)-4-[5-(1H-indol-6-yl)pyridin-3-yloxy]-1-azatricyclo[3.3.1.1³,⁷]decane;

(4r)-4-[5-(1H-indol-5-yl)pyridin-3-yloxy]-1-azatricyclo[3.3.1.1³,⁷]decane;

(4r)-4-[5-(1H-indol-6-yl)pyridin-3-yloxy]-1-azatricyclo[3.3.1.1³,⁷]decane; azatricyclo[3.3.1.1³,⁷]decane; and (4r)-4-[5-(1-benzofuran-5-yl)pyridin-3-yloxy]-1-azatricyclo[3.3.1.1³,⁷]decane.

Compounds of the invention may exist as stereoisomers wherein, asymmetric or chiral centers are present. These stereoisomers are "R" or "S" depending on the configuration of substituents around the chiral element. The terms "R" and "S" used herein are configurations as defined in IUPAC 1974 Recommendations for Section E, Fundamental Stereochemistry, Pure Appl. Chem., 1976, 45: 13-30. The invention contemplates various stereoisomers and mixtures thereof and are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

More particularly, the compounds of the invention can exist in the forms represented by formula (Ia) and (Ib)

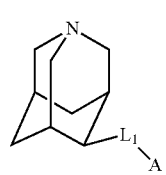

(Ia)

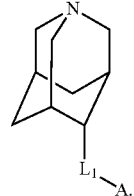

(Ib)

The aza-adamantane portion of isomer (Ia) and isomer (Ib) is not chiral, however the C-4 carbon at which $L_1$ is attached is considered pseudoasymmetric. Compounds represented by formula (Ia) and (Ib) are diastereomers. The configurational assignment of structures of formula (Ia) are assigned 4r in accordance with that described in Synthesis, 1992, 1080, Becker, D. P.; Flynn, D. L. and as defined in Stereochemistry of Organic Compounds, E. L. Eliel, S. H Wilen; John Wiley and Sons, Inc. 1994. In addition the configurational assignment of structures of formula (Ib) are assigned 4s using the same methods.

The isomers (Ia) and (Ib) may be synthesized separately using the individual stereoisomers according to the Schemes or the Experimentals described herein. Alternatively, isomers (Ia) and (Ib) may be synthesized together after which the individual isomers may be separated by chromatographic methods from the mixture of both isomers when mixtures of stereoisomers are used in the synthesis. The mixtures of isomers may also be separated through fractional crystallization of salts of amines contained in the compounds of formula (I) made with enantiomerically pure carboxylic acids.

It is contemplated that a mixture of both isomers may be used to modulate the effects of nAChRs. Furthermore, it is contemplated that the individual isomers of formula (Ia) and (Ib) may be used alone to modulate the effects of nAChRs. Therefore, it is contemplated that either a mixture of the compounds of formula (Ia) and (Ib) or the individual isomers alone represented by the compounds of formula (Ia) or (Ib) would be effective in modulating the effects of nAChRs, and more particularly α7 nAChRs, α4β2 nAChRs, or a combination of α7 nAChRs and α4β2 nAChRs and is thus within the scope of the invention.

More specifically, preferred compounds contemplated as part of the invention include

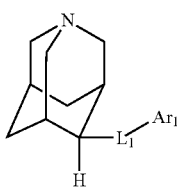

(IIa)

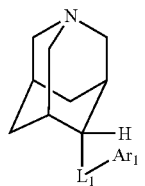

(IIb)

(IIIa)

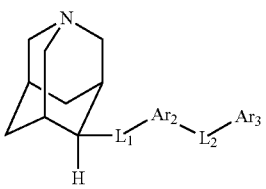

(IIIb)

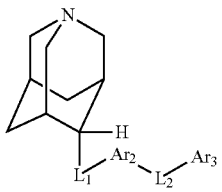

(IVa)

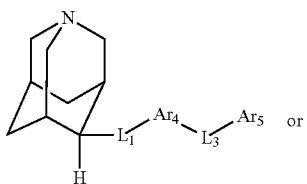

(IVb)

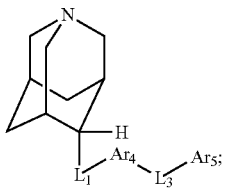

wherein $L_1$, $L_2$, $L_3$, $Ar_1$, $Ar_2$, $Ar_3$, $Ar_4$, and $Ar_5$ are defined herein.

In addition the use of compounds of formula (V)

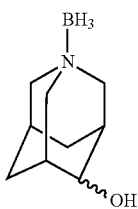

which may be used to generate compounds of formula (I) are contemplated to be within the scope of the invention.

Also within the scope of the invention are contemplated compounds of formula (VI) and compounds of formula (VII), (VI)

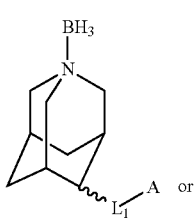

(VII)

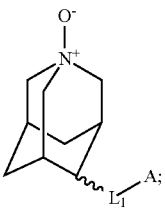

or a pharmaceutically acceptable salt or prodrug thereof, wherein $L_1$ is —O— or —$NR_a$—; A is —$Ar_1$, —$Ar_2$-$L_2$-$Ar_3$ or —$Ar_4$-$L_3$-$Ar_5$; $Ar_1$ is aryl or heteroaryl; $Ar_2$ is aryl or monocyclic heteroaryl; $Ar_3$ is aryl or heteroaryl; $Ar_4$ is a bicyclic heteroaryl; $Ar_5$ is aryl or heteroaryl; $L_2$ is a bond, —O—, —$NR_a$—, —$CH_2$—, or —C(O)$NR_a$—; $L_3$ is a bond, —O—, —$NR_a$— or —$CH_2$—; and $R_a$ is hydrogen or alkyl.

In addition, compounds of formula (VI) are useful as a prodrug of a compound of formula (I). Furthermore, compounds of formula (VII) also are useful as a prodrug of a compound of formula (I).

Specific embodiments contemplated as part of the invention include, but are not limited to compounds of formula (VI), for example:

(4r)-4-(5-bromopyridin-2-yloxy)-1-azatricyclo[3.3.1.1$^{3,7}$] decane N-borane complex;

(4s)-4-(6-chloropyridin-3-yloxy)-1-azatricyclo[3.3.1.1$^{3,7}$] decane N-borane complex;

(4s)-4-(6-nitropyridin-3-yloxy)-1-azatricyclo[3.3.1.1$^{3,7}$]decane N-borane complex;

(4r)-4-(6-nitropyridin-3-yloxy)-1-azatricyclo[3.3.1.1$^{3,7}$]decane N-borane complex;

(4s)-4-(5-bromothiazol-2-yloxy)-1-azatricyclo[3.3.1.1$^{3,7}$] decane N-borane complex;

(4s)-4-(5-phenyl-1,3,4-thiadiazol-2-yloxy)-1-azatricyclo [3.3.1.1$^{3,7}$]decane N-borane complex;

(4r)-4-(5-phenyl-1,3,4-thiadiazol-2-yloxy)-1-azatricyclo [3.3.1.1$^{3,7}$]decane N-borane complex;

(4s)-4-[5-(4-fluorophenyl)-1,3,4-thiadiazol-2-yloxy]-1-azatricyclo[3.3.1.1$^{3,7}$]decane N-borane complex;

(4r)-4-[5-(4-fluorophenyl)-1,3,4-thiadiazol-2-yloxy]-1-azatricyclo[3.3.1.1$^{3,7}$]decane N-borane complex;

(4s)-4-[5-(3-fluorophenyl)-1,3,4-thiadiazol-2-yloxy]-1-azatricyclo[3.3.1.1$^{3,7}$]decane N-borane complex;

(4r)-4-[5-(3-fluorophenyl)-1,3,4-thiadiazol-2-yloxy]-1-azatricyclo[3.3.1.1$^{3,7}$]decane N-borane complex;

(4s)-4-[5-(1H-indol-5-yl)-1,3,4-thiadiazol-2-yloxy]-1-azatricyclo[3.3.1.1$^{3,7}$]decane N-borane complex;

(4s)-4-(5-tert-butyl-1,3,4-thiadiazol-2-yloxy)-1-azatricyclo [3.3.1.1$^{3,7}$]decane N-borane complex;

(4r)-4-(5-tert-butyl-1,3,4-thiadiazol-2-yloxy)-1-azatricyclo [3.3.1.1$^{3,7}$]decane N-borane complex;

(4s)-4-(benzothiazol-2-yloxy)-1-azatricyclo[3.3.1.1$^{3,7}$]decane N-borane complex;

(4r)-4-(benzothiazol-2-yloxy)-1-azatricyclo[3.3.1.1$^{3,7}$]decane N-borane complex;

(4s)-4-(6-chlorobenzothiazol-2-yloxy)-1-azatricyclo [3.3.1.1$^{3,7}$]decane N-borane complex;

(4r)-4-(6-chlorobenzothiazol-2-yloxy)-1-azatricyclo [3.3.1.1$^{3,7}$]decane N-borane complex;

(4s)-4-(benzoxazol-2-yloxy)-1-azatricyclo[3.3.1.1$^{3,7}$]decane N-borane complex;

(4s)-4-(pyridin-3-yloxy)-1-azatricyclo[3.3.1.1$^{3,7}$]decane N-borane complex;

(4s)-4-[(1-oxidopyridin-3-yl)oxy]-1-azatricyclo[3.3.1.1$^{3,7}$] decane N-borane complex;

(4r)-4-(pyridin-3-yloxy)-1-azatricyclo[3.3.1.1$^{3,7}$]decane N-borane complex;
(4s)-4-[(2-chloropyridin-3-yl)oxy]-1-azatricyclo[3.3.1.1$^{3,7}$]decane N-borane complex;
(4s)-4-[(2-bromopyridin-3-yl)oxy]-1-azatricyclo[3.3.1.1$^{3,7}$]decane N-borane complex;
(4s)-4-[(4-chloropyridin-3-yl)oxy]-1-azatricyclo[3.3.1.1$^{3,7}$]decane N-borane complex;
(4s)-4-[(4-methylpyridin-3-yl)oxy]-1-azatricyclo[3.3.1.1$^{3,7}$]decane N-borane complex;
(4s)-4-{[4-(trifluoromethyl)pyridin-3-yl]oxy}-1-azatricyclo[3.3.1.1$^{3,7}$]decane N-borane complex;
(4s)-4-[(5-fluoropyridin-3-yl)oxy]-1-azatricyclo[3.3.1.1$^{3,7}$]decane N-borane complex;
(4s)-4-[(5-chloropyridin-3-yl)oxy]-1-azatricyclo[3.3.1.1$^{3,7}$]decane N-borane complex;
(4s)-4-[(5-bromopyridin-3-yl)oxy]-1-azatricyclo[3.3.1.1$^{3,7}$]decane N-borane complex;
(4s)-4-[(5-iodopyridin-3-yl)oxy]-1-azatricyclo[3.3.1.1$^{3,7}$]decane N-borane complex;
5-[(4 s)-1-azatricyclo[3.3.1.1$^{3,7}$]dec-4-yloxy]nicotinamide N-borane complex;
(4s)-4-{[5-(1H-pyrazol-4-yl)pyridin-3-yl]oxy}-1-azatricyclo[3.3.1.1$^{3,7}$]decane N-borane complex;
(4s)-4-{[5-(1-methyl-1H-pyrazol-4-yl)pyridin-3-yl]oxy}-1-azatricyclo[3.3.1.1$^{3,7}$]decane N-borane complex;
(4s)-4-{[5-(4-chlorophenyl)pyridin-3-yl]oxy}-1-azatricyclo[3.3.1.1$^{3,7}$]decane N-borane complex;
(4s)-4-(3,4'-bipyridin-5-yloxy)-1-azatricyclo[3.3.1.1$^{3,7}$]decane N-borane complex;
(4s)-4-[(5-pyrimidin-5-ylpyridin-3-yl)oxy)-1-azatricyclo[3.3.1.1$^{3,7}$]decane N-borane complex;
(4s)-4-[(6-chloropyridin-3-yl)oxy]-1-azatricyclo[3.3.1.1$^{3,7}$]decane N-borane complex;
(4r)-4-[(6-chloropyridin-3-yl)oxy]-1-azatricyclo[3.3.1.1$^{3,7}$]decane N-borane complex;
(4s)-4-(5-Fluoro-pyridin-2-yloxy)-1-aza-tricyclo[3.3.1.1$^{3,7}$]decane N-borane complex;
(4r)-4-(5-Fluoro-pyridin-2-yloxy)-1-aza-tricyclo[3.3.1.1$^{3,7}$]decane N-borane complex;
(4s)-4-[(6-bromopyridin-3-yl)oxy]-1-azatricyclo[3.3.1.1$^{3,7}$]decane N-borane complex N-borane complex;
5-[(4s)-1-azatricyclo[3.3.1.1$^{3,7}$]dec-4-yloxy]pyridine-2-carbonitrile N-borane complex N-borane complex;
(4s)-4-[(5,6-dibromopyridin-3-yl)oxy]-1-azatricyclo[3.3.1.1$^{3,7}$]decane N-borane complex N-borane complex;
(4s)-4-(pyridin-2-yloxy)-1-azatricyclo[3.3.1.1$^{3,7}$]decane N-borane complex N-borane complex;
(4s)-4-[(5-bromopyridin-2-yl)oxy]-1-azatricyclo[3.3.1.1$^{3,7}$]decane N-borane complex N-borane complex;
(4s)-4-[(4-bromopyridin-2-yl)oxy]-1-azatricyclo[3.3.1.1$^{3,7}$]decane N-borane complex N-borane complex;
(4s)-4-(3,3'-bipyridin-6-yloxy)-1-azatricyclo[3.3.1.1$^{3,7}$]decane N-borane complex N-borane complex;
(4s)-4-(3,4'-bipyridin-6-yloxy)-1-azatricyclo[3.3.1.1$^{3,7}$]decane N-borane complex N-borane complex;
(4r)-4-(3,4'-bipyridin-6-yloxy)-1-azatricyclo[3.3.1.1$^{3,7}$]decane N-borane complex N-borane complex;
(4s)-4-[(5-pyrimidin-5-ylpyridin-2-yl)oxy]-1-azatricyclo[3.3.1.1$^{3,7}$]decane N-borane complex N-borane complex;
(4s)-4-[(2-chloropyridin-4-yl)oxy]-1-azatricyclo[3.3.1.1$^{3,7}$]decane N-borane complex N-borane complex;
(4s)-4-[(6-methylpyridazin-3-yl)oxy]-1-azatricyclo[3.3.1.1$^{3,7}$]decane N-borane complex N-borane complex;
(4s)-4-(pyrimidin-2-yloxy)-1-azatricyclo[3.3.1.1$^{3,7}$]decane N-borane complex N-borane complex;
(4s)-4-[(5-bromopyrimidin-2-yl)oxy]-1-azatricyclo[3.3.1.1$^{3,7}$]decane N-borane complex N-borane complex;
(4s)-4-(pyrimidin-5-yloxy)-1-azatricyclo[3.3.1.1$^{3,7}$]decane N-borane complex N-borane complex;
(4s)-4-(pyrazin-2-yloxy)-1-azatricyclo[3.3.1.1$^{3,7}$]decane N-borane complex N-borane complex;
4-[(6-methylpyrazin-2-yl)oxy]-1-azatricyclo[3.3.1.1$^{3,7}$]decane N-borane complex N-borane complex;
(4r)-4-[(6-phenylpyrazin-2-yl)oxy]-1-azatricyclo[3.3.1.1$^{3,7}$]decane N-borane complex N-borane complex;
(4r)-4-(1,3-thiazol-2-yloxy)-1-azatricyclo[3.3.1.1$^{3,7}$]decane N-borane complex;
(4s)-4-({5-[4-(trifluoromethoxy)phenyl]-1,3-thiazol-2-yl}oxy)-1-azatricyclo[3.3.1.1$^{3,7}$]decane N-borane complex;
(4s)-4-[(5-pyrimidin-5-yl-1,3-thiazol-2-yl)oxy]-1-azatricyclo[3.3.1.1$^{3,7}$]decane N-borane complex;
(4s)-4-{[5-(1-trityl-1H-pyrazol-4-yl)-1,3-thiazol-2-yl]oxy}-1-azatricyclo[3.3.1.1$^{3,7}$]decane N-borane complex;
(4s)-4-[(4-bromo-1,3-thiazol-2-yl)oxy]-1-azatricyclo[3.3.1.1$^{3,7}$]decane N-borane complex; and
(4s)-4-[(4-chloro-1,3-thiazol-2-yl)oxy]-1-azatricyclo[3.3.1.1$^{3,7}$]decane N-borane complex.

Specific embodiments contemplated as part of the invention include, but are not limited to compounds of formula (VII), for example:
(4s)-4-[5-(1H-indol-5-yl)-thiazol-2-yloxy]-1-azatricyclo[3.3.1.1$^{3,7}$]decane-1-oxide;
(4s)-5-4-[2-(1-azatricyclo[3.3.1.1$^{3,7}$]decan-1-oxide-yloxy)thiazol-5-yl]-indolin-2-one; or
(4s)-4-(5-phenyl-1,3,4-thiadiazol-2-yloxy)-1-azatricyclo[3.3.1.1$^{3,7}$]decane-1-oxide.

Salt Properties

Particular salts of compounds of the invention also have been identified and are described herein. More particularly, such salts are (4s)-4-(5-phenyl-1,3,4-thiadiazol-2-yloxy)-1-azatricyclo[3.3.1.1$^{3,7}$]decane L-bitartrate anhydrate, L-bitartrate hydrate, dihydrogen phosphate anhydrate, dihydrogen phosphate hydrate, bisuccinate anhydrate, bisuccinate hydrate, hydrochloride quarterhydrate, hydrochloride sesquihydrate, dihydrogen citrate, and monohydrogen citrate.

(4s)-4-(5-Phenyl-1,3,4-thiadiazol-2-yloxy)-1-azatricyclo[3.3.1.1$^{3,7}$]decane L-bitartrate anhydrate crystalline solid can be identified by characteristic peaks in its powder X-ray diffraction pattern (FIG. 1). One with skill in the art of analytical chemistry would be able to readily identify (4s)-4-(5-phenyl-1,3,4-thiadiazol-2-yloxy)-1-azatricyclo[3.3.1.1$^{3,7}$]decane L-bitartrate anhydrate solid by as few as one characteristic peak in its powder X-ray diffraction pattern. Two-theta angle positions of characteristic peaks in a powder X-ray diffraction pattern of (4s)-4-(5-phenyl-1,3,4-thiadiazol-2-yloxy)-1-azatricyclo[3.3.1.1$^{3,7}$]decane L-bitartrate anhydrate are 4.96±0.20, 9.99±0.20, 11.77±0.20, 14.62±0.20, 14.99±0.20, 18.14±0.20, 18.44±0.20, 19.48±0.20, 20.05±0.20, 21.02±0.20, 21.38±0.20, 22.76±0.20, 24.74±0.20, 26.65±0.20, and 32.19±0.20.

Figure 2:
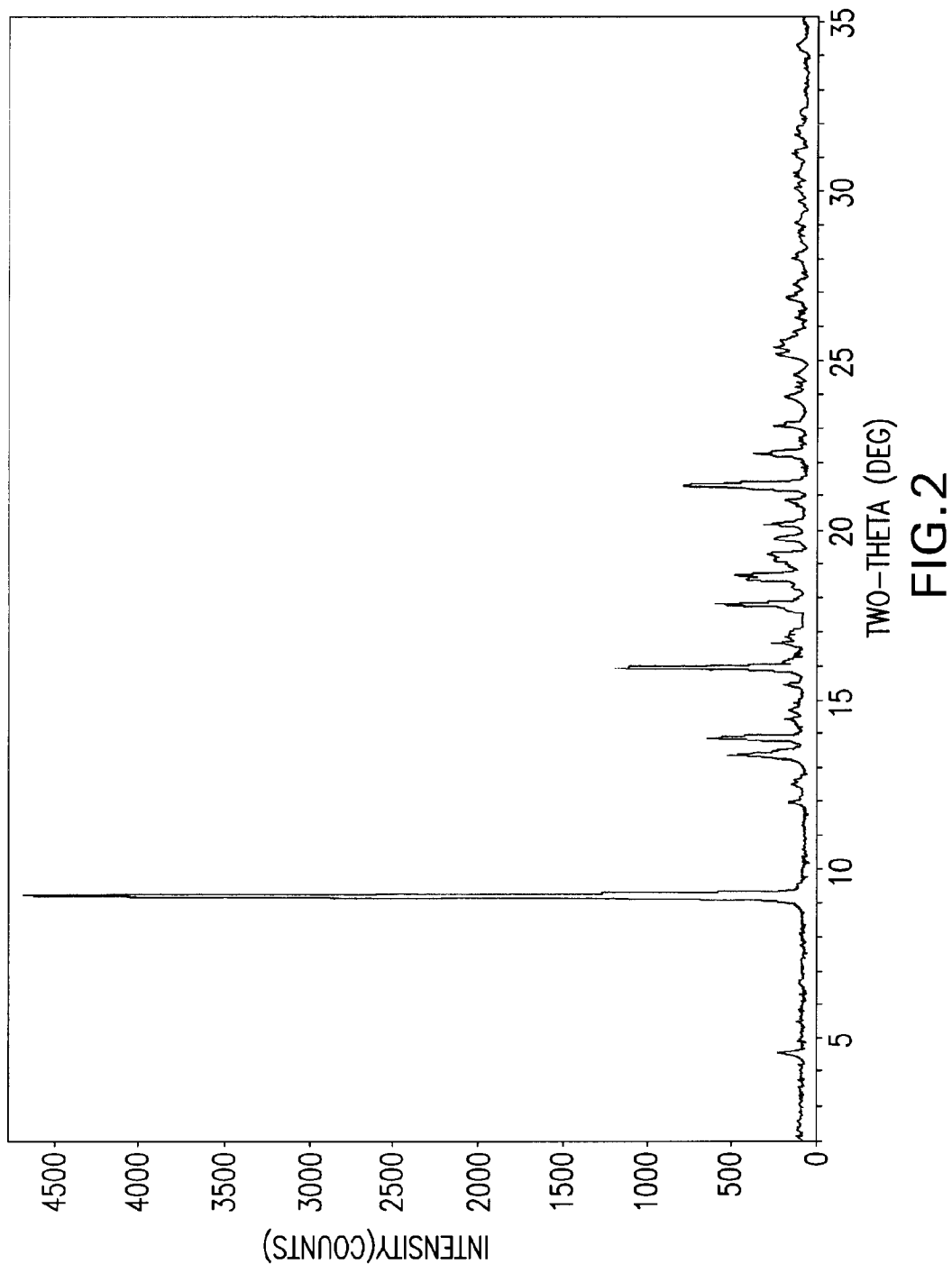
FIG. 2 is a powder X-ray diffraction pattern of a L-bitartrate hydrate of (4s)-4-(5-phenyl-1,3,4-thiadiazol-2-yloxy)-1-azatricyclo[3.3.1.1$^{3,7}$]decane.
Figure 2A:
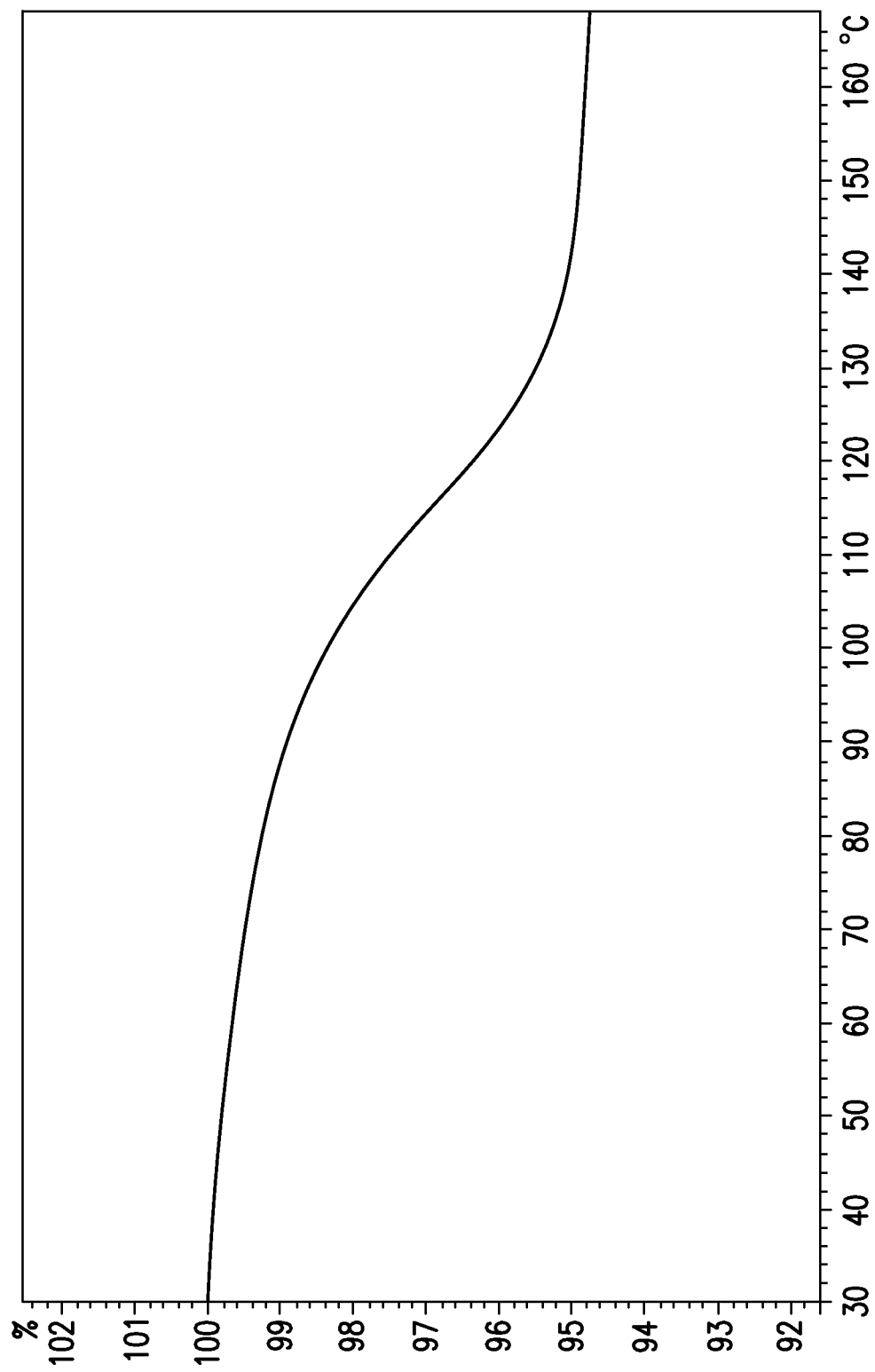
FIG. 2A is a thermogram of a L-bitartrate hydrate of (4s)-4-(5-phenyl-1,3,4-thiadiazol-2-yloxy)-1-azatricyclo[3.3.1.1$^{3,7}$]decane obtained by thermal gravimetric analysis (TGA).

(4s)-4-(5-Phenyl-1,3,4-thiadiazol-2-yloxy)-1-azatricyclo[3.3.1.1$^{3,7}$]decane L-bitartrate hydrate crystalline solid can be identified by characteristic peaks in its powder X-ray diffraction pattern (FIG. 2). One with skill in the art of analytical chemistry would be able to readily identify (4s)-4-(5-phenyl-1,3,4-thiadiazol-2-yloxy)-1-azatricyclo[3.3.1.1$^{3,7}$]decane L-bitartrate hydrate solid by as few as one characteristic peak in its powder X-ray diffraction pattern. Two-theta angle positions of characteristic peaks in a powder X-ray diffraction pattern of (4s)-4-(5-phenyl-1,3,4-thiadiazol-2-yloxy)-1-azatricyclo[3.3.1.1$^{3,7}$]decane L-bitartrate hydrate are 4.63±0.20, 9.26±0.20, 13.43±0.20, 13.91±0.20, 15.98±0.20, 17.86±0.20, 21.36±0.20, and 22.33±0.20. The TGA (FIG. 2A) shows the dehydration of (4s)-4-(5-phenyl-1,3,4-thiadiazol-2-yloxy)-1-azatricyclo[3.3.1.1$^{3,7}$]decane L-bitartrate hydrate.

Figure 3:
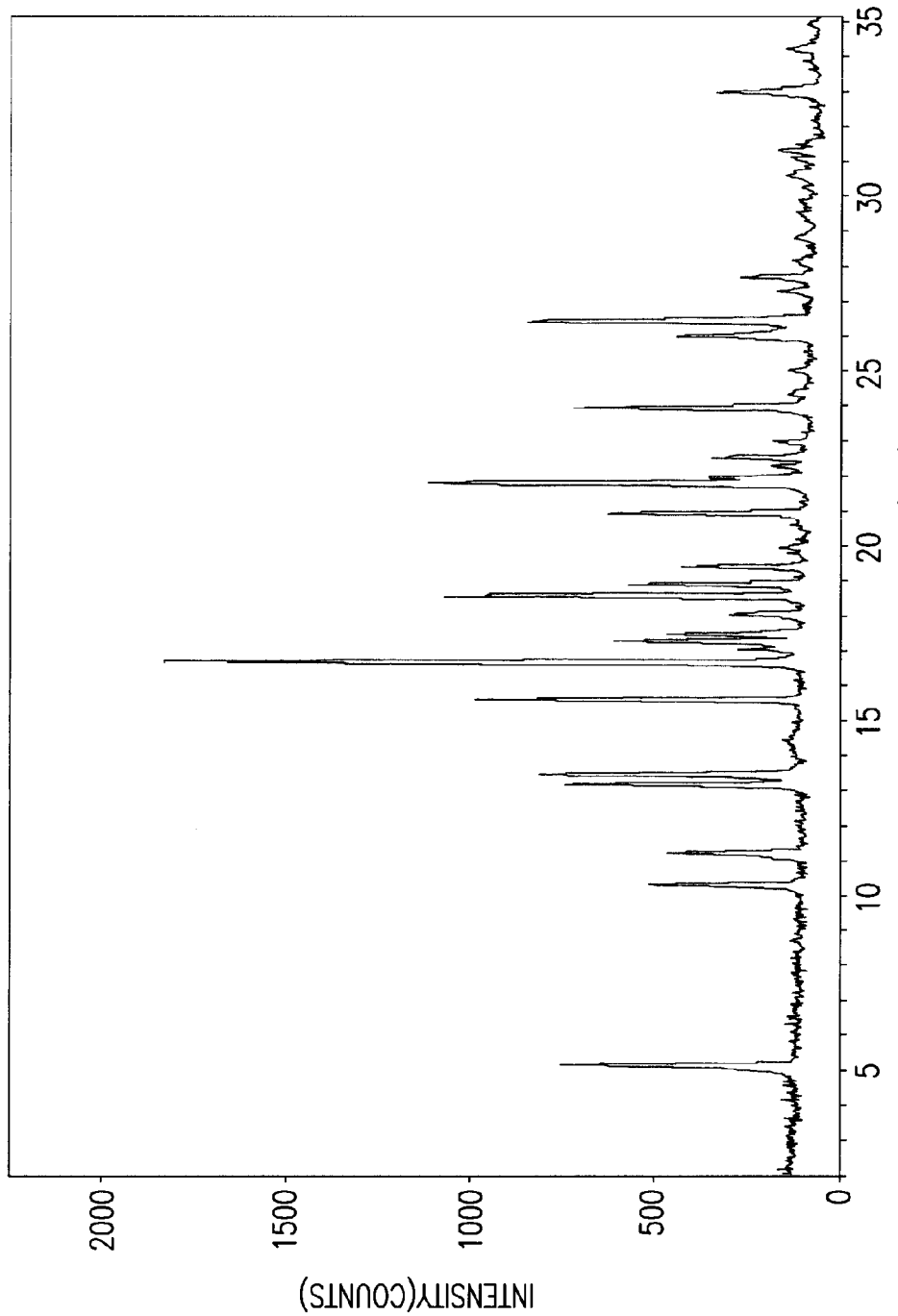
FIG. 3 is a powder X-ray diffraction pattern of an anhydrous dihydrogen phosphate of (4s)-4-(5-phenyl-1,3,4-thiadiazol-2-yloxy)-1-azatricyclo[3.3.1.1$^{3,7}$]decane.

(4s)-4-(5-Phenyl-1,3,4-thiadiazol-2-yloxy)-1-azatricyclo[3.3.1.1$^{3,7}$]decane dihydrogen phosphate anhydrate crystalline solid can be identified by characteristic peaks in its powder X-ray diffraction pattern (FIG. 3). One with skill in the art of analytical chemistry would be able to readily identify (4s)-4-(5-phenyl-1,3,4-thiadiazol-2-yloxy)-1-azatricyclo[3.3.1.1$^{3,7}$]decane dihydrogen phosphate anhydrate solid by as few as one characteristic peak in its powder X-ray diffraction pattern. Two-theta angle positions of characteristic peaks in a powder X-ray diffraction pattern of (4s)-4-(5-phenyl-1,3,4-thiadiazol-2-yloxy)-1-azatricyclo[3.3.1.1$^{3,7}$]decane dihydrogen phosphate anhydrate are 5.14±0.20, 10.31±0.20, 11.20±0.20, 13.17±0.20, 13.47±0.20, 15.61±0.20, 16.69±0.20, 17.27±0.20, 17.50±0.20, 18.56±0.20, 18.90±0.20, 19.41±0.20, 20.93±0.20, 21.80±0.20, 22.53±0.20, 23.96±0.20, 26.01±0.20, and 26.44±0.20.

Figure 4:
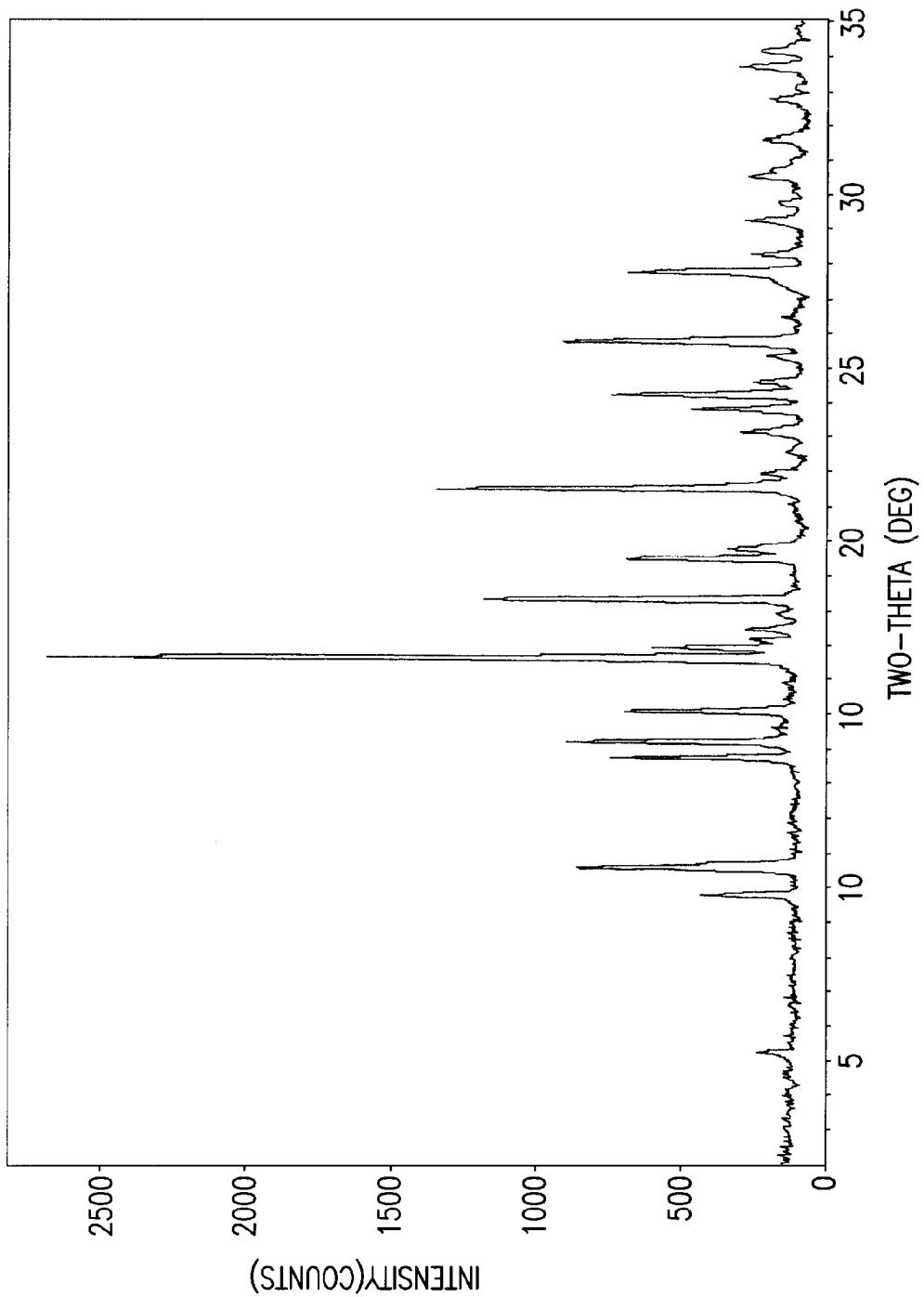
FIG. 4 is a powder X-ray diffraction pattern of a dihydrogen phosphate hydrate of (4s)-4-(5-phenyl-1,3,4-thiadiazol-2-yloxy)-1-azatricyclo[3.3.1.1$^{3,7}$]decane.
Figure 4A:
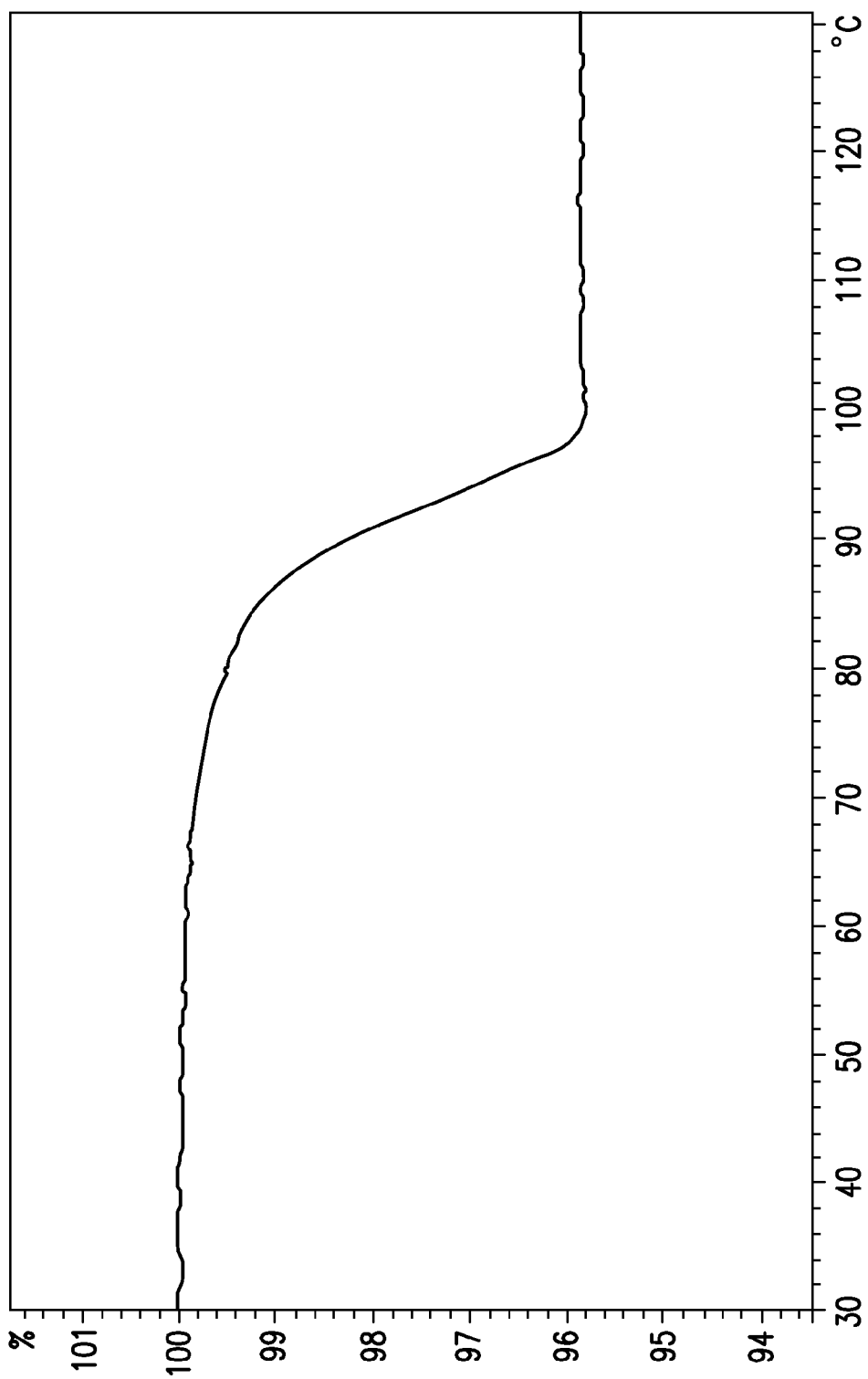
FIG. 4A is a thermogram of a dihydrogen phosphate hydrate of (4s)-4-(5-phenyl-1,3,4-thiadiazol-2-yloxy)-1-azatricyclo[3.3.1.1$^{3,7}$]decane obtained by thermal gravimetric analysis.

(4s)-4-(5-Phenyl-1,3,4-thiadiazol-2-yloxy)-1-azatricyclo[3.3.1.1$^{3,7}$]decane dihydrogen phosphate hydrate crystalline solid can be identified by characteristic peaks in its powder X-ray diffraction pattern (FIG. 4). One with skill in the art of analytical chemistry would be able to readily identify (4s)-4-(5-phenyl-1,3,4-thiadiazol-2-yloxy)-1-azatricyclo[3.3.1.1$^{3,7}$]decane dihydrogen phosphate hydrate solid by as few as one characteristic peak in its powder X-ray diffraction pattern. Two-theta angle positions of characteristic peaks in a powder X-ray diffraction pattern of (4s)-4-(5-phenyl-1,3,4-thiadiazol-2-yloxy)-1-azatricyclo[3.3.1.1$^{3,7}$]decane dihydrogen phosphate hydrate are 5.28±0.20, 9.82±0.20, 10.61±0.20, 13.79±0.20, 14.24±0.20, 15.13±0.20, 16.65±0.20, 16.95±0.20, 18.35±0.20, 19.52±0.20, 19.84±0.20, 21.55±0.20, 23.85±0.20, 24.26±0.20, and 25.80±0.20. The TGA (FIG. 4A) shows the dehydration of (4s)-4-(5-phenyl-1,3,4-thiadiazol-2-yloxy)-1-azatricyclo[3.3.1.1$^{3,7}$]decane dihydrogen phosphate hydrate.

Figure 5:
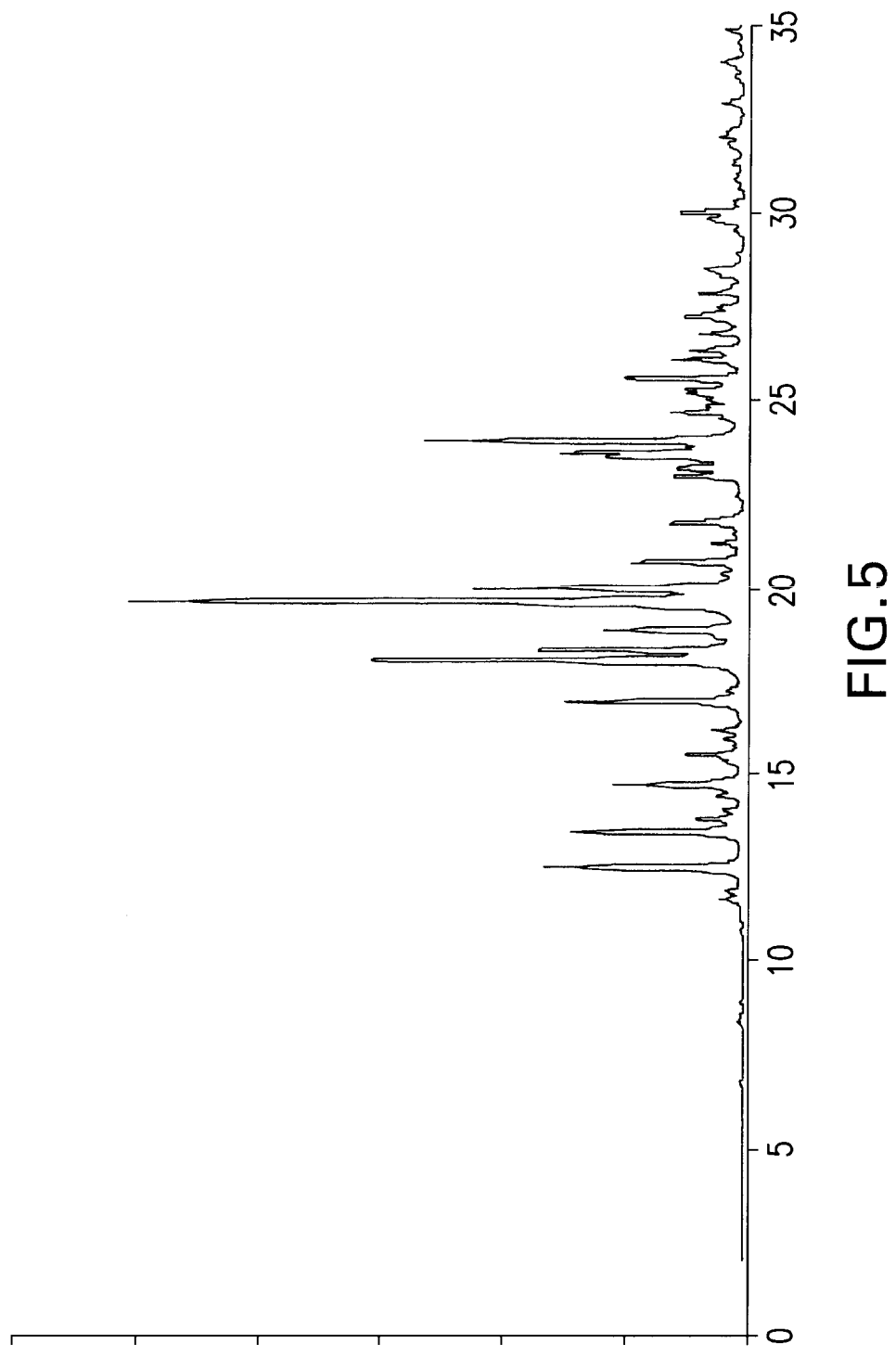
FIG. 5 is a powder X-ray diffraction pattern of an anhydrous bisuccinate of (4s)-4-(5-phenyl-1,3,4-thiadiazol-2-yloxy)-1-azatricyclo[3.3.1.1$^{3,7}$]decane.

(4s)-4-(5-Phenyl-1,3,4-thiadiazol-2-yloxy)-1-azatricyclo[3.3.1.1$^{3,7}$]decane bisuccinate anhydrate crystalline solid can be identified by characteristic peaks in its powder X-ray diffraction pattern (FIG. 5). One with skill in the art of analytical chemistry would be able to readily identify (4s)-4-(5-phenyl-1,3,4-thiadiazol-2-yloxy)-1-azatricyclo[3.3.1.1$^{3,7}$]decane bisuccinate anhydrate solid by as few as one characteristic peak in its powder X-ray diffraction pattern. Two-theta angle positions of characteristic peaks in a powder X-ray diffraction pattern of (4s)-4-(5-phenyl-1,3,4-thiadiazol-2-yloxy)-1-azatricyclo[3.3.1.1$^{3,7}$]decane bisuccinate anhydrate are 12.53±0.20, 13.50±0.20, 14.76±0.20, 16.98±0.20, 18.07±0.20, 18.34±0.20, 18.35±0.20, 18.88±0.20, 19.62±0.20, 19.67±0.20, 20.00±0.20, 20.71±0.20, 23.64±0.20, 23.96±0.20, 25.61±0.20, and 36.29±0.20. Crystallographic unit cell parameters of (4s)-4-(5-phenyl-1,3,4-thiadiazol-2-yloxy)-1-azatricyclo[3.3.1.1$^{3,7}$]decane bisuccinate anhydrate also were obtained and were determined as: a is 12.958(17) Å, b is 7.561(10) Å, c is 39.66(5) Å, and β is 94.54(2)° to afford a cell volume of 3873.51 Å$^3$, wherein a, b, and c are each a representative length of the crystal lattice and β is a unit cell angle. The salt crystallizes in the monoclinic P21/c space group.

Figure 6:
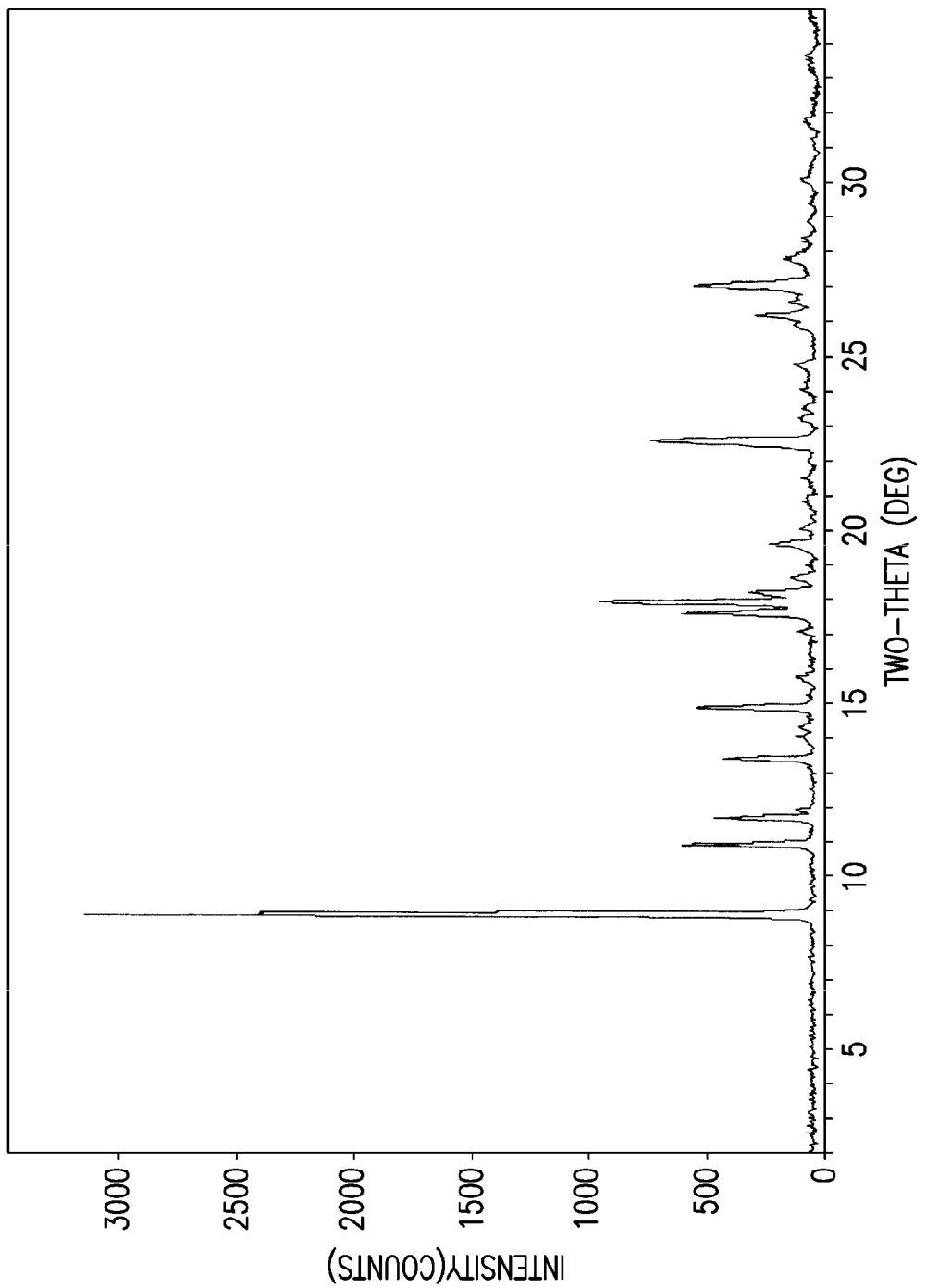
FIG. 6 is a powder X-ray diffraction pattern of a bisuccinate hydrate of (4s)-4-(5-phenyl-1,3,4-thiadiazol-2-yloxy)-1-azatricyclo[3.3.1.1$^{3,7}$]decane.
Figure 6A:
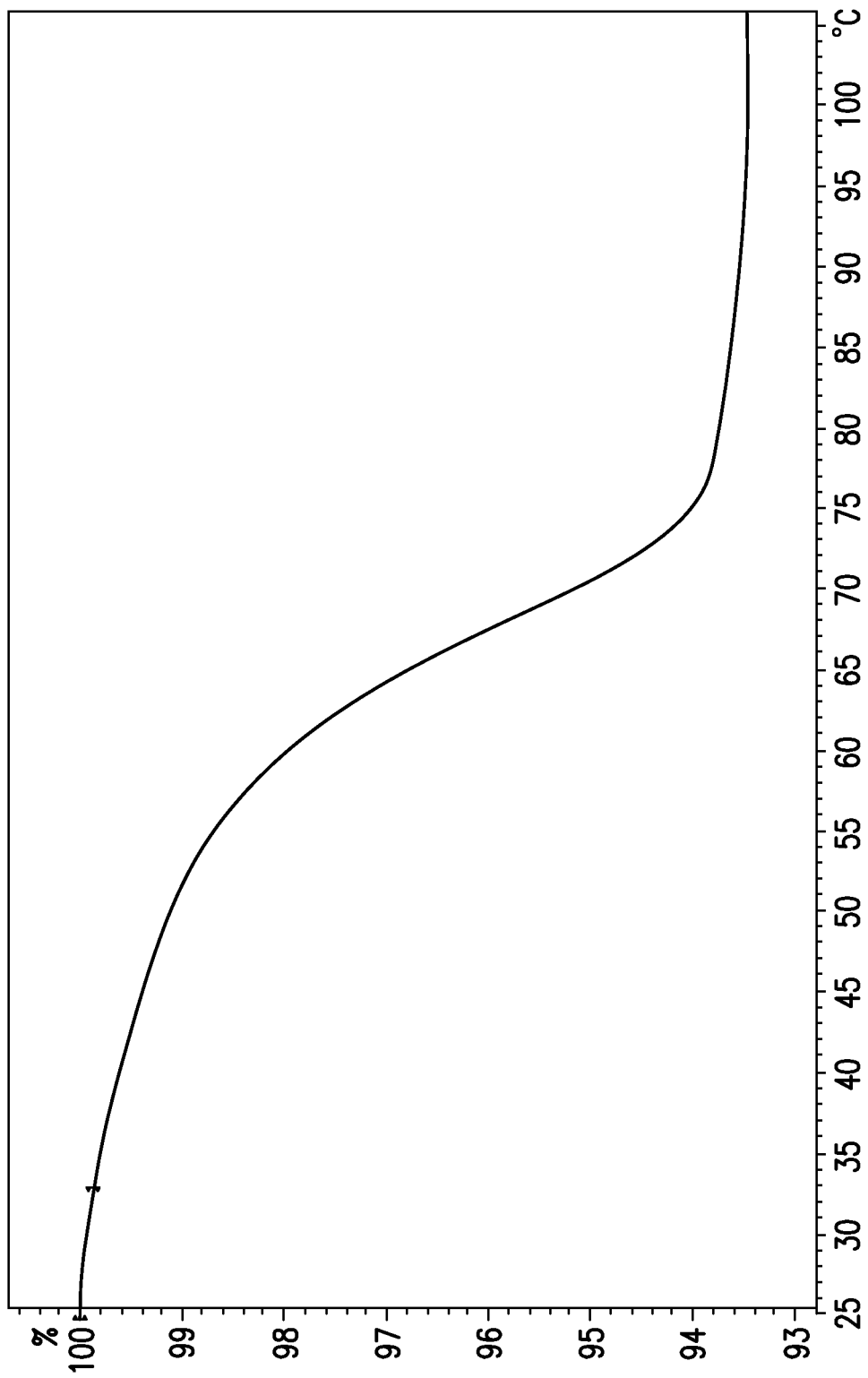
FIG. 6A is a thermogram of a bisuccinate hydrate of (4s)-4-(5-phenyl-1,3,4-thiadiazol-2-yloxy)-1-azatricyclo[3.3.1.1$^{3,7}$]decane obtained by thermal gravimetric analysis.

(4s)-4-(5-Phenyl-1,3,4-thiadiazol-2-yloxy)-1-azatricyclo[3.3.1.1$^{3,7}$]decane bisuccinate hydrate crystalline solid can be identified by characteristic peaks in its powder X-ray diffraction pattern (FIG. 6). One with skill in the art of analytical chemistry would be able to readily identify (4s)-4-(5-phenyl-1,3,4-thiadiazol-2-yloxy)-1-azatricyclo[3.3.1.1$^{3,7}$]decane bisuccinate hydrate solid by as few as one characteristic peak in its powder X-ray diffraction pattern. Two-theta angle positions of characteristic peaks in a powder X-ray diffraction pattern of (4s)-4-(5-phenyl-1,3,4-thiadiazol-2-yloxy)-1-azatricyclo[3.3.1.1$^{3,7}$]decane bisuccinate hydrate are 8.92±0.20, 10.94±0.20, 11.71±0.20, 13.41±0.20, 14.90±0.20, 17.61±0.20, 17.92±0.20, 18.19±0.20, 19.60±0.20, 22.58±0.20, 26.19±0.20, and 27.07±0.20. The TGA (FIG. 6A) shows the dehydration of (4s)-4-(5-phenyl-1,3,4-thiadiazol-2-yloxy)-1-azatricyclo[3.3.1.1$^{3,7}$]decane bisuccinate hydrate.

Figure 7:
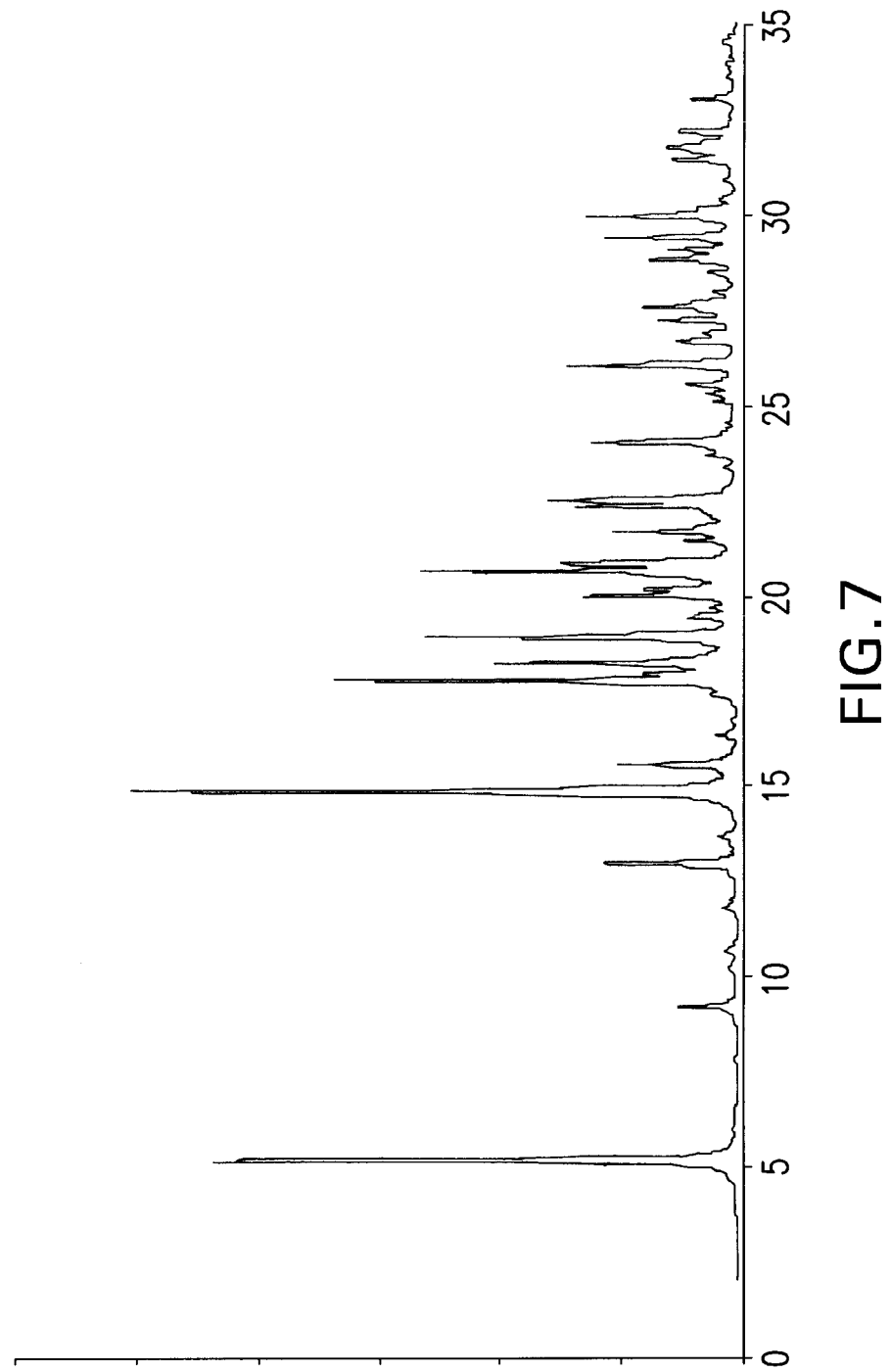
FIG. 7 is a powder X-ray diffraction pattern of a hydrochloride quarterhydrate of (4s)-4-(5-phenyl-1,3,4-thiadiazol-2-yloxy)-1-azatricyclo[3.3.1.1$^{3,7}$]decane.

(4s)-4-(5-Phenyl-1,3,4-thiadiazol-2-yloxy)-1-azatricyclo[3.3.1.1$^{3,7}$]decane hydrochloride quarterhydrate (1 salt: 0.25 water) crystalline solid can be identified by characteristic peaks in its powder X-ray diffraction pattern (FIG. 7). One with skill in the art of analytical chemistry would be able to readily identify (4s)-4-(5-phenyl-1,3,4-thiadiazol-2-yloxy)-1-azatricyclo[3.3.1.1$^{3,7}$]decane hydrochloride quarterhydrate solid by as few as one characteristic peak in its powder X-ray diffraction pattern. Two-theta angle positions of characteristic peaks in a powder X-ray diffraction pattern of (4s)-4-(5-phenyl-1,3,4-thiadiazol-2-yloxy)-1-azatricyclo[3.3.1.1$^{3,7}$]decane hydrochloride quarterhydrate are 5.19±0.20, 12.96±0.20, 13.00±0.20, 14.88±0.20, 14.98±0.20, 15.61±0.20, 17.79±0.20, 18.26±0.20, 18.93±0.20, 20.02±0.20, 20.67±0.20, 20.86±0.20, 21.72±0.20, 22.38±0.20, 22.55±0.20, 24.09±0.20, and 26.10±0.20. Crystallographic unit cell parameters of (4s)-4-(5-phenyl-1,3,4-thiadiazol-2-yloxy)-1-azatricyclo[3.3.1.1$^{3,7}$]decane hydrochloride quarterhydrate also were obtained and were determined as: a is 19.440(7) Å, b is 9.969(4) Å, c is 35.322(13) Å, and β is 105.325(17)° to afford a cell volume of 6601.91 Å$^3$, wherein a, b, and c are each a representative length of the crystal lattice and β is a unit cell angle. The salt crystallizes in the monoclinic P21/c space group.

Figure 8:
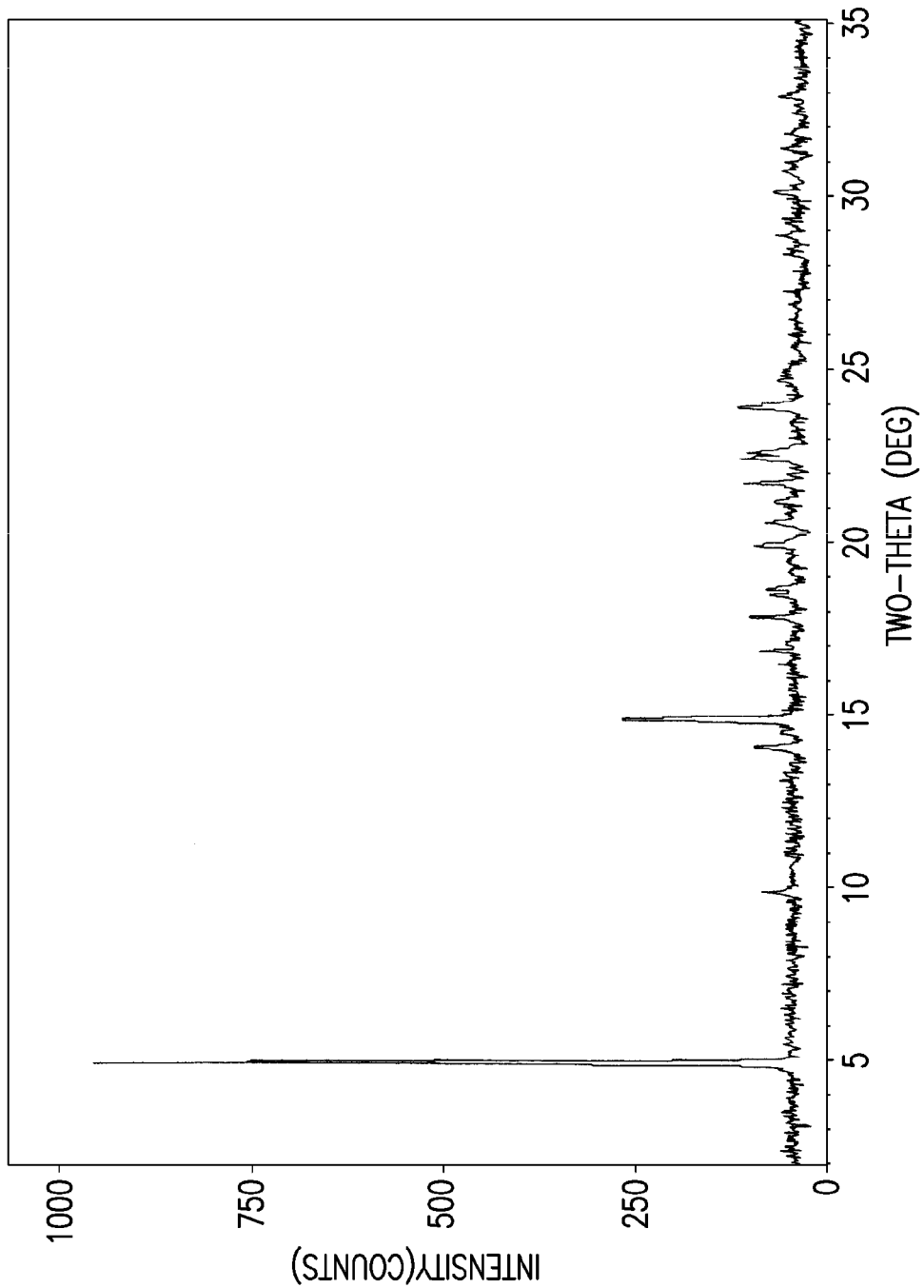
FIG. 8 is a powder X-ray diffraction pattern of a hydrochloride sesquihydrate of (4s)-4-(5-phenyl-1,3,4-thiadiazol-2-yloxy)-1-azatricyclo[3.3.1.1$^{3,7}$]decane.
Figure 8A:
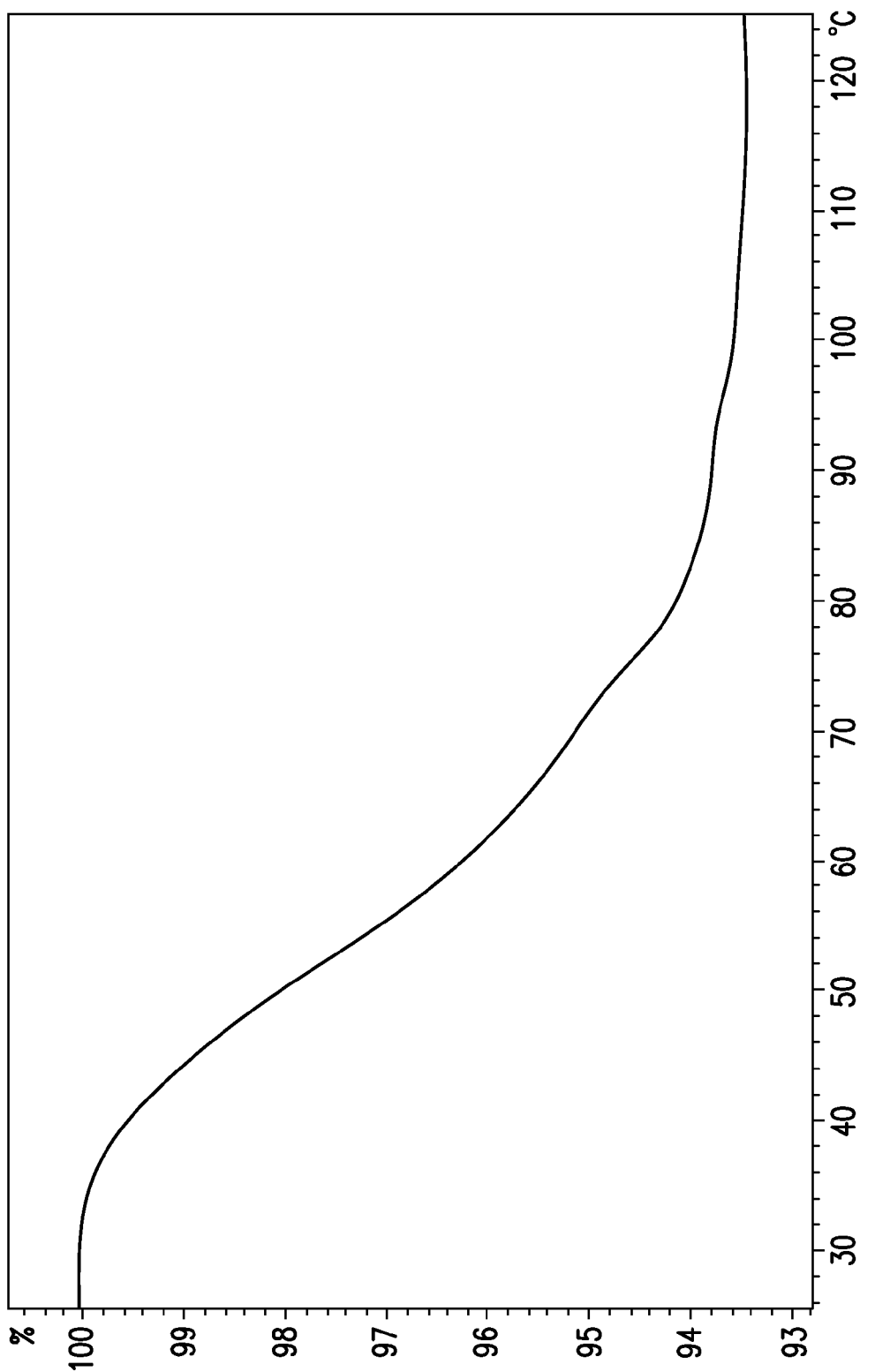
FIG. 8A is a thermogram of a hydrochloride sesquihydrate of (4s)-4-(5-phenyl-1,3,4-thiadiazol-2-yloxy)-1-azatricyclo[3.3.1.1$^{3,7}$]decane obtained by thermal gravimetric analysis.

(4s)-4-(5-Phenyl-1,3,4-thiadiazol-2-yloxy)-1-azatricyclo[3.3.1.1$^{3,7}$]decane hydrochloride sesquihydrate (1 salt:1.5 water) crystalline solid can be identified by characteristic peaks in its powder X-ray diffraction pattern (FIG. 8). One with skill in the art of analytical chemistry would be able to readily identify (4s)-4-(5-phenyl-1,3,4-thiadiazol-2-yloxy)-1-azatricyclo[3.3.1.1$^{3,7}$]decane hydrochloride sesquihydrate solid by as few as one characteristic peak in its powder X-ray diffraction pattern. Two-theta angle positions of characteristic peaks in a powder X-ray diffraction pattern of (4s)-4-(5-phenyl-1,3,4-thiadiazol-2-yloxy)-1-azatricyclo[3.3.1.1$^{3,7}$]decane hydrochloride sesquihydrate are 4.94±0.20, 9.93±0.20, 14.09±0.20, 14.90±0.20, 17.85±0.20, 19.92±0.20, 21.72±0.20, 22.43±0.20, 22.63±0.20, and 23.95±0.20. The TGA (FIG. 8A) shows the dehydration of (4s)-4-(5-phenyl-1,3,4-thiadiazol-2-yloxy)-1-azatricyclo[3.3.1.1$^{3,7}$]decane hydrochloride sesquihydrate.

Figure 9:
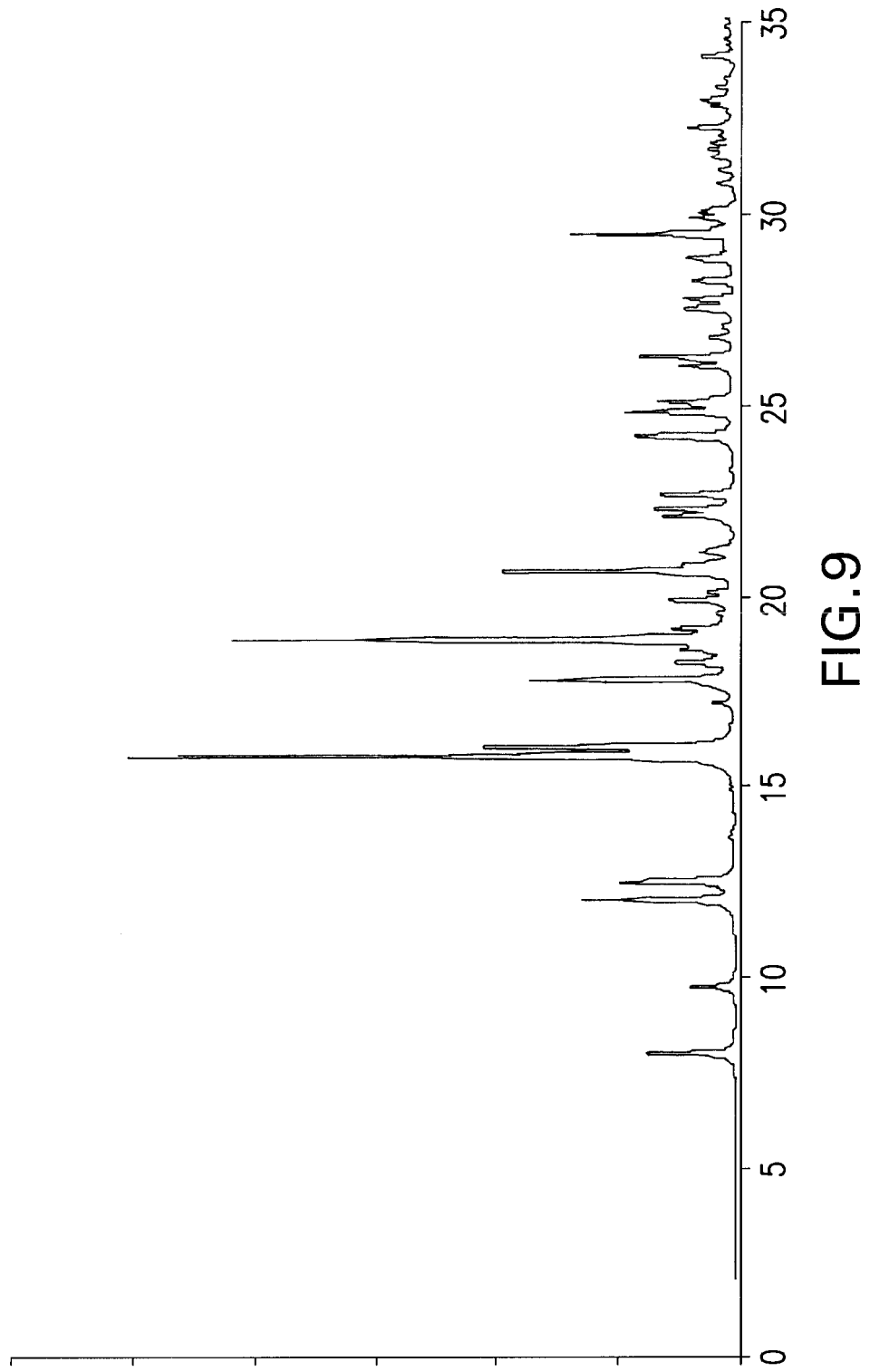
FIG. 9 is a powder X-ray diffraction pattern of a dihydrogen citrate of (4s)-4-(5-phenyl-1,3,4-thiadiazol-2-yloxy)-1-azatricyclo[3.3.1.1$^{3,7}$]decane.

(4s)-4-(5-Phenyl-1,3,4-thiadiazol-2-yloxy)-1-azatricyclo[3.3.1.1$^{3,7}$]decane dihydrogen citrate crystalline solid can be identified by characteristic peaks in its powder X-ray diffraction pattern (FIG. 9). One with skill in the art of analytical chemistry would be able to readily identify (4s)-4-(5-phenyl-1,3,4-thiadiazol-2-yloxy)-1-azatricyclo[3.3.1.1$^{3,7}$]decane dihydrogen citrate solid by as few as one characteristic peak in its powder X-ray diffraction pattern. Two-theta angle positions of characteristic peaks in a powder X-ray diffraction pattern of (4s)-4-(5-phenyl-1,3,4-thiadiazol-2-yloxy)-1-azatricyclo[3.3.1.1$^{3,7}$]decane dihydrogen citrate are 7.98±0.20, 11.98±0.20, 12.45±0.20, 15.76±0.20, 16.00±0.20, 17.75±0.20, 18.79±0.20, 18.82±0.20, 20.59±0.20, 22.25±0.20, 22.61±0.20, 24.16±0.20, 24.79±0.20, 25.06±0.20, 26.21±0.20, and 29.43±0.20. Crystallographic unit cell parameters of (4s)-4-(5-phenyl-1,3,4-thiadiazol-2-yloxy)-1-azatricyclo[3.3.1.1$^{3,7}$]decane dihydrogen citrate also were obtained and were determined as: a is 22.651(8) Å, b is 9.992(3) Å, c is 10.338(4) Å, and β is 101.961(5)° to afford a cell volume of 2288.99 Å$^3$, wherein a, b, and c are each a representative length of the crystal lattice and β is a unit cell angle. The salt crystallizes in the monoclinic P21/c space group.

Figure 10:
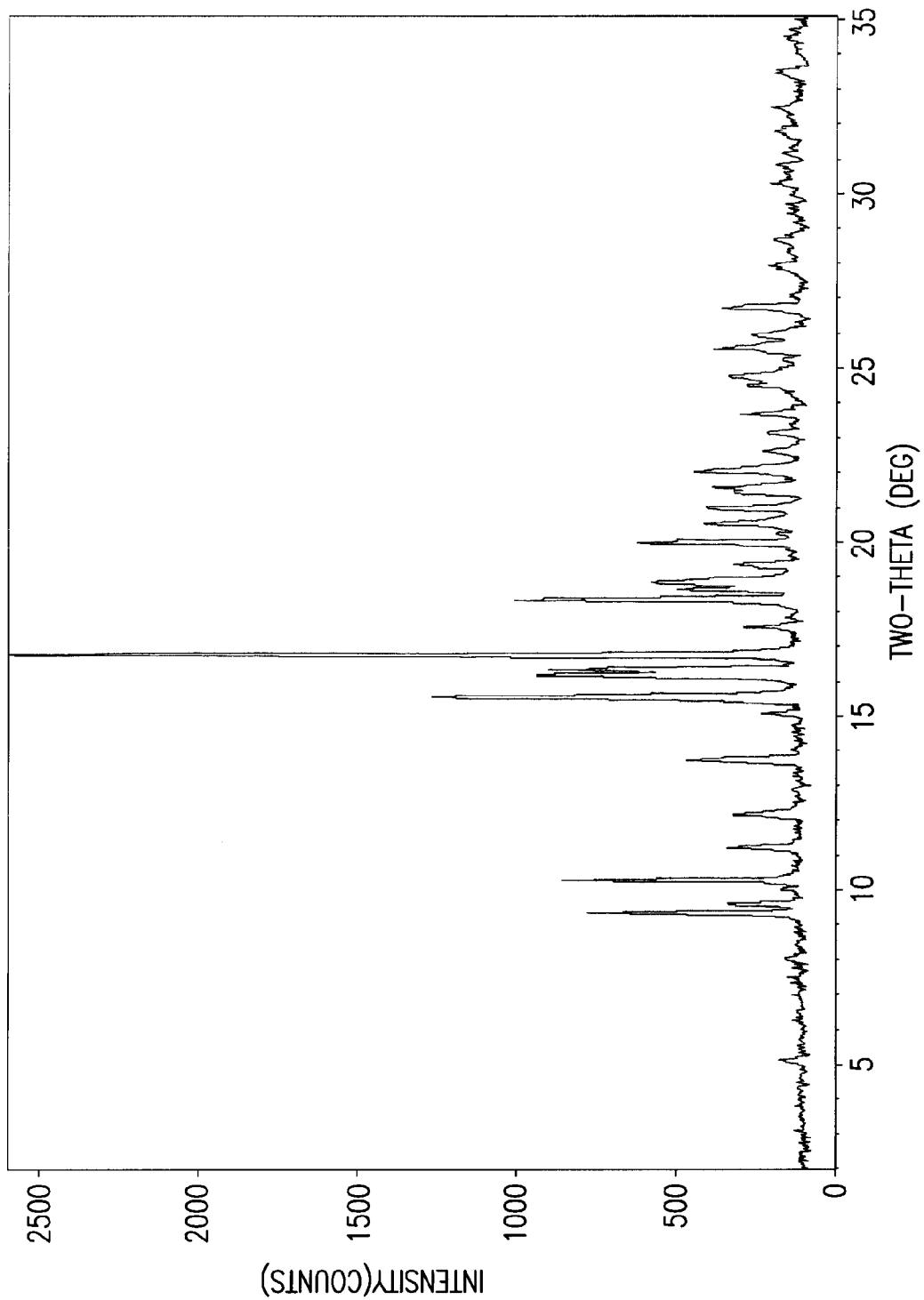
FIG. 10 is a powder X-ray diffraction pattern of a monohydrogen citrate of (4s)-4-(5-phenyl-1,3,4-thiadiazol-2-yloxy)-1-azatricyclo[3.3.1.1$^{3,7}$]decane.

(4s)-4-(5-Phenyl-1,3,4-thiadiazol-2-yloxy)-1-azatricyclo[3.3.1.1$^{3,7}$]decane monohydrogen citrate crystalline solid can be identified by characteristic peaks in its powder X-ray diffraction pattern (FIG. 10). One with skill in the art of analytical chemistry would be able to readily identify (4s)-4-(5-phenyl-1,3,4-thiadiazol-2-yloxy)-1-azatricyclo[3.3.1.1$^{3,7}$]decane monohydrogen citrate solid by as few as one characteristic peak in its powder X-ray diffraction pattern. Two-theta angle positions of characteristic peaks in a powder X-ray diffraction pattern of (4s)-4-(5-phenyl-1,3,4-thiadiazol-2-yloxy)-1-azatricyclo[3.3.1.1$^{3,7}$]decane monohydrogen citrate are 9.37±0.20, 9.62±0.20, 10.30±0.20, 11.24±0.20, 12.18±0.20, 13.73±0.20, 15.55±0.20, 16.17±0.20, 16.37±0.20, 16.76±0.20, 18.35±0.20, 18.67±0.20, 18.89±0.20, 19.98±0.20, 20.48±0.20, 20.94±0.20, 21.54±0.20, and 22.02±0.20.

Figure 11:
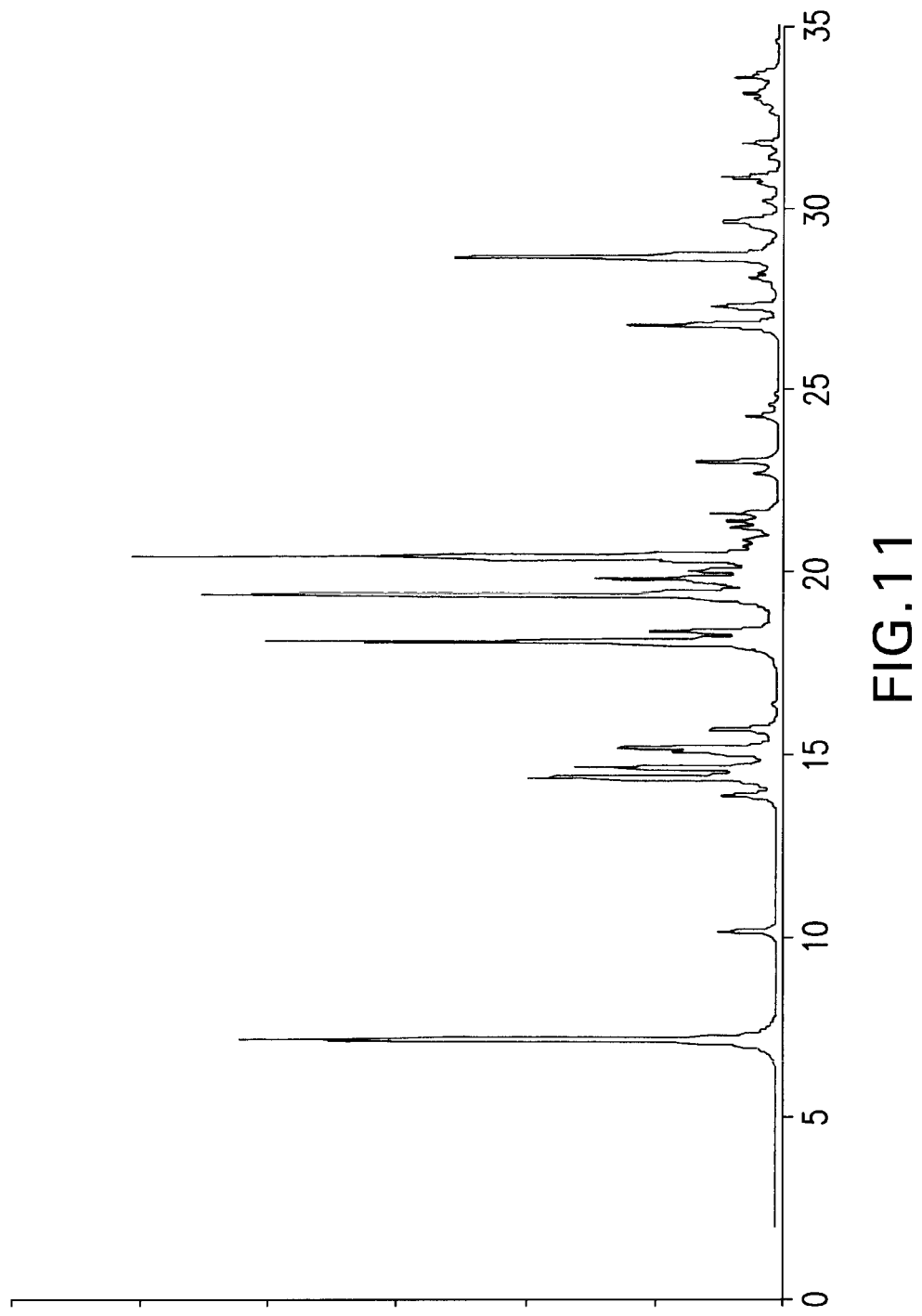
FIG. 11 is a powder X-ray diffraction pattern of the (4s)-4-(5-phenyl-1,3,4-thiadiazol-2-yloxy)-1-azatricyclo [3.3.1.1$^{3,7}$]decane free base.

(4s)-4-(5-Phenyl-1,3,4-thiadiazol-2-yloxy)-1-azatricyclo[3.3.1.1$^{3,7}$]decane free base can be identified by characteristic peaks in its powder X-ray diffraction pattern (FIG. 11). One with skill in the art of analytical chemistry would be able to readily identify (4s)-4-(5-phenyl-1,3,4-thiadiazol-2-yloxy)-1-azatricyclo[3.3.1.1$^{3,7}$]decane free base by as few as one characteristic peak in its powder X-ray diffraction pattern. Two-theta angle positions of characteristic peaks in a powder X-ray diffraction pattern of (4s)-4-(5-phenyl-1,3,4-thiadiazol-2-yloxy)-1-azatricyclo[3.3.1.1$^{3,7}$]decane free base are 7.18±0.20, 10.19±0.20, 13.90±0.20, 14.37±0.20, 14.40±0.20, 14.66±0.20, 15.09±0.20, 15.21±0.20, 18.13±0.20, 18.43±0.20, 19.41±0.20, 19.88±0.20 (two peaks), 20.09±0.20, 20.46±0.20, 21.66±0.20, 23.08±0.20, 26.84±0.20, 28.71±0.20, and 30.90±0.20. Crystallographic unit cell parameters of (4s)-4-(5-phenyl-1,3,4-thiadiazol-2-yloxy)-1-azatricyclo[3.3.1.1$^{3,7}$]decane free base also were obtained and were determined as: a is 6.4427(17) Å, b is 9.895(3) Å, c is 13.102(4) Å, and a is 70.145(4)°, β is 81.691(4)°, and γ is 73.391(4)° to afford a cell volume of 751.787 Å$^3$, wherein a, b, and c are each a representative length of the crystal lattice and α, β, and γ are each a unit cell angle. The salt crystallizes in the triclinic P-1 space group.

As used herein the term "substantially pure", when used in reference to a salt of (4s)-4-(5-phenyl-1,3,4-thiadiazol-2-yloxy)-1-azatricyclo[3.3.1.1$^{3,7}$]decane, refers to a salt that is greater than about 90% pure. The crystalline form of (4s)-4-(5-phenyl-1,3,4-thiadiazol-2-yloxy)-1-azatricyclo[3.3.1.1$^{3,7}$]decane does not contain more than about 10% of any other compound and, in particular, does not contain more than about 10% of any other form of (4s)-4-(5-phenyl-1,3,4-thiadiazol-2-yloxy)-1-azatricyclo[3.3.1.1$^{3,7}$]decane, such as amorphous, solvated forms, non-solvated forms, desolvated forms, and the enantiomer.

More preferably, a "substantially pure" salt refers to a salt that is greater than about 95% pure, wherein the crystalline form of (4s)-4-(5-phenyl-1,3,4-thiadiazol-2-yloxy)-1-azatricyclo[3.3.1.1$^{3,7}$]decane does not contain more than about 5% of any other compound and, in particular, does not contain more than about 5% of any other form of (4s)-4-(5-phenyl-1,3,4-thiadiazol-2-yloxy)-1-azatricyclo[3.3.1.1$^{3,7}$]decane, such as amorphous, solvated forms, non-solvated forms, desolvated forms, and the enantiomer.

Even more preferably, a "substantially pure" salt refers to a salt that is greater than about 97% pure, wherein the crystalline form of (4s)-4-(5-phenyl-1,3,4-thiadiazol-2-yloxy)-1-azatricyclo[3.3.1.1$^{3,7}$]decane does not contain more than about 3% of any other compound and, in particular, does not contain more than about 3% of any other form of (4s)-4-(5-phenyl-1,3,4-thiadiazol-2-yloxy)-1-azatricyclo[3.3.1.1$^{3,7}$]decane, such as amorphous, solvated forms, non-solvated forms, desolvated forms, and the enantiomer.

Compositions comprising (4s)-4-(5-phenyl-1,3,4-thiadiazol-2-yloxy)-1-azatricyclo[3.3.1.1$^{3,7}$]decane salts also are contemplated. A suitable pharmaceutical composition comprises a substantially pure (4s)-4-(5-phenyl-1,3,4-thiadiazol-2-yloxy)-1-azatricyclo[3.3.1.1$^{3,7}$]decane salt formulated together with one or more non-toxic pharmaceutically acceptable carriers as previously described for the compositions. Such compositions comprising (4s)-4-(5-phenyl-1,3,4-thiadiazol-2-yloxy)-1-azatricyclo[3.3.1.1$^{3,7}$]decane salts are administered and can be used in the methods of the invention as previously described for the compounds of the invention, except substituting a desired salt in place of a compound, which would readily understood by one with skill in the art.

Powder X-ray diffraction (PXRD) analysis of samples was conducted in the following manner. Samples for X-ray diffraction analysis were prepared by spreading the sample in a thin layer on the sample holder and gently flattening the sample with a microscope slide. For example, the sample may have been ground to a fine powder with mortar and pestle, or with glass microscope slides for limited quantity samples. Samples were run in one of three configurations: circular bulk holder, a quartz zero background plate, or hot stage mount (similar mounting to a zero background plate).

Diffraction patterns were collected using an Inel G3000 difrractometer equipped with an incident beam germanium monochromator to provide Cu-K$_{α1}$ radiation. The X-ray generator was operated at a voltage of 40 kV and a current of 30 mA. The Inel G3000 is equipped with a position sensitive detector that monitors all diffraction data simultaneously. The detector was calibrated by collecting the attenuated direct beam for seven seconds in 1 degree intervals across a 90 degree two theta range. The calibration was checked against a silicon line position reference standard (NIST 640c). Samples were placed on an aluminum sample holder and leveled with a glass slide.

Alternatively, X-ray powder diffraction can be performed using a Rigaku Miniflex diffractometer (30 kV and 15 mA; X-ray source: Cu; Range: 2.00-40.00° Two Theta; Scan rate: 1-5 degree/minute) or a Scintag X1 or X2 diffractometer (2 kW normal focus X-ray tube with either a liquid nitrogen or Peltier cooled germanium solid state detector; 45 kV and 40 mA; X-ray source: Cu; Range: 2.00-40.00° Two Theta; Scan Rate: 1-5 degree/minute).

Characteristic powder X-ray diffraction pattern peak positions are reported in terms of angular positions (two theta) with an allowable variability of ±0.20°. The variability of ±0.10° is intended to be used when comparing two powder X-ray diffraction patterns. In practice, if a diffraction pattern peak from one pattern is assigned a range of angular positions (two theta) which is the measured peak position ±0.20° and a diffraction pattern peak from another pattern is assigned a range of angular positions (two theta) which is measured peak position ±0.20° and if those ranges of peak position overlap, then the two peaks are considered to have the same angular position (two theta). For example, if a diffraction pattern peak from one pattern is determined to have a peak position of 5.20° for comparison purposes the allowable variability allows the peak to be assigned a position in the range of 5.00°-5.40°. If a comparison peak from the other diffraction pattern is determined to have a peak position of 5.35° and the allowable variability allows the peak to be assigned a position in the range of 5.15°-5.55°, then the two peaks being compared are considered to have the same angular position (two theta) because there is overlap between the two ranges of peak positions.

Single crystal X-ray diffraction analysis of samples was conducted in the following manner. Samples for X-ray diffraction analysis were prepared by affixing selected single crystals to glass pins with epoxy adhesive. X-ray diffraction data was collected using a Bruker SMART system with an APEX area detector (50 kv and 40 mA; X-ray source: Mo). Data were collected at −100° C.

Thermal gravimetric analysis of samples was conducted in the following manner. A Mettler Toledo Model TGA/SDTA 851e thermal gravimetric analysis instrument was used to determine the weight change against sample temperature. Experiments and analysis conducted with Mettler STARe software. The experimental parameters were: sample weight 2-20 mg, placed in an open aluminum pan; heating rate 10° C. per minute, $N_2$ purge flow rate 50 mL per minute. Samples were heated from 25° C. to 200° C. at a rate of 10° C. per minute.

METHODS OF THE INVENTION

Compounds and compositions of the invention are useful for modulating the effects of nAChRs, and more particularly α7 nAChRs. In particular, the compounds and compositions of the invention can be used for treating or preventing disorders modulated by α7 nAChRs. Typically, such disorders can be ameliorated by selectively modulating the α7 nAChRs in a mammal, preferably by administering a compound or composition of the invention, either alone or in combination with another active agent, for example, as part of a therapeutic regimen.

In addition, the invention relates to a method for treating or preventing conditions, disorders or deficits modulated by an α7 nicotinic acetylcholine receptor, an α4β2 nicotinic acetylcholine receptor or both α7 and α4β2 nicotinic acetylcholine receptor wherein the condition, disorder, or deficit is selected from the group consisting of a memory disorder, cognitive disorder, neurodegeneration, or neurodevelopmental disorder, or a combination thereof comprising administration of a therapeutically suitable amount of a compound of formula (I),

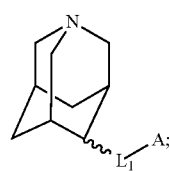

(I)

or a pharmaceutically acceptable salt or prodrug thereof, wherein $L_1$ is —O— or —$NR_a$—; A is —$Ar_1$, —$Ar_2$-$L_2$-$Ar_3$ or —$Ar_4$-$L_3$-$Ar_5$; $Ar_1$ is aryl or heteroaryl; $Ar_2$ is aryl or monocyclic heteroaryl; $Ar_3$ is aryl or heteroaryl; $Ar_4$ is a bicyclic heteroaryl; $Ar_5$ is aryl or heteroaryl; $L_2$ is a bond, —O—, —$NR_a$—, —$CH_2$—, —C(O)$NR_a$—; $L_3$ is a bond, —O—, —$NR_a$— or —$CH_2$—; and $R_a$ is hydrogen or alkyl.

The invention also contemplates the method for treating or preventing a condition or disorder modulated by an α7 nicotinic acetylcholine receptor comprising the step of administering a compound of the formula (I), wherein the condition or disorder is selected from a memory disorder, cognitive disorder, neurodegeneration, and neurodevelopmental disorder.

The invention also contemplates a method for treating or preventing a condition or disorder modulated by an α7 nicotinic acetylcholine receptor comprising the step of administering a compound of the formula (I), wherein the condition or disorder is selected from attention deficit disorder, attention deficit hyperactivity disorder (ADHD), Alzheimer's disease (AD), mild cognitive impairment, schizophrenia, senile dementia, AIDS dementia, Pick's disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain and inflammatory pain.

The invention also contemplates a method for treating or preventing a condition or disorder modulated by an α7 nicotinic acetylcholine receptor comprising the step of administering a compound of the formula (I), wherein the condition or disorder is schizophrenia.

The invention also contemplates a method for treating or preventing a condition or disorder modulated by an α7 nicotinic acetylcholine receptor comprising the step of administering a compound of the formula (I) in combination with an atypical antipsychotic.

The invention also contemplates a method for treating or preventing a condition or disorder modulated by an α7 nicotinic acetylcholine receptor comprising the step of administering a compound of the formula (I), wherein the condition or disorder is infertility, lack of circulation, need for new blood vessel growth associated with wound healing, more particularly circulation around a vascular occlusion, need for new blood vessel growth associated with vascularization of skin grafts, ischemia, inflammation, particularly those associated with rheumatoid arthritis, wound healing, and other complications associated with diabetes.

The invention also contemplates a method for treating or preventing a condition or disorder modulated both by α7 and α4β2 nicotinic acetylcholine receptors comprising the step of administering a compound of the formula (I), wherein the condition or disorder is selected from a group of disorders where both α7 and α4β2 nicotinic receptors are implicated. These include attention deficit disorder, attention deficit hyperactivity disorder (ADHD), Alzheimer's disease (AD), mild cognitive impairment, schizophrenia, senile dementia, AIDS dementia, Pick's disease, dementia associated with Lewy bodies, dementia associated with Down's syndrome, amyotrophic lateral sclerosis, Huntington's disease, inflammation, arthritis of various types, smoking cessation, nicotinic withdrawal syndrome, traumatic brain injury, acute pain, post-surgical pain, osteoarthritic pain, neuropathic and inflammatory chronic pain states.

Compounds for the method of the invention, including but not limited to those specified in the examples or otherwise specifically named, can modulate, and often possess an affinity for, nAChRs, and more particularly α7 nAChRs. As α7 nAChRs ligands, the compounds of the invention can be useful for the treatment or prevention of a number of α7 nAChR-mediated diseases or conditions. Certain compounds of the invention includes, in addition to affinity for α7 nAChRs, affinity for α4β2 nAChRs.

For example, α7 nAChRs have been shown to play a significant role in enhancing cognitive function, including aspects of learning, memory and attention (Levin, E. D., J. Neurobiol. 53: 633-640, 2002). As such, α7 ligands are suitable for the treatment of conditions and disorders related to memory and/or cognition including, for example, attention deficit disorder, attention deficit hyperactivity disorder (ADHD), Alzheimer's disease (AD), mild cognitive impairment, senile dementia, AIDS dementia, Pick's disease, dementia associated with Lewy bodies, and dementia associated with Down's syndrome, as well as cognitive deficits associated with schizophrenia.

In addition, α7-containing nAChRs have been shown to be involved in the cytoprotective effects of nicotine both in vitro (Jonnala, R. B. and Buccafusco, J. J., J. Neurosci. Res. 66: 565-572, 2001) and in vivo (Shimohama, S. et al., Brain Res. 779: 359-363, 1998). More particularly, neurodegeneration underlies several progressive CNS disorders, including, but not limited to, Alzheimer's disease, Parkinson's disease, amyotrophic lateral sclerosis, Huntington's disease, dementia with Lewy bodies, as well as diminished CNS function resulting from traumatic brain injury. For example, the impaired function of α7 nAChRs by β-amyloid peptides linked to Alzheimer's disease has been implicated as a key factor in development of the cognitive deficits associated with the disease (Liu, Q.-S., Kawai, H., Berg, D. K., PNAS 98: 4734-4739, 2001). α7 selective ligands can influence neuroprotective pathways leading to decreased phosphorylation of the tau protein, whose hyperphosphorylation is required for neurofibrillary tangle formation in various tau related pathologies such as Alzheimer's disease and various other dementias (Bitner et al., Soc. Neuroscience, 2006 abst 325.6). The activation of α7 nAChRs has been shown to block this neurotoxicity (Kihara, T. et al., J. Biol. Chem. 276: 13541-13546, 2001). As such, selective ligands that enhance α7 activity can counter the deficits of Alzheimer's and other neurodegenerative diseases.

Alpha-7 nAChRs also have been implicated in aspects of neurodevelopment, for example neurogenesis of the brain. (Falk, L. et al., Developmental Brain Research 142:151-160, 2003; Tsuneki, H., et al., J. Physiol. (London) 547:169-179, 2003; Adams, C. E., et al., Developmental Brain Research 139:175-187, 2002). As such, α7 nAChRs can be useful in preventing or treating conditions or disorders associated with impaired neurodevelopment, for example schizophrenia. (Sawa A., Mol. Med. 9:3-9, 2003).

Several compounds with high affinity for α4β2 neuronal nicotinic receptors (NNRs) have been shown to improve attentive and cognitive performance in preclinical models that are relevant to attention-deficit/hyperactivity disorder (ADHD), a disease characterized by core symptoms of hyperactivity, inattentiveness, and impulsivity. For example, ABT-418, a full agonist at α4β2 NNRs is efficacious in a variety of preclinical cognition models. ABT-418 administered transdermally, was shown in a controlled clinical trial in 32 adults to be effective in treating ADHD in general, and attentional/cognitive deficits in particular (Wilens, T. E.; Biederman, J.; Spencer, T. J.; Bostic, J.; Prince, J.; Monuteaux, M. C.; Soriano, J.; Fince, C.; Abrams, A.; Rater, M.; Polisner, D. The American Journal of Psychiatry (1999) 156(12), 1931-1937.). Likewise, ABT-418 showed a signal of efficacy in a pilot Alzheimer's disease trial. ABT-089, a α4β2 selective partial agonist, has been shown in rodent and primate animal models to improve attention, learning, and memory deficits. ABT-089 and another α4β2 agonist, ispronicline has shown efficacy in a pilot clinical trials. In addition to cognition, compounds that interact with α4β2 nAChRs such as ABT-594 and others are also efficacious in preclinical and clinical models of pain. As such, ligands that modulate both α7 and α4β2 activity can have broader spectrum of therapeutic efficacy in disease states such as those involving cognitive and attentive deficits, pain, neurodegenerative diseases and others.

Schizophrenia is a complex disease that is characterized by abnormalities in perception, cognition, and emotions. Significant evidence implicates the involvement of α7 nAChRs in this disease, including a measured deficit of these receptors in post-mortem patients (Sawa A., Mol. Med. 9:3-9, 2003; Leonard, S. Eur. J. Pharmacol. 393: 237-242, 2000). Deficits in sensory processing (gating) are one of the hallmarks of schizophrenia. These deficits can be normalized by nicotinic ligands that operate at the α7 nAChR (Adler L. E. et al., Schizophrenia Bull. 24: 189-202, 1998; Stevens, K. E. et al., Psychopharmacology 136: 320-327, 1998). More recent studies have shown that α4β2 nicotinic receptor stimulation also contributes to the effects of nicotine in the DBA/2 mouse model of sensory gating (Radek et al., Psychopharmacology (Berl). 2006 187:47-55. Thus, α7 and α7/α4β2 ligands demonstrate potential in the treatment schizophrenia.

Angiogenesis, a process involved in the growth of new blood vessels, is important in beneficial systemic functions, such as wound healing, vascularization of skin grafts, and enhancement of circulation, for example, increased circulation around a vascular occlusion. Non-selective nAChR agonists like nicotine have been shown to stimulate angiogenesis (Heeschen, C. et al., Nature Medicine 7: 833-839, 2001). Improved angiogenesis has been shown to involve activation of the α7 nAChR (Heeschen, C. et al., J. Clin. Invest. 110: 527-536, 2002). For example, improved conditions related to inflammation, ischemia, cardiac ischemia, and wound healing, for example in diabetic persons, have been associated with α7 nAChR activity (Jacobi, J., et al., Am. J. Pathol. 161:97-104, 2002). Therefore, nAChR ligands that are selective for the α7 subtype offer improved potential for stimulating angiogenesis with an improved side effect profile.

A population of α7 or α4β2 nAChRs in the spinal cord modulate neurotransmission transmission that have been associated with the pain-relieving effects of nicotinic compounds (Cordero-Erausquin, M. and Changeux, J.-P. PNAS 98:2803-2807, 2001). The α7 nAChR or and α7/α4β2 ligands demonstrate therapeutic potential for the treatment of pain states, including acute pain, post-surgical pain, as well as chronic pain states including inflammatory pain and neuropathic pain. Moreover, α7 nAChRs are expressed on the surface of primary macrophages that are involved in the inflammation response, and that activation of the α7 receptor inhibits release of TNF and other cytokines that trigger the inflammation response (Wang, H. et al Nature 421: 384-388, 2003). Therefore, selective α7 ligands demonstrate potential for treating conditions involving inflammation including those associated with various forms of arthritis.

The mammalian sperm acrosome reaction is an exocytosis process important in fertilization of the ovum by sperm. Activation of an α7 nAChR on the sperm cell has been shown to be essential for the acrosome reaction (Son, J. H. and Meizel, S. Biol. Reproduct. 68: 1348-1353 2003). Consequently, selective α7 agents demonstrate utility for treating fertility disorders.

Compounds of the invention are particularly useful for treating and preventing a condition or disorder affecting memory, cognition, neurodegeneration, neurodevelopment, and schizophrenia.

Cognitive impairment associated with schizophrenia often limits the ability of patients to function normally, a symptom not adequately treated by commonly available treatments, for example, treatment with an atypical antipsychotic. (Rowley, M. et al., J. Med. Chem. 44: 477-501, 2001). Such cognitive deficit has been linked to dysfunction of the nicotinic cholinergic system, in particular with decreased activity at α7 receptors. (Friedman, J. I. et al., Biol Psychiatry, 51: 349-357, 2002). Thus, activators of α7 receptors can provide useful treatment for enhancing cognitive function in schizophrenic patients who are being treated with atypical antipsychotics. Accordingly, the combination of an α7 nAChR ligand and an atypical antipsychotic would offer improved therapeutic utility. Specific examples of suitable atypical antipsychotics include, but are not limited to, clozapine, risperidone, olanzapine, quietapine, ziprasidone, zotepine, iloperidone, and the like.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide, or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.10 μg/kg body weight to about 10 mg/kg body weight. More preferable doses can be in the range of from about 0.10 μg/kg body weight to about 1 mg/kg body weight. If desired, the effective daily dose can be divided into multiple doses for purposes of administration. Consequently, single dose compositions may contain such amounts or submultiples thereof to make up the daily dose.

Methods for Preparing Compounds of the Invention

As used in the descriptions of the schemes and the examples, certain abbreviations are intended to have the following meanings: Bu for butyl; DMAP for 4-dimethylaminopyridine; DMF for dimethyl formamide; DME for 1,2-dimethoxyethane; EDAC for —N-(3-dimethylaminopropyl)-N'-ethylcarbodiimide hydrochloride, Et for ethyl; EtOAc for ethyl acetate; eq. for equivalents; HOBt for hydroxybenzotriazole; HPLC for high pressure liquid chromatography; mCPBA for m-chloroperbenzoic acid; Me for methyl; MeOH for methanol; OAc for acetoxy; OTf for trifluoromethanesulfonate; Pd/C for palladium on carbon; Ph for phenyl; THF for tetrahydrofuran; and TLC for thin layer chromatography.

The reactions exemplified in the schemes are performed in a solvent appropriate to the reagents and materials employed and suitable for the transformations being effected. The described transformations may require modifying the order of the synthetic steps or selecting one particular process scheme over another in order to obtain a desired compound of the invention, depending on the functionality present on the molecule.

Nitrogen protecting groups can be used for protecting amine groups present in the described compounds. Such methods, and some suitable nitrogen protecting groups, are described in Greene and Wuts (Protective Groups In Organic Synthesis, Wiley and Sons, 1999). For example, suitable nitrogen protecting groups include, but are not limited to, tert-butoxycarbonyl (Boc), benzyloxycarbonyl (Cbz), benzyl (Bn), acetyl, and trifluoroacetyl. More particularly, the Boc protecting group may be removed by treatment with an acid such as trifluoroacetic acid or hydrochloric acid. The Cbz and Bn protecting groups may be removed by catalytic hydrogenation. The acetyl and trifluoroacetyl protecting groups may be removed by a hydroxide ion.

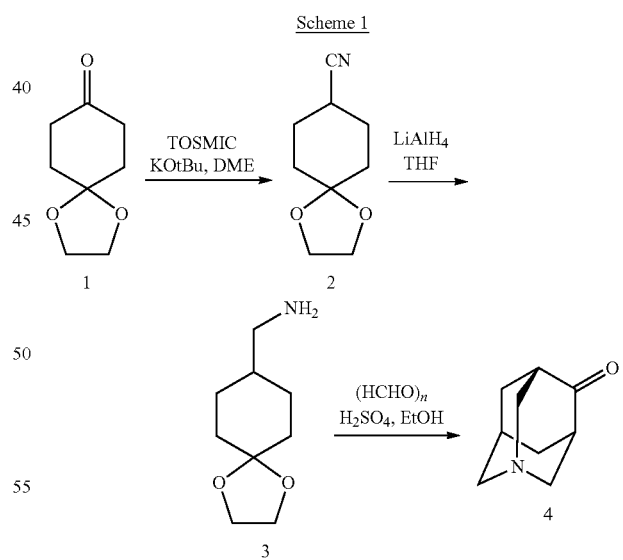

Scheme 1

As outlined in Scheme 1, compound of formula 1 (commercially available from Aldrich Chemical Co., [4746-97-8]) when treated with tosylmethyl isocyanide (TOSMIC, commercially available from Aldrich Chemical Co., [36635-61-7]) in the presence of a base such as potassium tert-butoxide in a solvent such as ethylene glycol dimethyl ether will provide the compound of formula 2. Compound of formula 2 when treated with lithium aluminum hydride in THF will provide the compound of formula 3. Compound of formula 3 when treated with paraformaldehyde along with sulfuric acid in ethanol will provide the compound of formula 4 (1-azaadamantan-4-one). A further description of the synthesis may be found in Synthesis, 1992, 1080, Becker, D. P.; Flynn, D. L.

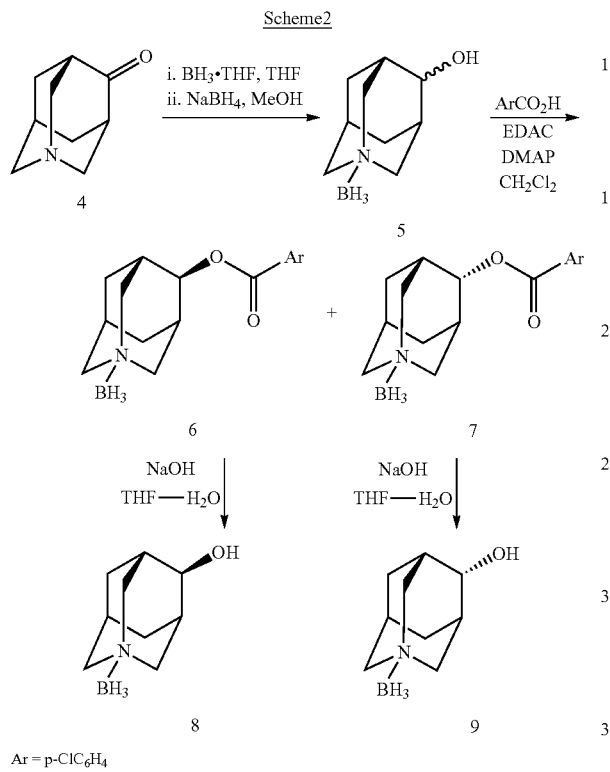

Ar = p-ClC$_6$H$_4$

As outlined in Scheme 2, compounds of formula 4 (1-azaadamantan-4-one) when treated with borane-THF complex in THF will provide the borane complexed amine, which when further treated with a reducing agent such as sodium borohydride in methanol will provide compounds of formula 5 which consists of a mixture of (r) and (s) isomers. The compound of formula 5 may be further treated according to the methods outlined in the Schemes 3-11 to obtain an (rs) mixture of the compound of formula (I), or the mixture may be separated into the individual (r) or (s) isomers and then treated according to the methods outlined in the Schemes 3-11 to generate a single (r) or (s) isomer of the compounds of formula (I). To effect the separation of the (r) isomer from the (s) isomer, the treatment of the compound of formula 5 with reagents such as a substituted benzoic acid (for example para-chlorobenzoic acid) and N-(3-dimethylaminopropyl)-N'-ethylcarbodiimide hydrochloride (EDAC) in the presence of 4-dimethyl aminopyridine in a solvent, such as dichloromethane, will provide compounds of formula 6 and 7. The mixture of compounds of formula 6 and 7 may be separated through the use of chromatographic procedures known to one skilled in the art. The individual isomers, the compound of formula 6 or the compound of formula 7, when further treated with sodium hydroxide in a mixture of THF and water will provide the compound of formula 8 or the compound of formula 9, respectively.

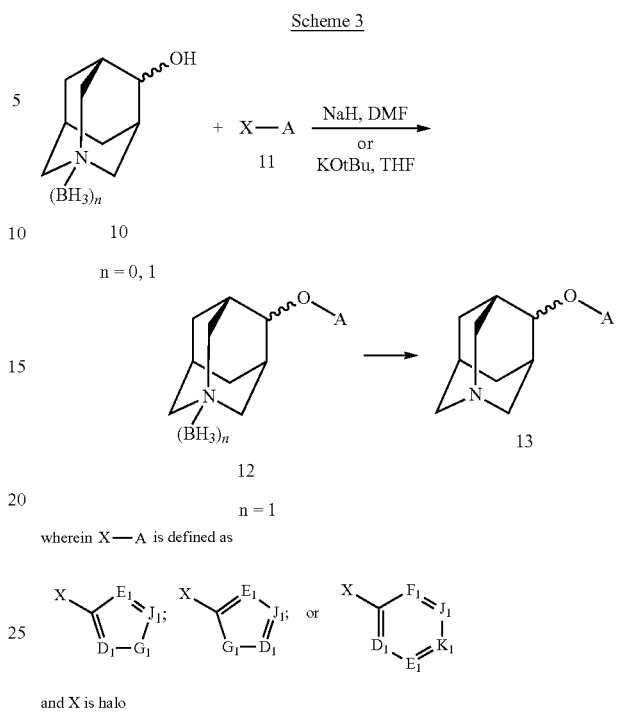

wherein X—A is defined as and X is halo

As outlined in Scheme 3, compounds of formula 10, which may be either the mixture of compounds of formula 8 and 9 or the individual isomers represented by the compound of formula 8 or the compound of formula 9, or the corresponding free amine lacking the borane group, when treated with sodium hydride in DMF, potassium tert butoxide, or potassium bis(trimethylsilylamide), in THF or DMSO followed by treatment with compounds of formula 11, wherein X is chloro, bromo, fluoro or iodo and A is as defined for compounds of formula (I), and more particularly for Ar$_1$ of compounds of formula (II) or similarly Ar$_2$ of compounds of formula (III), will provide compounds of formula 12. Compounds of formula 12 when treated with either aqueous hydrochloric acid in acetone or with palladium on carbon in methanol will provide compounds of formula 13 which are representative of compounds of the invention.

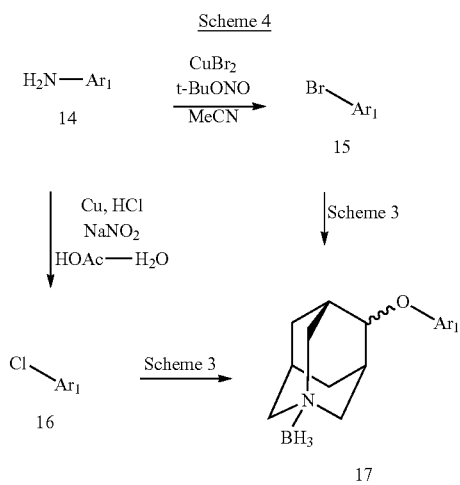

-continued

Wherein H$_2$N—Ar$_1$ is defined as

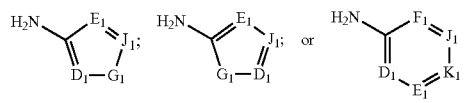

As shown in Scheme 4, compounds of formula 15 and 16 each represent compounds of formula A-X, wherein A is Ar$_1$ and is defined in formula (I) and X is chloro or bromo. Compounds of formula 15 and of formula 16 may be obtained from compounds of formula H$_2$N—Ar$_1$ as outlined. Compounds of formula H$_2$N—Ar$_1$ (formula 14) wherein D$_1$, E$_1$, F$_1$, J$_1$, and K$_1$ are each independently CR$_{1a}$ or N, G is —O—, —NR$_{1a}$, or —S—, R$_1$ is hydrogen, alkyl, alkoxy, alkoxycarbonyl, cyano, halo, nitro or —NR$_b$R$_c$, R$_{1a}$ is hydrogen or alkyl, R$_b$ and R$_c$ are each independently hydrogen, alkyl, alkoxycarbonyl or alkylcarbonyl, and n is 0, 1, 2 or 3 for groups shown in Scheme 4, when treated with cuprous bromide and tert butyl nitrite in acetonitrile will provide compounds of formula 15. Alternatively, compounds of formula 14, wherein Ar$_1$ is as defined above in Scheme 4 when treated with copper powder, aqueous hydrochloric acid, sodium nitrite in a solution of aqueous acetic acid will provide compounds of formula 16. Furthermore, when either compounds of formula 15 or compounds of formula 16 are subjected to the conditions outlined in Scheme 3 compounds of formula 17 which are representative of compounds of the invention which contain an A group that is defined as Ar$_1$ or Ar$_2$ in formula (I), will be provided.

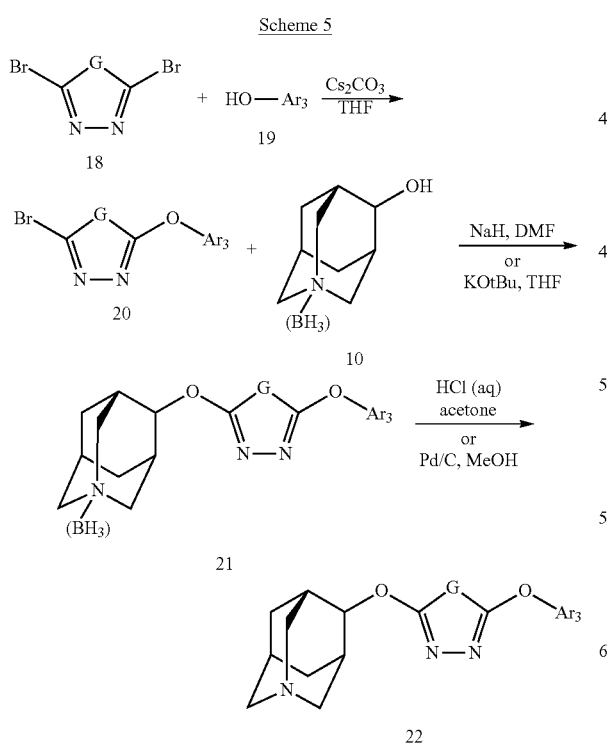

As outlined in Scheme 5, compounds of formula 18, wherein G is —O—, NR$_{1a}$, or —S—, and R$_{1a}$ is hydrogen or alkyl, when treated with compounds of formula 19, wherein Ar$_3$ as defined for compounds of formula (I), in the presence of cesium carbonate and a solvent such as but not limited to THF will provide compounds of formula 20, which are representative of compounds of formula A-X, (compounds of formula 11), described in Scheme 3, wherein A is —Ar$_2$-L$_2$-Ar$_3$ as defined in formula (I). When compounds of formula 20 and compounds of formula 10 are treated according to the conditions outlined in Scheme 3, compounds of formula 21 are obtained. When compounds of formula 21 are treated with aqueous hydrochloric acid in acetone or with palladium on carbon in methanol, compounds of formula 22 are obtained which are representative of compounds of the invention which contain an A group that is defined as Ar$_2$-L$_2$-Ar$_3$ in formula (I).

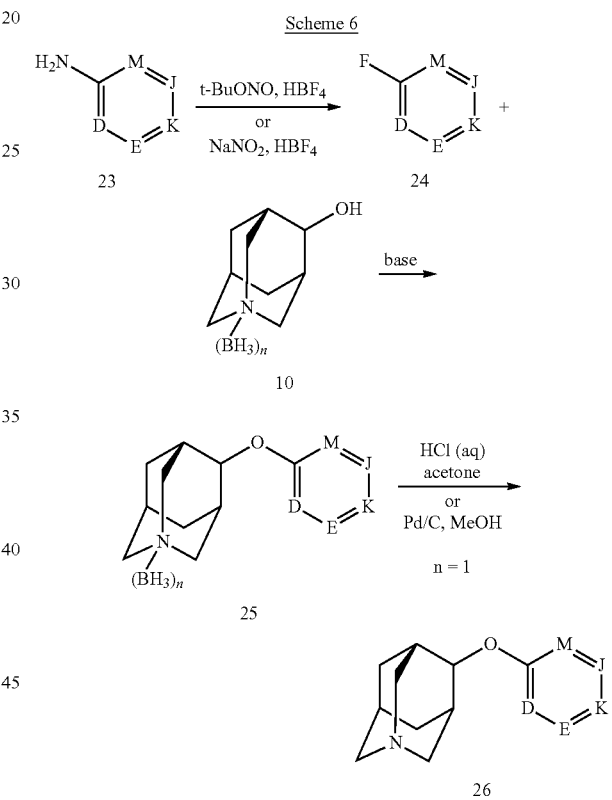

As outlined in Scheme 6, compounds of formula 23, wherein D, E, J, K, and M are each independently —CR$_{2a}$—, —CX$^2$—, or —N—, X$^2$ is halo, haloalkyl, cyano, or nitro, when treated with either tert-butyl nitrite and tetrafluoroboric acid, or sodium nitrite and tetrafluoroboric acid, will provide compounds of formula 24. Compounds of formula 24 when treated with compounds of formula 10 in the presence of a base such as but not limited to, either sodium hydride in DMF, potassium tert butoxide in THF or potassium bis(hexamethyldi-silylamine) in THF will provide compounds of formula 25. Compounds of formula 25 when treated with either aqueous hydrochloric acid in acetone or with palladium on carbon in methanol will provide compounds of formula 26 which are representative of compounds of the invention.

Scheme 7

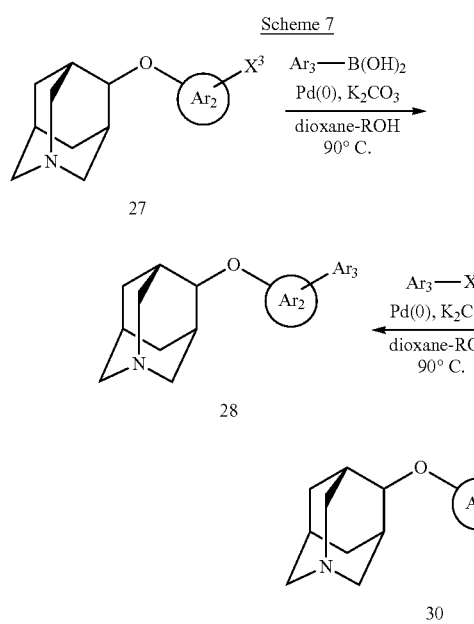

As outlined in Scheme 7, compounds of formula 27, wherein Ar$_2$ is defined in formula (I) and X$^3$ is halo or —O-trifluoromethanesulfonyl, which can be obtained according to the methods outlined in Schemes 3, 4, or 6, when heated in the presence of Ar$_3$-B(OH)$_2$, a palladium catalyst, as known to one skilled in the art, and potassium carbonate in a solvent such as, but not limited to, a mixture of dioxane and water or an alcoholic solvent such as ethanol under heated conditions, will provide compounds of formula 28 which is representative of compounds of the invention, wherein A is —Ar$_2$-L$_2$-Ar$_3$, and L$_2$ is a bond. Alternatively, compounds of formula 30, which contain a boronic acid or a boronic acid ester, wherein R$_X$ is hydrogen or alkyl, which may be obtained according to the methods described herein, when treated with Ar$_3$—X, wherein Ar$_3$ is defined in formula (I) and X is chloro, bromo or —O-trifluoromethane sulfonyl in the presence of a palladium catalyst as known to one skilled in the art and potassium carbonate in a mixture of solvents such as, but not limited to, a mixture of dioxane and an alcoholic solvent, for example ethanol, under heated conditions will also provide compounds of formula 28.

Scheme 8

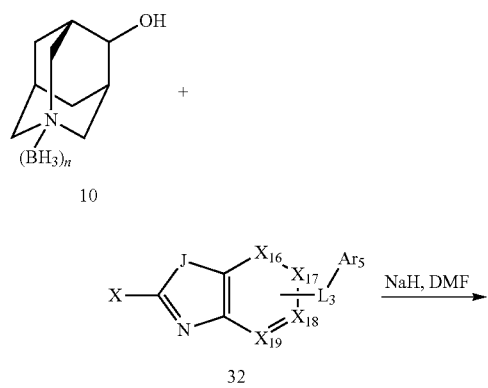

As outlined in Scheme 8, compounds of formula 10 when treated with compounds of formula 32, wherein X is chloro, bromo, or iodo, J is —O— or —S—, and X$_{16}$-X$_{19}$, L$_3$, and Ar$_5$ are as defined for compounds of formula (IV) in the presence of sodium hydride in DMF will provide compounds of formula 33. Compounds of formula 33 when treated with aqueous hydrochloric acid in acetone or with palladium on carbon in methanol will provide compounds of formula 34 which are representative of compounds of the invention wherein A is —Ar$_4$-L$_3$-Ar$_5$.

Scheme 9

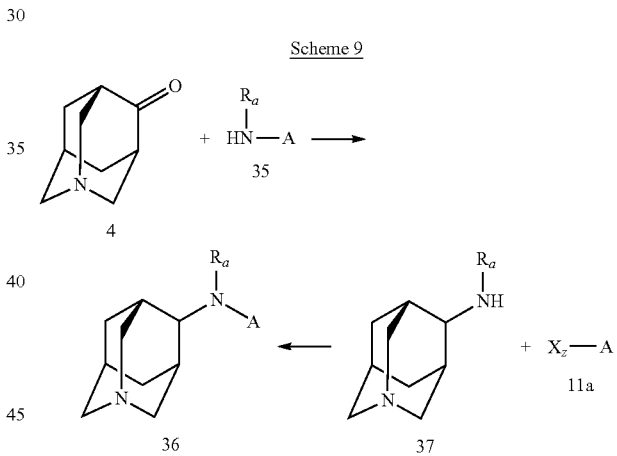

As outlined in Scheme 9, compounds of formula 4 when treated with compounds of formula 35 and a reducing agent such as but not limited to sodium triacetoxyborohydride will provide compounds of formula 36. Typical conditions for this transformation include stirring the compound of formula 4 and compound of formula 35 in a solvent such as THF in the presence of glacial acetic acid and/or magnesium sulfate followed by the addition of the reducing agent. Alternatively, compounds of formula 37, which can be obtained from the reductive amination of compounds of formula 4 with amine of formula R$_a$—NH$_2$, may be further treated with compounds of formula A-X$_z$ (compound 11a) wherein A is as defined in formula (I) and X$_z$ is halo or -OTf in the presence of a palladium catalyst such as but not limited to palladium tetrakis (triphenylphosphine) and a base such as but not limited to sodium carbonate will also provide compounds of formula 36 which are representative of compounds of the invention, wherein L$_1$ is —NR$_a$— in compounds of formula (I).

Scheme 10

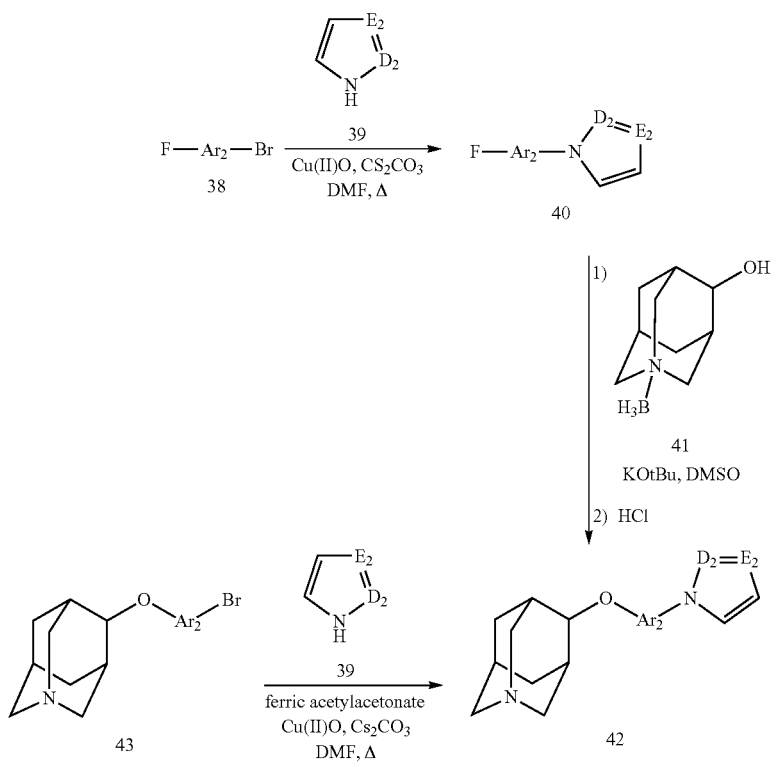

As outlined in Scheme 10, compounds of formula 38, wherein $Ar_2$, $E_2$, and $D_2$ are as defined for compounds of formula (III), when treated with compounds of formula 39, copper(II) oxide, and a base like cesium carbonate heated in solvent such as DMF supplies compounds of formula 40. Treatment of compounds of formula 41 with a base such as potassium t-butoxide in a solvent like dimethyl sulfoxide or tetrahydrofuran, then reacting with compounds of formula 40, and subsequent treatment with a hydrochloric acid in acetone provides compounds of formula 42. Alternatively, compounds of formula 42 can be prepared from compounds of formula 43 by treatment with compounds of formula 39 in the presence of ferric acetylacetonate, copper(II) oxide, a base like cesium carbonate and heated in a solvent like DMF.

Scheme 11

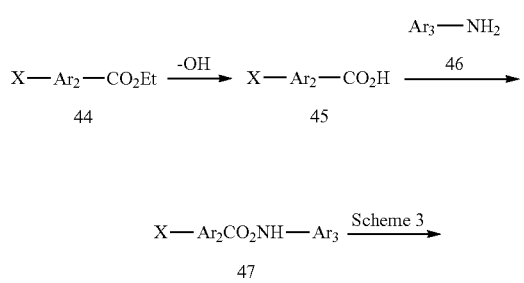

-continued

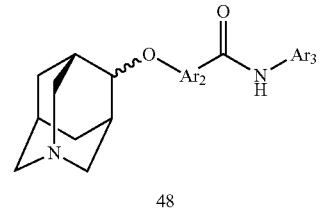

As outlined in Scheme 11, esters of formula 44, wherein $Ar_2$ is defined for compounds of formula (III) and X is halogen, when treated with a base such as sodium hydroxide, potassium hydroxide or lithium hydroxide in a solvent such as a mixture of water and ethanol at a temperature in the range of 25 to 40° C. for 30 minutes to 2 hours provides compounds of formula 45. Compounds of formula 45 can be coupled with compounds of formula 46 under amide bond forming conditions familiar to one skilled in the art to give compounds of formula 47. For example, compounds of formula 45 can be combined with compounds of formula 46, hydroxybenzotriazole, dimethylaminopyridine, and 1-(3-dimethylaminopropyl)-3-ethylcarbodiimide hydrochloride in a solvent, such as pyridine, to supply compounds of formula 47. Alternatively, compounds of formula 45 can be converted to the corresponding acid chloride by reacting in neat thionyl chloride. The acid chlorides can then be reacted with compounds of formula 46 in the presence of a base, such as triethylamine, in dichloromethane at or near room temperature to provide compounds of formula 47. Compounds of formula 47 can be converted to compounds of formula 48 using the conditions described in Scheme 3.

In addition, compounds of formula (I) may be converted to compounds of formula (VII) wherein the azaadamantane exists as an N-oxide by treatment with an oxidizing agent. Examples of the oxidizing agent include, but not limited to, aqueous hydrogen peroxide and m-chloroperbenzoic acid. The reaction is generally performed in a solvent such as, but not limited to, acetonitrile, water, dichloromethane, acetone or mixture thereof, preferably a mixture of acetonitrile and water, at a temperature from about 0° C. to about 80° C., for a period of about 1 hour to about 4 days.

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

The compounds of the invention have at least one basic nitrogen whereby the compound can be treated with an acid to form a desired salt. For example, a compound may be reacted with an acid to provide the desired salt. The salt may be collected by any suitable means. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, carbonic, fumaric, gluconic, acetic, propionic, salicylic, hydrochloric, hydrobromic, phosphoric, sulfuric, citric, or hydroxybutyric acid, camphorsulfonic, malic, phenylacetic, aspartic, glutamic, and the like. Preferred salts can include, but are not limited to, p-toluenesulfonate, L-bitartrate, dihydrogen phosphate, bisuccinate, hydrochloride, dihydrogen citrate, and monohydrogen citrate. Citrate salts are more preferred.

The compounds of the invention and processes for making compounds for the method of the invention will be better understood by reference to the following Examples, which are intended as an illustration of and not a limitation upon the scope of the invention.

EXAMPLES

Method A

Etherification

A solution of 1-azaadamantan-4-ol N-borane complex (1 eq.) and a heteroaryl halide (1.1 eq.) in anhydrous DMF (0.5-1 M) was chilled to between −20 and 0° C. and treated with sodium hydride (1.5 equiv; 95%, Aldrich). After 15 minutes, the cooling bath was removed and the mixture was allowed to warm to room temperature. When 1-azaadamantan-4-ol N-borane complex was consumed as determined by TLC analysis (generally 1-2 hours), the mixture was diluted with water and stirred for 1 hour. The resulting solid product was collected by filtration, washed with water, and dried under reduced pressure to afford the desired product.

Method B

Etherification

A solution of 1-azaadamantan-4-ol (or 1-azaadamantan-4-ol N-borane complex, 1 eq.) and a heteroaryl halide (1.1 eq.) in anhydrous tetrahydrofuran (~0.5 M) was chilled to 0° C. under a nitrogen atmosphere and treated with potassium tert-butoxide in THF (1.0 M; 1 eq.; Aldrich), added dropwise. The ice bath was removed, and the mixture was allowed to warm to room temperature overnight. After diluting with water, the mixture was extracted with chloroform (3×), and the combined extracts were purified by flash chromatography (silica gel eluting with a gradient of 5-10% MeOH—CHCl$_3$ containing 1% NH$_4$OH) to afford the desired product.

Method C

Acidic Deboronation

A suspension of the 1-azaadamantane N-borane complex (1 eq.) in acetone (~0.5 M) was chilled to 0° C. and treated with 3 N HCl (4 eq.). After 15 minutes, the ice bath was removed and the mixture was stirred until the borane complex was consumed as monitored by TLC (the borane complexes can be visualized with basic KMnO$_4$ stain). The pH of the solution was then adjusted with 5 N NaOH to ~pH 10, extracted with chloroform (3×), and dried over anhydrous magnesium sulfate, filtered, and concentrated under reduced pressure. The resulting material was purified by either flash chromatography [Analogix pre-packed silica gel cartridges, 5-50% gradient of ammonium hydroxide-methanol-chloroform (2:20:78) in chloroform] or by preparative HPLC [Waters® XTerra RP18 column, 5μ, 30×100 mm, flow rate 40 mL/minute, 5-95% gradient over 22 minutes of acetonitrile in buffer (0.1 M aqueous ammonium bicarbonate, adjusted to pH 10 with ammonium hydroxide)] to afford the desired product as its free base. (Stotter, P. L.; Friedman, M. D.; Dorsey, G. O.; Shiely, R. W.; Williams, R. F.; Minter, D. E. Heterocycles 1987, 25, 251).

Method D

Pd/C-Catalyzed Deboronation

A solution of the 1-azaadamantane N-borane complex in methanol was treated with 10% palladium on carbon (~10% by weight; Aldrich) until the starting material was consumed as indicated by TLC or HPLC (generally overnight). In some instances, the solution was warmed briefly to 50° C. to accelerate the reaction. The catalyst was removed by filtration and the product was purified by either flash chromatography [Analogix pre-packed silica gel cartridges, 5-50% gradient of ammonium hydroxide-methanol-chloroform (2:20:78) in chloroform] or by preparative HPLC [Waters® XTerra RP18 column, 5μ, 30×100 mm, flow rate 40 mL/minute, 5-95% gradient over 22 minutes of acetonitrile in buffer (0.1 M aqueous ammonium bicarbonate, adjusted to pH 10 with ammonium hydroxide)] to afford the desired product.

Method E

Suzuki Coupling

A flask with a septum cap was charged with the azaadamantane containing heteroaryl halide (1 eq.), a heteroaryl-boronic acid or heteroaryl-boronate ester (2 eq.), potassium carbonate (4 eq.), and tetrakis(triphenylphosphine)-palladium(0) (0.04 eq.; Strem). The flask was stoppered, evacuated, flushed with nitrogen, and charged with the solvent mixture 1,4-dioxane-water (3:1; ~0.1 M of the halide), added through the septum. The mixture was then warmed to 90° C. for 3-8 hours. Upon completion of the reaction, the mixture was diluted with EtOAc, washed with water, the extracts dried over magnesium sulfate and filtered. The resulting material was purified by preparative HPLC [Waters® XTerra RP18 column, 5µ, 30×100 mm, flow rate 40 mL/minute, 5-95% gradient of acetonitrile in buffer (0.1 M aqueous ammonium bicarbonate, adjusted to pH 10 with ammonium hydroxide), with UV detection at 254 nm]. Fractions containing the desired product were pooled, concentrated under vacuum, diluted with methanol or ethyl acetate, and filtered to afford the desired product.

Method F

Anhydrous Suzuki Coupling

A flask with a septum cap was charged with the heteroaryl halide (1 eq.), a heteroaryl-boronic acid or heteroaryl-boronate ester (2 eq.), potassium carbonate (3 eq.), [1,1'-bis(diphenylphosphino)ferrocene]dichloropalladium(II) complex with $CH_2Cl_2$ (0.2 eq.; Aldrich) and anhydrous 1,4-dioxane-ethanol (1:1; ~0.1 M of the halide). The mixture was flushed with nitrogen and warmed to 90° C. for 2 hours. After cooling, the mixture was concentrated and purified by preparative HPLC [Waters® XTerra RP18 column, 5µ, 30×100 mm, flow rate 40 mL/minute, 5-95% gradient of acetonitrile in buffer (0.1 M aqueous ammonium bicarbonate, adjusted to pH 10 with ammonium hydroxide), with UV detection at 254 nm]. Fractions containing the desired product were pooled, concentrated under vacuum, diluted with methanol or ethyl acetate, and filtered to afford the desired product as a free base.

Method G

Microwave Suzuki Coupling

In a microwave reaction tube were combined the heteroaryl halide (~0.1 mmol), the heteroaryl-boronic acid or heteroaryl-boronate ester (3 eq.), bis(triphenylphosphine)-palladium(II) chloride (0.1 eq.; Aldrich), and biphenyl-2-yldicyclohexylphosphane (0.03 eq.; Strem), followed by the solvents 1,4-dioxane (1.0 mL), ethanol (1.0 mL), and aqueous sodium carbonate (1.0 M; 1.0 mL). The tube was sealed, and the reaction was heated to 150° C. at 300 W for 10 minutes in a microwave reactor. After cooling to room temperature, the mixture was diluted with 5% $Na_2CO_3$ and extracted with $CHCl_3$ (3×). The combined organic extracts were washed with brine, dried ($Na_2SO_4$), filtered and concentrated under reduced pressure, and the resulting material was purified by preparative HPLC [Waters® XTerra RP18 column, 5µ, 30×100 mm, flow rate 40 mL/minute, 5-95% gradient of acetonitrile in buffer (0.1 M aqueous ammonium bicarbonate, adjusted to pH 10 with ammonium hydroxide] to afford the product as its free base. Alternatively, the product was purified by preparative HPLC under acidic conditions [Waters® XTerra RP18 column, 5µ, 30×100 mm, flow rate 40 mL/minute, 5-50% gradient of acetonitrile in 0.1% aq. TFA] to afford the trifluoroacetate salt.

Method H

Salt Formation

A rapidly stirring solution of the free base in ethyl acetate-ethanol, ethanol, or dioxane was treated with either p-toluenesulfonic acid monohydrate (1 eq.; Aldrich; added as a solution in ethyl acetate) or fumaric acid (1 eq., Aldrich; added as a solution in methanol) or HCl-dioxane (1-2 eq.; 4 M; Aldrich) at room temperature. After stirring for 2-16 hours, the precipitate was collected by filtration, rinsed with ethyl acetate, and dried to afford the title compound.

Method I

Etherification

A solution of 1-azaadamantan-4-ol (or 1-azaadamantan-4-ol N-borane complex, 1 eq.) and potassium tert-butoxide (1.1 eq.) in anhydrous dimethyl sulfoxide (~0.5 M) was stirred at room temperature for 1 hour. A heteroaryl halide (2.2 eq.) was added and the reaction mixture was stirred at room temperature overnight. The reaction mixture was purified by preparative HPLC on a Waters Nova-Pak® HR C18 6 µm 60 Å Prep-Pak® cartridge column (40×100 mm) using a gradient of 10% to 100% acetonitrile in 10 mM aqueous ammonium acetate over 12 minutes at a flow rate of 70 mL/minute to provide the desired compound.

Method J

Acidic Deboronation and Hydrochloride salt isolation

A suspension of the 1-azaadamantane N-borane complex (1 eq.) in acetone (~0.5 M) was chilled to 0° C. and treated with 3 N HCl (5-10 eq.). After 15 minutes, the ice bath was removed and the mixture was stirred until the borane complex was consumed as monitored by TLC (the borane complexes can be visualized with basic $KMnO_4$ stain). The reaction mixture was concentrated under reduced pressure. The resulting material was dissolved in MeOH (~0.1 M) and stirred for 30 minutes at room temperature. The reaction mixture was concentrated again. The residue was dissolved in a minimal amount of MeOH, then triturate by the slow addition of diethyl ether/MeOH 9:1 to afford the desired product as powder. The product was isolated by filtration, washed with additional diethyl ether and dried in a vacuum oven overnight.

Method K

Suzuki Coupling

A flask with a septum cap was charged with the azaadamantane-containing heteroaryl halide (1 eq.), a heteroaryl-boronic acid or heteroaryl-boronate ester (1.2-2.0 eq.), cesium carbonate (2.5 eq.), and dichlorobis(triphenylphosphine)-palladium(II) (0.05 eq.). The flask was stoppered, evacuated, flushed with nitrogen, and charged with DMF (~0.1 M of the halide), added through the septum. The mixture was then warmed to 65° C. for 18 hours. Upon completion of the reaction, the mixture was diluted with ethyl acetate, washed with water, and the extracts were dried over sodium sulfate and filtered. The resulting material was purified by preparative HPLC on a Waters Nova-Pak® HR C18 6 µm 60 Å Prep-Pak® cartridge column (40×100 mm) using a gradient of 10% to 100% acetonitrile in 10 mM aqueous ammonium acetate over 12 minutes at a flow rate of 70 mL/minute to provide the desired compound.

Method L

Removal of Acid Labile Protecting Groups

A mixture of the compound with an acid labile protecting group (e.g. trityl) (1 eq.) in acetone (~0.5 M) was chilled to 0°

C. and treated with 3 N HCl (4 eq.). After 15 minutes, the ice bath was removed and the mixture was stirred until the protecting group has cleaved as monitored by TLC. The pH of the solution was then adjusted with 5 N NaOH to ~pH 10, extracted with chloroform (3×), and dried over anhydrous magnesium sulfate, filtered, and concentrated under reduced pressure. The resulting material was purified by either flash chromatography [Analogix pre-packed silica gel cartridges, 5-50% gradient of ammonium hydroxide-methanol-chloroform (2:20:78) in chloroform] or by preparative HPLC [Waters® XTerra RP18 column, 5μ, 30×100 mm, flow rate 40 mL/min, 5-95% gradient over 22 minutes of acetonitrile in buffer (0.1 M aqueous ammonium bicarbonate, adjusted to pH 10 with ammonium hydroxide)] to afford the desired product as its free base.

Example 1

(4s)-4-(6-Chloropyridazin-3-yloxy)-1-azatricyclo [3.3.1.1$^{3,7}$]decane p-toluenesulfonate

Example 1A 4-(6-Chloropyridazin-3-yloxy)-1-azatricyclo [3.3.1.1$^{3,7}$]decane Prepared from 1-azaadamantan-4-ol (3:2 diastereomer mixture; 150 mg, 0.979 mmol; see WO 9215579) and 3,6-dichloropyridazine (182 mg, 1.22 mmol; Aldrich) according to Method B to afford the title compound as a mixture of stereoisomers: MS (DCI/NH$_3$) m/z=266 (M+H)$^+$.

Example 1B (4s)-4-(6-Chloropyridazin-3-yloxy)-1-azatricyclo [3.3.1.1$^{3,7}$]decane A portion of the mixture from Example 1A (100 mg, 0.38 mmol) was purified further by flash chromatography (25 g silica gel, 2-12% gradient of NH$_4$OH-MeOH (1:10) in CHCl$_3$) to provide the title compound as a single stereoisomer: TLC R$_f$=0.33 [silica gel, NH$_4$OH-MeOH—CHCl$_3$ (1:12:87)].

Example 1C (4r)-4-(6-Chloropyridazin-3-yloxy)-1-azatricyclo [3.3.1.1$^{3,7}$]decane A portion of the mixture from Example 1A (100 mg, 0.38 mmol) was purified further by flash chromatography (25 g silica gel, 2-12% gradient of NH$_4$OH-MeOH (1:10) in CHCl$_3$) to provide the title compound as a single stereoisomer: TLC R$_f$=0.28 [silica gel, NH$_4$OH-MeOH—CHCl$_3$ (1:12:87)].

Example 1D (4s)-4-(6-Chloropyridazin-3-yloxy)-1-azatricyclo [3.3.1.1$^{3,7}$]decane p-toluenesulfonate Prepared from the product of Example 1B (28 mg, 0.075 mmol) and p-toluenesulfonic acid monohydrate (0.016 g, 0.083 mmol; Aldrich) according to Method H: $^1$H NMR (300 MHz, methanol-D4) δ ppm 1.65 (s, 1H), 1.82 (d, J=12.5 Hz, 2H), 2.17 (s, 2H), 2.26 (d, J=12.5 Hz, 2H), 3.17 (d, J=12.5 Hz, 4H), 3.31 (d, J=13.9 Hz, 2H), 5.55 (t, J=3.2 Hz, 1H), 6.98 (d, J=9.2 Hz, 1H), 7.37 (d, J=9.2 Hz, 1H). MS (DCI/NH$_3$) m/z=226 (M+H)$^+$; Anal. Calcd. for C$_{13}$H$_{16}$ClN$_3$O.C$_7$H$_8$O$_3$S.0.3H$_2$O: C, 54.18; H, 5.59; N, 9.84. Found: C, 54.16; H, 5.55; N, 9.22.

Example 2

(4r)-4-(6-Chloropyridazin-3-yloxy)-1-azatricyclo [3.3.1.1$^{3,7}$]decane p-toluenesulfonate Prepared from the product of Example 1C (12 mg, 0.045 mmol) and p-toluenesulfonic acid monohydrate (9.5 mg, 0.049 mmol; Aldrich) according to Method H: $^1$H NMR (300 MHz, methanol-D4) δ ppm 1.74 (s, 1H), 2.00-2.23 (m, 6H), 3.02 (d, J=11.9 Hz, 2H), 3.18 (s, 2H), 3.51 (d, J=13.2 Hz, 2H), 5.57 (s, 1H), 7.00 (d, J=9.2 Hz, 1H), 7.38 (d, J=9.2 Hz, 1H). MS (DCI/NH$_3$) m/z=226 (M+H)$^+$; Anal. Calcd. for C$_{13}$H$_{16}$ClN$_3$O.C$_7$H$_8$O$_3$S: C, 54.85; H, 5.52; N, 9.59. Found: C, 54.46; H, 5.42; N, 9.37.

Example 3

(4s)-4-(6-Phenylpyridazin-3-yloxy)-1-azatricyclo [3.3.1.1$^{3,7}$]decane trifluoroacetate Prepared from the product of Example 1B (31 mg, 0.11 mmol) and phenylboronic acid (41 mg, 0.34 mmol; Aldrich) according to Method G, with purification by preparative HPLC [Waters® XTerra RP18 column, 5μ, 30×100 mm, flow rate 40 mL/minute, 5-50% gradient of acetonitrile in 0.1% aq. TFA] to afford the title compound: $^1$H NMR (300 MHz, methanol-D4) δ ppm 1.97 (d, J=12.5 Hz, 2H), 2.22 (s, 1H), 2.41 (d, J=13.2 Hz, 2H), 2.68 (s, 2H), 3.60 (s, 2H), 3.72 (s, 3H), 5.68 (s, 1H), 7.37 (d, J=9.2 Hz, 1H), 7.47-7.59 (m, 3H), 7.94-8.01 (m, 2H), 8.12 (d, J=9.2 Hz, 1H). MS (DCI/NH$_3$) m/z=308 (M+H)$^+$; Anal. Calcd. for C$_{19}$H$_{21}$N$_3$O.C$_2$HF$_3$O$_2$.0.5H$_2$O: C, 58.60; H, 5.39; N, 9.76. Found: C, 58.32; H, 4.98; N, 9.62.

Example 4

(4r)-4-(6-Phenylpyridazin-3-yloxy)-1-azatricyclo [3.3.1.1$^{3,7}$]decane hydrochloride The free base of the title compound was prepared from the product of Example 1C (50 mg, 0.19 mmol) and phenylboronic acid (46 mg, 0.37 mmol; Aldrich) according to Method G, followed by conversion to the HCl salt according to Method H: $^1$H NMR (300 MHz, methanol-D4) δ ppm 2.10-2.22 (m, 2H), 2.22-2.33 (m, 3H), 2.66 (s, 2H), 3.51 (d, J=12.5 Hz, 2H), 3.59 (s, 2H), 3.87 (d, J=12.5 Hz, 2H), 5.60 (t, J=3.4 Hz, 1H), 7.39 (d, J=9.5 Hz, 1H), 7.47-7.60 (m, 3H), 7.92-8.03 (m, 2H), 8.13 (d, J=9.5 Hz, 1H). MS (DCI/NH$_3$) m/z=308 (M+H)$^+$; Anal. Calcd. for C$_{19}$H$_{21}$N$_3$O.HCl.0.3H$_2$O: C, 65.34; H, 6.52; N, 12.03. Found: C, 65.33; H, 6.47; N, 12.01.

Example 5

(4s)-4-[6-(1H-indol-5-yl)pyridazin-3-yloxy]-1-azatricyclo[3.3.1.1$^{3,7}$]decane dihydrochloride The free base of the title compound was prepared from the product of Example 1B (46 mg, 0.17 mmol) and 5-indolylboronic acid (84 mg, 0.52 mmol; Maybridge) according to Method G, followed by conversion to the dihydrochloride salt according to Method H: $^1$H NMR (300 MHz, methanol-D4) δ ppm 2.01 (d, J=13.4 Hz, 2H), 2.25 (s, 1H), 2.41 (d, J=13.4 Hz, 2H), 2.71 (s, 2H), 3.62 (s, 2H), 3.75 (s, 4H), 5.63 (s, 1H), 6.68 (d, J=3.1 Hz, 1H), 7.44 (d, J=3.1 Hz, 1H), 7.62-7.69 (m, 1H), 7.71-7.80 (m, 1H), 7.90 (d, J=9.5 Hz, 1H), 8.27 (s, 1H), 8.62 (d, J=9.5 Hz, 1H). MS (DCI/NH$_3$) m/z=374 (M+H)$^+$; Anal. Calcd. for C$_{21}$H$_{22}$N$_4$O.2HCl.1.4H$_2$O: C, 56.74; H, 6.08; N, 12.60. Found: C, 56.74; H, 6.05; N, 12.44.

Example 6

(4r)-4-[6-(1H-indol-5-yl)pyridazin-3-yloxy]-1-azatricyclo[3.3.1.1$^{3,7}$]decane dihydrochloride The free base of the title compound was prepared from the product of Example 1C (31 mg, 0.11 mmol) and coupled with 5-indolylboronic acid (55 mg, 0.34 mmol; Maybridge) according to Method G. This material was converted to the dihydrochloride salt according to Method H: $^1$H NMR (300 MHz, methanol-D4) δ ppm 2.15 (d, J=12.5 Hz, 2H), 2.25-2.39 (m, 3H), 2.69 (s, 2H), 3.55 (d, J=11.9 Hz, 2H), 3.61 (s, 2H), 3.89 (d, J=12.9 Hz, 2H), 5.52 (t, J=3.2 Hz, 1H), 6.70 (d, J=3.1 Hz, 1H), 7.46 (d, J=3.1 Hz, 1H), 7.65-7.78 (m, 2H), 7.99 (d, J=9.5 Hz, 1H), 8.30 (d, J=2.0 Hz, 1H), 8.72 (d, J=9.5 Hz, 1H). MS (DCI/NH$_3$) m/z=347 (M+H)$^+$; Anal. Calcd. for C$_{21}$H$_{22}$N$_4$O.2HCl.H$_2$O: C, 57.67; H, 5.99; N, 12.81. Found: C, 57.49; H, 5.94; N, 12.56.

Example 7

(4s)-4-[6-(1-Benzothien-5-yl)pyridazin-3-yloxy]-1-azatricyclo[3.3.1.1$^{3,7}$]decane bis(trifluoroacetate)

Prepared from the product mixture of Example 1A (125 mg, 0.470 mmol) and 2-benzo[b]thiophen-5-yl-4,4,5,5-tetramethyl-[1,3,2]dioxaborolane (171 mg, 0.658 mmol; Maybridge) according to Method G. The desired stereoisomer was separated by preparative HPLC [Waters® XTerra RP18 column, 5μ, 30×100 mm, flow rate 40 mL/minute, 5-50% gradient of acetonitrile in 0.1% aq. TFA] to afford the title compound: $^1$H NMR (300 MHz, methanol-D4) δ ppm 1.98 (d, J=12.5 Hz, 2H), 2.23 (s, 1H), 2.42 (d, J=13.6 Hz, 2H), 2.69 (s, 2H), 3.60 (s, 2H), 3.73 (s, 4H), 5.70 (s, 1H), 7.39 (d, J=9.5 Hz, 1H), 7.50 (d, J=5.4 Hz, 1H), 7.68 (d, J=5.4 Hz, 1H), 7.95-8.02 (m, 1H), 8.03-8.11 (m, 1H), 8.21 (d, J=9.5 Hz, 1H), 8.45 (s, 1H). MS (DCI/NH$_3$) m/z=364 (M+H)$^+$; Anal. Calcd. for C$_{21}$H$_{21}$N$_3$OS.1.4C$_2$HF$_3$O$_2$: C, 54.65; H, 4.32; N, 8.03 Found: C, 54.61; H, 4.09; N, 8.04.

Example 8

(4r)-4-[6-(1-Benzothien-5-yl)pyridazin-3-yloxy]-1-azatricyclo[3.3.1.1$^{3,7}$]decane bis(trifluoroacetate)

Separation of the stereoisomers in Example 7 by preparative HPLC provided the title compound: $^1$H NMR (300 MHz, methanol-D4) δ ppm 2.12-2.34 (m, 5H), 2.67 (s, 2H), 3.51 (d, J=12.2 Hz, 2H), 3.59 (s, 2H), 3.88 (d, J=12.5 Hz, 2H), 5.61 (t, J=3.4 Hz, 1H), 7.38 (d, J=9.2 Hz, 1H), 7.50 (d, J=5.1 Hz, 1H), 7.67 (d, J=5.4 Hz, 1H), 7.96-8.01 (m, 1H), 8.04-8.09 (m, 1H), 8.21 (d, J=9.5 Hz, 1H), 8.44 (d, J=1.4 Hz, 1H). MS (DCI/NH$_3$) m/z=364 (M+H)$^+$; Anal. Calcd. for C$_{21}$H$_{21}$N$_3$OS.1.1C$_2$HF$_3$O$_2$.0.25H$_2$O: C, 56.47; H, 4.62; N, 8.52. Found: C, 56.56; H, 4.33; N, 8.54.

Example 9

(4r)-4-(5-Bromopyridin-2-yloxy)-1-azatricyclo[3.3.1.1$^{3,7}$]decane p-toluenesulfonate

Example 9A

1-Azaadamantan-4-ol N-borane complex

A solution of 1-azaadamantan-4-one (29 g, 190 mmol; see Becker, D. P.; Flynn, D. L. *Synthesis* 1992, 1080) in anhydrous tetrahydrofuran (200 mL) was chilled in an ice-water bath and treated with borane-THF complex (1.0 M in THF; 200 mL, 200 mmol; Aldrich), added dropwise. After stirring for 30 minutes, the mixture was diluted with methanol (1000 mL) and carefully treated with sodium borohydride (8.8 g, 230 mmol; Aldrich), keeping the internal temperature about 5-7° C. The mixture was stirred for 2 hours, and then the ice bath was removed and stirring was continued for 4 hours. The volatile components were removed on the rotary evaporator and the residue was dissolved in chloroform (~500 mL) and washed with saturated aqueous sodium carbonate. The aqueous layer was extracted with chloroform and the organic phases were dried over magnesium sulfate and filtered. The resulting material was purified by flash chromatography (Analogix 400 g 65×220 mm silica gel column, 5-95% gradient of ethyl acetate in hexanes over 50 minutes) to afford an inseparable 3.7:1.0 mixture of isomers [according to integration of $^1$H NMR signals (chloroform-D) at δ3.96 (t, major) and δ3.82 (t, minor)] (33 g, 200 mmol; 100% yield). The product spot can be visualized on the TLC plate (silica gel) using KMnO$_4$ stain.

Example 9B (4s)-4-(4-Chlorobenzoyloxy)-1-azatricyclo[3.3.1.1$^{3,7}$]decane N-borane complex

Example 9C (4r)-4-(4-Chlorobenzoyloxy)-1-azatricyclo[3.3.1.1$^{3,7}$]decane N-borane complex A solution of the product of Example 9A (28 g, 170 mmol; 3.2:1.0 mixture of diastereomers), 4-chlorobenzoic acid (28.0 g, 179 mmol; Aldrich), and 4-dimethylaminopyridine (4.2 g, 34 mmol; Aldrich) in dichloromethane (700 mL) was chilled to 0° C. and treated with N-(3-dimethylaminopropyl)-N'-ethylcarbodiimide hydrochloride (EDAC; 42.0 g, 219 mmol; Aldrich). After 1 hour, the mixture was warmed to room temperature and stirred overnight. The solution was washed quickly with 1 M HCl (200 mL) followed by saturated sodium bicarbonate, dried over magnesium sulfate and filtered. The resulting material was purified in ~5 g batches by flash chromatography (Analogix 400 g 65×220 mm silica gel column, 5-55% gradient of ethyl acetate in hexanes over 45 minutes).

Example 9B (4s) stereoisomer: TLC R$_f$=0.49 (silica gel, 3:1 hexanes-EtOAc). $^1$H NMR (300 MHz, chloroform-D) δ ppm 1.76 (d, J=12.5 Hz, 2H), 2.06 (s, 1H), 2.16-2.33 (m, 4H), 3.12-3.32 (m, 6H), 5.26 (t, J=3.2 Hz, 1H), 7.45 (dt, J=8.7, 2.4, 2.1 Hz, 2H), 8.00 (dt, J=8.7, 2.4, 2.1 Hz, 2H). MS (DCI/NH$_3$) m/z=321/323 (M+H)$^+$. Anal. Calcd. for C$_{16}$H$_{21}$BClNO$_2$: C, 62.88; H, 6.93; N, 4.58. Found: C, 63.00; H, 6.80; N, 4.50.

Example 9C (4r) stereoisomer: TLC $R_f$=0.34 (silica gel, 3:1 hexanes-EtOAc). $^1$H NMR (300 MHz, chloroform-D) δ ppm 1.84-2.11 (m, 5H), 2.24 (s, 2H), 3.03 (d, J=12.5 Hz, 2H), 3.14 (s, 2H), 3.46 (d, J=13.2 Hz, 2H), 5.16 (t, J=3.2 Hz, 1H), 7.39-7.51 (m, 2H), 7.89-8.05 (m, 2H). MS (DCI/NH$_3$) m/z=321/323 (M+H)$^+$. Anal. Calcd. for C$_{16}$H$_{21}$BClNO$_2$: C, 62.88; H, 6.93; N, 4.58. Found: C, 62.83; H, 6.95; N, 4.53.

Example 9D (4r)-4-(1-Azatricyclo[3.3.1.1$^{3,7}$]decan-4-ol) N-borane complex A suspension of the product of Example 9C (10.0 g, 32.7 mmol) in tetrahydrofuran (20 mL) was treated with 5 M sodium hydroxide (20 mL) and the mixture was warmed to 50° C. for 4 hours. The mixture was diluted with chloroform and washed with water, and the aqueous phase was reextracted with additional chloroform. The product was purified by flash chromatography (Analogix 80 g 40×170 mm silica gel column, 10-95% gradient of ethyl acetate in hexanes) to afford the product: $^1$H NMR (300 MHz, methanol-D4) δ ppm 0.82-2.02 (br m, 3H), 1.76 (d, J=11.9 Hz, 2H), 1.83-1.99 (m, 6H), 2.81 (d, J=12.2 Hz, 2H), 3.00 (s, 2H), 3.37 (d, J=12.9 Hz, 2H), 3.82 (s, 1H). MS (DCI/NH$_3$) m/z=183 (M+H)$^+$.

Example 9E (4r)-4-(5-Bromopyridin-2-yloxy)-1-azatricyclo[3.3.1.1$^{3,7}$]decane N-borane complex Prepared from the product of Example 9D (500 mg, 2.99 mmol) and 2-chloro-5-bromopyridine (1.15 g, 5.99 mmol; Aldrich) according to Method B to provide material, which was carried on without additional purification: MS (DCI/NH$_3$) m/z=309/311 (M-BH$_3$+H)$^+$.

Example 9F (4r)-4-(5-Bromopyridin-2-yloxy)-1-azatricyclo[3.3.1.1$^{3,7}$]decane Prepared from the product of Example 9E (732 mg, 2.11 mmol) according to Method C to afford the title compound: $^1$H NMR (300 MHz, methanol-D4) δ ppm 1.73 (s, 1H), 1.95-2.07 (m, 4H), 2.11-2.22 (m, 2H), 2.96 (d, J=12.9 Hz, 2H), 3.13 (s, 2H), 3.45 (d, J=12.9 Hz, 2H), 5.28 (t, J=3.2 Hz, 1H), 6.80 (d, J=8.8 Hz, 1H), 7.78 (dd, J=8.8, 2.7 Hz, 1H), 8.17 (d, J=2.7 Hz, 1H). MS (DCI/NH$_3$) m/z=309/311 (M+H)$^+$.

Example 9G (4r)-4-(5-Bromopyridin-2-yloxy)-1-azatricyclo[3.3.1.1$^{3,7}$]decane p-toluenesulfonate Prepared from the product of Example 9F (70 mg, 0.23 mmol) according to Method H: $^1$H NMR (300 MHz, methanol-D4) δ ppm 2.02-2.14 (m, 2H), 2.16-2.26 (m, 3H), 2.36 (s, 3H), 2.49 (s, 2H), 3.44 (d, J=11.9 Hz, 2H), 3.55 (s, 2H), 3.79 (d, J=12.2 Hz, 2H), 5.31 (t, J=3.6 Hz, 1H), 6.85 (dd, J=8.8, 0.7 Hz, 1H), 7.19-7.26 (m, 2H), 7.70 (ddd, J=8.3, 1.9, 1.7 Hz, 2H), 7.84 (dd, J=8.6, 2.5 Hz, 1H), 8.21 (dd, J=2.7, 0.7 Hz, 1H). MS (DCI/NH$_3$) m/z=309/311 (M+H)$^+$. Anal. Calcd. for C$_{14}$H$_{17}$BrN$_2$O.C$_7$H$_8$O$_3$S: C, 52.39; H, 5.23; N, 5.82. Found: C, 52.29; H, 5.17; N, 5.73.

Example 10

(4s)-4-(5-Phenylpyridin-2-yloxy)-1-azatricyclo[3.3.1.1$^{3,7}$]decane p-toluenesulfonate

Example 10A (4s)-4-(1-Azatricyclo[3.3.1.1$^{3,7}$]decan-4-ol) N-borane complex A suspension of the product of Example 9B (25.0 g, 81.8 mmol) in tetrahydrofuran (50 mL) was treated with 5 M sodium hydroxide (50 mL). After 1 hour, the mixture was warmed to 50° C. for 3 hours Most of the solvent was removed on the rotary evaporator, and the residue was purified by flash chromatography (Analogix 220 g 65×120 mm silica gel column, 5-95% gradient of ethyl acetate in hexanes) to afford the product: $^1$H NMR (300 MHz, methanol-D4) δ ppm 0.87-2.09 (br m, 3H; BH$_3$), 1.59 (d, J=12.5 Hz, 2H), 1.78-1.98 (m, 2H), 2.22 (d, J=12.5 Hz, 2H), 2.97-3.18 (m, 6H), 3.96 (t, J=3.4 Hz, 1H). MS (DCI/NH$_3$) m/z=183 (M+H)$^+$.

Example 10B (4s)-4-(1-Azatricyclo[3.3.1.1$^{3,7}$]decan-4-ol)

A solution of the product of Example 10A (1.00 g, 6.00 mmol) in acetone (30 mL) was chilled to 0° C. and treated with 3 N HCl (10 mL). After 10 minutes, the ice bath was removed and the mixture was stirred for 4 hours. The solution was concentrated to dryness on the rotary evaporator and azeotroped with methanol (3×). The resulting white solid was suspended in EtOAc (25 mL), cooled to 0° C., and anhydrous ammonia was bubbled into the mixture for about 1 minute. After stirring for an additional 15 minutes, the mixture was filtered, rinsed with EtOAc, and concentrated to afford the product: $^1$H NMR (300 MHz, chloroform-D) δ ppm 1.51-1.84 (m, 5H), 2.26 (d, J=11.9 Hz, 2H), 2.36 (s, 1H), 2.99 (d, J=12.9 Hz, 2H), 3.09 (s, 2H), 3.25 (d, J=13.6 Hz, 2H), 4.00 (s, 1H). MS (ESI) m/z=154 (M+H)$^+$.

Example 10C (4s)-4-(5-Bromopyridin-2-yloxy)-1-azatricyclo[3.3.1.1$^{3,7}$]decane Prepared from the hydrochloride salt of the product of Example 10B (220 mg, 1.16 mmol) and 2,5-dibromopyridine (550 mg, 2.30 mmol; Aldrich) using excess potassium tert-butoxide in THF (2.4 mL, 2.4 mmol; 1.0 M; Aldrich) according to Method B: MS (DCI/NH$_3$) m/z=309/311 (M+H)$^+$.

Example 10D (4s)-4-(5-Phenylpyridin-2-yloxy)-1-azatricyclo[3.3.1.1$^{3,7}$]decane p-toluenesulfonate The free base of the title compound was prepared from the product of Example 10C (45 mg, 0.14 mmol) and phenylboronic acid (25 mg, 0.20 mmol) according to Method F, and converted to the p-toluenesulfonate salt using the procedure of Method H: $^1$H NMR (300 MHz, methanol-D4) δ ppm 1.94 (d, J=13.2 Hz, 2H), 2.20 (s, 1H), 2.36 (s, 5H), 2.41 (s, 1H), 2.57 (s, 2H), 3.58 (s, 2H), 3.70 (s, 4H), 5.47 (t, J=3.4 Hz, 1H), 7.09 (d, J=8.5 Hz, 1H), 7.22 (d, J=7.8 Hz, 2H), 7.30-7.41 (m, 1H), 7.42-7.51 (m, 2H), 7.56-7.63 (m, 2H), 7.67-7.75 (m, 2H), 8.07 (dd, J=8.6, 2.5 Hz, 1H), 8.40 (d, J=2.4 Hz, 1H). MS (DCI/NH$_3$) m/z=307 (M+H)$^+$; Anal. Calcd. for C$_{20}$H$_{22}$N$_2$O.1.3C$_7$H$_8$O$_3$S.0.5H$_2$O: C, 64.81; H, 6.24; N, 5.19 Found: C, 64.77; H, 6.30; N, 5.15.

Example 11

(4r)-4-(5-Phenylpyridin-2-yloxy)-1-azatricyclo[3.3.1.1$^{3,7}$]decane p-toluenesulfonate

Example 11A (4r)-4-(5-Phenylpyridin-2-yloxy)-1-azatricyclo[3.3.1.1$^{3,7}$]decane Prepared from the product of Example 9F (496 mg, 1.60 mmol) and phenylboronic acid (480 mg, 3.1 mmol; Aldrich) according to Method E: $^1$H NMR (300 MHz, methanol-D4) δ ppm 1.75 (s, 1H), 2.00-2.25 (m, 6H), 2.98 (d, J=12.9 Hz, 2H), 3.15 (s, 2H), 3.51 (d, J=12.9 Hz, 2H), 5.33 (s, 1H), 6.90-6.96 (m, 1H), 7.30-7.38 (m, 1H), 7.40-7.48 (m, 2H), 7.54-7.61 (m, 2H), 7.94 (dd, J=8.6, 2.5 Hz, 1H), 8.35 (d, J=2.4 Hz, 1H). MS (ESI) m/z=307 (M+H)$^+$.

Example 11B (4r)-4-(5-Phenylpyridin-2-yloxy)-1-azatricyclo[3.3.1.1$^{3,7}$]decane p-toluenesulfonate Prepared from the product of Example 11A (277 mg, 0.904 mmol) according to Method H: $^1$H NMR (300 MHz, methanol-D4) δ ppm 2.07-2.19 (m, 2H), 2.20-2.31 (m, 3H), 2.36 (s, 5H), 2.56 (s, 2H), 3.49 (d, J=12.5 Hz, 2H), 3.57 (s, 2H), 3.85 (d, J=12.2 Hz, 2H), 5.38 (t, J=3.4 Hz, 1H), 7.16 (d, J=8.5 Hz, 1H), 7.23 (d, J=8.1 Hz, 3H), 7.34-7.42 (m, 1H), 7.43-7.52 (m, 2H), 7.58-7.64 (m, 2H), 7.66-7.74 (m, 3H), 8.14 (dd, J=8.8, 2.7 Hz, 1H), 8.45 (d, J=2.4 Hz, 1H). MS (DCI/NH$_3$) m/z=307 (M+H)$^+$; Anal. Calcd. for C$_{20}$H$_{22}$N$_2$O.C$_7$H$_8$O$_3$S: C, 67.76; H, 6.32; N, 5.85.
Found: C, 67.70; H, 6.39; N, 5.74.

Example 12

(4s)-4-[5-(1H-Indol-5-yl)pyridin-2-yloxy]-1-azatricyclo[3.3.1.1$^{3,7}$]decane

Prepared from the product of Example 10C (45 mg, 0.14 mmol) and 5-indolylboronic acid (33 mg, 0.204 mmol; Maybridge) according to Method G: MS (DCI/NH$_3$) m/z=346 (M+H)$^+$.

Example 13

(4r)-4-[5-(1H-Indol-5-yl)pyridin-2-yloxy]-1-azatricyclo[3.3.1.1$^{3,7}$]decane

Prepared from the product of Example 9F (45 mg, 0.14 mmol) and 5-indolylboronic acid (33 mg, 0.204 mmol; Maybridge) according to Method E: $^1$H NMR (300 MHz, CHCl$_3$) δ ppm 1.76-1.86 (m, 2H), 2.26 (s, 2H), 2.39 (d, J=11.5 Hz, 2H), 3.26-3.44 (m, 5H), 5.37 (t, J=3.2 Hz, 1H), 6.61 (t, J=2.5 Hz, 1H), 6.85 (d, J=8.5 Hz, 1H), 7.25-7.30 (m, 1H), 7.31-7.41 (m, 1H), 7.48 (d, J=8.5 Hz, 1H), 7.77 (s, 1H), 7.86 (dd, J=8.5, 2.7 Hz, 1H). MS (DCI/NH$_3$) m/z=346 (M+H)$^+$; Anal. Calcd. for C$_{22}$H$_{22}$N$_3$O.1.6H$_2$O: C, 70.79; H, 6.80; N, 11.26. Found: C, 70.78; H, 6.44; N, 10.91.

Example 14

(4r)-4-[5-(Benzothien-5-yl)pyridin-2-yloxy]-1-azatricyclo[3.3.1.1$^{3,7}$]decane p-toluenesulfonate

Example 14A (4r)-4-[5-(Benzothien-5-yl)pyridin-2-yloxy]-1-azatricyclo[3.3.1.1$^{3,7}$]decane Prepared from the product of Example 9F (45 mg, 0.14 mmol) and 2-benzo[b]thiophen-5-yl-4,4,5,5-tetramethyl-[1,3,2]dioxaborolane (53 mg, 0.204 mmol; Maybridge), according to Method E: MS (DCI/NH$_3$) m/z=363 (M+H)$^+$.

Example 14B (4r)-4-[5-(1-Benzothien-5-yl)pyridin-2-yloxy]-1-azatricyclo[3.3.1.1$^{3,7}$]decane p-toluenesulfonate Prepared from the product of Example 14A (50 mg, 0.14 mmol) according to Method H: $^1$H NMR (300 MHz, methanol-D4) δ ppm 1.94 (d, J=12.9 Hz, 2H), 2.20 (s, 1H), 2.34-2.46 (m, 5H), 2.58 (s, 2H), 3.58 (s, 2H), 3.69 (s, 4H), 5.48 (t, J=3.1 Hz, 1H), 7.00 (dd, J=8.5, 0.7 Hz, 1H), 7.22 (d, J=8.1 Hz, 2H), 7.44 (dd, J=5.6, 0.8 Hz, 1H), 7.57 (dd, J=8.5, 1.4 Hz, 1H), 7.62 (d, J=5.4 Hz, 1H), 7.70 (d, J=8.1 Hz, 2H), 7.98 (d, J=8.5 Hz, 1H), 8.03-8.10 (m, 2H), 8.44 (dd, J=2.5, 0.8 Hz, 1H). MS (DCI/NH$_3$) m/z=363 (M+H)$^+$. Anal. Calcd. for C$_{22}$H$_{22}$N$_2$OS.C$_7$H$_8$O$_3$S: C, 65.14; H, 5.66; N, 5.24. Found: C, 64.78; H, 5.26; N, 5.18.

Example 15

(4s)-4-(6-Chloropyridin-3-yloxy)-1-azatricyclo[3.3.1.1$^{3,7}$]decane p-toluenesulfonate

Example 15A (4s)-4-(6-Chloropyridin-3-yloxy)-1-azatricyclo[3.3.1.1$^{3,7}$]decane N-borane complex A mixture of the product of Example 10A (1.00 g, 5.99 mmol), 2-chloro-5-iodopyridine (1.44 g, 6.01 mmol; Aldrich), copper(I) iodide (110 mg, 0.60 mmol; Aldrich), o-phenanthroline (220 mg, 1.2 mmol; Aldrich), and cesium carbonate (3.9 g, 12 mmol; Aldrich) in toluene (6 mL) was heated to 110° C. with vigorous stirring for 3 days. The black mixture was cooled to room temperature, diluted with dichloromethane, and filtered through diatomaceous earth. The crude material was purified by flash chromatography (Analogix 34 g silica gel column, 5-60% gradient of ethyl acetate in hexanes) to afford the title compound: $^1$H NMR (300 MHz, methanol-D4) δ ppm 1.65-1.75 (m, 2H), 1.96 (s, 1H), 2.16-2.27 (m, 4H), 3.14 (s, 2H), 3.16-3.27 (m, 4H), 4.76 (t, J=3.1 Hz, 1H), 7.36 (dd, J=8.8, 0.7 Hz, 1H), 7.52 (dd, J=8.8, 3.1 Hz, 1H), 8.12 (dd, J=3.1, 0.7 Hz, 1H). MS (DCI/NH$_3$) m/z=279/281 (M+H)$^+$.

Example 15B (4s)-4-(6-Chloropyridin-3-yloxy)-1-azatricyclo[3.3.1.1$^{3,7}$]decane Prepared from the product of Example 15A (210 mg, 0.60 mmol) according to Method C: $^1$H NMR (300 MHz, methanol-D4) δ ppm 1.67 (s, 1H), 1.83 (d, J=12.9 Hz, 2H), 2.04 (s, 2H), 2.31 (d, J=12.2 Hz, 2H), 3.08-3.18 (m, 4H), 3.22-3.27 (m, 2H), 4.75 (t, J=3.2 Hz, 1H), 7.35 (dd, J=8.8, 0.7 Hz, 1H), 7.50 (dd, J=8.8, 3.1 Hz, 1H), 8.10 (d, J=3.1 Hz, 1H). MS (DCI/NH$_3$) m/z=265/267 (M+H)$^+$.

Example 15C (4s)-4-(6-Chloropyridin-3-yloxy)-1-azatricyclo[3.3.1.1$^{3,7}$]decane p-toluenesulfonate Prepared from the product of Example 15B (40 mg, 0.15 mmol) according to Method H: $^1$H NMR (300 MHz, methanol-D4) δ ppm 1.90 (d, J=13.2 Hz, 2H), 2.18 (s, 1H), 2.30-2.41 (m, 5H), 2.46 (s, 2H), 3.56 (s, 2H), 3.57-3.74 (m, 4H), 4.88 (t, J=3.4 Hz, 1H), 7.20-7.25 (m, 2H), 7.39 (d, J=8.8 Hz, 1H), 7.55 (dd, J=8.8, 3.1 Hz, 1H), 7.70 (dt, J=8.1, 1.9 Hz, 2H), 8.17 (dd, J=3.1, 0.7 Hz, 1H). MS (DCI/NH$_3$) m/z=265/267 (M+H)$^+$. Anal. Calcd. for C$_{14}$H$_{17}$ClN$_2$O.C$_7$H$_8$O$_3$S.0.05H$_2$O: C, 57.61; H, 5.78; N, 6.40. Found: C, 57.23; H, 5.71; N, 6.34.

Example 16

(4s)-4-(6-Nitropyridin-3-yloxy)-1-azatricyclo[3.3.1.1$^{3,7}$]decane hydrochloride Example 16A (4s)-4-(6-Nitropyridin-3-yloxy)-1-azatricyclo[3.3.1.1$^{3,7}$]decane N-borane complex Prepared from the product of Example 10A (419 g, 2.51 mmol) and 5-fluoro-2-nitropyridine (420 mg, 2.9 mmol; see US Patent Appl. 20040209886) according to Method A: $^1$H NMR (300 MHz, chloroform-D) δ ppm 1.68-1.78 (m, 2H), 2.07 (s, 1H), 2.20-2.35 (m, 4H), 3.19-3.34 (m, 6H), 4.74 (t, J=3.4 Hz, 1H), 7.42 (dd, J=9.0, 2.9 Hz, 1H), 8.26-8.31 (m, 2H). MS (DCI/NH$_3$) m/z=290 (M+H)$^+$.

Example 16B (4s)-4-(6-Nitropyridin-3-yloxy)-1-azatricyclo[3.3.1.1$^{3,7}$]decane hydrochloride Prepared from the product of Example 16A (599 mg, 2.07 mmol) according to Method C. The product precipitated from the reaction mixture, so it was collected by filtration and dried to afford the title compound: $^1$H NMR (300 MHz, methanol-D4) δ ppm 1.95 (d, J=12.5 Hz, 2H), 2.21 (s, 1H), 2.38 (d, J=13.6 Hz, 2H), 2.53 (s, 2H), 3.59 (s, 2H), 3.61-3.79 (m, 4H), 5.11 (t, J=3.4 Hz, 1H), 7.80 (dd, J=9.2, 2.7 Hz, 1H), 8.31-8.38 (m, 2H). MS (+ESI) m/z=276 (M+H)$^+$.

Example 17

(4s)-4-(6-Aminopyridin-3-yloxy)-1-azatricyclo[3.3.1.1$^{3,7}$]decane dihydrochloride Example 17A (4s)-4-(6-Aminopyridin-3-yloxy)-1-azatricyclo[3.3.1.1$^{3,7}$]decane A solution of the product of Example 16B (380 mg, 1.2 mmol) in THF-MeOH (10 mL, 1:1) was treated with Raney nickel (401 mg, 6.83 mmol) under an atmosphere of hydrogen (60 psi), and the mixture was warmed to 50° C. for 1 hour. After removing the catalyst by filtration, the product was purified by preparative HPLC [Waters® XTerra RP18 column, 5μ, 30×100 mm, flow rate 40 mL/minutes, 5-95% gradient of acetonitrile in buffer (0.1 M aqueous ammonium bicarbonate, adjusted to pH 10 with ammonium hydroxide), with UV detection at 254 nm]. Fractions containing the desired compound were pooled, concentrated under vacuum, diluted with methanol, and filtered to afford the title compound: $^1$H NMR (300 MHz, methanol-D4) δ ppm 1.66 (s, 1H), 1.80 (d, J=12.5 Hz, 2H), 1.99 (s, 2H), 2.28-2.39 (m, 2H), 3.01-3.12 (m, 4H), 3.24 (ddd, J=14.1, 2.4, 2.2 Hz, 2H), 4.45 (t, J=3.2 Hz, 1H), 6.57 (dd, J=9.2, 0.7 Hz, 1H), 7.27 (dd, J=9.0, 2.9 Hz, 1H), 7.67 (dd, J=3.1, 0.7 Hz, 1H). MS (+ESI) m/z=246 (M+H)$^+$.

Example 17B (4s)-4-(6-Aminopyridin-3-yloxy)-1-azatricyclo[3.3.1.1$^{3,7}$]decane dihydrochloride Prepared from the product of Example 17A (81 mg, 0.33 mmol) and HCl-dioxane (160 μL, 0.66 mmol; Aldrich, 4.0 M) according to Method H: $^1$H NMR (300 MHz, methanol-D4) δ ppm 1.92 (d, J=12.2 Hz, 2H), 2.19 (s, 1H), 2.34 (d, J=13.2 Hz, 2H), 2.46 (s, 2H), 3.56 (s, 2H), 3.58-3.74 (m, 4H), 4.77 (t, J=3.2 Hz, 1H), 7.04 (dd, J=9.5, 0.7 Hz, 1H), 7.73 (dd, J=3.1, 0.7 Hz, 1H), 7.89 (dd, J=9.5, 2.7 Hz, 1H). MS (+ESI) m/z=246 (M+H)$^+$. Anal. Calcd. for C$_{14}$H$_{19}$N$_3$O.2HCl.0.5H$_2$O: C, 51.38; H, 6.78; N, 12.84. Found: C, 51.06; H, 6.47; N, 12.68.

Example 18

(4r)-4-(6-Nitropyridin-3-yloxy)-1-azatricyclo[3.3.1.1$^{3,7}$]decane p-toluenesulfonate Example 18A (4r)-4-(6-Nitropyridin-3-yloxy)-1-azatricyclo[3.3.1.1$^{3,7}$]decane N-borane complex Prepared from the product of Example 9D (500 g, 2.99 mmol) and 5-fluoro-2-nitropyridine (500 mg, 3.5 mmol; see US Patent Appl. 20040209886) according to Method A: $^1$H NMR (300 MHz, chloroform-D) δ ppm 1.84-1.95 (m, 2H), 2.01-2.13 (m, 3H), 2.30 (s, 2H), 3.00 (d, J=12.5 Hz, 2H), 3.15 (s, 2H), 3.48 (d, J=13.6 Hz, 2H), 4.60 (t, J=3.2 Hz, 1H), 7.43 (dd, J=8.8, 3.1 Hz, 1H), 8.24-8.30 (m, 2H). MS (DCI/NH$_3$) m/z=290 (M+H)$^+$.

Example 18B (4r)-4-(6-Nitropyridin-3-yloxy)-1-azatricyclo[3.3.1.1$^{3,7}$]decane Prepared from the product of Example 18A (599 mg, 2.07 mmol) according to Method C: $^1$H NMR (300 MHz, methanol-D4): δ ppm 1.76 (s, 1H), 2.00-2.13 (m, 4H), 2.16-2.28 (m, 2H), 2.99 (d, J=12.9 Hz, 2H), 3.15 (s, 2H), 3.48 (d, J=12.9 Hz, 2H), 4.96 (t, J=3.2 Hz, 1H), 7.70 (dd, J=9.0, 2.9 Hz, 1H), 8.25-8.36 (m, 2H). MS (+ESI) m/z=276 (M+H)$^+$.

Example 18C (4r)-4-(6-Nitropyridin-3-yloxy)-1-azatricyclo[3.3.1.1$^3$:]decane p-toluenesulfonate Prepared from the product of Example 18B (25 mg, 0.091 mmol) and p-toluenesulfonic acid monohydrate (17 mg, 0.091 mmol; Aldrich) according to Method H: $^1$H NMR (300 MHz, methanol-D4) δ ppm 2.07-2.30 (m, 5H), 2.36 (s, 3H), 2.51 (s, 2H), 3.47 (d, J=11.9 Hz, 2H), 3.56 (s, 2H), 3.83 (d, J=12.5 Hz, 2H), 5.01 (t, J=3.4 Hz, 1H), 7.23 (d, J=8.1 Hz, 2H), 7.70 (d, J=8.1 Hz, 2H), 7.79 (dd, J=9.0, 2.9 Hz, 1H), 8.31-8.37 (m, 2H). MS (+ESI) m/z=276 (M+H)$^+$. Anal. Calcd. for $C_{14}H_{17}N_3O_3C_7H_8O_3S.0.9H_2O$: C, 54.39; H, 5.83; N, 9.06. Found: C, 54.32; H, 5.87; N, 8.97.

Example 19

(4r)-4-(6-Aminopyridin-3-yloxy)-1-azatricyclo[3.3.1.1$^{3,7}$]decane dihydrochloride

Example 19A (4r)-4-(6-Aminopyridin-3-yloxy)-1-azatricyclo[3.3.1.1$^{3,7}$]decane A solution of the product of Example 18B (322 mg, 1.17 mmol) in THF-MeOH (10 mL, 1:1) was treated with Raney nickel (400 mg, 6.82 mmol) under an atmosphere of hydrogen (60 psi), and the mixture was warmed to 50° C. for 1 hours. After removing the catalyst by filtration, the product was purified by preparative HPLC [Waters® XTerra RP18 column, 5μ, 30×100 mm, flow rate 40 mL/minute 5-95% gradient of acetonitrile in buffer (0.1 M aqueous ammonium bicarbonate, adjusted to pH 10 with ammonium hydroxide), with UV detection at 254 nm]. Fractions containing the desired compound were pooled, concentrated under vacuum, diluted with methanol, and filtered to afford the title compound: $^1$H NMR (300 MHz, methanol-D4) δ ppm 1.71 (s, 1H), 1.89-2.01 (m, 4H), 2.10-2.20 (m, 2H), 2.93 (dd, J=12.5, 1.0 Hz, 2H), 3.11 (s, 2H), 3.49 (d, J=12.9 Hz, 2H), 4.45 (t, J=3.4 Hz, 1H), 6.57 (dd, J=8.8, 0.7 Hz, 1H), 7.26 (dd, J=9.0, 2.9 Hz, 1H), 7.65 (dd, J=3.1, 0.7 Hz, 1H). MS (+ESI) m/z=246 (M+H)$^+$.

Example 19B (4r)-4-(6-Aminopyridin-3-yloxy)-1-azatricyclo[3.3.1.1$^{3,7}$]decane dihydrochloride Prepared from the product of Example 19A (50 mg, 0.20 mmol) and HCl-dioxane (100 μL, 0.41 mmol; Aldrich, 4.0 M) according to Method H: $^1$H NMR (300 MHz, methanol-D4) δ ppm 2.00-2.12 (m, 2H), 2.16-2.29 (m, 3H), 2.46 (s, 2H), 3.45 (d, J=12.2 Hz, 2H), 3.55 (s, 2H), 3.81 (d, J=12.2 Hz, 2H), 4.64 (t, J=3.4 Hz, 1H), 7.03 (dd, J=9.5, 0.7 Hz, 1H), 7.72 (d, J=2.7 Hz, 1H), 7.89 (dd, J=9.7, 2.9 Hz, 1H). MS (+ESI) m/z=246 (M+H)$^+$. Anal. Calcd. for $C_{14}H_{19}N_3O.2HCl.1.1H_2O$: C, 49.74; H, 6.92; N, 12.43. Found: C, 49.57; H, 6.75; N, 12.37.

Example 20

(4s)-4-(5-Bromothiazol-2-yloxy)-1-azatricyclo[3.3.1.1$^{3,7}$]decane p-toluenesulfonate

Example 20A (4s)-4-(5-Bromothiazol-2-yloxy)-1-azatricyclo[3.3.1.1$^{3,7}$]decane N-borane complex Prepared from the product of Example 10A (1.67 g, 10.0 mmol) and 2,5-dibromothiazole (2.90 g, 11.9 mmol; Aldrich) according to Method A: $^1$H NMR (300 MHz, chloroform-D) δ ppm 1.69 (d, J=12.2 Hz, 2H), 2.01 (s, 1H), 2.19 (d, J=12.9 Hz, 2H), 2.39 (s, 2H), 3.13-3.25 (m, 6H), 5.19 (t, J=3.4 Hz, 1H), 7.03 (s, 1H). MS (DCI/NH$_3$) m/z=329/331 (M+H)$^+$.

Example 20B (4s)-4-(5-Bromothiazol-2-yloxy)-1-azatricyclo[3.3.1.1$^{3,7}$]decane Prepared from the product of Example 20A (3.1 g, 9.4 mmol) according to Method C: $^1$H NMR (300 MHz, methanol-D4) δ ppm 1.68 (s, 1H), 1.87 (d, J=11.5 Hz, 2H), 2.10-2.31 (m, 4H), 3.04-3.17 (m, 6H), 5.22 (t, J=3.4 Hz, 1H), 7.11 (s, 1H).

Example 20C (4s)-4-(5-Bromothiazol-2-yloxy)-1-azatricyclo[3.3.1.1$^{3,7}$]decane p-toluenesulfonate Prepared from the product of Example 20B (80 mg, 0.25 mmol) according to Method H: $^1$H NMR (300 MHz, methanol-D4) δ ppm 1.94 (d, J=13.2 Hz, 2H), 2.18 (s, 2H), 2.28 (d, J=13.2 Hz, 2H), 2.37 (s, 3H), 2.61 (s, 2H), 3.56 (s, 2H), 3.57-3.74 (m, 4H), 5.37 (t, J=3.2 Hz, 1H), 7.15 (s, 1H), 7.23 (d, J=8.1 Hz, 2H), 7.70 (d, J=8.1 Hz, 2H). Anal. Calcd. for $C_{12}H_{15}BrN_2OS.C_7H_8O_3S.0.5H_2O$: C, 45.97; H, 4.87; N, 5.64. Found: C, 45.64; H, 4.63; N, 5.57.

Example 21

(4s)-4-(Thiazol-2-yloxy)-1-azatricyclo[3.3.1.1$^{3,7}$]decane p-toluenesulfonate

Example 21A (4s)-4-(Thiazol-2-yloxy)-1-azatricyclo[3.3.1.1$^{3,7}$]decane

A solution of the product of Example 20B (93 mg, 0.30 mmol) in ethanol (3 mL) was treated with 10% Pd/C (10 mg; Aldrich) under a hydrogen balloon with vigorous stirring for 7 hours. The mixture was filtered to remove the catalyst, rinsing with methanol. The compound was purified by preparative HPLC [Waters® XTerra RP18 5μ column, 30×100 mm, flow rate 40 mL/minute, 5-95% gradient of acetonitrile in buffer (0.1 M aqueous ammonium bicarbonate, adjusted to pH 10 with ammonium hydroxide) over 22 minutes, with UV detection at 254 nm]. Fractions containing the desired product were pooled and concentrated under vacuum to afford the title compound: $^1$H NMR (300 MHz, methanol-D4) δ ppm 1.68 (s, 1H), 1.87 (d, J=11.9 Hz, 2H), 2.18 (s, 2H), 2.27 (d, J=12.9 Hz, 2H), 3.04-3.17 (m, 6H), 5.16 (t, J=3.4 Hz, 1H), 6.88 (d, J=3.7 Hz, 1H), 7.12 (d, J=3.7 Hz, 1H). MS (DCI/NH$_3$) m/z=237 (M+H)$^+$.

Example 21B (4s)-4-(Thiazol-2-yloxy)-1-azatricyclo[3.3.1.1$^{3,7}$]decane p-toluenesulfonate Prepared from the product of Example 21A (30 mg, 0.13 mmol) according to Method H: $^1$H NMR (300 MHz, methanol-D4) δ ppm 1.94 (d, J=13.2 Hz, 2H), 2.18 (s, 1H), 2.31 (d, J=13.6 Hz, 2H), 2.37 (s, 3H), 2.61 (s, 2H), 3.56 (s, 2H), 3.58-3.74 (m, 4H), 5.33 (t, J=3.4 Hz, 1H), 6.94 (d, J=3.7 Hz, 2H), 7.15 (d, J=4.1 Hz, 1H), 7.23 (d, J=7.8 Hz, 2H), 7.71 (d, J=8.5 Hz, 2H). MS (DCI/NH$_3$) m/z=237 (M+H)$^+$; Anal.

Calcd. for $C_{12}H_{16}N_2OS \cdot C_7H_8O_3S$: C, 55.86; H, 5.92; N, 6.86. Found: C, 55.48; H, 5.95; N, 6.84.

Example 22

(4s)-4-(5-Phenylthiazol-2-yloxy)-1-azatricyclo[3.3.1.1$^{3,7}$]decane p-toluenesulfonate Example 22A (4s)-4-(5-Phenylthiazol-2-yloxy)-1-azatricyclo[3.3.1.1$^{3,7}$]decane Prepared from the product of Example 20B (100 mg, 0.317 mmol) and phenylboronic acid (80 mg, 0.66 mmol; Aldrich) according to Method E: $^1$H NMR (300 MHz, methanol-D4) δ ppm 1.70 (s, 1H), 1.89 (d, J=11.9 Hz, 2H), 2.18-2.35 (m, 4H), 3.09-3.19 (m, 4H), 5.22 (t, J=3.4 Hz, 1H), 7.25-7.32 (m, 1H), 7.34-7.42 (m, 3H), 7.47-7.53 (m, 2H). MS (DCI/NH$_3$) m/z=313 (M+H)$^+$.

Example 22B (4s)-4-(5-Phenylthiazol-2-yloxy)-1-azatricyclo[3.3.1.1$^{3,7}$]decane p-toluenesulfonate Prepared from the product of Example 22A (85 mg, 0.27 mmol) according to Method H: $^1$H NMR (300 MHz, methanol-D4) δ ppm 1.96 (d, J=13.2 Hz, 2H), 2.20 (s, 1H), 2.28-2.39 (m, 5H), 2.66 (s, 2H), 3.58 (s, 2H), 3.60-3.76 (m, 4H), 5.38 (t, J=3.2 Hz, 1H), 7.23 (d, J=7.8 Hz, 2H), 7.27-7.34 (m, 1H), 7.35-7.42 (m, 2H), 7.44 (s, 1H), 7.48-7.54 (m, 2H). MS (DCI/NH$_3$) m/z=313 (M+H)$^+$. Anal. Calcd. for $C_{18}H_{20}N_2OS \cdot C_7H_8O_3S$: C, 61.96; H, 5.82; N, 5.78. Found: C, 61.71; H, 5.74; N, 5.71.

Example 23

(4s)-4-[5-(4-Methoxyphenyl)-thiazol-2-yloxy]-1-azatricyclo[3.3.1.1$^{3,7}$]decane p-toluenesulfonate Example 23A (4s)-4-[5-(4-Methoxyphenyl)-thiazol-2-yloxy]-1-azatricyclo[3.3.1.1$^{3,7}$]decane Prepared from the product of Example 20B (100 mg, 0.317 mmol) and 4-methoxyphenylboronic acid (100 mg, 0.66 mmol; Aldrich) according to Method E: $^1$H NMR (300 MHz, methanol-D4) δ ppm 1.69 (s, 1H), 1.89 (d, J=11.9 Hz, 2H), 2.21 (s, 2H), 2.29 (d, J=12.9 Hz, 2H), 3.08-3.17 (m, 4H), 3.26-3.29 (m, 2H), 3.81 (s, 3H), 5.18 (t, J=3.4 Hz, 1H), 6.91-6.97 (m, 2H), 7.26 (s, 1H), 7.42 (ddd, J=9.3, 2.7, 2.5 Hz, 2H). MS (DCI/NH$_3$) m/z=343 (M+H)$^+$.

Example 23B (4s)-4-[5-(4-Methoxyphenyl)-thiazol-2-yloxy]-1-azatricyclo[3.3.1.1$^{3,7}$]decane p-toluenesulfonate Prepared from the product of Example 23A (87 mg, 0.25 mmol) according to Method H: $^1$H NMR (300 MHz, methanol-D4) δ ppm 1.95 (d, J=12.9 Hz, 2H), 2.19 (s, 1H), 2.32 (d, J=13.6 Hz, 2H), 2.36 (s, 3H), 2.64 (s, 2H), 3.57 (s, 2H), 3.59-3.76 (m, 4H), 3.81 (s, 3H), 5.34 (t, J=3.4 Hz, 1H), 6.90-6.99 (m, 2H), 7.23 (d, J=8.5 Hz, 2H), 7.29 (s, 1H), 7.39-7.47 (m, 2H), 7.71 (d, J=8.1 Hz, 2H). MS (ESI) m/z=343 (M+H)$^+$. Anal. Calcd. for $C_{19}H_{22}N_2O_2S \cdot C_7H_8O_3S$: C, 60.68; H, 5.88; N, 5.44. Found: C, 60.57; H, 5.87; N, 5.37.

Example 24

(4s)-4-[5-(3-Chlorophenyl)-thiazol-2-yloxy]-1-azatricyclo[3.3.1.1$^{3,7}$]decane p-toluenesulfonate Example 24A (4s)-4-[5-(3-Chlorophenyl)-thiazol-2-yloxy]-1-azatricyclo[3.3.1.1$^{3,7}$]decane Prepared from the product of Example 20B (100 mg, 0.317 mmol) and 3-chlorophenylboronic acid (100 mg, 0.66 mmol; Aldrich) according to Method E: $^1$H NMR (300 MHz, methanol-D4) δ ppm 1.69 (s, 1H), 1.89 (d, J=12.5 Hz, 2H), 2.18-2.35 (m, 4H), 3.08-3.18 (m, 4H), 3.26-3.29 (m, 2H), 5.24 (t, J=3.2 Hz, 1H), 7.29 (dt, J=8.1, 1.6 Hz, 1H), 7.36 (t, J=7.8 Hz, 1H), 7.43 (ddd, J=7.6, 1.5, 1.4 Hz, 1H), 7.48 (s, 1H), 7.54 (t, J=1.7 Hz, 1H). MS (ESI) m/z=347/349 (M+H)$^+$.

Example 24B (4s)-4-[5-(3-Chlorophenyl)-thiazol-2-yloxy]-1-azatricyclo[3.3.1.1$^{3,7}$]decane p-toluenesulfonate Prepared from the product of Example 24A (96 mg, 0.28 mmol) according to Method H: $^1$H NMR (300 MHz, methanol-D4) δ ppm 1.96 (d, J=13.2 Hz, 2H), 2.20 (s, 1H), 2.27-2.39 (m, 5H), 2.66 (s, 2H), 3.58 (s, 2H), 3.61-3.76 (m, 4H), 5.40 (t, J=3.2 Hz, 1H), 7.23 (d, J=8.5 Hz, 2H), 7.31 (dt, J=7.8, 1.7 Hz, 1H), 7.37 (t, J=7.5 Hz, 1H), 7.44 (dt, J=7.5, 1.7 Hz, 1H), 7.51 (s, 1H), 7.55 (t, J=1.9 Hz, 1H), 7.67-7.75 (m, 2H). MS (ESI) m/z=347/349 (M+H)$^+$. Anal. Calcd. for $C_{18}H_{19}ClN_2OS \cdot C_7H_8O_3S \cdot 0.2H_2O$: C, 57.45; H, 5.28; N, 5.36. Found: C, 57.13; H, 5.31; N, 5.10.

Example 25

(4)-4-[5-(3-Chloro-4-methoxyphenyl)-thiazol-2-yloxy]-1-azatricyclo[3.3.1.1$^{3,7}$]decane p-toluenesulfonate Example 25A (4s)-4-[5-(3-Chloro-4-methoxyphenyl)-thiazol-2-yloxy]-1-azatricyclo[3.3.1.1$^{3,7}$]decane Prepared from the product of Example 20B (100 mg, 0.317 mmol) and 3-chloro-4-methoxyphenyl-boronic acid (120 mg, 0.63 mmol; Aldrich) according to Method E: $^1$H NMR (300 MHz, methanol-D4) δ ppm 1.70 (s, 1H), 1.89 (d, J=11.9 Hz, 2H), 2.17-2.35 (m, 4H), 3.09-3.18 (m, 4H), 3.26-3.30 (m, 2H), 3.90 (s, 3H), 5.21 (t, J=3.4 Hz, 1H), 7.09 (d, J=8.8 Hz, 1H), 7.32 (s, 1H), 7.40 (dd, J=8.5, 2.4 Hz, 1H), 7.53 (d, J=2.4 Hz, 1H). MS (ESI) m/z=3771379 (M+H)$^+$.

Example 25B (4s)-4-[5-(3-Chloro-4-methoxyphenyl)-thiazol-2-yloxy]-1-azatricyclo[3.3.1.1$^{3,7}$]decane p-toluenesulfonate Prepared from the product of Example 25A (105 mg, 0.278 mmol) according to Method H: $^1$H NMR (300 MHz, methanol-D4) δ ppm 1.96 (d, J=13.2 Hz, 2H), 2.20 (s, 1H), 2.32 (d, J=12.9 Hz, 2H), 2.36 (s, 3H), 2.65 (s, 2H), 3.58 (s, 2H), 3.60-3.76 (m, 4H), 3.91 (s, 3H), 5.37 (t, J=3.2 Hz, 1H), 7.10 (d, J=8.8 Hz, 1H), 7.23 (d, J=8.1 Hz, 2H), 7.35 (s, 1H), 7.41 (dd, J=8.5, 2.4 Hz, 1H), 7.54 (d, J=2.4 Hz, 1H), 7.71 (d, J=8.1 Hz, 2H). MS (ESI) m/z=377/379 (M+H)$^+$. Anal. Calcd. for $C_{19}H_{21}ClN_2O_2S.C_7H_8O_3S.0.2H_2O$: C, 56.50; H, 5.36; N, 5.07. Found: C, 56.15; H, 5.40; N, 5.02.

Example 26

(4s)-4-[5-(4-Fluorophenyl)-thiazol-2-yloxy]-1-azatricyclo[3.3.1.1$^{3,7}$]decane p-toluenesulfonate The free base was prepared from the product of Example 20B (75 mg, 0.24 mmol) and 4-fluorophenyl-boronic acid (73 mg, 0.46 mmol; Aldrich) according to Method E, and then converted to the salt by the procedure of Method H: $^1$H NMR (300 MHz, methanol-D4) δ ppm 1.91-2.01 (m, 2H), 2.19 (s, 1H), 2.32 (d, J=13.5 Hz, 2H), 2.36 (s, 3H), 2.64 (s, 2H), 3.52-3.77 (m, 6H) 5.38 (s, 1H), 7.14 (d, J=24.1 Hz, 2H), 7.37-7.40 (m, 1H), 7.48-7.58 (m, 2H), 7.70 (d, J=8.1 Hz, 2H). MS (DCI/NH$_3$) m/z=331. Anal. Calcd. for $C_{18}H_{19}FN_2OS.C_7H_8O_3S$: C, 59.74; H, 5.41; N, 5.57. Found: C, 53.36; H, 5.13; N, 5.50.

Example 27

(4s)-4-[5-(3,5-Difluorophenyl)-thiazol-2-yloxy]-1-azatricyclo[3.3.1.1$^{3,7}$]decane p-toluenesulfonate The free base was prepared from the product of Example 20B (75 mg, 0.24 mmol) and coupled with 3,5-difluorophenyl-boronic acid (75 mg, 0.46 mmol; Aldrich) according to Method E, and then converted to the salt by the procedure of Method H: $^1$H NMR (300 MHz, methanol-D4) δ ppm 1.96 (d, J=15.2 Hz, 2H), 2.18 (s, 1H), 2.32 (d, J=14.9 Hz, 2H), 2.36 (s, 3H), 2.63 (s, 2H), 3.49-3.76 (m, 6H), 5.41 (s, 1H), 6.79-6.97 (m, 1H), 7.15-7.19 (m, 2H), 7.21-7.24 (m, 2H), 7.58 (s, 1H), 7.71 (m, 2H). MS (DCI/NH$_3$) m/z=349. Anal. Calcd. for $C_{18}H_{18}F_2N_2OS.C_7H_8SO_3$: C, 57.68; H, 5.03; N, 5.38. Found: C, 55.49; H, 5.17; N, 5.14.

Example 28

(4s)-4-[5-(1H-Indol-5-yl)-thiazol-2-yloxy]-1-azatricyclo[3.3.1.1$^{3,7}$]decane p-toluenesulfonate

Example 28A (4s)-4-[5-(1H-Indol-5-yl)-thiazol-2-yloxy]-1-azatricyclo[3.3.1.1$^{3,7}$]decane Prepared from the product of Example 20B (110 mg, 0.349 mmol) and 5-indolylboronic acid (140 mg, 0.72 mmol; Frontier) according to Method E: MS (DCI/NH$_3$) m/z=352.

Example 28B (4s)-4-[5-(1H-Indol-5-yl)-thiazol-2-yloxy]-1-azatricyclo[3.3.1.1$^{3,7}$]decane p-toluenesulfonate Prepared from the product of Example 28A (72 mg, 0.20 mmol) according to Method H: $^1$H NMR (300 MHz, methanol-D4) δ ppm 1.96 (d, J=13.6 Hz, 2H), 2.20 (s, 1H), 2.29-2.38 (m, 5H), 2.65 (s, 2H), 3.59-3.75 (m, 6H), 5.34 (t, J=3.2 Hz, 1H), 6.46 (d, J=3.4 Hz, 1H), 7.19-7.32 (m, 5H), 7.40 (d, J=8.5 Hz, 1H), 7.65-7.74 (m, 3H). MS (DCI/NH$_3$) m/z=352 (M+H)$^+$; Anal. Calcd. for $C_{20}H_{21}N_3OS.C_7H_8O_3S.0.25H_2O$: C, 61.40; H, 5.63; N, 7.96 Found: C, 61.36; H, 5.64; N, 7.86.

Example 29

(4s)-4-[5-(1H-Indol-5-yl)-thiazol-2-yloxy]-1-azatricyclo[3.3.1.1$^{3,7}$]decane-1-oxide A solution of the product of Example 28A (105 mg, 0.30 mmol) in methanol (4 mL) was treated with 3-chloroperbenzoic acid (mCPBA; 70-75%; 71.0 mg, 0.30 mmol; Aldrich) and stirred at ambient temperature for 4 hours. The resulting material was purified by preparative HPLC [Waters® XTerra RP18 column, 5μ, 30×100 mm, flow rate 40 mL/minutes, 5-95% gradient of acetonitrile in buffer (0.1 M aqueous ammonium bicarbonate, adjusted to pH 10 with ammonium hydroxide] to afford the title compound: $^1$H NMR (300 MHz, methanol-D4) δ ppm 1.70-2.02 (m, 2H), 2.10-2.29 (m, 1H), 2.29-2.47 (m, 1H), 2.58-2.78 (m, 2H), 3.57-3.67 (m, 5H), 5.32 (t, J=3.3 Hz, 1H), 6.46 (d, J=3.0 Hz, 1H), 7.26 (d, J=3.3 Hz, 1H), 7.27-7.31 (m, 2H), 7.36-7.42 (m, 1H), 7.66 (d, J=1.3 Hz, 1H). MS (DCI/NH$_3$) m/z=368 (M+H)$^+$.

Example 30

(4s)-5-4-[2-(1-Azatricyclo[3.3.1.1$^{3,7}$]decan-4-yloxy)thiazol-5-yl]-indolin-2-one Prepared from the product of Example 20B (200 mg, 0.63 mmol) and 5-(4,4,5,5-tetramethyl-1,3,2-dioxaborolan-2-yl)-indolin-2-one (260 mg, 1.0 mmol; see US Patent Appl. 20050245531) according to Method E: $^1$H NMR (300 MHz, methanol-D4) δ ppm 1.52-1.79 (m, 1H), 1.80-2.00 (m, 2H), 2.07-2.43 (m, 4H), 3.00-3.20 (m, 5H), 3.35 (s, 2H), 5.20 (t, J=3.2 Hz, 1H), 6.90 (d, J=8.1 Hz, 1H), 7.30 (s, 1H), 7.35 (dd, J=8.1, 2.0 Hz, 1H), 7.43 (d, J=1.7 Hz, 1H). MS (DCI/NH$_3$) m/z=368 (M+H)$^+$.

Example 31

(4s)-5-4-[2-(1-Azatricyclo[3.3.1.1$^{3,7}$]decan-1-oxide-4-yloxy)thiazol-5-yl]-indolin-2-one A solution of the product of Example 30 (100 mg, 0.27 mmol) in methanol (4 mL) was treated with 3-chloroperbenzoic acid (mCPBA; 70-75%; 71.0 mg, 0.30 mmol; Aldrich) and stirred at ambient temperature for 4 hours. The resulting material was purified by preparative HPLC [Waters® XTerra RP18 column, 5μ, 30×100 mm, flow rate 40 mL/minutes, 5-95% gradient of acetonitrile in buffer (0.1 M aqueous ammonium bicarbonate, adjusted to pH 10 with ammonium hydroxide] to afford the title compound: $^1$H NMR (300 MHz, methanol-D4) δ ppm 1.71-1.94 (m, 2H), 2.07-2.26 (m, 2H), 2.29-2.45 (m, 1H), 2.58-2.80 (m, 2H), 3.44-3.75 (m, 8H), 5.34 (t, J=3.2 Hz, 1H), 6.90 (d, J=8.1 Hz, 1H), 7.32 (s, 1H), 7.35 (dd, J=8.1, 1.7 Hz, 1H), 7.43 (d, J=1.3 Hz, 1H). MS (DCI/NH$_3$) m/z=384 (M+H)$^+$.

Example 32

(4s)-4-[5-(2-Trifluoromethyl-1H-indol-5-yl)-thiazol-2-yloxy]-1-azatricyclo[3.3.1.1$^{3,7}$]decane p-toluenesulfonate The free base of the title compound was prepared from the product of Example 20B (100 mg, 0.30 mmol) and 5-(4,4,5,5-tetramethyl-1,3,2-dioxaborolan-2-yl)-2-(trifluoromethyl)-

1H-indole (197 mg, 0.64 mmol; US Patent Appl 2005043347) according to Method E, and then converted to the salt according to the procedure of Method H: $^1$H NMR (300 MHz, methanol-D4) δ ppm 1.96 (d, J=12.2 Hz, 2H), 2.13 (s, 1H), 2.32 (s, 2H), 2.36 (s, 3H), 2.60 (s, 2H), 3.48-3.71 (m, 6H), 5.35 (s, 1H), 6.91 (s, 1H), 7.22 (d, J=7.8 Hz, 2H), 7.34-7.39 (m, 1H), 7.48 (s, 2H), 7.71 (d, J=8.1 Hz, 2H), 7.78 (s, 1H). MS (DCI/NH$_3$) m/z=420 (M+H)$^+$. Anal. Calcd. for $C_{21}H_{20}F_3N_3OS \cdot C_7H_8O_3S$: C, 56.84; H, 4.77; N, 7.10. Found: C, 55.39; H, 4.57; N, 7.02.

Example 33

(4s)-4-[5-(1H-Indol-4-yl)-thiazol-2-yloxy]-1-azatricyclo[3.3.1.1$^{3,7}$]decane p-toluenesulfonate The free base of the title compound was prepared from the product of Example 20B (110 mg, 0.349 mmol) and indole-4-boronic acid (120 mg, 0.72 mmol; Frontier) according to Method E, and then converted to the salt according to the procedure of Method H: $^1$H NMR (300 MHz, methanol-D4) δ ppm 1.97 (d, J=12.2 Hz, 2H), 2.21 (s, 1H), 2.28-2.44 (m, 5H), 2.68 (s, 2H), 3.58 (s, 2H), 3.62-3.77 (m, 4H), 5.39 (s, 1H), 6.71 (dd, J=3.4, 1.0 Hz, 1H), 7.09-7.19 (m, 2H), 7.23 (d, J=7.8 Hz, 2H), 7.34 (d, J=3.1 Hz, 1H), 7.37-7.43 (m, 1H), 7.47 (s, 1H), 7.71 (d, J=8.1 Hz, 2H). MS (DCI/NH$_3$) m/z=352 (M+H)$^+$; Anal. Calcd. for $C_{20}H_{21}N_3OS \cdot C_7H_8O_3S \cdot 0.2H_2O$: C, 61.50; H, 5.62; N, 7.97 Found: C, 61.48; H, 5.59; N, 7.91.

Example 34

(4s)-4-[5-(1H-Indol-6-yl)-thiazol-2-yloxy]-1-azatricyclo[3.3.1.1$^{3,7}$]decane p-toluenesulfonate The free base of the title compound was prepared from the product of Example 20B (110 mg, 0.349 mmol) and indole-6-boronic acid (120 mg, 0.72 mmol; Frontier) according to Method E, and then converted to the salt according to the procedure of Method H: $^1$H NMR (300 MHz, methanol-D4) δ ppm 1.96 (d, J=14.2 Hz, 2H), 2.21 (s, 1H), 2.28-2.46 (m, 5H), 2.66 (s, 2H), 3.58 (s, 2H), 3.61-3.77 (m, 4H), 5.35 (t, J=3.2 Hz, 1H), 6.45 (dd, J=3.1, 1.0 Hz, 1H), 7.12-7.25 (m, 3H), 7.27 (d, J=3.1 Hz, 1H), 7.35 (s, 1H), 7.45-7.51 (m, 1H), 7.55 (d, J=8.1 Hz, 1H), 7.71 (d, J=8.1 Hz, 2H). MS (DCI/NH$_3$) m/z=352 (M+H)$^+$. Anal. Calcd. for $C_{20}H_{21}N_3OS \cdot C_7H_8O_3S \cdot 0.2H_2O$: C, 61.50; H, 5.62; N, 7.97. Found: C, 61.48; H, 5.59; N, 7.91.

Example 35

(4s)-4-[5-(1H-Indol-3-yl)-thiazol-2-yloxy]-1-azatricyclo[3.3.1.1$^{3,7}$]decane p-toluenesulfonate

Example 35A (4s)-4-[5-(1-Benzenesulfonyl-1H-indol-3-yl)]-thiazol-2-yloxy]-1-azatricyclo[3.3.1.1$^{3,7}$]decane Prepared from the product of Example 20B (110 mg, 0.349 mmol) and 1-phenylsulfonyl-1H-indol-3-ylboronic acid (220 mg, 0.72 mmol; Aldrich) according to Method E: MS (DCI/NH$_3$) m/z=492 (M+H)$^+$.

Example 35B (4s)-4-[5-(1H-Indol-3-yl)-thiazol-2-yloxy]-1-azatricyclo[3.3.1.1$^{3,7}$]decane p-toluenesulfonate A solution of the product of Example 35A (150 mg, 0.31 mmol) and potassium carbonate (100 mg, 0.76 mmol) in methanol (3 mL) was heated to reflux for 90 minutes. After cooling, the solvent was removed, the residue was dissolved in water, and the mixture was extracted with ethyl acetate (3×). The combined extracts were washed with brine, dried (Na$_2$SO$_4$), filtered and concentrated to afford the free base of the title compound. This material was converted to the salt according to Method H: $^1$H NMR (300 MHz, methanol-D4) δ ppm 1.96 (d, J=12.9 Hz, 2H), 2.21 (s, 1H), 2.30-2.40 (m, 5H), 2.66 (s, 2H), 3.58 (s, 2H), 3.62-3.79 (m, 4H), 5.35 (t, J=3.6 Hz, 1H), 7.08-7.25 (m, 4H), 7.29 (s, 1H), 7.39-7.44 (m, 1H), 7.45 (s, 1H), 7.67-7.77 (m, 3H). MS (DCI/NH$_3$) m/z=352 (M+H)$^+$; Anal. Calcd. for $C_{20}H_{21}N_3OS \cdot C_7H_8O_3S$: C, 61.93; H, 5.58; N, 8.02. Found: C, 61.56; H, 5.20; N, 7.77.

Example 36

(4s)-4-[5-(Pyridin-4-yl)-thiazol-2-yloxy]-1-azatricyclo[3.3.1.1$^{3,7}$]decane bis(p-toluenesulfonate)

Example 36A (4s)-4-[5-(Pyridin-4-yl)-thiazol-2-yloxy]-1-azatricyclo[3.3.1.1$^{3,7}$]decane Prepared from the product of Example 20B (100 mg, 0.317 mmol) and 4-pyridylboronic acid (100 mg, 0.814 mmol; Aldrich) according to Method E: $^1$H NMR (300 MHz, methanol-D4) δ ppm 1.70 (s, 1H), 1.90 (d, J=11.9 Hz, 2H), 2.19-2.34 (m, 4H), 3.09-3.19 (m, 4H), 5.31 (t, J=3.2 Hz, 1H), 7.53-7.58 (m, 2H), 7.78 (s, 1H), 8.46-8.52 (m, 2H). MS (DCI/NH$_3$) m/z=314 (M+H)$^+$.

Example 36B (4s)-4-[5-(Pyridin-4-yl)-thiazol-2-yloxy]-1-azatricyclo[3.3.1.1$^{3,7}$]decane bis(p-toluenesulfonate)

Prepared from the product of Example 36A (77 mg, 0.24 mmol) and p-toluenesulfonic acid monohydrate (93 mg, 0.49 mmol; Aldrich) according to Method H: $^1$H NMR (300 MHz, methanol-D4) δ ppm 1.98 (d, J=12.5 Hz, 2H), 2.22 (s, 1H), 2.26-2.39 (m, 8H), 2.69 (s, 2H), 3.59 (s, 2H), 3.63-3.78 (m, 4H), 5.57 (t, J=3.2 Hz, 1H), 7.22 (d, J=8.5 Hz, 4H), 7.67-7.74 (m, 4H), 8.12-8.17 (m, 2H), 8.25 (s, 1H), 8.67-8.73 (m, 2H). MS (ESI) m/z=314 (M+H)$^+$. Anal. Calcd. for $C_{17}H_{19}N_3OS \cdot 2C_7H_8O_3S \cdot 0.2H_2O$: C, 56.29; H, 5.39; N, 6.35. Found: C, 56.03; H, 5.29; N, 6.12.

Example 37

(4s)-4-[5-(Furan-2-yl)-thiazol-2-yloxy]-1-azatricyclo[3.3.1.1$^{3,7}$]decane bis(p-toluenesulfonate)

The free base of the title compound was prepared from the product of Example 20B (101 mg, 0.32 mmol) and 2-furylboronic acid (53 mg, 0.48 mmol; Aldrich) according to Method E, and then converted to the salt according to the procedure of Method H: $^1$H NMR (300 MHz, methanol-D4) δ ppm 1.96 (d, J=12.5 Hz, 2H), 2.19 (s, 1H), 2.33 (d, J=13.6 Hz, 2H), 2.36 (s, 3H), 2.64 (s, 2H), 3.52-3.77 (m, 6H), 5.36 (s, 1H), 6.52 (d, J=21.0 Hz, 2H), 7.22 (d, J=8.1 Hz, 2H), 7.33 (s, 1H), 7.51 (d, J=1.4 Hz, 1H), 7.70 (d, J=8.1 Hz, 2H). MS (DCI/NH$_3$) m/z=304 (M+H)$^+$. Anal. Calcd. for $C_{16}H_{17}N_2O_2S \cdot C_7H_8O_3S$: C, 58.21; H, 5.52; N, 5.90. Found: C, 55.59; H, 5.18; N, 5.55.

Example 38

(4s)-4-[5-(Furan-3-yl)-thiazol-2-yloxy]-1-azatricyclo[3.3.1.1$^{3,7}$]decane bis(p-toluenesulfonate)

The free base of the title compound was prepared from the product of Example 20B (101 mg, 0.32 mmol) and 3-furylboronic acid (106 mg, 0.99 mmol; Aldrich) according to Method E, and then converted to the salt according to the procedure of Method H: $^1$H NMR (300 MHz, methanol-D4) δ ppm 1.96 (d, J=12.5 Hz, 2H), 2.19 (s, 1H), 2.33 (d, J=13.6 Hz, 2H), 2.36 (s, 3H), 2.64 (s, 2H), 3.52-3.77 (m, 6H), 5.36 (s, 1H), 7.16 (s, 1H), 7.23 (d, J=8.1 Hz, 3H), 7.67-7.74 (m, 4H). MS (DCI/NH$_3$) m/z=304 (M+H)$^+$. Anal. Calcd. for C$_{16}$H$_{17}$N$_2$O$_2$S.C$_7$H$_8$O$_3$S: C, 58.21; H, 5.52; N, 5.90. Found: C, 55.77; H, 4.99; N, 5.57.

Example 39

(4s)-4-[5-(Thien-3-yl)-thiazol-2-yloxy]-1-azatricyclo[3.3.1.1$^{3,7}$]decane bis(p-toluenesulfonate)

The free base of the title compound was prepared from the product of Example 20B (110 mg, 0.35 mmol) and 3-thiopheneboronic acid (77 mg, 0.60 mmol; Aldrich) according to Method E, and then converted to the salt according to the procedure of Method H: $^1$H NMR (300 MHz, methanol-D4) δ ppm 1.96 (d, J=12.5 Hz, 2H), 2.19 (s, 1H), 2.32 (d, J=13.9 Hz, 2H), 2.36 (s, 3H), 2.64 (s, 2H), 3.51-3.78 (m, 6H), 5.36 (s, 1H), 7.22 (d, J=8.4 Hz, 2H), 7.30 (dd, J=5.1, 1.4 Hz, 1H), 7.34 (s, 1H), 7.42-7.52 (m, 2H), 7.70 (d, J=8.1 Hz, 2H). MS (DCI/NH$_3$) m/z=320 (M+H)$^+$. Anal. Calcd. for C$_{16}$H$_{17}$N$_2$OS$_2$.C$_7$H$_8$SO$_3$: C, 53.74; H, 5.13; N, 8.55. Found: C, 53.51; H, 5.37; N, 10.89.

Example 40

(4s)-4-[5-(Pyrazol-4-yl)-thiazol-2-yloxy]-1-azatricyclo[3.3.1.1$^{3,7}$]decane bis(p-toluenesulfonate)

Prepared from the product of Example 20B (111 mg, 0.315 mmol) and 4-(4,4,5,5-tetramethyl-1,3,2-dioxaborolan-2-yl)-1-trityl-1H-pyrazole (272 mg, 0.624 mmol; JP 2005232071) according to Method E, followed by deprotection using the procedure or Method L, and salt formation according to Method H: $^1$H NMR (300 MHz, methanol-D4) δ ppm 1.96 (d, J=12.5 Hz, 2H), 2.19 (s, 1H), 2.32 (d, J=13.9 Hz, 2H), 2.36 (s, 3H), 2.64 (s, 2H), 3.51-3.78 (m, 6H), 5.36 (s, 1H), 7.13-7.31 (m, 3H), 7.71 (d, J=8.4 Hz, 2H), 7.80 (s, 2H). MS (DCI/NH$_3$) m/z=304 (M+H)$^+$.

Example 41

(4s)-4-(5-Bromo-1,3,4-thiadiazol-2-yloxy)-1-azatricyclo[3.3.1.1$^{3,7}$]decane p-toluenesulfonate

Example 41A (4s)-4-(5-Bromo-1,3,4-thiadiazol-2-yloxy)-1-azatricyclo[3.3.1.1$^{3,7}$]decane N-borane complex Prepared from the product of Example 10A (1.3 g, 8.0 mmol) and 2,5-dibromo-1,3,4-thiadiazole (2.1 g, 8.8 mmol; prepared as described in Yasuda, T.; Imase, T.; Sasaki, S.; Yamamoto, T. *Macromolecules* 2005, 38, 1500) according to Method A: $^1$H NMR (300 MHz, chloroform-D) δ ppm 1.72 (d, J=11.9 Hz, 2H), 2.03 (s, 1H), 2.17 (d, J=12.9 Hz, 2H), 2.48 (s, 2H), 3.15-3.26 (m, 6H), 5.34 (t, J=3.6 Hz, 1H).

Example 41B (4s)-4-(5-Bromo-1,3,4-thiadiazol-2-yloxy)-1-azatricyclo[3.3.1.1$^{3,7}$]decane Prepared from the product of Example 41A (1.35 g, 4.09 mmol) according to Method C: $^1$H NMR (300 MHz, methanol-D4) δ ppm 1.68 (s, 1H), 1.84-1.95 (m, 2H), 2.24 (s, 4H), 3.07-3.17 (m, 4H), 3.25-3.29 (m, 2H), 5.34 (t, J=3.1 Hz, 1H). MS (ESI) m/z=316/318 (M+H)$^+$.

Example 41C (4s)-4-(5-Bromo-1,3,4-thiadiazol-2-yloxy)-1-azatricyclo[3.3.1.1$^{3,7}$]decane p-toluenesulfonate Prepared from the product of Example 41B (80 mg, 0.25 mmol) according to Method H: $^1$H NMR (300 MHz, methanol-D4) δ ppm 1.96 (d, J=14.2 Hz, 2H), 2.19 (s, 1H), 2.30 (d, J=13.9 Hz, 2H), 2.36 (s, 3H), 2.68 (s, 2H), 3.57 (s, 2H), 3.59-3.76 (m, 4H), 5.47 (t, J=3.4 Hz, 1H), 7.23 (d, J=7.8 Hz, 2H), 7.66-7.74 (m, 2H). MS (ESI) m/z=316/318 (M+H)$^+$. Anal. Calcd. for C$_{11}$H$_{14}$BrN$_3$OS.C$_7$H$_8$O$_3$S: C, 44.26; H, 4.54; N, 8.60. Found: C, 44.35; H, 4.58; N, 8.61.

Example 42

(4s)-4-(1,3,4-Thiadiazol-2-yloxy)-1-azatricyclo[3.3.1.1$^{3,7}$]decane p-toluenesulfonate

Example 42A (4s)-4-(1,3,4-Thiadiazol-2-yloxy)-1-azatricyclo[3.3.1.1$^{3,7}$]decane A solution of the product of Example 41B (100 mg, 0.32 mmol) in ethanol (3 mL) was treated with 10% Pd/C (10 mg; Aldrich) under a hydrogen balloon with vigorous stirring for 3 days. Since the reaction did not go to completion, it was filtered to remove the catalyst, rinsed with ethanol, and resubjected to the reaction conditions with fresh Pd/C. After 6 hours, the mixture was filtered and the compound was purified by preparative HPLC [Waters® XTerra RP18 5μ column, 30×100 mm, flow rate 40 mL/minute, 5-95% gradient of acetonitrile in buffer (0.1 M aqueous ammonium bicarbonate, adjusted to pH 10 with ammonium hydroxide) over 22 minutes, with UV detection at 254 nm]. Fractions containing the desired product were pooled and concentrated under vacuum to afford the title compound: $^1$H NMR (300 MHz, methanol-D4) δ ppm 1.69 (s, 1H), 1.90 (d, J=13.6 Hz, 2H), 2.20-2.33 (m, 4H), 3.07-3.20 (m, 4H), 5.30 (t, J=2.9 Hz, 1H), 8.88 (s, 1H). MS (DCI/NH$_3$) m/z=238 (M+H)$^+$.

Example 42B (4s)-4-(1,3,4-Thiadiazol-2-yloxy)-1-azatricyclo[3.3.1.1$^{3,7}$]decane p-toluenesulfonate Prepared from the product of Example 42A (38 mg, 0.16 mmol) according to Method H: $^1$H NMR (300 MHz, methanol-D4) δ ppm 1.96 (d, J=12.5 Hz, 2H), 2.20 (s, 1H), 2.31 (d, J=13.2 Hz, 2H), 2.37 (s, 3H), 2.70 (s, 2H), 3.58 (s, 2H), 3.61-3.77 (m, 4H), 5.46 (t, J=3.2 Hz, 1H), 7.23 (d, J=8.5 Hz, 2H), 7.71 (d, J=8.1 Hz, 2H), 8.94 (s, 1H). MS (DCI/NH$_3$)

m/z=238 (M+H)⁺. Anal. Calcd. for C₁₁H₁₅N₃OS.C₇H₈O₃S.0.3H₂O: C, 52.10; H, 5.73; N, 10.13. Found: C, 51.94; H, 5.69; N, 9.76.

Example 43

(4s)-4-(5-Phenyl-1,3,4-thiadiazol-2-yloxy)-1-azatricyclo[3.3.1.1$^{3,7}$]decane

Example 43A

1-Azaadamantan-4-ol N-borane complex

A solution of azaadamantan-4-one (29 g, 190 mmol, see Becker, D. P.; Flynn, D. L. Synthesis, 1992, 1080) in anhydrous tetrahydrofuran (200 mL) was chilled in an ice-water bath and treated with borane-THF complex (1.0 M in THF; 200 mL, 200 mmol; Aldrich), added dropwise. After stirring for 30 minutes, the reaction mixture was diluted with methanol (1000 mL) and carefully treated with sodium borohydride (8.8 g, 230 mmol; Aldrich), keeping the internal temperature about 5-7° C. The reaction was stirred for 2 hours, and then the ice bath was removed and stirring was continued for 4 hours. The volatile components were removed on the rotary evaporator and the residue was dissolved in chloroform (~500 mL) and washed with saturated aqueous sodium carbonate. The aqueous layer was extracted with chloroform and the organic phases were dried over magnesium sulfate. The resulting material was purified by flash chromatography (Analogix 400 g 65×220 mm silica gel column, 5-95% gradient of ethyl acetate in hexanes over 50 minutes) to afford an inseparable 3.7:1.0 mixture of isomers [according to integration of ¹H NMR signals (CDCl₃) at δ3.96 (t, major) and δ3.82 (t, minor)]. The product spot can be visualized on the TLC plate (silica gel) using KMnO₄ stain.

Example 43B

4-Chlorobenzoic acid (4s)-1-azatricyclo[3.3.1.1$^{3,7}$]dec-4-yl ester N-borane complex and Example 43C 4-Chlorobenzoic acid (4r)-1-azatricyclo[3.3.1.1$^{3,7}$]dec-4-yl ester N-borane complex A solution of 1-azaadamantan-4-ol N-borane complex (28 g, 170 mmol; 3.2:1.0 mixture of diastereomers), 4-chlorobenzoic acid (28.0 g, 179 mmol; Aldrich), and 4-dimethylaminopyridine (4.2 g, 34 mmol; Aldrich) in dichloromethane (700 mL) was chilled to 0° C. and treated with N-(3-dimethylaminopropyl)-N'-ethylcarbodiimide hydrochloride (42.0 g, 219 mmol; Aldrich). After 1 hour, the reaction mixture was warmed to room temperature and stirred overnight. The solution was washed quickly with 1 M HCl (200 mL) followed by saturated sodium bicarbonate, and dried over magnesium sulfate. The resulting material was purified in 5 g batches by flash chromatography (Analogix 400 g 65×220 mm silica gel column, 5-55% gradient of ethyl acetate in hexanes over 45 minutes).

Example 43B: Major (4s) isomer: TLC R$_f$=0.49 (silica gel, 3:1 hexanes-EtOAc). ¹H NMR (300 MHz, CDCl₃) δ ppm 1.76 (d, J=12.5 Hz, 2H), 2.06 (s, 1H), 2.16-2.33 (m, 4H), 3.12-3.32 (m, 6H), 5.26 (t, J=3.2 Hz, 1H), 7.45 (dt, J=8.7, 2.4, 2.1 Hz, 2H), 8.00 (dt, J=8.7, 2.4, 2.1 Hz, 2H). MS (DCI/NH₃) m/e 321/323 (M+H)⁺. Anal. Calculated for C₁₆H₂₁BClNO₂: C, 62.88; H, 6.93; N, 4.58. Found C, 63.00; H, 6.80; N, 4.50.

Example 43C: Minor (4r) isomer: TLC R$_f$=0.34 (silica gel, 3:1 hexanes-EtOAc). ¹H NMR (300 MHz, CDCl₃) δ ppm 1.84-2.11 (m, 5H), 2.24 (s, 2H), 3.03 (d, J=12.5 Hz, 2H), 3.14 (s, 2H), 3.46 (d, J=13.2 Hz, 2H), 5.16 (t, J=3.2 Hz, 1H), 7.39-7.51 (m, 2H), 7.89-8.05 (m, 2H). MS (DCI/NH₃) m/e 321/323 (M+H)⁺. Anal. Calculated for C₁₆H₂₁BClNO₂: C, 62.88; H, 6.93; N, 4.58. Found C, 62.83; H, 6.95; N, 4.53.

Example 43D (4s)-1-Azatricyclo[3.3.1.1$^{3,7}$]decan-4-ol N-borane complex

A suspension of 4-chlorobenzoic acid (4s)-1-azatricyclo[3.3.1.1$^{3,7}$]dec-4-yl ester N-borane complex (Example 43B, 25.0 g, 81.8 mmol) in tetrahydrofuran (50 mL) was treated with 5 M sodium hydroxide (50 mL). After 1 hour, the reaction mixture was warmed to 50° C. for 3 hours. Most of the solvent was removed on the rotary evaporator, and the residue was purified by flash chromatography (Analogix 220 g 65×120 mm silica gel column, 5-95% gradient of ethyl acetate in hexanes) to afford the title product: ¹H NMR (300 MHz, methanol-d4) δ ppm 0.87-2.09 (br m, 3H; BH₃), 1.59 (d, J=12.5 Hz, 2H), 1.78-1.98 (m, 2H), 2.22 (d, J=12.5 Hz, 2H), 2.97-3.18 (m, 6H), 3.96 (t, J=3.4 Hz, 1H). MS (DCI/NH₃) m/e 183 (M+H)⁺.

Example 43E

2-Chloro-5-phenyl-[1,3,4]thiadiazole

A stirred suspension of 2-amino-5-phenyl-[1,3,4]thiadiazole (6.45 g, 36.4 mmol; Aldrich) and copper (230 mg, 3.6 mmol; Aldrich) in hydrochloric acid (36 mL, 12 M) and glacial acetic acid (180 mL) was chilled to 0° C. and treated with a solution of sodium nitrite (2.64 g, 38.2 mmol; Aldrich) in water (12 mL), added dropwise over 40 minutes. After stirring at room temperature for 4 hours, the mixture was poured into ice water. The aqueous solution was extracted with chloroform (3×), and the combined extracts were washed sequentially with 5% sodium bicarbonate and brine, and dried over sodium sulfate. The crude product was filtered through a short silica gel plug with chloroform to afford the title product: ¹H NMR (300 MHz, CDCl₃) δ ppm 7.46-7.55 (m, 3H), 7.85-7.93 (m, 2H). MS (DCI/NH₃) m/e 197/199 (M+H)⁺.

Example 43F (4s)-4-(5-Phenyl-[1,3,4]thiadiazol-2-yloxy)-1-azatricyclo[3.3.1.1$^{3,7}$]decane N-borane complex A solution of (4s)-1-azatricyclo[3.3.1.1$^{3,7}$]decan-4-ol N-borane complex (Example 43D, 2.31 g, 13.8 mmol) and 2-chloro-5-phenyl-[1,3,4]thiadiazole (Example 43E, 2.78 g, 14.1 mmol) in anhydrous DMF (20 mL) was chilled to 0° C. and treated with sodium hydride (500 mg, 20.8 mmol; Aldrich, 95%). Vigorous bubbling was observed, and the solution turned orange. After 15 minutes, the cooling bath was removed and the reaction was stirred for 4 hours. The reaction mixture was diluted with water and stirred overnight. The resulting precipitate was collected by filtration, washed with water, and dried under vacuum to afford the title product: ¹H NMR (300 MHz, CDCl₃) δ ppm 1.73 (d, J=12.5 Hz, 2H), 2.04 (s, 1H), 2.22 (d, J=13.2 Hz, 2H), 2.54 (s, 2H), 3.17-3.28 (m, 6H), 5.38 (t, J=3.6 Hz, 1H), 7.42-7.51 (m, 3H), 7.77-7.87 (m, 2H). MS (+ESI) m/e 328 (M+H)+.

Example 43G (4s)-4-(5-Phenyl-[1,3,4]thiadiazol-2-yloxy)-1-azatricyclo[3.3.1.1$^{3,7}$]decane (A-913958.0)

A suspension of (4s)-4-(5-phenyl-[1,3,4]thiadiazol-2-yloxy)-1-azatricyclo[3.3.1.1$^{3,7}$]decane N-borane complex (Example 43F, 580 mg, 1.77 mmol) in acetone (18 mL) was chilled to 0° C. and treated with 3 N HCl (6 mL). The suspension slowly cleared, and then a precipitate began to form. After 20 minutes, the ice bath was removed and the mixture was stirred for 2 hours. The solution was then basified with 5 N NaOH to pH 10, extracted with chloroform (3×), and dried over anhydrous magnesium sulfate. The resulting material was purified by flash chromatography [Analogix 34 g 25 mm silica gel column, 5-50% gradient of ammonium hydroxide-methanol-chloroform (2:20:78) in chloroform]. It was purified further by preparative HPLC [Waters XTerra RP18 5μ column, 30×100 mm, flow rate 40 mL/min, 5-95% gradient of acetonitrile in buffer (0.1 M ammonium bicarbonate, adjusted to pH 10 with ammonium hydroxide) over 22 minutes, with UV detection at 254 nm]. Fractions containing the desired product (center of peak only) were pooled and concentrated to afford the title product: $^1$H NMR (300 MHz, methanol-d4) δ ppm 1.71 (s, 1H), 1.92 (d, J=12.5 Hz, 2H), 2.29 (s, 4H), 3.10-3.21 (m, 4H), 3.30-3.38 (m, 2H), 5.35 (t, J=3.1 Hz, 1H), 7.46-7.54 (m, 3H), 7.80-7.89 (m, 2H). MS (+ESI) m/e 314 (M+H)+. Anal. Calculated for $C_{17}H_{19}NO_3S$: C, 65.15; H, 6.11; N, 13.41. Found C, 64.94; H, 6.10; N, 13.41.

Example 44

(4s)-4-(5-Phenyl-1,3,4-thiadiazol-2-yloxy)-1-azatricyclo[3.3.1.1$^{3,7}$]decane-1-oxide A solution of the product of Example 43B (50 mg, 0.16 mmol) in methanol (3 mL) was chilled to 0° C. and treated with 3-chloroperbenzoic acid (70-75%; 39 mg, 0.16 mmol; Aldrich). After 30 minutes the ice bath was removed and stirring was continued overnight. The mixture was concentrated, and the residue was purified by flash chromatography (Analogix 15 g silica gel column, 5-50% gradient of ammonium hydroxide-methanol-chloroform (2:20:78) in chloroform) to afford the title compound: $^1$H NMR (300 MHz, methanol-D4) δ ppm 1.85 (d, J=13.2 Hz, 2H), 2.20 (d, J=12.9 Hz, 2H), 2.37 (s, 1H), 2.77 (s, 2H), 3.50-3.59 (m, 4H), 3.63-3.72 (m, 2H), 5.49 (t, J=3.6 Hz, 1H), 7.48-7.55 (m, 3H), 7.82-7.88 (m, 2H). MS (+ESI) m/z=330 (M+H)+.

Example 45

(4r)-4-(5-Phenyl-1,3,4-thiadiazol-2-yloxy)-1-azatricyclo[3.3.1.1$^{3,7}$]decane fumarate

Example 45A (4r)-4-(5-Phenyl-1,3,4-thiadiazol-2-yloxy)-1-azatricyclo[3.3.1.1$^{3,7}$]decane N-borane complex Prepared from the product of Example 9D (500 mg, 2.99 mmol) and 2-chloro-5-phenyl-1,3,4-thiadiazole (600 mg, 3.05 mmol; WO 2003094831) according to Method A: $^1$H NMR (300 MHz, chloroform-D) δ ppm 1.87-2.08 (m, 5H), 2.51 (s, 2H), 3.00 (dd, J=13.4, 1.2 Hz, 2H), 3.14 (s, 2H), 3.46 (d, J=13.6 Hz, 2H), 5.31 (t, J=3.4 Hz, 1H), 7.43-7.49 (m, 3H), 7.80-7.85 (m, 2H). MS (+ESI) m/z=328 (M+H)+.

Example 45B (4r)-4-(5-Phenyl-1,3,4-thiadiazol-2-yloxy)-1-azatricyclo[3.3.1.1$^{3,7}$]decane Prepared from the product of Example 45A (960 mg, 2.90 mmol) according to Method C: $^1$H NMR (300 MHz, methanol-D4) δ ppm 1.76 (s, 1H), 2.06 (d, J=11.9 Hz, 2H), 2.17-2.29 (m, 4H), 3.04 (d, J=12.9 Hz, 2H), 3.16 (s, 2H), 3.45 (d, J=13.6 Hz, 2H), 5.37 (s, 1H), 7.47-7.53 (m, 3H), 7.81-7.88 (m, 2H). MS (DCI/NH$_3$) m/z=314 (M+H)+.

Example 45C (4r)-4-(5-Phenyl-1,3,4-thiadiazol-2-yloxy)-1-azatricyclo[3.3.1.1$^{3,7}$]decane fumarate Prepared from the product of Example 45B (860 mg, 2.74 mmol) and fumaric acid (318 mg, 2.74 mmol; Aldrich) according to Method H: $^1$H NMR (300 MHz, methanol-D4) δ ppm 2.06-2.32 (m, 5H), 2.70 (s, 2H), 3.49 (d, J=12.5 Hz, 2H), 3.56 (s, 2H), 3.80 (d, J=12.2 Hz, 2H), 5.42 (t, J=3.4 Hz, 1H), 6.69 (s, 2H), 7.49-7.55 (m, 3H), 7.82-7.88 (m, 2H). MS (+ESI) m/z=314 (M+H)+. Anal. Calcd. for $C_{17}H_{19}NO_3S \cdot C_4H_4O_4$: C, 58.73; H, 5.40; N, 9.78. Found: C, 58.79; H, 5.52; N, 9.70.

Example 46

(4s)-4-[5-(4-Fluorophenyl)-1,3,4-thiadiazol-2-yloxy]-1-azatricyclo[3.3.1.1$^{3,7}$]decane p-toluenesulfonate

Example 46A (4s)-4-[5-(4-Fluorophenyl)-1,3,4-thiadiazol-2-yloxy]-1-azatricyclo[3.3.1.1$^{3,7}$]decane N-borane complex Prepared from the product of Example 10A (254 mg, 1.5 mmol) and 2-bromo-5-(4-fluorophenyl)-1,3,4-thiadiazole (402 mg, 1.5 mmol; WO 2003044020) according to Method A: $^1$H NMR (300 MHz, chloroform-D) δ ppm 1.26 (s, 1H), 1.74 (d, J=12.2 Hz, 2H), 2.05 (s, 1H), 2.22 (d, J=13.2 Hz, 1H), 2.54 (s, 2H), 3.17-3.33 (m, 6H), 5.33-5.47 (m, 1H), 7.08-7.24 (m, 2H), 7.76-7.96 (m, 2H). MS (DCI/NH$_3$) m/z=346 (M+H)+.

Example 46B (4s)-4-[5-(4-Fluorophenyl)-1,3,4-thiadiazol-2-yloxy]-1-azatricyclo[3.3.1.1$^{3,7}$]decane p-toluenesulfonate The product of Example 46A (204 mg, 0.59 mmol) was deprotected according to Method C and converted to the p-toluenesulfonate salt by the procedure of Method H: $^1$H NMR (300 MHz, methanol-D4) δ ppm 1.99 (d, J=13.6 Hz, 2H), 2.21 (s, 1H), 2.32 (s, 2H), 2.36 (s, 3H), 2.73 (s, 2H), 3.52-3.81 (m, 6H), 5.52 (s, 1H), 7.19-7.32 (m, 4H), 7.71 (d, J=8.1 Hz, 2H), 7.85-7.95 (m, 2H). MS (DCI/NH$_3$) m/z=332 (M+H)+. Anal. Calcd. for $C_{17}H_{18}FN_3OS \cdot C_7H_8O_3S$: C, 57.24; H, 5.20; N, 8.34.
Found: C, 56.08; H, 5.16; N, 8.31.

Example 47

(4r)-4-[5-(4-Fluorophenyl)-1,3,4-thiadiazol-2-yloxy]-1-azatricyclo[3.3.1.1$^{3,7}$]decane p-toluenesulfonate

Example 47A (4r)-4-[5-(4-Fluorophenyl)-1,3,4-thiadiazol-2-yloxy]-1-azatricyclo[3.3.1.1$^{3,7}$]decane N-borane complex Prepared from the product of Example 9D (203 mg, 1.22 mmol) and 2-bromo-5-(4-fluorophenyl)-1,3,4-thiadiazole (316 mg, 1.22 mmol; see WO 2003044020) according to Method A: $^1$H NMR (300 MHz, chloroform-D) δ ppm 1.70 (s, 1H), 1.96-2.08 (m, 2H), 2.12-2.23 (m, 4H), 3.01 (d, J=12.9 Hz, 2H), 3.16 (s, 2H), 3.49 (d, J=13.2 Hz, 2H), 5.46 (s, 1H), 7.08-7.19 (m, 2H), 7.75-7.87 (m, 2H). MS (DCI/NH$_3$) m/z=346 (M+H)$^+$.

Example 47B (4r)-4-[5-(4-Fluorophenyl)-1,3,4-thiadiazol-2-yloxy]-1-azatricyclo[3.3.1.1$^{3,7}$]decane p-toluenesulfonate The product of Example 47A (204 mg, 0.59 mmol) was deprotected according to Method C and converted to the p-toluenesulfonate salt by the procedure of Method H: $^1$H NMR (300 MHz, methanol-D4) δ ppm 2.05-2.32 (m, 5H), 2.36 (s, 3H), 2.71 (s, 2H), 3.42-3.63 (m, 4H), 3.81 (d, J=12.5 Hz, 2H), 5.41 (s, 1H), 7.18-7.32 (m, 4H), 7.70 (d, J=8.1 Hz, 2H), 7.90 (dd, J=8.9, 5.2 Hz, 2H). MS (DCI/NH$_3$) m/z=332 (M+H)$^+$. Anal. Calcd. for C$_{17}$H$_{18}$FN$_3$OS.C$_7$H$_8$O$_3$S: C, 57.21; H, 5.20; N, 8.34.
Found: C, 55.19; H, 5.40; N, 8.02.

Example 48

(4s)-4-[5-(3-Fluorophenyl)-1,3,4-thiadiazol-2-yloxy]-1-azatricyclo[3.3.1.1$^{3,7}$]decane p-toluenesulfonate

Example 48A

2-Bromo-5-(3-fluorophenyl)-1,3,4-thiadiazole

A vigorously stirred suspension of copper (II) bromide (1.37 g, 0.615 mmol; Acros) and amyl nitrite (1.20 g, 10.2 mmol) in acetonitrile (20 mL) was treated with 5-(3-fluorophenyl)-1,3,4-thiadiazol-2-ylamine (1.00 g, 0.512 mmol; Aldrich), added in portions. The mixture was stirred overnight, quenched with saturated ammonium chloride, and extracted with ether (2×). The combined organic phases were dried (MgSO$_4$), filtered, concentrated, and the residue was purified by flash chromatography (Analogix 12 g silica gel column, 5-85% gradient of ethyl acetate in hexanes) to afford the title compound: $^1$H NMR (300 MHz, methanol-D4) δ ppm 7.29-7.38 (m, 1H), 7.57 (td, J=8.1, 5.8 Hz, 1H), 7.71-7.79 (m, 2H). MS (+ESI) m/z=259/261 (M+H)$^+$.

Example 48B (4s)-4-[5-(3-Fluorophenyl)-1,3,4-thiadiazol-2-yloxy]-1-azatricyclo[3.3.1.1$^{3,7}$]decane N-borane complex Prepared from the product of Example 10A (257 mg, 1.5 mmol) and the product of Example 48A (398 mg, 1.5 mmol) according to Method A: $^1$H NMR (300 MHz, chloroform-D) δ ppm 1.26 (s, 1H), 1.74 (d, J=12.2 Hz, 2H), 2.05 (s, 1H), 2.22 (d, J=13.2 Hz, 1H), 2.54 (s, 2H), 3.17-3.33 (m, 6H), 5.33-5.47 (m, 1H), 7.10-7.25 (m, 1H), 7.37-7.53 (m, 1H), 7.54-7.70 (m, 2H). MS (DCI/NH$_3$) m/z=346 (M+H)$^+$.

Example 48C (4s)-4-[5-(3-Fluorophenyl)-1,3,4-thiadiazol-2-yloxy]-1-azatricyclo[3.3.1.1$^{3,7}$]decane p-toluenesulfonate The product of Example 48B (245 mg, 0.71 mmol) was deprotected according to Method C and converted to the p-toluenesulfonate salt by the procedure of Method H: $^1$H NMR (300 MHz, methanol-D4) δ ppm 1.99 (d, J=13.6 Hz, 2H), 2.21 (s, 1H), 2.32 (s, 2H), 2.36 (s, 3H), 2.73 (s, 2H), 3.52-3.81 (m, 6H), 5.52 (s, 1H), 7.23 (d, J=8.5 Hz, 2H), 7.25-7.32 (m, 1H), 7.49-7.58 (m, 1H), 7.62-7.73 (m, 4H). MS (DCI/NH$_3$) m/z=332 (M+H)$^+$. Anal. Calcd. for C$_{17}$H$_{18}$FN$_3$OS.C$_7$H$_8$O$_3$S: C, 57.24; H, 5.20; N, 8.34. Found: C, 56.97; H, 4.90; N, 8.22.

Example 49

(4r)-4-[5-(3-Fluorophenyl)-1,3,4-thiadiazol-2-yloxy]-1-azatricyclo[3.3.1.1$^{3,7}$]decane p-toluenesulfonate

Example 49A (4r)-4-[5-(3-Fluorophenyl)-1,3,4-thiadiazol-2-yloxy]-1-azatricyclo[3.3.1.1$^{3,7}$]decane N-borane complex Prepared from the product of Example 9D (203 mg, 1.38 mmol) and the product of Example 48A (398 mg, 1.5 mmol) according to Method A: $^1$H NMR (300 MHz, chloroform-D) δ ppm 1.70 (s, 1H), 1.96-2.08 (m, 2H), 2.12-2.23 (m, 4H), 3.01 (d, J=12.9 Hz, 2H), 3.16 (s, 2H), 3.49 (d, J=13.2 Hz, 2H), 5.46 (s, 1H), 7.08-7.19 (m, 2H), 7.75-7.87 (m, 2H). MS (DCI/NH$_3$) m/z=346 (M+H)$^+$.

Example 49B (4r)-4-[5-(3-Fluorophenyl)-1,3,4-thiadiazol-2-yloxy]-1-azatricyclo[3.3.1.1$^{3,7}$]decane p-toluenesulfonate The product of Example 49A (245 mg, 0.71 mmol) was deprotected according to Method C and converted to the p-toluenesulfonate salt by the procedure of Method H: $^1$H NMR (300 MHz, methanol-D$_4$) δ ppm 2.05-2.32 (m, 5H), 2.36 (s, 3H), 2.71 (s, 2H), 3.42-3.63 (m, 4H), 3.81 (d, J=12.5 Hz, 2H), 5.41 (s, 1H), 7.18-7.32 (m, 4H), 7.70 (d, J=8.1 Hz, 2H), 7.90 (dd, J=8.9, 5.3 Hz, 2H). MS (DCI/NH$_3$) m/z=332 (M+H)$^+$. Anal. Calcd. for C$_{17}$H$_{18}$FN$_3$OS.C$_7$H$_8$O$_3$S: C, 57.21; H, 5.20; N, 8.34.
Found: C, 55.19; H, 5.40; N, 8.02.

Example 50

(4s)-4-[5-(1H-Indol-5-yl)-1,3,4-thiadiazol-2-yloxy]-1-azatricyclo[3.3.1.1$^{3,7}$]decane p-toluenesulfonate Example 50A (4s)-4-[5-(1H-Indol-5-yl)-1,3,4-thiadiazol-2-yloxy]-1-azatricyclo[3.3.1.1$^{3,7}$]decane N-borane complex Prepared from the product of Example 10A (131 mg, 0.785 mmol) and 2-bromo-5-(1h-indol-5-yl)-1,3,4-thiadiazole (200 mg, 0.714 mmol; see WO 2003044020) according to Method B, with purification by flash chromatography (Analogix 80 g 40×120 mm silica gel column, 5-95% gradient of ethyl acetate in hexanes) to afford the title compound: $^1$H NMR (300 MHz, chloroform-D) δ ppm 1.73 (d, J=12.5 Hz, 2H), 2.05 (s, 1H), 2.24 (d, J=12.9 Hz, 2H), 2.55 (s, 2H), 3.18-3.27 (m, 6H), 5.36 (t, J=3.6 Hz, 1H), 6.64 (ddd, J=3.4, 2.0, 1.0 Hz, 1H), 7.29 (dd, J=3.2, 2.5 Hz, 1H), 7.46 (ddd, J=8.6, 0.8, 0.7 Hz, 1H), 7.75 (dd, J=8.5, 1.7 Hz, 1H), 8.04-8.07 (m, 1H), 8.35 (s, 1H). MS (+ESI) m/z=353 (M+H)$^+$.

Example 50B (4s)-4-[5-(1H-Indol-5-yl)-1,3,4-thiadiazol-2-yloxy]-1-azatricyclo[3.3.1.1$^{3,7}$]decane p-toluenesulfonate The free base of the title compound was prepared from the product of Example 50A (140 mg, 0.38 mmol) according to Method D, and then converted to the p-toluenesulfonate salt using the procedure of Method H: $^1$H NMR (300 MHz, methanol-D4) δ ppm 1.99 (d, J=12.5 Hz, 2H), 2.22 (s, 1H), 2.29-2.40 (m, 5H), 2.73 (s, 2H), 3.59 (s, 2H), 3.63-3.79 (m, 4H), 5.47 (t, J=3.2 Hz, 1H), 6.56 (dd, J=3.2, 0.8 Hz, 1H), 7.19-7.27 (m, 2H), 7.34 (d, J=3.4 Hz, 1H), 7.49 (ddd, J=8.6, 0.8, 0.7 Hz, 1H), 7.63 (dd, J=8.5, 1.7 Hz, 1H), 7.71 (ddd, J=8.3, 2.0, 1.9 Hz, 2H), 8.04 (dd, J=1.7, 0.7 Hz, 1H). MS (+ESI) m/z=353 (M+H)$^+$. Anal. Calcd. for C$_{19}$H$_{20}$N$_4$OS.C$_7$H$_8$O$_3$S.0.2H$_2$O: C, 59.12; H, 5.42; N, 10.61. Found: C, 58.77; H, 5.11; N, 10.35.

Example 51

(4s)-4-[5-(1H-Indol-6-yl)-1,3,4-thiadiazol-2-yloxy]-1-azatricyclo[3.3.1.1$^{3,7}$]decane p-toluenesulfonate Example 51A (4s)-4-[5-(1H-Indol-6-yl)-1,3,4-thiadiazol-2-yloxy]-1-azatricyclo[3.3.1.1$^{3,7}$]decane Prepared from the product of Example 41B (100 mg, 0.316 mmol) and indole-6-boronic acid (102 mg, 0.632 mmol; Frontier) according to Method F: $^1$H NMR (300 MHz, methanol-D4) δ ppm 1.71 (s, 1H), 1.92 (d, J=12.2 Hz, 2H), 2.26-2.37 (m, 5H), 3.12-3.22 (m, 5H), 5.33 (t, J=3.1 Hz, 1H), 6.52 (d, J=3.1 Hz, 1H), 7.39 (d, J=3.1 Hz, 1H), 7.47 (dd, J=8.3, 1.5 Hz, 1H), 7.64 (d, J=8.1 Hz, 1H), 7.87-7.92 (m, 1H). MS (+ESI) m/z=353 (M+H)$^+$.

Example 51B (4s)-4-[5-(1H-Indol-6-yl)-1,3,4-thiadiazol-2-yloxy]-1-azatricyclo[3.3.1.1$^{3,7}$]decane p-toluenesulfonate Prepared from the product of Example 51A (18 mg, 0.052 mmol) according to Method H: $^1$H NMR (300 MHz, methanol-D4) δ ppm 1.99 (d, J=12.5 Hz, 2H), 2.22 (s, 1H), 2.30-2.41 (m, 5H), 2.73 (s, 2H), 3.59 (s, 2H), 3.64-3.78 (m, 4H), 5.49 (t, J=3.4 Hz, 1H), 6.53 (dd, J=3.2, 0.8 Hz, 1H), 7.23 (d, J=7.8 Hz, 2H), 7.40 (d, J=3.1 Hz, 1H), 7.48 (dd, J=8.1, 1.7 Hz, 1H), 7.65 (d, J=8.5 Hz, 1H), 7.71 (ddd, J=8.3, 2.0, 1.9 Hz, 2H), 7.89-7.92 (m, 1H). MS (+ESI) m/z=353 (M+H)$^+$. Anal. Calcd. for C$_{19}$H$_{20}$N$_4$OS.C$_7$H$_8$O$_3$S.1.5H$_2$O: C, 56.61; H, 5.66; N, 10.16. Found: C, 56.65; H, 5.49; N, 9.89.

Example 52

(4s)-4-[5-(1H-Indol-4-yl)-1,3,4-thiadiazol-2-yloxy]-1-azatricyclo[3.3.1.1$^{3,7}$]decane p-toluenesulfonate The free base of the title compound was prepared from the product of Example 41B (190 mg, 0.60 mmol) and indole-4-boronic acid (192 mg, 1.19 mmol; Frontier) according to Method F, and converted to the p-toluenesulfonate salt using the procedure of Method H: $^1$H NMR (300 MHz, methanol-D4) δ ppm 1.96 (d, J=12.5 Hz, 2H), 2.19 (s, 1H), 2.33 (d, J=13.5 Hz, 2H), 2.36 (s, 3H), 2.64 (s, 2H), 3.52-3.77 (m, 6H), 5.36 (s, 1H), 7.04 (d, J=3.0 Hz, 1H), 7.17-7.27 (m, 3H), 7.43 (d, J=3.4 Hz, 1H), 7.49 (d, J=6.7 Hz, 1H), 7.58 (d, J=8.1 Hz, 1H), 7.70 (d, J=8.1 Hz, 2H). MS (DCI/NH$_3$) m/z=354 (M+H)$^+$. Anal. Calcd. for C$_{19}$H$_{20}$N$_4$OS.C$_7$H$_8$O$_3$S: C, 59.92; H, 5.38; N, 10.68. Found: C, 56.90; H, 5.11; N, 10.13.

Example 53

(4s)-4-[5-(Benzothien-5-yl)-1,3,4-thiadiazol-2-yloxy]-1-azatricyclo[3.3.1.1$^{3,7}$]decane p-toluenesulfonate The free base of the title compound was prepared from the product of Example 41B (193 mg, 0.60 mmol) and 2-(benzo[b]thiophen-5-yl)-4,4,5,5-tetramethyl-1,3,2-dioxaborolane (317 mg, 0.74 mmol; Maybridge) according to Method F, and converted to the p-toluenesulfonate salt using the procedure of Method H: $^1$H NMR (300 MHz, methanol-D4) δ ppm 1.96 (d, J=12.5 Hz, 2H), 2.19 (s, 1H), 2.33 (d, J=13.6 Hz, 2H), 2.36 (s, 3H), 2.64 (s, 2H), 3.52-3.77 (m, 6H), 5.36 (s, 1H), 7.22 (d, J=8.8 Hz, 2H), 7.49 (d, J=5.4 Hz, 1H), 7.67-7.75 (m, 3H), 7.85 (dd, J=8.4, 1.7 Hz, 1H), 8.05 (d, J=8.8 Hz, 1H), 8.32 (d, J=1.7 Hz, 1H). MS (DCI/NH$_3$) m/z=370 (M+H)$^+$. Anal. Calcd. for C$_{19}$H$_{19}$N$_3$OS$_2$.C$_7$H$_8$O$_3$S: C, 57.65; H, 5.02; N, 7.76. Found: C, 56.45; H, 4.59; N, 7.45.

Example 54

(4s)-4-[5-(Pyrazol-4-yl)-1,3,4-thiadiazol-2-yloxy]-1-azatricyclo[3.3.1.1$^{3,7}$]decane bis(p-toluenesulfonate)

Example 54A (4s)-4-[5-(1-Trityl-1H-pyrazol-4-yl)-1,3,4-thiadiazol-2-yloxy]-1-azatricyclo[3.3.1.1$^{3,7}$]decane Prepared from the product of Example 41B (120 mg, 0.38 mmol) and 4-(4,4,5,5-tetramethyl-1,3,2-dioxaborolan-2-yl)-1-trityl-1H-pyrazole (335 mg, 0.77 mmol; JP 2005232071)

according to Method F: $^1$H NMR (300 MHz, chloroform-D) δ ppm 1.70 (s, 1H), 1.96-2.08 (m, 2H), 2.12-2.23 (m, 4H), 3.01 (d, J=12.9 Hz, 2H), 3.16 (s, 2H), 3.49 (d, J=13.2 Hz, 2H), 5.46 (s, 1H), 7.16 (dd, J=6.8, 3.0 Hz, 6H), 7.29-7.38 (m, 9H), 7.87 (s, 1H), 7.95 (s, 1H). MS (DCI/NH$_3$) m/z=546 (M+H)$^+$.

Example 54B (4s)-4-[5-(Pyrazol-4-yl)-1,3,4-thiadiazol-2-yloxy]-1-azatricyclo[3.3.1.1$^{3,7}$]decane bis(p-toluenesulfonate)

The free base of the title compound was prepared from the product of Example 54A (100 mg, 0.18 mmol) according to Method L, and then converted to the p-toluenesulfonate salt using the procedure of Method H: $^1$H NMR (300 MHz, methanol-D4) δ ppm 1.99 (d, J=13.6 Hz, 2H), 2.21 (s, 1H), 2.32 (s, 2H), 2.36 (s, 3H), 2.73 (s, 2H), 3.52-3.81 (m, 6H), 5.52 (s, 1H), 7.23 (d, J=8.1 Hz, 2H), 7.71 (d, J=8.1 Hz, 2H), 8.09 (br.s, 2H). MS (DCI/NH$_3$) m/z=304 (M+H)$^+$. Anal. Calcd. for C$_{14}$H$_{17}$N$_5$OS.C$_7$H$_8$O$_3$S: C, 53.03; H, 5.30; N, 14.73. Found: C, 52.48; H, 5.03; N, 14.46.

Example 55

(4s)-4-(5-Phenoxy-1,3,4-thiadiazol-2-yloxy)-1-azatricyclo[3.3.1.1$^{3,7}$]decane p-toluenesulfonate Example 55A 2-Bromo-5-phenoxy-1,3,4-thiadiazole A solution of 2,5-dibromo-1,3,4-thiadiazole (1.00 g, 4.10 mmol; prepared as described in Yasuda, T.; Imase, T.; Sasaki, S.; Yamamoto, T. Macromolecules 2005, 38, 1500) and phenol (188 mg, 2.00 mmol; Aldrich) in anhydrous tetrahydrofuran (4 mL) was treated with cesium carbonate (2.0 g, 6.0 mmol) and heated to reflux for 5 hours. The mixture was cooled to room temperature, diluted with chloroform, filtered through Celite, and the residue was purified by flash chromatography (Analogix 40×120 mm 80 g silica gel column, chloroform) to afford the title compound: $^1$H NMR (300 MHz, chloroform-D) δ ppm 7.28-7.35 (m, 3H), 7.41-7.49 (m, 2H). MS (+ESI) m/z=257/259 (M+H)$^+$.

Example 55B (4s)-4-(5-Phenoxy-1,3,4-thiadiazol-2-yloxy)-1-azatricyclo[3.3.1.1$^{3,7}$]decane The coupling of the product of Example 10A (100 mg, 0.599 mmol) and the product of Example 55A (180 mg, 0.700 mmol) was performed according to Method A, and the resulting product was converted to the title compound using the procedures of Method C followed by using the procedure of Method H: $^1$H NMR (300 MHz, methanol-D4) δ ppm 1.95 (d, J=13.2 Hz, 2H), 2.18 (s, 1H), 2.29 (d, J=13.9 Hz, 2H), 2.36 (s, 3H), 2.66 (s, 2H), 3.56 (s, 2H), 3.58-3.74 (m, 4H), 5.41 (t, J=3.4 Hz, 1H), 7.19-7.26 (m, 2H), 7.28-7.36 (m, 3H), 7.43-7.51 (m, 2H), 7.68-7.73 (m, 2H). MS (+ESI) m/z=330 (M+H)$^+$. Anal. Calcd. for C$_{17}$H$_{19}$N$_3$O$_2$S.C$_7$H$_8$O$_3$S.0.5H$_2$O: C, 56.45; H, 5.53; N, 8.23. Found: C, 56.11; H, 5.38; N, 8.02.

Example 56

(4s)-4-(5-tert-Butyl-1,3,4-thiadiazol-2-yloxy)-1-azatricyclo[3.3.1.1$^{3,7}$]decane p-toluenesulfonate Example 56A (4s)-4-(5-tert-Butyl-1,3,4-thiadiazol-2-yloxy)-1-azatricyclo[3.3.1.1$^{3,7}$]decane N-borane complex Prepared from the product from Example 10A (515 mg, 3.1 mmol) and 2-bromo-5-tert-butyl-1,3,4-thiadiazole (682 mg, 3.1 mmol; see JP 58140084) according to Method A: $^1$H NMR (300 MHz, methanol-D4) δ ppm 1.26 (s, 1H), 1.42 (s, 9H), 1.74 (d, J=12.2 Hz, 2H), 2.05 (s, 1H), 2.22 (d, J=13.2 Hz, 1H), 2.54 (s, 2H), 3.17-3.33 (m, 6H), 5.33-5.47 (m, 1H). MS (DCI/NH$_3$) m/z=308 (M+H)$^+$.

Example 56B (4s)-4-(5-tert-Butyl-1,3,4-thiadiazol-2-yloxy)-1-azatricyclo[3.3.1.1$^{3,7}$]decane p-toluenesulfonate The free base of the title compound was prepared from the product of Example 56A (929 mg, 3.02 mmol) according to Method C, and then converted to the p-toluenesulfonate salt using the procedure of Method H: $^1$H NMR (300 MHz, methanol-D4) δ ppm 1.42 (s, 9H) 1.99 (d, J=13.6 Hz, 2H), 2.21 (s, 1H), 2.32 (s, 2H), 2.36 (s, 3H), 2.73 (s, 2H), 3.52-3.81 (m, 6H), 5.52 (s, 1H), 7.23 (d, J=7.8 Hz, 2H), 7.70 (d, J=8.1 Hz, 2H). MS (DCI/NH$_3$) m/z=294 (M+H)$^+$. Anal. Calcd. for C$_{15}$H$_{23}$N$_3$OS.C$_7$H$_8$O$_3$S: C, 56.75; H, 6.71; N, 9.02. Found: C, 56.62; H, 6.81; N, 8.98.

Example 57

(4r)-4-(5-tert-Butyl-1,3,4-thiadiazol-2-yloxy)-1-azatricyclo[3.3.1.1$^{3,7}$]decane p-toluenesulfonate Example 57A (4r)-4-(5-tert-Butyl-1,3,4-thiadiazol-2-yloxy)-1-azatricyclo[3.3.1.1$^{3,7}$]decane N-borane complex Prepared from the product from Example 9D (200 mg, 1.2 mmol) and 2-bromo-5-tert-butyl-1,3,4-thiadiazole (270 mg, 1.2 mmol; see JP 58140084) according to Method A: $^1$H NMR (300 MHz, chloroform-D) δ ppm 1.42 (s, 9H), 1.70 (s, 1H), 1.96-2.08 (m, 2H), 2.12-2.23 (m, 4H), 3.01 (d, J=12.9 Hz, 2H), 3.16 (s, 2H), 3.49 (d, J=13.2 Hz, 2H), 5.46 (s, 1H). MS (DCI/NH$_3$) m/z=308 (M+H)$^+$.

Example 57B (4r)-4-(5-tert-Butyl-1,3,4-thiadiazol-2-yloxy)-1-azatricyclo[3.3.1.1$^{3,7}$]decane p-toluenesulfonate The free base of the title compound was prepared from the product of Example 57A (106 mg, 0.34 mmol) according to Method C, and then converted to the p-toluenesulfonate salt using the procedure of Method H: $^1$H NMR (300 MHz, methanol-D4) δ ppm 1.42 (s, 9H), 2.05-2.32 (m, 5H), 2.36 (s, 3H), 2.71 (s, 2H), 3.42-3.63 (m, 4H), 3.81 (d, J=12.5 Hz, 2H), 5.41 (s, 1H), 7.23 (d, J=7.8 Hz, 2H), 7.70 (d, J=8.1 Hz, 2H).

MS (DCI/NH$_3$) m/z=294 (M+H)$^+$. Anal. Calcd. for C$_{15}$H$_{23}$N$_3$OS.C$_7$H$_8$O$_3$S: C, 56.75; H, 6.71; N, 9.02. Found: C, 54.04; H, 6.43; N, 8.41.

Example 58

(4s)-4-(5-Phenyl-1,3,4-oxadiazol-2-yloxy)-1-azatricyclo[3.3.1.1$^{3,7}$]decane p-toluenesulfonate

Example 58A (4s)-4-(5-Phenyl-1,3,4-oxadiazol-2-yloxy)-1-azatricyclo[3.3.1.1$^{3,7}$]decane N-borane complex Prepared from the product of Example 10A (100 mg, 0.599 mmol) and 2-bromo-5-phenyl-1,3,4-oxadiazole (148 mg, 0.658 mmol; Vachl, P.; Toth, L. M. Tetrahedron Lett. 2004, 45, 7157) according to Method A, followed by conversion to the free amine using the procedure of Method C: $^1$H NMR (300 MHz, methanol-D4) δ ppm 1.71 (s, 1H), 1.94 (d, J=13.6 Hz, 2H), 2.25-2.37 (m, 4H), 3.09-3.21 (m, 4H), 5.25 (t, J=3.2 Hz, 1H), 7.49-7.59 (m, 3H), 7.90-7.99 (m, 2H). MS (+ESI) m/z=298 (M+H)$^+$.

Example 58B (4s)-4-(5-Phenyl-1,3,4-oxadiazol-2-yloxy)-1-azatricyclo[3.3.1.1$^{3,7}$]decane p-toluenesulfonate Prepared from the product of Example 58A (77 mg, 1.77 mmol) according to Method H: $^1$H NMR (300 MHz, methanol-D4) δ ppm 2.00 (d, J=13.6 Hz, 2H), 2.23 (s, 1H), 2.30-2.41 (m, 5H), 2.73 (s, 2H), 3.60 (s, 2H), 3.63-3.80 (m, 4H), 5.36 (t, J=3.4 Hz, 1H), 7.23 (d, J=7.8 Hz, 2H), 7.51-7.63 (m, 3H), 7.67-7.74 (m, 2H), 7.92-7.99 (m, 2H). MS (+ESI) m/z=298 (M+H)$^+$.

Example 59

(4r)-4-(5-Phenyl-1,3,4-oxadiazol-2-yloxy)-1-azatricyclo[3.3.1.1$^{3,7}$]decane p-toluenesulfonate

Example 59A (4r)-4-(5-Phenyl-1,3,4-oxadiazol-2-yloxy)-1-azatricyclo[3.3.1.1$^{3,7}$]decane N-borane complex Prepared from the product of Example 9D (100 mg, 0.599 mmol) and 2-bromo-5-phenyl-1,3,4-oxadiazole (148 mg, 0.658 mmol; Vachl, P.; Toth, L. M. Tetrahedron Lett. 2004, 45, 7157) according to Method A, followed by conversion to the free amine using the procedure of Method C: $^1$H NMR (300 MHz, methanol-D4) δ ppm 1.76 (s, 1H), 2.05 (d, J=11.9 Hz, 2H), 2.19-2.30 (m, 4H), 3.05 (d, J=12.9 Hz, 2H), 3.17 (s, 2H), 3.46 (d, J=13.2 Hz, 2H), 5.27 (s, 1H), 7.49-7.59 (m, 3H), 7.91-7.97 (m, 2H). MS (+ESI) m/z=298 (M+H)$^+$.

Example 59B (4r)-4-(5-Phenyl-1,3,4-oxadiazol-2-yloxy)-1-azatricyclo[3.3.1.1$^{3,7}$]decane p-toluenesulfonate Prepared from the product of Example 59A (45 mg, 0.15 mmol) according to Method H: $^1$H NMR (300 MHz, methanol-D4) δ ppm 2.05-2.17 (m, 2H), 2.21-2.34 (m, 3H), 2.36 (s, 3H), 2.73 (s, 2H), 3.53 (d, J=12.5 Hz, 2H), 3.59 (s, 2H), 3.82 (d, J=12.5 Hz, 2H), 5.27 (t, J=3.6 Hz, 1H), 7.23 (d, J=7.8 Hz, 2H), 7.50-7.63 (m, 3H), 7.70 (d, J=8.5 Hz, 2H), 7.90-7.98 (m, 2H). MS (+ESI) m/z=298 (M+H)$^+$. Anal. Calcd. for C$_{17}$H$_{19}$N$_3$O$_2$: C, 61.39; H, 5.80; N, 8.95. Found: C, 61.11; H, 5.83; N, 8.91.

Example 60

(4s)-4-(Benzothiazol-2-yloxy)-1-azatricyclo[3.3.1.1$^{3,7}$]decane p-toluenesulfonate

Example 60A (4s)-4-(Benzothiazol-2-yloxy)-1-azatricyclo[3.3.1.1$^{3,7}$]decane N-borane complex Prepared from the product of Example 10A (100 mg, 0.599 mmol) and 2-chlorobenzothiazole (102 mg, 0.599 mmol; Aldrich) according to Method A: $^1$H NMR (300 MHz, chloroform-D) δ ppm 1.71 (d, J=12.9 Hz, 2H), 2.00-2.07 (m, 1H), 2.25 (d, J=13.2 Hz, 2H), 2.50 (s, 2H), 3.18-3.35 (m, 6H), 5.43 (t, J=3.4 Hz, 1H), 7.21-7.28 (m, 1H), 7.34-7.41 (m, 1H), 7.63-7.68 (m, 2H). MS (+ESI) m/z=301 (M+H)$^+$.

Example 60B (4s)-4-(Benzothiazol-2-yloxy)-1-azatricyclo[3.3.1.1$^{3,7}$]decane Prepared from the product of Example 60A (180 mg, 0.60 mmol) according to Method C: $^1$H NMR (300 MHz, methanol-D4) δ ppm 1.70 (s, 1H), 1.86-1.95 (m, 2H), 2.23-2.35 (m, 4H), 3.13-3.22 (m, 4H), 5.43 (t, J=3.1 Hz, 1H), 7.25 (ddd, J=8.3, 7.0, 1.0 Hz, 1H), 7.37 (td, J=7.7, 1.2 Hz, 1H), 7.59-7.64 (m, 1H), 7.70-7.75 (m, 1H). MS (+ESI) m/z=287 (M+H)$^+$.

Example 60C (4s)-4-(Benzothiazol-2-yloxy)-1-azatricyclo[3.3.1.1$^{3,7}$]decane p-toluenesulfonate Prepared from the product of Example 60B (131 mg, 0.457 mmol) according to Method H: $^1$H NMR (300 MHz, methanol-D4) δ ppm 1.97 (d, J=12.5 Hz, 2H), 2.21 (s, 1H), 2.28-2.39 (m, 5H), 2.71 (s, 2H), 3.59 (s, 2H), 3.64-3.78 (m, 4H), 5.57 (t, J=3.6 Hz, 1H), 7.22 (d, J=8.1 Hz, 2H), 7.28 (td, J=7.6, 1.4 Hz, 1H), 7.40 (td, J=7.6, 1.4 Hz, 1H), 7.61-7.65 (m, 1H), 7.71 (dt, J=8.4, 1.9 Hz, 2H), 7.74-7.78 (m, 1H). MS (+ESI) m/z=287 (M+H)$^+$. Anal. Calcd. for C$_{16}$H$_{18}$N$_2$OS.C$_7$H$_8$O$_3$S.0.2H$_2$O: C, 59.77; H, 5.76; N, 6.06. Found: C, 59.63; H, 5.81; N, 5.76.

Example 61

(4r)-4-(Benzothiazol-2-yloxy)-1-azatricyclo[3.3.1.1$^{3,7}$]decane p-toluenesulfonate

Example 61A (4r)-4-(Benzothiazol-2-yloxy)-1-azatricyclo[3.3.1.1$^{3,7}$]decane N-borane complex Prepared from the product of Example 9D (100 mg, 0.599 mmol) and 2-chlorobenzothiazole (102 mg, 0.599 mmol; Aldrich) according to Method A: $^1$H NMR (300 MHz, chloroform-D) δ ppm 1.90-2.09 (m, 5H), 2.46 (s, 2H), 2.99 (d, J=12.9 Hz, 2H), 3.14 (s, 2H), 3.48 (d, J=13.2 Hz, 2H), 5.33 (t, J=3.2 Hz, 1H), 7.24 (ddd, J=8.3, 7.0, 1.0 Hz, 1H), 7.33-7.41 (m, 1H), 7.62-7.69 (m, 2H). MS (+ESI) m/z=287 (M+H)$^+$.

Example 61B (4r)-4-(Benzothiazol-2-yloxy)-1-azatricyclo[3.3.1.1$^{3,7}$]decane Prepared from the product of Example 61A (180 mg, 0.60 mmol) according to Method C: $^1$H NMR (300 MHz, methanol-D4) δ ppm 1.72-1.80 (m, 1H), 2.02-2.14 (m, 2H), 2.15-2.29 (m, 4H), 3.03 (dd, J=13.1, 1.2 Hz, 2H), 3.16 (s, 2H), 3.46 (d, J=13.2 Hz, 2H), 5.41-5.48 (m, 1H), 7.25 (td, J=7.7, 1.2 Hz, 1H), 7.37 (td, J=7.8, 1.4 Hz, 1H), 7.62 (dt, J=8.1, 0.7 Hz, 1H), 7.72 (dd, J=7.6, 1.2 Hz, 1H) MS (+ESI) m/z=287 (M+H)$^+$.

Example 61C (4r)-4-(Benzothiazol-2-yloxy)-1-azatricyclo[3.3.1.1$^{3,7}$]decane p-toluenesulfonate Prepared from the product of Example 61B (123 mg, 0.429 mmol) according to Method H: $^1$H NMR (300 MHz, methanol-D4) δ ppm 2.07-2.19 (m, 2H), 2.20-2.31 (m, 3H), 2.36 (s, 3H), 2.69 (s, 2H), 3.50 (d, J=12.5 Hz, 2H), 3.57 (s, 2H), 3.80 (d, J=12.5 Hz, 2H), 5.49 (t, J=3.4 Hz, 1H), 7.22 (d, J=8.1 Hz, 2H), 7.28 (td, J=7.6, 1.0 Hz, 1H), 7.40 (td, J=7.8, 1.4 Hz, 1H), 7.63-7.79 (m, 4H) MS (+ESI) m/z=287 (M+H)$^+$. Anal. Calcd. for $C_{16}H_{18}N_2OS \cdot C_7H_8O_3S$: C, 60.24; H, 5.71; N, 6.11. Found: C, 60.36; H, 5.73; N, 6.18.

Example 62

(4s)-4-(6-Chlorobenzothiazol-2-yloxy)-1-azatricyclo[3.3.1.1$^{3,7}$]decane p-toluenesulfonate

Example 62A (4s)-4-(6-Chlorobenzothiazol-2-yloxy)-1-azatricyclo[3.3.1.1$^{3,7}$]decane N-borane complex Prepared from the product of Example 10A (102 mg, 0.610 mmol) and 2,6-dichlorobenzothiazole (122 mg, 0.599 mmol; Aldrich) according to Method A: $^1$H NMR (300 MHz, chloroform-D) δ ppm 1.72 (d, J=12.2 Hz, 2H), 2.04 (s, 1H), 2.24 (d, J=12.9 Hz, 2H), 2.48 (s, 2H), 3.17-3.34 (m, 6H), 5.41 (t, J=3.6 Hz, 1H), 7.33 (dd, J=9.0, 2.2 Hz, 1H), 7.56 (d, J=8.5 Hz, 1H), 7.63 (d, J=2.0 Hz, 1H). MS (+ESI) m/z=335/337 (M+H)$^+$.

Example 62B (4s)-4-(6-Chlorobenzothiazol-2-yloxy)-1-azatricyclo[3.3.1.1$^{3,7}$]decane Prepared from the product of Example 62A (184 mg, 0.55 mmol) according to Method C: $^1$H NMR (300 MHz, chloroform-D) δ ppm 1.65 (s, 1H), 1.79-1.89 (m, 2H), 2.19-2.35 (m, 4H), 3.12-3.22 (m, 4H), 3.27-3.36 (m, 2H), 5.43 (t, J=3.2 Hz, 1H), 7.31 (dd, J=8.6, 2.2 Hz, 1H), 7.55 (d, J=8.5 Hz, 1H), 7.61 (d, J=2.0 Hz, 1H).

Example 62C (4s)-4-(6-Chlorobenzothiazol-2-yloxy)-1-azatricyclo[3.3.1.1$^{3,7}$]decane p-toluenesulfonate Prepared from the product of Example 62B (138 mg, 0.430 mmol) according to Method H: $^1$H NMR (300 MHz, methanol-D4) δ ppm 1.97 (d, J=12.9 Hz, 2H), 2.21 (s, 1H), 2.27-2.39 (m, 5H), 2.71 (s, 2H), 3.58 (s, 2H), 3.63-3.78 (m, 4H), 5.58 (t, J=3.4 Hz, 1H), 7.22 (d, J=8.5 Hz, 2H), 7.39 (dd, J=8.6, 2.2 Hz, 1H), 7.59 (d, J=8.8 Hz, 1H), 7.70 (d, J=8.1 Hz, 2H), 7.82 (d, J=2.0 Hz, 1H). MS (+ESI) m/z=321/323 (M+H)$^+$. Anal. Calcd. for $C_{16}H_{17}ClN_2OS \cdot C_7H_8O_3S$: C, 56.03; H, 5.11; N, 5.68. Found: C, 56.12; H, 5.14; N, 5.65.

Example 63

(4r)-4-(6-Chlorobenzothiazol-2-yloxy)-1-azatricyclo[3.3.1.1$^{3,7}$]decane p-toluenesulfonate

Example 63A (4r)-4-(6-Chlorobenzothiazol-2-yloxy)-1-azatricyclo[3.3.1.1$^{3,7}$]decane N-borane complex Prepared from the product of Example 9D (102 mg, 0.610 mmol) and 2,6-dichlorobenzothiazole (122 mg, 0.599 mmol; Aldrich) according to Method A: $^1$H NMR (300 MHz, chloroform-D) δ ppm 1.88-2.10 (m, 5H), 2.45 (s, 2H), 2.99 (dd, J=13.2, 1.4 Hz, 2H), 3.14 (s, 2H), 3.46 (d, J=13.2 Hz, 2H), 5.31 (t, J=3.4 Hz, 1H), 7.33 (dd, J=8.5, 2.0 Hz, 1H), 7.55 (d, J=8.5 Hz, 1H), 7.64 (d, J=2.0 Hz, 1H). MS (+ESI) m/z=321/323 (M+H—BH$_3$)$^+$.

Example 63B (4r)-4-(6-Chlorobenzothiazol-2-yloxy)-1-azatricyclo[3.3.1.1$^{3,7}$]decane Prepared from the product of Example 63A (190 mg, 0.57 mmol) according to Method C: $^1$H NMR (300 MHz, chloroform-D) δ ppm 1.67-1.78 (m, 2H), 1.98-2.23 (m, 5H), 3.00 (dd, J=13.2, 1.0 Hz, 2H), 3.16 (s, 2H), 3.51 (d, J=13.2 Hz, 2H), 5.46 (s, 1H), 7.28-7.34 (m, 1H), 7.56 (d, J=8.8 Hz, 1H), 7.62 (d, J=2.7 Hz, 1H). MS (+ESI) m/z=321/323 (M+H)$^+$.

Example 63C (4r)-4-(6-Chlorobenzothiazol-2-yloxy)-1-azatricyclo[3.3.1.1$^{3,7}$]decane p-toluenesulfonate Prepared from the product of Example 63B (152 mg, 0.474 mmol) according to Method H: $^1$H NMR (300 MHz, methanol-D4) δ ppm 2.07-2.19 (m, 2H), 2.20-2.31 (m, 3H), 2.36 (s, 3H), 2.68 (s, 2H), 3.50 (d, J=11.9 Hz, 2H), 3.57 (s, 2H), 3.79 (d, J=12.5 Hz, 2H), 5.50 (t, J=3.4 Hz, 1H), 7.22 (d, J=7.8 Hz, 2H), 7.39 (dd, J=8.6, 2.2 Hz, 1H), 7.61 (d, J=8.8 Hz, 1H), 7.70 (ddd, J=8.3, 2.0, 1.9 Hz, 2H), 7.81 (d, J=2.4 Hz, 1H). MS (+ESI) m/z=321/323 (M+H)$^+$. Anal. Calcd. for $C_{16}H_{17}ClN_2OS \cdot C_7H_8O_3S \cdot 0.4H_2O$: C, 55.22; H, 5.20; N, 5.60. Found: C, 55.00; H, 5.19; N, 5.64.

Example 64

(4s)-4-(Benzoxazol-2-yloxy)-1-azatricyclo[3.3.1.1$^{3,7}$]decane p-toluenesulfonate

Example 64A (4s)-4-(Benzoxazol-2-yloxy)-1-azatricyclo[3.3.1.1$^{3,7}$]decane N-borane complex Prepared from the product of Example 10A (103 mg, 0.616 mmol) and 2-chlorobenzoxazole (100 mg, 0.86 mmol; Aldrich) according to Method A: ¹H NMR (300 MHz, chloroform-D) δ ppm 1.74 (d, J=12.2 Hz, 2H), 2.06 (s, 1H), 2.27 (d, J=12.9 Hz, 2H), 2.50 (s, 2H), 3.19-3.34 (m, 6H), 5.29 (t, J=3.4 Hz, 1H), 7.17-7.30 (m, 2H), 7.35-7.40 (m, 1H), 7.48 (dd, J=7.5, 1.7 Hz, 1H).

Example 64B (4s)-4-(Benzoxazol-2-yloxy)-1-azatricyclo[3.3.1.1$^{3,7}$]decane

Prepared from the product of Example 64A (141 mg, 0.496 mmol) according to Method D: ¹H NMR (300 MHz, methanol-D4) δ ppm 1.71 (s, 1H), 1.87-1.98 (m, 2H), 2.23-2.36 (m, 4H), 3.11-3.22 (m, 4H), 3.32-3.39 (m, 2H), 5.32 (t, J=2.9 Hz, 1H), 7.17-7.31 (m, 2H), 7.39-7.46 (m, 2H). MS (+ESI) m/z=271 (M+H)⁺.

Example 64C (4s)-4-(Benzothiazol-2-yloxy)-1-azatricyclo[3.3.1.1$^{3,7}$]decane p-toluenesulfonate Prepared from the product of Example 64B (124 mg, 0.459 mmol) and p-toluenesulfonic acid monohydrate (87 mg, 0.46 mmol; Aldrich) according to Method H: ¹H NMR (300 MHz, methanol-D4) δ ppm 2.00 (d, J=13.2 Hz, 2H), 2.23 (s, 1H), 2.29-2.41 (m, 5H), 2.72 (s, 2H), 3.60 (s, 2H), 3.63-3.80 (m, 4H), 5.43 (t, J=3.4 Hz, 1H), 7.18-7.34 (m, 4H), 7.45 (dd, J=7.5, 1.4 Hz, 2H), 7.71 (ddd, J=8.3, 2.0, 1.9 Hz, 2H). MS (+ESI) m/z=271 (M+H)⁺. Anal. Calcd. for C$_{16}$H$_{18}$N$_2$O$_2$·C$_7$H$_8$O$_3$S·H$_2$O: C, 59.98; H, 6.13; N, 6.08. Found: C, 59.77; H, 6.18; N, 6.33.

Example 65

(4s)-4-N-(6-Chloropyridin-3-yl)-1-azatricyclo[3.3.1.1$^{3,7}$]decan-4-amine hydrochloride Example 65A (4s)-4-N-(6-Chloropyridin-3-yl)-1-azatricyclo[3.3.1.1$^{3,7}$]decan-4-amine Example 65B (4r)-4-N-(6-Chloropyridin-3-yl)-1-azatricyclo[3.3.1.1$^{3,7}$]decan-4-amine A solution of 1-azatricyclo[3.3.1.1$^{3,7}$]decan-4-one (1.51 g, 10 mmol; see Becker, D. P.; Flynn, D. L. Synthesis 1992, 1080) in HOAc (50 mL) was treated with 3-amino-6-chloropyridine (1.90 g, 15 mmol; Aldrich), anhydrous Na$_2$SO$_4$ (18.5 g, 0.13 mol; Aldrich), and NaBH(OAc)$_3$ (4.22 g, 20 mmol; Aldrich) and was stirred at ambient temperature for 10 hours. After the reaction was complete, the solid was filtered off, and the filtrate was concentrated. The residue was carefully basified with saturated aqueous Na$_2$CO$_3$ (pH 10), extracted with CHCl$_3$ (3×100 mL), and the combined extracts were purified by flash chromatography [silica gel, ammonium hydroxide-methanol-chloroform (2:10:90)] to afford the title compounds:

Example 65A (4s) stereoisomer: ¹H NMR (300 MHz, methanol-D4) δ ppm 1.74-1.94 (m, 4H), 1.97-2.10 (m, 2H), 2.18-2.43 (m, 2H), 3.23-3.28 (m, 2H), 3.33-3.45 (m, 4H), 3.78 (s, 1H), 6.84-7.36 (m, 2H), 7.69-7.94 (m, 1H). MS (DCI/NH$_3$) m/z=264/266 (M+H)⁺.

Example 65B (4r) stereoisomer: ¹H NMR (300 MHz, methanol-D4) δ ppm 1.71-1.93 (m, 4H), 2.02-2.26 (m, 4H), 2.90-3.03 (m, 2H), 3.08-3.16 (m, 2H), 3.35-3.46 (m, 2H) 3.67 (s, 1H), 7.03-7.10 (m, 1H), 7.11-7.17 (m, 1H), 7.74 (d, J=3.05 Hz, 1H). MS (DCI/NH$_3$) m/z=264 (M+H)⁺.266 (M+H)⁺.

Example 65C (4s)-4-N-(6-Chloropyridin-3-yl)-1-azatricyclo[3.3.1.1$^{3,7}$]decan-4-amine hydrochloride Prepared from the product of Example 65A (100 mg, 0.38 mmol) according to Method H: ¹H NMR (300 MHz, methanol-D4) δ ppm 1.81-2.10 (m, 2H), 2.11-2.23 (m, 1H), 2.23-2.48 (m, 4H), 3.50-3.60 (m, 2H), 3.64-3.81 (m, 4H), 3.98 (s, 1H), 7.36-7.56 (m, 2H), 7.98 (d, J=2.7 Hz, 1H). MS (DCI/NH$_3$) m/z=264/266 (M+H)⁺. Anal. Calcd. for C$_{14}$H$_{18}$ClN$_3$·1.15HCl·1.65H$_2$O: C, 50.13; H, 6.75; N, 12.53. Found: C, 50.01; H, 6.35; N, 12.15.

Example 66

(4r)-4-N-(6-Chloropyridin-3-yl)-1-azatricyclo[3.3.1.1$^{3,7}$]decan-4-amine trihydrochloride Prepared from the product of Example 65B (100 mg, 0.38 mmol) according to Method H: ¹H NMR (300 MHz, methanol-D4) δ ppm 2.08-2.52 (m, 7H), 3.40-3.61 (m, 4H), 3.75-3.90 (m, 3H), 7.54-7.68 (m, 2H), 8.03 (d, J=3.0 Hz, 1H). MS (DCI/NH$_3$) m/z=264/266 (M+H)⁺. Anal. Calcd. for C$_{14}$H$_{18}$ClN$_3$·3.15HCl·1.2H$_2$O: C, 42.01; H, 5.93; N, 10.50. Found: C, 42.29; H, 5.56; N, 10.10.

Example 67

(4s)-4-N-(6-Phenylpyridin-3-yl)-1-azatricyclo[3.3.1.1$^{3,7}$]decan-4-amine dihydrochloride Example 67A (4s)-4-N-(6-Phenylpyridin-3-yl)-1-azatricyclo[3.3.1.1$^{3,7}$]decan-4-amine Prepared from the product of Example 65A (200 mg, 0.76 mmol) and phenylboronic acid (121 mg, 1.0 mmol; Aldrich) according to Method E: ¹H NMR (300 MHz, methanol-D4) δ ppm 1.58-1.77 (m, 1H), 1.78-1.92 (m, 2H), 1.90-2.02 (m, 2H), 2.16-2.42 (m, 3H), 3.06-3.41 (m, 7H), 3.75 (s, 1H), 7.17 (dd, J=8.6, 2.8 Hz, 1H), 7.26-7.34 (m, 1H), 7.59-7.70 (m, 3H), 7.73-7.83 (m, 2H), 8.09 (d, J=2.7 Hz, 1H). MS (DCI/NH$_3$) m/z=306 (M+H)⁺.

Example 67B (4s)-4-N-(6-Phenylpyridin-3-yl)-1-azatricyclo[3.3.1.1$^{3,7}$]decan-4-amine dihydrochloride Prepared from the product of Example 67A (150 mg, 0.49 mmol) according to Method H: ¹H NMR (300 MHz, methanol-D4) δ ppm 1.93-2.08 (m, 2H), 2.15-2.26 (m, 1H), 2.26-2.51 (m, 4H), 3.55-3.63 (m, 2H), 3.66-3.82 (m, 4H), 4.12-4.19 (m, 1H), 7.52-7.70 (m, 3H), 7.76-7.85 (m, 2H), 7.99 (dd, J=9.2, 2.7 Hz, 1H), 8.08 (d, J=9.2 Hz, 1H), 8.20 (d, J=2.7 Hz, 1H). MS (DCI/NH$_3$) m/z=306 (M+H)⁺. Anal. Calcd. for C$_{20}$H$_{23}$N$_3$·2HCl·0.9H$_2$O: C, 60.25; H, 7.08; N, 9.58. Found: C, 60.24; H, 6.92; N, 9.47.

Example 68

(4s)-4-N-[6-(Indol-5-yl)-pyridin-3-yl]-1-azatricyclo[3.3.1.1$^{3,7}$]decan-4-amine dihydrochloride

Example 68A (4s)-4-N-[6-(Indol-5-yl)-pyridin-3-yl]-1-azatricyclo[3.3.1.1$^{3,7}$]decan-4-amine Prepared from the product of Example 65A (200 mg, 0.76 mmol) and 5-indolylboronic acid (160 mg, 1.0 mmol; Aldrich) according to Method E: $^1$H NMR (300 MHz, methanol-D4) δ ppm 1.62-1.76 (m, 1H), 1.80-1.90 (m, 2H), 1.93-2.02 (m, 2H), 2.21-2.39 (m, 2H), 3.13-3.17 (m, 2H), 3.18-3.30 (m, 4H), 3.77-3.86 (m, 1H), 6.49 (d, J=4.0 Hz, 1H), 7.18 (dd, J=8.6, 2.8 Hz, 1H), 7.24 (d, J=3.4 Hz, 1H), 7.41 (d, J=8.4 Hz, 1H), 7.52-7.62 (m, 2H), 7.95 (s, 1H), 8.06 (d, J=2.4 Hz, 1H). MS (DCI/NH$_3$) m/z=345 (M+H)$^+$.

Example 68B (4s)-4-N-[6-(Indol-5-yl)-pyridin-3-yl]-1-azatricyclo[3.3.1.1$^{3,7}$]decan-4-amine dihydrochloride Prepared from the product of Example 68A (110 mg, 0.32 mmol) according to Method H: $^1$H NMR (300 MHz, methanol-D4) δ ppm 1.88-2.07 (m, 2H), 2.13-2.28 (m, 1H), 2.28-2.51 (m, 4H), 3.55-3.63 (m, 2H), 3.68-3.83 (m, 4H), 4.09-4.14 (m, 1H), 6.62 (d, J=3.0 Hz, 1H), 7.40 (d, J=3.0 Hz, 1H), 7.54 (dd, J=8.8, 2.1 Hz 1H), 7.60-7.65 (m, 1H), 7.97 (dd, J=9.2, 2.7 Hz 1H), 8.03-8.16 (m, 2H). MS (DCI/NH$_3$) m/z=345 (M+H)$^+$. Anal. Calcd. for C$_{20}$H$_{23}$N$_3$.2HCl.2.5H$_2$O: C, 57.14; H, 6.76; N, 12.12. Found: C, 57.22; H, 6.63; N, 11.77.

Example 69

(4s)-4-N-(5-Bromopyridin-3-yl)-1-azatricyclo[3.3.1.1$^{3,7}$]decan-4-amine dihydrochloride

Example 69A (4s)-4-N-(5-Bromopyridin-3-yl)-1-azatricyclo[3.3.1.1$^{3,7}$]decan-4-amine Prepared from 1-azatricyclo[3.3.1.1$^{3,7}$]decan-4-one (1.51 g, 10 mmol; see Becker, D. P.; Flynn, D. L. Synthesis 1992, 1080) and 3-amino-5-bromopyridine (2.06 g, 12 mmol; Aldrich) according to the procedure described in Example 65A: $^1$H NMR (300 MHz, methanol-D4) δ ppm 1.81-1.99 (m, 2H), 2.02-2.15 (m, 1H), 2.17-2.40 (m, 4H), 3.44-3.51 (m, 2H), 3.53-3.66 (m, 4H), 3.91 (s, 1H), 7.26-7.41 (m, 1H), 7.84 (d, J=1.7 Hz, 1H), 8.01 (d, J=2.7 Hz, 1H). MS (DCI/NH$_3$) m/z=308/310 (M+H)$^+$.

Example 69B (4s)-4-N-(5-Bromopyridin-3-yl)-1-azatricyclo[3.3.1.1$^{3,7}$]decan-4-amine dihydrochloride Prepared from the product of Example 69A (50 mg, 0.16 mmol) according to Method H: $^1$H NMR (300 MHz, methanol-D4) δ ppm 1.89-2.04 (m, 2H), 2.15-2.49 (m, 5H), 3.53-3.61 (m, 2H), 3.64-3.81 (m, 4H), 4.08 [s (br.), 1H], 8.03 (dd, J=2.37, 1.70 Hz, 1H), 8.20 (d, J=1.36 Hz, 1H), 8.28 (d, J=2.37 Hz, 1H). MS (DCI/NH$_3$) m/z=308/310 (M+H)$^+$. Anal. Calcd. for C$_{14}$H$_{18}$BrN$_3$.2HCl.1.1H$_2$O: C, 41.94; H, 5.58; N, 10.48. Found: C, 42.13; H, 5.26; N, 10.13.

Example 70

(4s)-4-N-[5-(Indol-5-yl)-pyridin-3-yl]-1-azatricyclo[3.3.1.1$^{3,7}$]decan-4-amine Prepared from the product of Example 69A (150 mg, 0.50 mmol) and 5-indolylboronic acid (160 mg, 1.0 mmol; Aldrich) according to Method E: $^1$H NMR (300 MHz, methanol-D4) δ ppm 1.59-1.77 (m, 1H), 1.79-1.93 (m, 2H), 1.93-2.07 (m, 2H), 2.28-2.32 (m, 2H), 3.10-3.32 (m, 6H), 3.88 (s, 1H), 6.51 (dd, J=3.0, 0.7 Hz, 1H), 7.27 (d, J=3.4 Hz, 1H), 7.30-7.34 (m, 1H), 7.36 (d, J=1.7 Hz, 1H), 7.47 (d, J=8.3 Hz, 1H), 7.78 (d, J=1.0 Hz, 1H), 7.93 (d, J=2.4 Hz, 1H), 8.03 (d, J=1.7 Hz, 1H). MS (DCI/NH$_3$) m/z=345 (M+H)$^+$.

Example 71

(4s)-4-N-[5-(Indol-6-yl)-pyridin-3-yl]-1-azatricyclo[3.3.1.1$^{3,7}$]decan-4-amine bis(trifluoroacetate)

Prepared from the product of Example 69A (100 mg, 0.325 mmol) and 6-indolylboronic acid (130 mg, 0.807 mmol; Frontier) according to Method F, with HPLC purification using the acidic conditions to afford the trifluoroacetate salt: $^1$H NMR (300 MHz, methanol-D4) δ ppm 1.95-2.04 (m, 2H), 2.18-2.45 (m, 5H), 3.59 (m, 2H), 3.72 (m, 4H), 4.15 (s, 1H), 6.53 (dd, J=3.2, 0.8 Hz, 1H), 7.33-7.41 (m, 2H), 7.68-7.77 (m, 2H), 8.03-8.07 (m, 1H), 8.10 (d, J=2.4 Hz, 1H), 8.32 (d, J=1.0 Hz, 1H). MS (DCI/NH$_3$) m/z=345 (M+H)$^+$. Anal. Calcd. for C$_{22}$H$_{24}$N$_4$.2.3C$_2$HF$_3$O$_2$.H$_2$O: C, 51.22; H, 4.41; N, 8.98. Found: C, 51.17; H, 4.75; N, 8.98.

Example 72

(4s)-4-N-[5-(Indol-4-yl)-pyridin-3-yl]-1-azatricyclo[3.3.1.1$^{3,7}$]decan-4-amine fumarate The free base of the title compound was prepared from the product of Example 69A (100 mg, 0.325 mmol) and 4-indolylboronic acid (130 mg, 0.807 mmol; Frontier) according to Method F, followed by conversion to the fumarate salt using the procedure of Method H: $^1$H NMR (300 MHz, methanol-D4) δ ppm 1.90-1.95 (m, 2H), 2.15-2.19 (m, 1H), 2.32-2.45 (m, 4H), 3.50-3.58 (m, 2H), 3.62-3.73 (m, 4H), 4.04 (s, 1H), 6.56 (dd, J=3.2, 0.8 Hz, 1H), 6.69 (s, 2H), 7.09 (dd, J=7.1, 1.0 Hz, 1H), 7.16-7.24 (m, 1H), 7.32 (d, J=3.4 Hz, 1H), 7.41-7.45 (m, 2H), 8.04 (d, J=2.7 Hz, 1H), 8.12 (d, J=1.7 Hz, 1H). MS (DCI/NH$_3$) m/z=345 (M+H)$^+$. Anal. Calcd. for C$_{22}$H$_{24}$N$_4$.1.5C$_4$H$_4$O$_4$.0.7H$_2$O: C, 63.31; H, 5.96; N, 10.55. Found: C, 63.05; H, 5.95; N, 10.74.

Example 73

(4s)-4-N-[5-(3-Methylphenyl)-pyridin-3-yl]-1-azatricyclo[3.3.1.1$^{3,7}$]decan-4-amine fumarate The free base of the title compound was prepared from product of Example 69A (100 mg, 0.325 mmol) and m-tolylboronic acid (110 mg, 0.808 mmol; Aldrich) according to Method F, followed by conversion to the fumarate salt using the procedure of Method H: $^1$H NMR (300 MHz, methanol-D4) δ ppm 1.83-1.98 (m, 2H), 2.08-2.26 (m, 1H), 2.27-2.40 (m, 4H), 2.41 (s, 3H), 3.50-3.59 (m, 2H), 3.60-3.80 (m, 4H), 3.97-4.08 (m, 1H), 6.70 (s, 2H), 7.17-7.59 (m, 5H), 7.93-8.18 (m, 2H). MS (DCI/NH$_3$) m/z=320 (M+H)$^+$. Anal. Calcd. for C$_{21}$H$_{25}$N$_3$.2C$_4$H$_4$O$_4$.1.6H$_2$O: C, 60.01; H, 6.29; N, 7.24. Found: C, 59.88; H, 6.55; N, 7.54.

Example 74

(4s)-4-N-[5-(3-Chlorophenyl)-pyridin-3-yl]-1-azatricyclo[3.3.1.1$^{3,7}$]decan-4-amine bis(trifluoroacetate)

Prepared from the product of Example 69A (100 mg, 0.325 mmol) and m-chlorophenylboronic acid (101 mg, 0.650 mmol; Aldrich) according to the procedure of Method F: $^1$H NMR (300 MHz, methanol-D4) δ ppm 1.86-2.06 (m, 2H), 2.15-2.26 (m, 1H), 2.26-2.54 (m, 4H), 3.53-3.65 (m, 2H), 3.64-3.83 (m, 4H), 4.14 (s, 1H), 7.48-7.58 (m, 2H), 7.60-7.70 (m, 1H), 7.74-7.80 (m, 1H), 7.89 (s, 1H), 8.10-8.24 (m, 2H). MS (DCI/NH$_3$) m/z=340/342 (M+H)$^+$. Anal. Calcd. for C$_{20}$H$_{22}$N$_3$Cl.2.5C$_2$F$_3$O$_2$H.1.2H$_2$O: C, 46.44; H, 4.19; N, 6.50. Found: C, 46.23; H, 4.17; N, 6.67.

Example 75

(4s)-4-N-[5-(3-Chlorophenylphen-3-yl)-pyridin-3-yl]-1-azatricyclo[3.3.1.1$^{3,7}$]decan-4-amine bis(trifluoroacetate)

Prepared from the product of Example 69A (100 mg, 0.325 mmol) and m-chlorophenylboronic acid (101 mg, 0.650 mmol; Aldrich) according to the procedure of Method F: $^1$H NMR (300 MHz, methanol-D4) δ ppm 1.88-2.11 (m, 2H), 2.15-2.28 (m, 1H), 2.27-2.49 (m, 4H), 3.54-3.64 (m, 2H), 3.65-3.87 (m, 4H), 4.07-4.28 (m, 1H), 7.36-7.44 (m, 1H), 7.48 (t, J=7.8 Hz, 1H), 7.61-7.70 (m, 2H), 7.71-7.76 (m, 2H), 7.78 (dt, J=7.7, 1.6 Hz, 1H), 7.94 (t, J=1.7 Hz, 1H), 8.00 (s, 1H), 8.19 (s, 1H), 8.37 (s, 1H). MS (DCI/NH$_3$) m/z=416/418 (M+H)$^+$. Anal. Calcd. for C$_{26}$H$_{26}$N$_3$Cl.2.2C$_2$HF$_3$O$_2$: C, 54.76; H, 4.26; N, 6.30. Found: C, 54.75; H, 4.15; N, 6.12.

Example 76

(4s)-4-(Pyridin-3-yloxy)-1-azatricyclo[3.3.1.1$^{3,7}$]decane hydrochloride

Example 76A (4s)-4-(Pyridin-3-yloxy)-1-azatricyclo[3.3.1.1$^{3,7}$]decane N-borane complex Prepared from the product of Example 10A (84.2 mg, 0.51 mmol) and 3-fluoropyridine (66 µL, 0.77 mmol) according to Method I: $^1$H NMR (300 MHz, chloroform-D) δ ppm 1.65-1.69 (m, 2H), 2.03 (br s, 1H), 2.26-2.31 (m, 4H), 3.19-3.27 (m, 6H), 4.58 (t, J=3.2 Hz, 1H), 7.23-7.24 (m, 2H), 8.25-8.27 (m, 1H), 8.34-8.36 (m, 1H). MS (DCI/NH$_3$) m/z=245 (M+H)$^+$.

Example 76B (4s)-4-(Pyridin-3-yloxy)-1-azatricyclo[3.3.1.1$^{3,7}$]decane hydrochloride Prepared from the product of Example 76A (69.8 mg, 0.27 mmol) according to Method J: $^1$H NMR (300 MHz, methanol-D4) δ ppm 1.94-1.99 (m, 2H), 2.22 (br s, 1H), 2.35-2.38 (m, 2H), 2.55 (br s, 2H), 3.60 (s, 2H), 3.64-3.77 (m, 4H), 5.15 (t, J=3.2 Hz, 1H), 8.02 (dd, J=9.0, 5.6 Hz, 1H), 8.34-8.38 (m, 1H), 8.50 (d, J=5.4 Hz, 1H), 8.77 (d, J=2.7 Hz, 1H). MS (DCI/NH$_3$) m/z=231 (M+H)$^+$. Anal. Calcd. for C$_{14}$H$_{18}$N$_2$O.2.05HCl: C, 55.12; H, 6.62; N, 9.18; Cl, 23.82. Found: C, 54.91; H, 6.79; N, 9.04; Cl, 23.59.

Example 77

(4s)-4-[(1-Oxidopyridin-3-yl)oxy]-1-azatricyclo[3.3.1.1$^{3,7}$]decane hydrochloride Example 77A (4s)-4-[(1-Oxidopyridin-3-yl)oxy]-1-azatricyclo[3.3.1.1$^{3,7}$]decane N-borane complex Prepared from the product of Example 10A (85.2 mg, 0.51 mmol) and 3-fluoropyridine N-oxide (87.2 mg, 0.77 mmol) according to Method I: $^1$H NMR (300 MHz, chloroform-D) δ ppm 1.67-1.71 (m, 2H), 2.03 (br s, 1H), 2.19-2.26 (m, 4H), 3.15-3.27 (m, 6H), 4.54 (t, J=3.4 Hz, 1H), 6.88 (dd, J=8.7, 2.4 Hz, 1H), 7.19 (dd, J=8.7, 6.4 Hz, 1H), 7.91-7.93 (m, 1H), 8.00 (t, J=2.0 Hz, 1H). MS (DCI/NH$_3$) m/z=261 (M+H)$^+$.

Example 77B (4s)-4-[(1-Oxidopyridin-3-yl)oxy]-1-azatricyclo[3.3.1.1$^{3,7}$]decane hydrochloride Prepared from the product of Example 77A (100.4 mg, 0.39 mmol) according to Method J: $^1$H NMR (300 MHz, methanol-D4) δ ppm 1.93-1.97 (m, 2H), 2.21 (br s, 1H), 2.33-2.38 (m, 2H), 2.53 (br s, 2H), 3.58 (s, 2H), 3.64-3.76 (m, 4H), 5.08 (t, J=3.4 Hz, 1H), 7.78 (dd, J=8.8, 6.1 Hz, 1H), 7.88 (ddd, J=8.8, 2.4, 1.0 Hz, 1H), 8.37 (ddd, J=6.1, 1.9, 1.0 Hz, 1H), 8.66 (app t, J=2.0 Hz, 1H). MS (DCI/NH$_3$) m/z=247 (M+H)$^+$. Anal. Calcd. for C$_{14}$H$_{18}$N$_2$O$_2$.2 HCl.0.6H$_2$O: C, 50.95; H, 6.47; N, 8.49; Cl, 21.48. Found: C, 51.18; H, 6.39; N, 8.48; Cl, 21.27.

Example 78

(4r)-4-(Pyridin-3-yloxy)-1-azatricyclo[3.3.1.1$^{3,7}$]decane hydrochloride

Example 78A (4r)-4-(Pyridin-3-yloxy)-1-azatricyclo[3.3.1.1$^{3,7}$]decane N-borane complex Prepared from the product of Example 9D (85.0 mg, 0.51 mmol) and 3-fluoropyridine (66 µL, 0.77 mmol) according to Method I: $^1$H NMR (300 MHz, chloroform-D) δ ppm 1.83-1.87 (m, 2H), 1.99-2.14 (m, 3H), 2.26 (br s, 2H), 2.29-2.96 (m, 2H), 3.12 (s, 2H), 3.49-3.53 (m, 2H), 4.44 (t, J=3.2 Hz, 1H), 7.23-7.24 (m, 2H), 8.26 (t, J=3.0 Hz, 1H), 8.33-8.34 (m, 1H). MS (DCI/NH$_3$) m/z=245 (M+H)$^+$.

Example 78B (4r)-4-(Pyridin-3-yloxy)-1-azatricyclo[3.3.1.1$^{3,7}$]decane hydrochloride Prepared from the product of Example 78A (81.0 mg, 0.33 mmol) according to Method J: $^1$H NMR (300 MHz, methanol-D4) δ ppm 2.12-2.16 (m, 2H), 2.25-2.29 (m, 2H), 2.54 (br s, 2H), 3.47-3.51 (m, 2H), 3.58 (s, 2H), 3.83-3.87 (m, 2H), 5.07 (t, J=3.4 Hz, 1H), 8.05 (dd, J=8.72, 5.55 Hz, 1H), 8.37-8.41 (m, 1H), 8.50-8.52 (m, 1H), 8.79 (d, J=2.78 Hz, 1H). MS (DCI/NH$_3$) m/z=231 (M+H)$^+$. Anal. Calcd. for C$_{14}$H$_{18}$N$_2$O.2.1HCl: C, 54.80; H, 6.60; N, 9.13; Cl, 24.26. Found: C, 54.72; H, 6.87; N, 9.06; Cl, 24.37.

Example 79

(4s)-4-[(2-Chloropyridin-3-yl)oxy]-1-azatricyclo[3.3.1.1$^{3,7}$]decane hydrochloride

Example 79A (4s)-4-[(2-Chloropyridin-3-yl)oxy]-1-azatricyclo[3.3.1.1$^{3,7}$]decane N-borane complex Prepared from the product of Example 10A (85.1 mg, 0.51 mmol) and 2-chloro-3-fluoropyridine (141.6 mg, 1.08 mmol) according to Method I: $^1$H NMR (300 MHz, chloroform-D) δ ppm 1.66-1.70 (m, 2H), 2.06 (br s, 1H), 2.26 (br s, 2H), 2.35-2.40 (m, 2H), 3.16-3.28 (m, 6H), 4.62 (t, J=3.4 Hz, 1H), 7.20-7.21 (m, 2H), 8.04-8.06 (m, 1H). MS (DCI/NH$_3$) m/z=294 (M+NH$_3$–H)$^+$.

Example 79B (4s)-4-[(2-Chloropyridin-3-yl)oxy]-1-azatricyclo[3.3.1.1$^{3,7}$]decane hydrochloride Prepared from the product of Example 79A (110.6 mg, 0.40 mmol) according to Method J: $^1$H NMR (300 MHz, methanol-D4) δ ppm 1.92-1.96 (m, 2H), 2.22 (br s, 1H), 2.41-2.48 (m, 4H), 3.58 (s, 2H), 3.62-3.74 (m, 4H), 5.02 (t, J=3.2 Hz, 1H), 7.38 (dd, J=8.3, 4.8 Hz, 1H), 7.69 (dd, J=8.1, 1.4 Hz, 1H), 8.01 (dd, J=4.8, 1.6 Hz, 1H). MS (DCI/NH$_3$) m/z=265 (M+H)$^+$. Anal. Calcd. for C$_{14}$H$_{17}$ClN$_2$O.1.65 HCl.0.4H$_2$O: C, 50.63; H, 5.90; N, 8.43; Cl, 28.29. Found: C, 50.80; H, 5.66; N, 8.43; Cl, 28.29.

Example 80

(4s)-4-[(2-Bromopyridin-3-yl)oxy]-1-azatricyclo[3.3.1.1$^{3,7}$]decane hydrochloride

Example 80A (4s)-4-[(2-Bromopyridin-3-yl)oxy]-1-azatricyclo[3.3.1.1$^{3,7}$]decane N-borane complex Prepared from the product of Example 10A (88.0 mg, 0.53 mmol) and 2-bromo-3-fluoropyridine (146.3 mg, 0.83 mmol) according to Method I: $^1$H NMR (300 MHz, chloroform-D) δ ppm 1.67-1.71 (m, 2H), 2.06 (br s, 1H), 2.27 (br s, 2H), 2.38-2.42 (m, 2H), 3.17-3.29 (m, 6H), 4.64 (t, J=3.4 Hz, 1H), 7.13-7.16 (m, 1H), 7.20-7.24 (m, 1H), 8.04 (dd, J=4.4, 1.6 Hz, 1H). MS (DCI/NH$_3$) m/z=323 (M+H)$^+$.

Example 80B (4s)-4-[(2-Bromopyridin-3-yl)oxy]-1-azatricyclo[3.3.1.1$^{3,7}$]decane hydrochloride Prepared from the product of Example 80A (92.7 mg, 0.29 mmol) according to Method J: $^1$H NMR (300 MHz, methanol-D4) δ ppm 1.92-1.96 (m, 2H), 2.22 (br s, 1H), 2.44-2.49 (m, 4H), 3.58 (s, 2H), 3.63-3.75 (m, 4H), 5.05 (t, J=3.2 Hz, 1H), 7.43 (dd, J=8.5, 4.8 Hz, 1H), 7.67 (dd, J=8.3, 1.5 Hz, 1H), 8.02 (dd, J=4.8, 1.4 Hz, 1H). MS (DCI/NH$_3$) m/z=309 (M+H)$^+$. Anal. Calcd. for C$_{14}$H$_{17}$BrN$_2$O.2HCl: C, 44.00; H, 5.01; N, 7.33. Found: C, 44.00; H, 5.16; N, 7.23.

Example 81

(4s)-4-[(4-Chloropyridin-3-yl)oxy]-1-azatricyclo[3.3.1.1$^{3,7}$]decane hydrochloride

Example 81A (4s)-4-[(4-Chloropyridin-3-yl)oxy]-1-azatricyclo[3.3.1.1$^{3,7}$]decane N-borane complex Prepared from the product of Example 10A (81.0 mg, 0.49 mmol) and 4-chloro-3-fluoropyridine (131.7 mg, 1.00 mmol) according to Method I: $^1$H NMR (300 MHz, chloroform-D) δ ppm 1.67-1.71 (m, 2H), 2.05 (br s, 1H), 2.31-2.38 (m, 4H), 3.16-3.28 (m, 6H), 4.69 (t, J=3.4 Hz, 1H), 7.36 (d, J=5.1 Hz, 1H), 7.19 (d, J=5.1 Hz, 1H), 8.29 (s, 1H). MS (DCI/NH$_3$) m/z=294 (M+NH$_3$–H)$^+$.

Example 81B (4s)-4-[(4-Chloropyridin-3-yl)oxy]-1-azatricyclo[3.3.1.1$^{3,7}$]decane hydrochloride Prepared from the product of Example 81A (88.6 mg, 0.32 mmol) according to Method J: $^1$H NMR (300 MHz, methanol-D4) δ ppm 1.96-2.00 (m, 2H), 2.24 (br s, 1H), 2.40-2.44 (m, 2H), 2.57 (br s, 2H), 3.60 (s, 2H), 3.66-3.77 (m, 4H), 5.21 (t, J=3.4 Hz, 1H), 7.98 (d, J=5.9 Hz, 1H), 8.40 (d, J=5.6 Hz, 1H), 8.80 (s, 1H). MS (DCI/NH$_3$) m/z=265 (M+H)$^+$. Anal. Calcd. for C$_{14}$H$_{17}$ClN$_2$O.1.75 HCl.1.65H$_2$O: C, 46.93; H, 6.20; N, 7.82; Cl, 27.21. Found: C, 47.03; H, 5.90; N, 7.82; Cl, 26.92.

Example 82

(4s)-4-[(4-Methylpyridin-3-yl)oxy]-1-azatricyclo[3.3.1.1$^{3,7}$]decane hydrochloride

Example 82A (4s)-4-[(4-Methylpyridin-3-yl)oxy]-1-azatricyclo[3.3.1.1$^{3,7}$]decane N-borane complex Prepared from the product of Example 10A (82.7 mg, 0.50 mmol) and 3-fluoro-4-methylpyridine (117.7 mg, 1.06 mmol) according to Method I: $^1$H NMR (300 MHz, chloroform-D) δ ppm 1.67-1.71 (m, 2H), 2.03 (br s, 1H), 2.24-2.31 (m, 7H), 3.19-3.28 (m, 6H), 4.65 (t, J=3.2 Hz, 1H), 7.11 (d, J=4.8 Hz, 1H), 8.13-8.14 (m, 2H). MS (DCI/NH$_3$) m/z=259 (M+H)$^+$.

Example 82B (4s)-4-[(4-Methylpyridin-3-yl)oxy]-1-azatricyclo[3.3.1.1$^{3,7}$]decane hydrochloride Prepared from the product of Example 82A (46.0 mg, 0.18 mmol) according to Method J: $^1$H NMR (300 MHz, methanol-D4) δ ppm 1.97-2.02 (m, 2H), 2.24 (br s, 1H), 2.34-2.38 (m, 2H), 2.58-2.60 (m, 5H), 3.60 (s, 2H), 3.69-3.79 (m, 4H), 5.18 (t, J=3.4 Hz, 1H), 7.93 (d, J=5.6 Hz, 1H), 8.40 (d, J=5.6 Hz, 1H), 8.73 (s, 1H). MS (DCI/NH$_3$) m/z=245 (M+H)$^+$.

Anal. Calcd. for $C_{15}H_{20}N_2O.2$ HCl.1.15$H_2O$: C, 53.31; H, 7.25; N, 8.29; Cl, 20.98. Found: C, 53.34; H, 7.27; N, 8.31; Cl, 20.81.

Example 83

(4s)-4-{[4-(Trifluoromethyl)pyridin-3-yl]oxy}-1-azatricyclo[3.3.1.1$^{3,7}$]decane hydrochloride Example 83A (4s)-4-{[4-(Trifluoromethyl)pyridin-3-yl]oxy}-1-azatricyclo[3.3.1.1$^{3,7}$]decane N-borane complex Prepared from the product of Example 10A (86.0 mg, 0.52 mmol) and 3-fluoro-4-(trifluoromethyl)pyridine (139.1 mg, 0.84 mmol) according to Method I: $^1$H NMR (300 MHz, chloroform-D) δ ppm 1.67-1.71 (m, 2H), 2.04 (br s, 1H), 2.26-2.35 (m, 4H), 3.20-3.31 (m, 6H), 4.82 (t, J=3.2 Hz, 1H), 7.50 (d, J=4.8 Hz, 1H), 8.39-8.43 (m, 2H). MS (DCI/NH$_3$) m/z=313 (M+H)$^+$.

Example 83B (4s)-4-{[4-(Trifluoromethyl)pyridin-3-yl]oxy}-1-azatricyclo[3.3.1.1$^{3,7}$]decane hydrochloride Prepared from the product of Example 83A (76.3 mg, 0.24 mmol) according to Method J: $^1$H NMR (300 MHz, methanol-D4) δ ppm 1.93-1.97 (m, 2H), 2.21 (br s, 1H), 2.33-2.38 (m, 2H), 2.57 (br s, 2H), 3.59 (s, 2H), 3.65-3.71 (m, 4H), 5.22 (t, J=3.2 Hz, 1H), 7.69 (d, J=4.8 Hz, 1H), 8.42 (d, J=4.8 Hz, 1H), 8.70 (s, 1H). MS (DCI/NH$_3$) m/z=299 (M+H)$^+$. Anal. Calcd. for $C_{15}H_{17}F_3N_2O.1.15$ HCl.0.55$H_2O$: C, 51.45; H, 5.54; N, 8.00; Cl, 11.64. Found: C, 51.60; H, 5.72; N, 8.03; Cl, 11.59.

Example 84

(4s)-4-[(5-Fluoropyridin-3-yl)oxy]-1-azatricyclo[3.3.1.1$^{3,7}$]decane hydrochloride Example 84A (4s)-4-[(5-Fluoropyridin-3-yl)oxy]-1-azatricyclo[3.3.1.1$^{3,7}$]decane N-borane complex Prepared from the product of Example 10A (84.2 mg, 0.50 mmol) and 3,5-difluoropyridine (100.2 mg, 0.87 mmol) according to Method I: $^1$H NMR (300 MHz, chloroform-D) δ ppm 1.66-1.71 (m, 2H), 2.03 (br s, 1H), 2.24-2.27 (m, 4H), 3.19-3.28 (m, 6H), 4.58 (t, J=3.2 Hz, 1H), 6.98 (dt, J=10.2, 2.4 Hz, 1H), 8.15 (d, J=2.4 Hz, 1H), 8.18-8.19 (m, 1H). MS (DCI/NH$_3$) m/z=263 (M+H)$^+$.

Example 84B (4s)-4-[(5-Fluoropyridin-3-yl)oxy]-1-azatricyclo[3.3.1.1$^{3,7}$]decane hydrochloride Prepared from the product of Example 84A (105.8 mg, 0.40 mmol) according to Method J: $^1$H NMR (300 MHz, methanol-D4) δ ppm 1.93-1.97 (m, 2H), 2.21 (br s, 1H), 2.34-2.39 (m, 2H), 2.54 (br s, 2H), 3.59 (s, 2H), 3.65-3.76 (m, 4H), 5.10 (t, J=3.2 Hz, 1H), 8.09 (dt, J=10.2, 2.4 Hz, 1H), 8.48 (dd, J=2.3, 1.4 Hz, 1H), 8.58 (d, J=2.3 Hz, 1H). MS (DCI/NH$_3$) m/z=249 (M+H)$^+$. Anal. Calcd. for $C_{14}H_{17}FN_2O.1.85$ HCl: C, 53.25; H, 6.02; N, 8.87; Cl, 20.77. Found: C, 53.03; H, 5.97; N, 8.87; Cl, 20.48.

Example 85

(4s)-4-[(5-Chloropyridin-3-yl)oxy]-1-azatricyclo[3.3.1.1$^{3,7}$]decane hydrochloride Example 85A (4s)-4-[(5-Chloropyridin-3-yl)oxy]-1-azatricyclo[3.3.1.1$^{3,7}$]decane N-borane complex Prepared from the product of Example 10A (85.9 mg, 0.51 mmol) and 3,5-dichloropyridine (108.0 mg, 0.73 mmol) according to Method I: $^1$H NMR (300 MHz, chloroform-D) δ ppm 1.66-1.70 (m, 2H), 2.03 (br s, 1H), 2.23-2.27 (m, 4H), 3.19-3.28 (m, 6H), 4.58 (t, J=3.2 Hz, 1H), 7.23-7.25 (m, 1H), 8.23-8.24 (m, 2H). MS (DCI/NH$_3$) m/z=279 (M+H)$^+$.

Example 85B (4s)-4-[(5-Chloropyridin-3-yl)oxy]-1-azatricyclo[3.3.1.1$^{3,7}$]decane hydrochloride Prepared from the product of Example 85A (57.7 mg, 0.21 mmol) according to Method J: $^1$H NMR (300 MHz, methanol-D4) δ ppm 1.92-1.96 (m, 2H), 2.21 (br s, 1H), 2.34-2.39 (m, 2H), 2.51 (br s, 2H), 3.58 (s, 2H), 3.63-3.75 (m, 4H), 5.06 (t, J=3.4 Hz, 1H), 8.09-8.10 (m, 1H), 8.45 (d, J=1.98 Hz, 1H), 8.54 (d, J=2.38 Hz, 1H). MS (DCI/NH$_3$) m/z=265 (M+H)$^+$. Anal. Calcd. for $C_{14}H_{17}ClN_2O.2$ HCl: C, 49.80; H, 5.67; N, 8.30; Cl, 31.50. Found: C, 49.64; H, 5.82; N, 8.15; Cl, 31.30.

Example 86

(4s)-4-[(5-Bromopyridin-3-yl)oxy]-1-azatricyclo[3.3.1.1$^{3,7}$]decane hydrochloride Example 86A (4s)-4-[(5-Bromopyridin-3-yl)oxy]-1-azatricyclo[3.3.1.1$^{3,7}$]decane N-borane complex Prepared from the product of Example 10A (85.3 mg, 0.51 mmol) and 3-bromo-5-fluoropyridine (141.8 mg, 0.81 mmol) according to Method I: $^1$H NMR (300 MHz, chloroform-D) δ ppm 1.66-1.70 (m, 2H), 2.03 (br s, 1H), 2.23-2.26 (m, 4H), 3.19-3.28 (m, 6H), 4.57 (t, J=3.2 Hz, 1H), 7.39-7.40 (m, 1H), 8.26 (d, J=2.7 Hz, 1H), 8.23 (d, J=2.0 Hz, 1H). MS (DCI/NH$_3$) m/z=323 (M+H)$^+$.

Example 86B (4s)-4-[(5-Bromopyridin-3-yl)oxy]-1-azatricyclo[3.3.1.1$^{3,7}$]decane hydrochloride Prepared from the product of Example 86A (105.1 mg, 0.33 mmol) according to Method J: $^1$H NMR (300 MHz, methanol-D4) δ ppm 1.92-1.96 (m, 2H), 2.21 (br s, 1H), 2.34-2.38 (m, 2H), 2.51 (br s, 2H), 3.58 (s, 2H), 3.64-3.75 (m, 4H), 5.07 (t, J=3.6 Hz, 1H), 8.26-8.27 (m, 1H), 8.55-8.62 (m, 2H). MS (DCI/NH$_3$) m/z=309 (M+H)$^+$. Anal. Calcd. for $C_{14}H_{17}BrN_2O.1.85$ HCl: C, 44.54; H, 5.06; N, 7.42. Found: C, 44.51; H, 4.99; N, 7.36.

Example 87

(4s)-4-[(5-Iodopyridin-3-yl)oxy]-1-azatricyclo[3.3.1.1$^{3,7}$]decane hydrochloride

Example 87A (4s)-4-[(5-Iodopyridin-3-yl)oxy]-1-azatricyclo[3.3.1.1$^{3,7}$]decane N-borane complex Prepared from the product of Example 10A (86.3 mg, 0.52 mmol) and 3-fluoro-5-iodopyridine (186.1 mg, 0.84 mmol) according to Method I: $^1$H NMR (300 MHz, chloroform-D) δ ppm 1.66-1.70 (m, 2H), 2.03 (br s, 1H), 2.23-2.26 (m, 4H), 3.19-3.28 (m, 6H), 4.56 (t, J=3.2 Hz, 1H), 7.57-7.57 (m, 1H), 8.28 (d, J=2.7 Hz, 1H), 8.46 (d, J=1.7 Hz, 1H). MS (DCI/NH$_3$) m/z=371 (M+H)$^+$.

Example 87B (4s)-4-[(5-Iodopyridin-3-yl)oxy]-1-azatricyclo[3.3.1.1$^{3,7}$]decane hydrochloride Prepared from the product of Example 87A (67.3 mg, 0.18 mmol) according to Method J: $^1$H NMR (300 MHz, methanol-D4) δ ppm 1.91-1.95 (m, 2H), 2.20 (br s, 1H), 2.34-2.38 (m, 2H), 2.50 (br s, 2H), 3.56 (s, 2H), 3.64-3.75 (m, 4H), 5.07 (t, J=3.2 Hz, 1H), 8.43-8.45 (m, 1H), 8.62 (d, J=2.4 Hz, 1H), 8.66 (d, J=1.6 Hz, 1H). MS (DCI/NH$_3$) m/z=357 (M+H)$^+$. Anal. Calcd. for C$_{14}$H$_{17}$IN$_2$O.2.25 HCl: C, 38.30; H, 4.62; N, 6.34. Found: C, 38.37; H, 4.43; N, 6.39.

Example 88

5-[(4s)-1-Azatricyclo[3.3.1.1$^{3,7}$]dec-4-yloxy]nicotinamide hydrochloride

Example 88A

5-[(4s)-1-Azatricyclo[3.3.1.1$^{3,7}$]dec-4-yloxy]nicotinamide N-borane complex

Prepared from the product of Example 10A (86.0 mg, 0.52 mmol) and 5-fluoronicotinamide (102.0 mg, 0.73 mmol) according to Method I: $^1$H NMR (300 MHz, chloroform-D) δ ppm 1.66-1.70 (m, 2H), 2.04 (br s, 1H), 2.23-2.26 (m, 4H), 3.19-3.23 (m, 6H), 4.58 (t, J=3.2 Hz, 1H), 7.54-7.56 (m, 1H), 8.49 (d, J=2.7 Hz, 1H), 8.59 (d, J=1.7 Hz, 1H). MS (DCI/NH$_3$) m/z=288 (M+H)$^+$.

Example 88B

5-[(4s)-1-Azatricyclo[3.3.1.1$^{3,7}$]dec-4-yloxy]nicotinamide hydrochloride

Prepared from the product of Example 88A (16.9 mg, 0.059 mmol) according to Method J: $^1$H NMR (300 MHz, methanol-D4) δ ppm 1.94-1.99 (m, 2H), 2.23 (br s, 1H), 2.37-2.41 (m, 2H), 2.57 (br s, 2H), 3.60 (s, 2H), 3.67-3.77 (m, 4H), 5.19 (t, J=3.39 Hz, 1H), 8.53 (dd, J=2.7, 1.4 Hz, 1H), 8.83 (d, J=2.7 Hz, 1H), 8.85 (d, J=1.7 Hz, 1H). MS (DCI/NH$_3$) m/z=274 (M+H)$^+$. Anal. Calcd. for C$_{15}$H$_{19}$N$_3$O$_2$.2.65 HCl: C, 48.70; H, 5.90; N, 11.36. Found: C, 48.45; H, 6.17; N, 11.44.

Example 89

(4s)-4-{[5-(1H-Pyrazol-4-yl)pyridin-3-yl]oxy}-1-azatricyclo[3.3.1.1$^{3,7}$]decane hydrochloride

Example 89A (4s)-4-{[5-(1-Trityl-1H-pyrazol-4-yl)pyridin-3-yl]oxy}-1-azatricyclo[3.3.1.1$^{3,7}$]decane N-borane complex Prepared from the product of Example 86A (83.6 mg, 0.26 mmol) and 4-(4,4,5,5-tetramethyl-1,3,2-dioxaborolan-2-yl)-1-trityl-1H-pyrazole (155.3 mg, 0.36 mmol) according to Method K: $^1$H NMR (300 MHz, chloroform-D) δ ppm 1.76-1.81 (m, 2H), 1.90 (br s, 1H), 2.23-2.26 (m, 4H), 3.22-3.26 (m, 4H), 3.34-3.39 (m, 2H), 4.65 (t, J=3.2 Hz, 1H), 7.17-7.22 (m, 6H), 7.32-7.37 (m, 9H), 7.66 (s, 1H), 7.94 (s, 1H), 8.16 (d, J=2.7 Hz, 1H), 8.32 (d, J=2.0 Hz, 1H). MS (DCI/NH$_3$) m/z=539 (M-BH$_3$+H)$^+$.

Example 89B (4s)-4-{[5-(1H-Pyrazol-4-yl)pyridin-3-yl]oxy}-1-azatricyclo[3.3.1.1$^{3,7}$]decane hydrochloride Prepared from the product of Example 89A (47.0 mg, 0.085 mmol) according to Method J: $^1$H NMR (300 MHz, methanol-D4) δ ppm 1.95-1.99 (m, 2H), 2.23 (br s, 1H), 2.39-2.43 (m, 2H), 2.57 (br s, 2H), 3.60 (s, 2H), 3.68-3.78 (m, 4H), 5.24 (t, J=3.2 Hz, 1H), 8.34 (s, 2H), 8.47-8.48 (m, 1H), 8.55 (d, J=2.4 Hz, 1H), 8.77 (d, J=1.4 Hz, 1H). MS (DCI/NH$_3$) m/z=297 (M+H)$^+$. Anal. Calcd. for C$_{17}$H$_{20}$N$_4$O.2 HCl.2H$_2$O: C, 50.38; H, 6.47; N, 13.82. Found: C, 50.51; H, 6.57; N, 13.76.

Example 90

(4s)-4-{[5-(1-Methyl-1H-pyrazol-4-yl)pyridin-3-yl]oxy}-1-azatricyclo[3.3.1.1$^{3,7}$]decane hydrochloride

Example 90A (4s)-4-{[5-(1-Methyl-1H-pyrazol-4-yl)pyridin-3-yl]oxy}-1-azatricyclo[3.3.1.1$^{3,7}$]decane N-borane complex Prepared from the product of Example 86A (102.7 mg, 0.32 mmol) and 1-methyl-4-(4,4,5,5-tetramethyl-1,3,2-dioxaborolan-2-yl)-1H-pyrazole (94.7 mg, 0.46 mmol) according to Method K: $^1$H NMR (300 MHz, chloroform-D) δ ppm 1.66-1.70 (m, 2H), 2.04 (br s, 1H), 2.28-2.32 (m, 4H), 3.19-3.28 (m, 6H), 3.97 (s, 3H), 4.63 (t, J=3.2 Hz, 1H), 7.26-7.28 (m, 1H), 7.66 (s, 1H), 7.76 (s, 1H), 8.18 (d, J=2.8 Hz, 1H), 8.39 (d, J=2.0 Hz, 1H). MS (DCI/NH$_3$) m/z=325 (M+H)$^+$.

Example 90B (4s)-4-{[5-(1-Methyl-1H-pyrazol-4-yl)pyridin-3-yl]oxy}-1-azatricyclo[3.3.1.1$^{3,7}$]decane hydrochloride Prepared from the product of Example 90A (92.2 mg, 0.28 mmol) according to Method J: $^1$H NMR (300 MHz, methanol-D4) δ ppm 1.95-1.99 (m, 2H), 2.23 (br s, 1H), 2.38-2.42 (m, 2H), 2.57 (br s, 2H), 3.60 (s, 2H), 3.70-3.79 (m, 4H), 3.98 (s, 3H), 5.26 (t, J=3.2 Hz, 1H), 8.13 (s, 1H), 8.39 (s, 1H), 8.46-8.47 (m, 1H), 8.57 (d, J=2.4 Hz, 1H), 8.73 (d, J=1.6 Hz, 1H). MS (DCI/NH$_3$) m/z=311 (M+H)$^+$. Anal. Calcd. for C$_{18}$H$_{22}$N$_4$O.2 HCl.1.55H$_2$O: C, 52.57; H, 6.67; N, 13.62; Cl, 17.24.

Found: C, 52.79; H, 6.62; N, 13.44; Cl, 17.03.

Example 91

(4s)-4-{[5-(1H-Pyrazol-1-yl)pyridin-3-yl]oxy}-1-azatricyclo[3.3.1.1$^{3,7}$]decane

Example 91A

3-Fluoro-5-(1H-pyrazol-1-yl)pyridine

3-Bromo-5-fluoropyridine (300 mg, 1.705 mmol), 1H-pyrazole (180 mg, 2.64 mmol), ferric acetylacetonate (181 mg, 0.511 mmol), copper(II) oxide (13.6 mg, 0.170 mmol) and cesium carbonate (1.11 g, 3.41 mmol) were suspended in DMF (2.0 mL). The reaction mixture was stirred at 90° C. for 60 hours. After cooling to room temperature, the reaction mixture was partitioned between ethyl acetate (3×30 mL) and water (100 mL). The organic layers were combined, washed with brine (50 mL) and dried (sodium sulfate). It was then concentrated and the residue was purified by silica gel flash chromatography to afford the titled compound: $^1$H NMR (400 MHz, methanol-D4) δ ppm 6.55-6.65 (m, 1H), 7.80 (d, J=1.2 Hz, 1H), 8.10 (dt, J=9.9, 2.3 Hz, 1H), 8.38 (d, J=2.5 Hz, 1H), 8.42 (d, J=1.5 Hz, 1H), 8.93 (s, 1H). MS (ESI) m/z=163 (M+H)$^+$. Anal. Calcd. for C$_8$H$_6$FN3.0.15CH$_3$OH: C, 61.99; H, 4.48; N, 32.42. Found: C, 62.30; H, 4.12; N, 32.21.

Example 91B (4s)-4-{[5-(1H-Pyrazol-1-yl)pyridin-3-yl]oxy}-1-azatricyclo[3.3.1.1$^{3,7}$]decane bishydrochloride The product of Example 10A (23.7 mg, 0.142 mmol) and potassium tert-butoxide (18.2 mg, 0.162 mmol) were dissolved in dimethyl sulfoxide (0.3 mL) and stirred at 25° C. for 1 hour. A solution of the product of Example 91A (22 mg, 0.135 mmol) in DMSO (0.3 mL) was added dropwise. The reaction mixture was stirred at 25° C. for 18 hours. The mixture was dissolved in DMF (2 mL), filtered and purified by preparative HPLC [Waters® XTerra RP18 5 μm column, 30×100 mm, flow rate 40 mL/minutes, 5-95% gradient of acetonitrile in buffer (0.1 M aqueous ammonium bicarbonate, adjusted to pH 10 with ammonium hydroxide) over 22 minutes, with UV detection at 254 nm]. Fractions containing the desired product were pooled, concentrated under vacuum and then processed as described in Method C. The resulting mixture in 3 N HCl was concentrated to dryness and stirred in 10:1 diethyl ether/MeOH. The precipitate was filtered and dried under vacuum to afford the titled compound: $^1$H NMR (400 MHz, methanol-D4) δ ppm 1.98 (m, 2H), 2.24 (br s, 1H), 2.41 (m, 2H), 2.60 (br s, 2H), 3.61 (br s, 2H), 3.70-3.80 (m, 4H), 5.33 (t, J=3.2 Hz, 1H), 6.65-6.71 (m, 1H), 7.88 (d, J=1.5 Hz, 1H), 8.56-8.77 (m, 3H), 9.04 (s, 1H). MS (ESI) m/z=297 (M+H)$^+$. Anal. Calcd. for C$_{17}$H$_{20}$N$_4$O.2HCl.1.6H$_2$O: C, 51.29; H, 6.38; N, 14.07; Cl, 17.81. Found: C, 51.21; H, 6.18; N, 13.87; Cl, 17.96.

Example 92

(4s)-4-{[5-(4-Chlorophenyl)pyridin-3-yl]oxy}-1-azatricyclo[3.3.1.1$^{3,7}$]decane hydrochloride

Example 92A (4s)-4-{[5-(4-Chlorophenyl)pyridin-3-yl]oxy}-1-azatricyclo[3.3.1.1$^{3,7}$]decane N-borane complex Prepared from the product of Example 86A (82.6 mg, 0.26 mmol) and 4-chlorophenylboronic acid (66.3 mg, 0.42 mmol) according to Method K: $^1$H NMR (300 MHz, chloroform-D) δ ppm 1.67-1.71 (m, 2H), 2.03 (br s, 1H), 2.28-2.32 (m, 4H), 3.19-3.28 (m, 6H), 4.66 (t, J=3.2 Hz, 1H), 7.35-7.37 (m, 1H), 7.44-7.51 (m, 4H), 8.32 (d, J=2.8 Hz, 1H), 8.46 (d, J=2.0 Hz, 1H). MS (DCI/NH$_3$) m/z=355 (M+H)$^+$.

Example 92B (4s)-4-{[5-(4-Chlorophenyl)pyridin-3-yl]oxy}-1-azatricyclo[3.3.1.1$^{3,7}$]decane hydrochloride Prepared from the product of Example 92A (52.4 mg, 0.15 mmol) according to Method J: $^1$H NMR (300 MHz, methanol-D4) δ ppm 1.95-1.99 (m, 2H), 2.24 (br s, 1H), 2.40-2.44 (m, 2H), 2.59 (br s, 2H), 3.60 (s, 2H), 3.68-3.78 (m, 4H), 5.26 (t, J=3.2 Hz, 1H), 7.58-7.62 (m, 2H), 7.81-7.85 (m, 2H), 8.51 (dd, J=2.7, 1.4 Hz, 1H), 8.74 (d, J=2.7 Hz, 1H), 8.79 (d, J=1.4 Hz, 1H). MS (DCI/NH$_3$) m/z=341 (M+H)$^+$. Anal. Calcd. for C$_{20}$H$_{21}$ClN$_2$O.2 HCl.1.5H$_2$O: C, 54.50; H, 5.95; N, 6.36; Cl, 24.13.

Found: C, 54.80; H, 5.86; N, 6.31; Cl, 23.79.

Example 93

(4s)-4-(3,4'-Bipyridin-5-yloxy)-1-azatricyclo[3.3.1.1$^{3,7}$]decane hydrochloride

Example 93A

5-Fluoro-3,4'-bipyridine

Prepared from 3-bromo-5-fluoropyridine (439.0 mg, 2.50 mmol) and pyridin-4-ylboronic acid (509.9 mg, 3.73 mmol) according to Method K, except the product was purified by silica gel chromatography (ethyl acetate, R$_f$=0.21) instead of preparative HPLC: $^1$H NMR (300 MHz, chloroform-D) δ ppm 7.50-7.51 (m, 2H), 7.65 (dt, J=9.1, 2.4 Hz, 1H), 8.56 (d, J=2.8 Hz, 1H), 8.73-8.76 (m, 3H). MS (DCI/NH$_3$) m/z=175 (M+H)$^+$.

Example 93B (4s)-4-(3,4'-Bipyridin-5-yloxy)-1-azatricyclo[3.3.1.1$^{3,7}$]decane N-borane complex Prepared from the product of Example 10A (84.0 mg, 0.50 mmol) and the product of Example 93A (111.3 mg, 0.64 mmol) according to Method I: $^1$H NMR (300 MHz, chloroform-D) δ ppm 1.68-1.72 (m, 2H), 2.05 (br s, 1H), 2.30-2.32 (m, 4H), 3.20-3.30 (m, 6H), 4.68 (t, J=3.1 Hz, 1H), 7.43-7.44 (m, 1H), 7.48-7.50 (m, 2H), 8.40 (d, J=2.7 Hz, 1H), 8.53 (d, J=1.7 Hz, 1H), 8.72-8.74 (m, 2H). MS (DCI/NH$_3$) m/z=322 (M+H)$^+$.

Example 93C (4s)-4-(3,4'-Bipyridin-5-yloxy)-1-azatricyclo[3.3.1.1$^{3,7}$]decane hydrochloride Prepared from the product of Example 93B (141.8 mg, 0.44 mmol) according to Method J: $^1$H NMR (300 MHz, methanol-D4) δ ppm 1.95-1.99 (m, 2H), 2.24 (br s, 1H), 2.41-2.45 (m, 2H), 2.59 (br s, 2H), 3.60 (s, 2H), 3.70-3.78 (m, 4H), 5.31 (t, J=3.39 Hz, 1H), 8.52-8.54 (m, 1H), 8.57-8.60 (m, 2H), 8.82 (d, J=2.71 Hz, 1H), 8.95 (d, J=1.36 Hz, 1H), 9.00-9.02 (m, 2H). MS (DCI/NH$_3$) m/z=308 (M+H)$^+$. Anal. Calcd. for C$_{19}$H$_{21}$N$_3$O.3 HCl.2H$_2$O: C, 50.40; H, 6.23; N, 9.28. Found: C, 50.70; H, 6.23; N, 9.23.

Example 94

(4s)-4-[(5-Pyrimidin-5-ylpyridin-3-yl)oxy]-1-azatricyclo[3.3.1.1$^{3,7}$]decane hydrochloride

Example 94A (4s)-4-[(5-Pyrimidin-5-ylpyridin-3-yl)oxy]-1-azatricyclo[3.3.1.1$^{3,7}$]decane N-borane complex Prepared from the product of Example 86A (101.0 mg, 0.31 mmol) and pyrimidin-5-ylboronic acid (53.1 mg, 0.43 mmol) according to Method K: $^1$H NMR (300 MHz, chloroform-D) δ ppm 1.68-1.73 (m, 2H), 2.06 (br s, 1H), 2.30-2.32 (m, 4H), 3.20-3.30 (m, 6H), 4.70 (t, J=3.1 Hz, 1H), 7.40-7.41 (m, 1H), 8.44 (d, J=2.7 Hz, 1H), 8.49 (d, J=2.0 Hz, 1H), 8.98 (s, 2H), 9.29 (s, 1H). MS (DCI/NH$_3$) m/z=323 (M+H)$^+$.

Example 94B (4s)-4-[(5-Pyrimidin-5-ylpyridin-3-yl)oxy]-1-azatricyclo[3.3.1.1$^{3,7}$]decane hydrochloride Prepared from the product of Example 94A (24.0 mg, 0.074 mmol) according to Method J: $^1$H NMR (300 MHz, methanol-D4) δ ppm 1.95-1.99 (m, 2H), 2.24 (br s, 1H), 2.41-2.45 (m, 2H), 2.59 (br s, 2H), 3.60 (s, 2H), 3.70-3.78 (m, 4H), 5.31 (t, J=3.4 Hz, 1H), 8.66-8.68 (m, 1H), 8.88 (d, J=2.4 Hz, 1H), 8.94 (d, J=1.6 Hz, 1H), 9.26 (s, 2H), 9.32 (s, 1H). MS (DCI/NH$_3$) m/z=309 (M+H)$^+$.

Example 95

(4r)-4-(6-Chloro-pyridin-3-yloxy)-1-aza-tricyclo[3.3.1.1$^{3,7}$]decane hydrochloride

Examples 95A1, 95A2, 95A3, and 95A4

(4s)-4-(6-Chloro-pyridin-3-yloxy)-1-aza-tricyclo[3.3.1.1$^{3,7}$]decane N-borane complex (95A1), (4r)-4-(6-Chloro-pyridin-3-yloxy)-1-aza-tricyclo[3.3.1.1$^{3,7}$]decane N-borane complex (95A2)

(4s)-4-(5-Fluoro-pyridin-2-yloxy)-1-aza-tricyclo[3.3.1.1$^{3,7}$]decane N-borane complex (95A3), and (4r)-4-(5-Fluoro-pyridin-2-yloxy)-1-aza-tricyclo[3.3.1.1$^{3,7}$]decane N-borane complex (95A4)

A solution of the product of Example 9A (2.4:1 diastereomer mixture; 3.34 g, 20 mmol) in dry THF (40 mL) was treated with potassium bis(trimethylsilyl)amide (4.0 g, 20 mmol), and the mixture was stirred at room temperature for 1 hour. 2-Chloro-5-fluoropyridine (2.6 g, 20 mmol) was added, and the mixture was heated at 60° C. for 2 hours. The mixture was purified by flash chromatography [200 g silica gel, eluting with hexanes-ethyl acetate (100% to 60% gradient over 72 minutes at 40 mL/minute flow rate)]. Four products were collected: (4s)-4-(6-chloro-pyridin-3-yloxy)-1-aza-tricyclo[3.3.1.1$^{3,7}$]decane N-borane complex (95A1); (4r)-4-(6-chloro-pyridin-3-yloxy)-1-aza-tricyclo[3.3.1.1$^{3,7}$]decane N-borane complex (95A2); (4s)-4-(5-fluoro-pyridin-2-yloxy)-1-aza-tricyclo[3.3.1.1$^{3,7}$]decane N-borane complex (95A3); and (4r)-4-(5-fluoro-pyridin-2-yloxy)-1-aza-tricyclo[3.3.1.1$^{3,7}$]decane N-borane complex (95A4).

Example 95B (4r)-4-(6-Chloro-pyridin-3-yloxy)-1-aza-tricyclo[3.3.1.1$^{3,7}$]decane Prepared from the product of Example 95A2 (750 mg, 2.69 mmol) according to Method C to provide the titled compound: $^1$H NMR (300 MHz, methanol-D4) δ ppm 1.75 (s, 1H), 1.97-2.08 (m, 4H), 2.14-2.25 (m, 2H), 2.95 (s, 1H), 2.99 (s, 1H), 3.14 (s, 2H), 3.45 (s, 1H), 3.49 (s, 1H), 4.74 (s, 1H), 7.33-7.38 (m, 1H), 7.45-7.52 (m, 1H), 8.09 (d, J=3.1 Hz, 1H). MS (DCI/NH$_3$) m/e=265/267 (M+H)$^+$.

Example 95C (4r)-4-(6-Chloro-pyridin-3-yloxy)-1-aza-tricyclo[3.3.1.1$^{3,7}$]decane Hydrochloride Prepared from the product of Example 95B (120 mg, 0.453 mmol) according to Method H to provide the titled compound: $^1$H NMR (300 MHz, methanol-D4) δ ppm 2.04-2.29 (m, 5H), 2.47 (s, 2H), 3.43 (s, 1H), 3.46 (s, 1H), 3.55 (s, 2H), 3.80 (s, 1H), 3.84 (s, 1H), 4.81 (t, J=3.4 Hz, 1H), 7.40 (d, J=8.8 Hz, 1H), 7.57 (dd, J=8.8, 3.4 Hz, 1H), 8.18 (d, J=3.1 Hz, 1H). MS (DCI/NH$_3$) m/e=265, 267 (M+H)$^+$. Anal. calcd. for C$_{14}$H$_{17}$N$_2$ClO.1.5HCl: C, 52.64; H, 5.84; N, 8.77. Found C, 52.44; H, 5.86; N, 8.68.

Example 96

(4s)-4-[(6-Bromopyridin-3-yl)oxy]-1-azatricyclo[3.3.1.1$^{3,7}$]decane hydrochloride

Example 96A (4s)-4-[(6-Bromopyridin-3-yl)oxy]-1-azatricyclo[3.3.1.1$^{3,7}$]decane N-borane complex Prepared from the product of Example 10A (81.6 mg, 0.49 mmol) and 2-bromo-5-fluoropyridine (160.8 mg, 0.91 mmol) according to Method I: $^1$H NMR (300 MHz, chloroform-D) δ ppm 1.65-1.69 (m, 2H), 2.03 (br s, 1H), 2.20-2.26 (m, 4H), 3.15-3.27 (m, 6H), 4.54 (t, J=3.1 Hz, 1H), 7.13 (dd, J=8.8, 3.1 Hz, 1H), 7.40 (d, J=8.8 Hz, 1H), 8.09 (d, J=3.4 Hz, 1H). MS (DCI/NH$_3$) m/z=323 (M+H)$^+$.

Example 96B (4s)-4-[(6-Bromopyridin-3-yl)oxy]-1-azatricyclo[3.3.1.1$^{3,7}$]decane hydrochloride Prepared from the product of Example 96A (111.3 mg, 0.35 mmol) according to Method J: $^1$H NMR (300 MHz, methanol-D4) δ ppm 1.89-1.93 (m, 2H), 2.19 (br s, 1H), 2.34-2.38 (m, 2H), 2.47 (br s, 2H), 3.56-3.72 (m, 6H), 4.90 (t, J=3.4 Hz, 1H), 7.47 (dd, J=8.7, 3.2 Hz, 1H), 7.54 (d, J=9.1 Hz, 1H), 8.18 (d, J=3.2 Hz, 1H). MS (DCI/NH$_3$) m/z=309 (M+H)$^+$. Anal. Calcd. for C$_{14}$H$_{17}$BrN$_2$O.1.2 HCl: C, 47.62; H, 5.17; N, 7.94. Found: C, 47.62; H, 5.17; N, 7.90.

Example 97

5-[(4s)-1-Azatricyclo[3.3.1.1$^{3,7}$]dec-4-yloxy]pyridine-2-carbonitrile hydrochloride Example 97A 5-[(4s)-1-Azatricyclo[3.3.1.1$^{3,7}$]dec-4-yloxy]pyridine-2-carbonitrile N-borane complex Prepared from the product of Example 10A (88.1 mg, 0.53 mmol) and 5-fluoropicolinonitrile (61.5 mg, 0.50 mmol) according to Method I: $^1$H NMR (300 MHz, chloroform-D) δ ppm 1.69-1.73 (m, 2H), 2.06 (br s, 1H), 2.22-2.27 (m, 4H), 3.21-3.30 (m, 6H), 4.68 (t, J=3.1 Hz, 1H), 7.24-7.28 (m, 1H), 7.66 (d, J=8.7 Hz, 1H), 8.41 (d, J=3.6 Hz, 1H). MS (DCI/NH$_3$) m/z=287 (M+NH$_4$)$^+$.

Example 97B

5-[(4s)-1-Azatricyclo[3.3.1.1$^{3,7}$]dec-4-yloxy]pyridine-2-carbonitrile hydrochloride Prepared from the product of Example 97A (54.8 mg, 0.20 mmol) according to Method J: $^1$H NMR (300 MHz, methanol-D4) δ ppm 1.91-1.95 (m, 2H), 2.20 (br s, 1H), 2.34-2.39 (m, 2H), 2.50 (br s, 2H), 3.57 (s, 2H), 3.61-3.74 (m, 4H), 5.04 (t, J=3.4 Hz, 1H), 7.64 (dd, J=8.8, 3.1 Hz, 1H), 7.85 (d, J=8.8 Hz, 1H), 8.49 (d, J=3.1 Hz, 1H). MS (DCI/NH$_3$) m/z=256 (M+H)$^+$. Anal. Calcd. for C$_{15}$H$_{17}$N$_3$O.HCl.H$_2$O: C, 61.75; H, 6.22; N, 14.40; Cl, 12.15. Found: C, 61.64; H, 6.41; N, 14.36; Cl, 12.24.

Example 98

(4s)-4-[(5-Thien-2-ylpyridin-2-yl)oxy]-1-azatricyclo[3.3.1.1$^{3,7}$]decane

The free base of the title compound was prepared from the product of Example 10C (50 mg, 0.16 mmol) and 2-thiophene boronic acid (29 mg, 0.23 mmol; Aldrich) according to Method G, and converted to the p-toluenesulfonate salt using the procedure of Method H: $^1$H NMR (300 MHz, methanol-D4) δ ppm 1.92 (d, J=13.6 Hz, 2H), 2.19 (s, 1H), 2.32-2.46 (m, 6H), 2.55 (s, 2H), 3.57 (s, 2H), 3.68 (s, 4H), 5.46 (s, 1H), 6.93 (d, J=8.5 Hz, 1H), 7.10 (dd, J=5.1, 3.4 Hz, 1H), 7.22 (d, J=8.5 Hz, 2H), 7.37 (dd, J=15.3, 4.4 Hz, 2H), 7.70 (d, J=8.1 Hz, 2H), 7.97 (dd, J=8.6, 2.5 Hz, 1H), 8.38 (d, J=2.7 Hz, 1H). MS (DCI/NH$_3$) m/z=313 (M+H)$^+$.

Example 99

(4s)-4-[6-(1H-Indol-5-yl)-pyridin-3-yloxy]-1-azatricyclo[3.3.1.1$^{3,7}$]decane dihydrochloride Prepared from the product of Example 15B (165 mg, 0.623 mmol) and 1H-indol-5-ylboronic acid using the microwave Suzuki coupling Method G and the salt formation Method H to provide the titled compound: $^1$H NMR (300 MHz, methanol-D4) δ ppm 1.96 (s, 1H), 2.00 (s, 1H), 2.24 (s, 1H), 2.40 (s, 1H), 2.44 (s, 1H), 2.59 (s, 2H), 3.61 (s, 2H), 3.74 (s, 4H), 5.19 (t, J=3.2 Hz, 1H), 6.66 (dd, J=3.2, 0.8 Hz, 1H), 7.43 (d, J=3.4 Hz, 1H), 7.59-7.64 (m, 1H), 7.64-7.68 (m, 1H), 8.16 (dd, J=1.9, 0.8 Hz, 1H), 8.31-8.35 (m, 1H), 8.36-8.41 (m, 1H), 8.61 (d, J=2.0 Hz, 1H). MS (DCI/NH$_3$) m/e=346 (M+H)$^+$. Anal. calcd. for C$_{22}$H$_{23}$N$_3$O.2HCl.H$_2$O: C, 60.55; H, 6.24; N, 9.63. Found C, 60.71; H, 6.38; N, 9.39.

Example 100

(4r)-4-[6-(1H-Indol-5-yl)-pyridin-3-yloxy]-1-azatricyclo[3.3.1.1$^{3,7}$]decane trifluoroacetate Prepared from the product of Example 95B (135 mg, 0.510 mmol) and 1H-indol-5-ylboronic acid using the microwave Suzuki coupling Method G and the salt formation Method H to provide the titled compound: $^1$H NMR (300 MHz, methanol-D4) δ ppm 2.06-2.30 (m, 5H), 2.52 (s, 2H), 3.44 (s, 1H), 3.49 (s, 1H), 3.57 (s, 2H), 3.86 (s, 1H), 3.90 (s, 1H), 4.84-4.86 (m, 1H), 6.52 (d, J=3.1 Hz, 1H), 7.26-7.30 (m, 1H), 7.46 (d, J=8.5 Hz, 1H), 7.59-7.67 (m, 2H), 7.83 (d, J=8.8 Hz, 1H), 8.06 (s, 1H), 8.37 (d, J=2.7 Hz, 1H). MS (DCI/NH$_3$) m/e=346 (M+H)$^+$. Anal. calcd. for C$_{22}$H$_{23}$N$_3$O.1.17C$_2$HF$_3$O$_2$: C, 61.05; H, 5.09; N, 8.78. Found C, 60.98; H, 4.98; N, 8.75.

Example 101

(4s)-4-[6-(1H-Indol-6-yl)-pyridin-3-yloxy]-1-azatricyclo[3.3.1.1$^{3,7}$]decane trihydrochloride Prepared from the product of Example 15B (115 mg, 0.434 mmol) and 1H-indol-6-ylboronic acid using the microwave Suzuki coupling Method G and the salt formation Method H to provide the titled compound: $^1$H NMR (300 MHz, methanol-D4) δ ppm 1.93-2.05 (m, 2H), 2.24 (s, 1H), 2.40 (s, 1H), 2.44 (s, 1H), 2.59 (s, 2H), 3.61 (s, 2H), 3.67-3.81 (m, 4H), 5.19 (t, J=3.2 Hz, 1H), 6.61 (d, J=3.1 Hz, 1H), 7.48-7.55 (m, 2H), 7.82 (d, J=8.5 Hz, 1H), 7.97 (s, 1H), 8.31-8.36 (m, 1H), 8.36-8.42 (m, 1H), 8.62 (d, J=2.4 Hz, 1H). MS (DCI/NH$_3$) m/e=346 (M+H)$^+$. Anal. calcd. for C$_{22}$H$_{23}$N$_3$O.3HCl.0.3H$_2$O: C, 57.42; H, 5.83; N, 9.13. Found C, 57.46; H, 5.98; N, 9.01.

Example 102

(4r)-4-[6-(1H-Indol-6-yl)-pyridin-3-yloxy]-1-azatricyclo[3.3.1.1$^{3,7}$]decane dihydrochloride Prepared from the product of Example 95B (125 mg, 0.472 mmol) and 1H-indol-6-ylboronic acid using microwave Suzuki Coupling Method G and the salt formation Method H to provide the titled compound: $^1$H NMR (300 MHz, methanol-D4) δ ppm 2.11-2.34 (m, 5H), 2.58 (s, 2H), 3.49 (s, 1H), 3.54 (s, 1H), 3.60 (s, 2H), 3.87 (s, 1H), 3.92 (s, 1H), 5.09 (t, J=3.4 Hz, 1H), 6.61 (dd, J=3.2, 0.8 Hz, 1H), 7.49-7.54 (m, 2H), 7.83 (d, J=8.5 Hz, 1H), 7.98 (s, 1H), 8.32-8.38 (m, 1H), 8.38-8.43 (m, 1H), 8.61 (d, J=2.7 Hz, 1H). MS (DCI/NH$_3$) m/e=346 (M+H)$^+$. Anal. calcd. for C$_{22}$H$_{23}$N$_3$O.2HCl.2.2H$_2$O: C, 57.69; H, 6.47; N, 9.17. Found C, 57.35; H, 6.26; N, 8.95.

Example 103

5-{5-[(4s)-1-azatricyclo[3.3.1.1$^{3,7}$]dec-4-yloxy]pyridin-2-yl}-1,3-dihydro-2H-indol-2-one dihydrochloride Prepared from the product of Example 15B (185 mg, 0.699 mmol) and 5-(4,4,5,5-tetramethyl-1,3,2-dioxaborolan-2-yl)

indolin-2-one using the microwave Suzuki coupling Method G and the salt formation Method H to provide the titled compound: $^1$H NMR (300 MHz, methanol-D4) δ ppm 1.93-2.00 (m, 2H), 2.23 (s, 1H), 2.39 (s, 1H), 2.43 (s, 1H), 2.56 (s, 2H), 3.58-3.78 (m, 8H), 5.09-5.16 (m, 1H), 7.10 (d, J=8.5 Hz, 1H), 7.73-7.82 (m, 2H), 8.10-8.23 (m, 2H), 8.57 (d, J=2.7 Hz, 1H). MS (DCI/NH$_3$) m/e=362 (M+H)$^+$. Anal. calcd. for C$_{22}$H$_{23}$N$_3$O$_2$.2HCl.H$_2$O: C, 58.64; H, 6.02; N, 9.29. Found C, 58.64; H, 5.99; N, 9.11.

Example 104

(4r)-4-[6-(Benzofuran-5-yl)-pyridin-3-yloxy]-1-aza-tricyclo[3.3.1.1$^{3,7}$]decane trifluoroacetate Prepared from the product of Example 95B (165 mg, 0.623 mmol) and 2-(benzofuran-5-yl)-4,4,5,5-tetramethyl-1,3,2-dioxaborolane using the microwave Suzuki coupling Method G and the salt formation Method H to provide the titled compound: $^1$H NMR (300 MHz, methanol-D4) δ ppm 2.07-2.30 (m, 5H), 2.52 (s, 2H), 3.45 (s, 1H), 3.49 (s, 1H), 3.57 (s, 2H), 3.86 (s, 1H), 3.90 (s, 1H), 4.87 (t, J=3.2 Hz, 1H), 6.91 (d, J=3.1 Hz, 1H), 7.58 (d, J=8.8 Hz, 1H), 7.63 (dd, J=8.8, 3.1 Hz, 1H), 7.79-7.88 (m, 3H), 8.13 (d, J=1.4 Hz, 1H), 8.42 (d, J=2.4 Hz, 1H). MS (DCI/NH$_3$) m/e=347 (M+H)$^+$. Anal. calcd. for C$_{22}$H$_{22}$N$_2$O$_2$.1.15C$_2$HF$_3$O$_2$: C, 61.12; H, 4.89; N, 5.87. Found C, 60.98; H, 4.74; N, 5.87.

Example 105

(4s)-4-[(5,6-Dibromopyridin-3-yl)oxy]-1-azatricyclo[3.3.1.1$^{3,7}$]decane hydrochloride Example 105A (4s)-4-[(5,6-Dibromopyridin-3-yl)oxy]-1-azatricyclo[3.3.1.1$^{3,7}$]decane N-borane complex Prepared from the product of Example 10A (108.6 mg, 0.65 mmol) and 2,3-dibromo-5-fluoropyridine (24.5 mg, 0.96 mmol) according to Method I: $^1$H NMR (300 MHz, chloroform-D) δ ppm 1.67-1.70 (m, 2H), 2.03 (br s, 1H), 2.22-2.24 (m, 4H), 3.19-3.28 (m, 6H), 4.55 (t, J=3.1 Hz, 1H), 7.49 (d, J=2.7 Hz, 1H), 8.06 (d, J=2.7 Hz, 1H). MS (DCI/NH$_3$) m/z=401 (M+H)$^+$.

Example 105B (4s)-4-[(5,6-Dibromopyridin-3-yl)oxy]-1-azatricyclo[3.3.1.1$^{3,7}$]decane hydrochloride Prepared from the product of Example 105A (142.3 mg, 0.35 mmol) according to Method J: $^1$H NMR (300 MHz, methanol-D4) δ ppm 1.89-1.93 (m, 2H), 2.18 (br s, 1H), 2.33-2.37 (m, 2H), 2.46 (br s, 2H), 3.56-3.71 (m, 6H), 4.92 (t, J=3.2 Hz, 1H), 7.91 (d, J=2.8 Hz, 1H), 8.19 (d, J=2.8 Hz, 1H). MS (DCI/NH$_3$) m/z=387 (M+H)$^+$. Anal. Calcd. for C$_{14}$H$_{16}$Br$_2$N$_2$O.1.5 HCl: C, 37.98; H, 3.98; N, 6.33. Found: C, 37.98; H, 4.07; N, 6.30.

Example 106

(4s)-4-(Pyridin-2-yloxy)-1-azatricyclo[3.3.1.1$^{3,7}$]decane hydrochloride

Example 106A (4s)-4-(Pyridin-2-yloxy)-1-azatricyclo[3.3.1.1$^{3,7}$]decane N-borane complex Prepared from the product of Example 10A (101.3 mg, 0.61 mmol) and 2-chloropyridine (120 mg, 1.06 mmol) according to Method I: $^1$H NMR (300 MHz, chloroform-D) δ ppm 1.63-1.67 (m, 2H), 2.01 (br s, 1H), 2.23-2.29 (m, 4H), 3.17-3.30 (m, 6H), 5.29 (t, J=3.1 Hz, 1H), 6.77 (d, J=8.3 Hz, 1H), 6.85-6.89 (m, 1H), 7.56-7.62 (m, 1H), 8.11 (dd, J=5.2, 2.0 Hz, 1H). MS (DCI/NH$_3$) m/z=260 (M+NH$_3$–H)$^+$.

Example 106B (4s)-4-(Pyridin-2-yloxy)-1-azatricyclo[3.3.1.1$^{3,7}$]decane hydrochloride Prepared from the product of Example 106A (53.7 mg, 0.22 mmol) according to Method J: $^1$H NMR (300 MHz, methanol-D4) δ ppm 1.96-2.00 (m, 2H), 2.23 (br s, 1H), 2.34-2.39 (m, 2H), 2.58 (br s, 2H), 3.59 (s, 2H), 3.67-3.71 (m, 4H), 5.44 (t, J=3.4 Hz, 1H), 7.30-7.34 (m, 1H), 7.42 (d, J=8.7 Hz, 1H), 8.16-8.22 (m, 1H), 8.30-8.32 (m, 1H). MS (DCI/NH$_3$) m/z=231 (M+H)$^+$. Anal. Calcd. for C$_{14}$H$_{18}$N$_2$O.2 HCl: C, 55.45; H, 6.65; N, 9.24; Cl, 23.38. Found: C, 55.43; H, 6.67; N, 9.10; Cl, 23.49.

Example 107

(4s)-4-(5-Fluoro-pyridin-2-yloxy)-1-aza-tricyclo[3.3.1.1$^{3,7}$]decane dihydrochloride Prepared from the product of Example 95A3 (4s)-4-(5-fluoro-pyridin-2-yloxy)-1-aza-tricyclo[3.3.1.1$^{3,7}$]decane N-borane complex (200 mg, 0.763 mmol) using the acid deboronation Method C and the salt formation Method H to provide the titled compound: $^1$H NMR (300 MHz, methanol-D4) δ ppm 1.89 (s, 1H), 1.94 (s, 1H), 2.18 (s, 1H), 2.33 (s, 1H), 2.37 (s, 1H), 2.52 (s, 2H), 3.56 (s, 2H), 3.61-3.72 (m, 4H), 5.38 (t, J=3.2 Hz, 1H), 6.94 (dd, J=9.3, 3.9 Hz, 1H), 7.58 (ddd, J=9.2, 7.8, 3.1 Hz, 1H), 8.01 (d, J=3.1 Hz, 1H). MS (DCI/NH$_3$) m/e=249 (M+H)$^+$. Anal. calcd. for C$_{14}$H$_{17}$N$_2$FO.2.9HCl.H$_2$O: C, 45.20; H, 5.93; N, 7.53. Found C, 45.29; H, 6.11; N, 7.48.

Example 108

(4s)-4-[(5-Bromopyridin-2-yl)oxy]-1-azatricyclo[3.3.1.1$^{3,7}$]decane hydrochloride Example 108A (4s)-4-[(5-Bromopyridin-2-yl)oxy]-1-azatricyclo[3.3.1.1$^{3,7}$]decane N-borane complex Prepared from the product of Example 10A (419.0 mg, 2.51 mmol) and 5-bromo-2-chloropyridine (592.4 mg, 3.08 mmol) according to Method I, except the product was purified by silica gel chromatography (2.5% ethyl acetate in dichloromethane, R$_f$=0.39) instead of preparative HPLC: $^1$H NMR (300 MHz, chloroform-D) δ ppm 1.63-1.67 (m, 2H), 1.99 (br s, 1H), 2.23-2.29 (m, 4H), 3.17-3.28 (m, 6H), 5.22 (t, J=3.1 Hz, 1H), 6.69 (d, J=8.8 Hz, 1H), 7.67 (dd, J=8.8, 2.0 Hz, 1H), 8.15 (d, J=2.0 Hz, 1H). MS (DCI/NH$_3$) m/z=338 (M+NH$_3$–H)$^+$.

Example 108B (4s)-4-[(5-Bromopyridin-2-yl)oxy]-1-azatricyclo[3.3.1.1$^{3,7}$]decane hydrochloride Prepared from the product of Example 108A (151.9 mg, 0.47 mmol) according to Method J: $^1$H NMR (300 MHz, methanol-D4) δ ppm 1.90-1.94 (m, 2H), 2.18 (br s, 1H), 2.33-2.37 (m, 2H), 2.52 (br s, 2H), 3.54-3.71 (m, 6H), 5.41 (t, J=3.2 Hz, 1H), 6.85 (d, J=8.8 Hz, 1H), 7.84 (dd, J=8.8, 2.7 Hz, 1H), 8.19 (d, J=2.7 Hz, 1H). MS (DCI/NH$_3$) m/z=309 (M+H)$^+$. Anal. Calcd. for C$_{14}$H$_{17}$BrN$_2$O.1.15 HCl: C, 47.89; H, 5.21; N, 7.98. Found: C, 47.91; H, 5.14; N, 7.84.

Example 109

(4s)-4-[(4-Bromopyridin-2-yl)oxy]-1-azatricyclo [3.3.1.1$^{3,7}$]decane hydrochloride Example 109A (4s)-4-[(4-Bromopyridin-2-yl)oxy]-1-azatricyclo [3.3.1.1$^{3,7}$]decane N-borane complex Prepared from the product of Example 10A (86.7 mg, 0.51 mmol) and 4-bromo-2-fluoropyridine (166.3 mg, 0.95 mmol) according to Method I: $^1$H NMR (300 MHz, chloroform-D) δ ppm 1.63-1.67 (m, 2H), 2.00 (br s, 1H), 2.20-2.28 (m, 4H), 3.17-3.28 (m, 6H), 5.27 (t, J=3.4 Hz, 1H), 7.00 (d, J=1.6 Hz, 1H), 7.04 (dd, J=4.8, 1.6 Hz, 1H), 7.94 (d, J=4.8 Hz, 1H). MS (DCI/NH$_3$) m/z=338 (M+NH$_3$–H)$^+$.

Example 109B (4s)-4-[(4-Bromopyridin-2-yl)oxy]-1-azatricyclo [3.3.1.1$^{3,7}$]decane hydrochloride Prepared from the product of Example 109A (41.8 mg, 0.13 mmol) according to Method J: $^1$H NMR (300 MHz, methanol-D4) δ ppm 1.90-1.94 (m, 2H), 2.19 (br s, 1H), 2.33-2.38 (m, 2H), 2.53 (br s, 2H), 3.57 (br s, 2H), 3.62-3.72 (m, 4H), 5.44 (t, J=3.4 Hz, 1H), 7.17-7.21 (m, 2H), 8.01 (d, J=5.4 Hz, 1H). MS (DCI/NH$_3$) m/z=309 (M+H)$^+$. Anal. Calcd. for C$_{14}$H$_{17}$BrN$_2$O.1.15 HCl: C, 47.89; H, 5.21; N, 7.98.
Found: C, 47.99; H, 5.06; N, 7.82.

Example 110

(4s)-4-(3,3'-Bipyridin-6-yloxy)-1-azatricyclo [3.3.1.1$^{3,7}$]decane hydrochloride Example 110A (4s)-4-(3,3'-Bipyridin-6-yloxy)-1-azatricyclo [3.3.1.1$^{3,7}$]decane N-borane complex Prepared from the product of Example 108A (118.8 mg, 0.37 mmol) and pyridin-3-ylboronic acid (69.3 mg, 0.56 mmol) according to Method K: $^1$H NMR (300 MHz, chloroform-D) δ ppm 1.66-1.70 (m, 2H), 2.02 (br s, 1H), 2.26-2.34 (m, 4H), 3.19-3.32 (m, 6H), 5.35 (t, J=3.2 Hz, 1H), 6.88-6.91 (m, 1H), 7.38 (dd, J=7.9, 4.8 Hz, 1H), 7.80-7.83 (m, 2H), 8.34 (d, J=2.0 Hz, 1H), 8.61 (dd, J=4.8. 1.6 Hz, 1H), 8.79 (d, J=2.0 Hz, 1H). MS (DCI/NH$_3$) m/z=322 (M+H)$^+$.

Example 110B (4s)-4-(3,3'-Bipyridin-6-yloxy)-1-azatricyclo [3.3.1.1$^{3,7}$]decane hydrochloride Prepared from the product of Example 110A (58.5 mg, 0.18 mmol) according to Method J: $^1$H NMR (300 MHz, methanol-D4) δ ppm 1.94-1.98 (m, 2H), 2.22 (br s, 1H), 2.37-2.41 (m, 2H), 2.59 (br s, 2H), 3.59 (br s, 2H), 3.66-3.75 (m, 4H), 5.56 (t, J=3.4 Hz, 1H), 7.12 (d, J=8.7 Hz, 1H), 8.14-8.22 (m, 2H), 8.61 (d, J=2.8 Hz, 1H), 8.83 (d, J=6.0 Hz, 1H), 8.88-8.92 (m, 1H), 9.19 (d, J=2.4 Hz, 1H). MS (DCI/NH$_3$) m/z=308 (M+H)$^+$. Anal. Calcd. for C$_{19}$H$_{21}$N$_3$O.2 HCl.H$_2$O: C, 57.29; H, 6.33; N, 10.55; Cl, 17.80. Found: C, 57.21; H, 6.42; N, 10.46; Cl, 17.63.

Example 111

(4s)-4-(3,4'-Bipyridin-6-yloxy)-1-azatricyclo [3.3.1.1$^{3,7}$]decane hydrochloride Example 111A 6-Fluoro-3,4'-bipyridine Prepared from 5-bromo-2-fluoropyridine (881 mg, 5.00 mmol) and pyridin-4-ylboronic acid (979 mg, 7.96 mmol) according to Method K, except the product was purified by silica gel chromatography (10% ethanol in ethyl acetate, R$_f$=0.32) instead of preparative HPLC: $^1$H NMR (300 MHz, chloroform-D) δ ppm 7.08 (dd, J=8.5, 3.0 Hz, 1H), 7.48-7.50 (m, 2H), 8.01-8.07 (m, 1H), 8.51 (d, J=2.7 Hz, 1H), 8.72-8.74 (m, 2H). MS (DCI/NH$_3$) m/z=175 (M+H)$^+$.

Example 111B (4s)-4-(3,4'-Bipyridin-6-yloxy)-1-azatricyclo [3.3.1.1$^{3,7}$]decane N-borane complex Prepared from the product of Example 10A (101.1 mg, 0.62 mmol) and the product of Example 111A (107.3 mg, 0.62 mmol) according to Method I: $^1$H NMR (300 MHz, chloroform-D) δ ppm 1.66-1.70 (m, 2H), 2.02 (br s, 1H), 2.25-2.34 (m, 4H), 3.19-3.32 (m, 6H), 5.35 (t, J=3.2 Hz, 1H), 6.90 (d, J=8.5 Hz, 1H), 7.47-7.49 (m, 2H), 7.88 (dd, J=8.6, 2.5 Hz, 1H), 8.43 (d, J=2.4 Hz, 1H), 8.67-8.68 (m, 2H). MS (DCI/NH$_3$) m/z=322 (M+H)$^+$.

Example 111C (4s)-4-(3,4'-Bipyridin-6-yloxy)-1-azatricyclo [3.3.1.1$^{3,7}$]decane hydrochloride Prepared from the product of Example 111B (134.6 mg, 0.42 mmol) according to Method J: $^1$H NMR (300 MHz, methanol-D4) δ ppm 1.95-1.99 (m, 2H); 2.22 (br s, 1H); 2.37-2.41 (m, 2H), 2.60 (br s, 2H); 3.36 (br s, 2H); 3.71 (br s, 4H); 5.61 (t, J=3.2 Hz, 1H); 7.15 (d, J=8.8 Hz, 1H); 8.36-8.42 (m, 3H); 8.83-8.87 (m, 3H). MS (DCI/NH$_3$) m/z=308 (M+H)$^+$. Anal. Calcd. for C$_{19}$H$_{21}$N$_3$O.1.8 HCl.1.45H$_2$O: C, 57.17; H, 6.49; N, 10.53; Cl, 15.99. Found: C, 57.43; H, 6.85; N, 10.17; Cl, 16.12.

Example 112

(4r)-4-(3,4'-Bipyridin-6-yloxy)-1-azatricyclo [3.3.1.1$^{3,7}$]decane hydrochloride Example 112A (4r)-4-(3,4'-Bipyridin-6-yloxy)-1-azatricyclo [3.3.1.1$^{3,7}$]decane N-borane complex Prepared from the product of Example 9D (100.1 mg, 0.60 mmol) and the product of Example 111A (109.6 mg, 0.63 mmol) according to Method I: ¹H NMR (300 MHz, chloroform-D) δ ppm 1.97-2.03 (m, 5H), 2.31 (br s, 2H), 2.94-2.99 (m, 2H), 3.13 (s, 2H), 3.49-3.53 (m, 2H), 5.24 (t, J=2.8 Hz, 1H), 6.92 (d, J=8.5 Hz, 1H), 7.46-7.48 (m, 2H), 7.88 (dd, J=8.8, 2.7 Hz, 1H), 8.42 (d, J=2.4 Hz, 1H), 8.67-8.68 (m, 2H). MS (DCI/NH$_3$) m/z=322 (M+H)$^+$.

Example 112B (4r)-4-(3,4'-Bipyridin-6-yloxy)-1-azatricyclo[3.3.1.1$^{3,7}$]decane hydrochloride Prepared from the product of Example 112A (123.8 mg, 0.39 mmol) according to Method J: ¹H NMR (300 MHz, methanol-D4) δ ppm 2.11-2.17 (m, 2H), 2.24-2.28 (m, 3H), 2.57 (br s, 2H), 3.46-3.52 (m, 2H), 3.58 (br s, 2H), 3.83-3.87 (m, 2H), 5.52 (t, J=2.8 Hz, 1H); 7.15 (d, J=8.8 Hz, 1H); 8.35-8.42 (m, 3H); 8.85-8.86 (m, 3H). MS (DCI/NH$_3$) m/z=308 (M+H)$^+$. Anal. Calcd. for C$_{19}$H$_{21}$N$_3$O.2.4 HCl.2.25 H$_2$O: C, 52.41; H, 6.46; N, 9.65; Cl, 19.54. Found: C, 52.28; H, 6.33; N, 9.54; Cl, 19.69.

Example 113

(4s)-4-[(5-Pyrimidin-5-ylpyridin-2-yl)oxy]-1-azatricyclo[3.3.1.1$^{3,7}$]decane hydrochloride Example 113A (4s)-4-[(5-Pyrimidin-5-ylpyridin-2-yl)oxy]-1-azatricyclo[3.3.1.1$^{3,7}$]decane N-borane complex Prepared from the product of Example 108A (102.3 mg, 0.32 mmol) and pyridin-3-ylboronic acid (61.1 mg, 0.49 mmol) according to Method K: ¹H NMR (300 MHz, chloroform-D) δ ppm 1.67-1.71 (m, 2H), 2.03 (br s, 1H), 2.25-2.34 (m, 4H), 3.19-3.32 (m, 6H), 5.36 (t, J=3.1 Hz, 1H), 6.94 (d, J=8.7 Hz, 1H), 7.82 (dd, J=8.7, 2.8 Hz, 1H), 8.35 (d, J=2.8 Hz, 1H), 8.91 (s, 2H), 9.22 (s, 1H). MS (DCI/NH$_3$) m/z=323 (M+H)$^+$.

Example 113B (4s)-4-[(5-Pyrimidin-5-ylpyridin-2-yl)oxy]-1-azatricyclo[3.3.1.1$^{3,7}$]decane hydrochloride Prepared from the product of Example 113A (58.5 mg, 0.18 mmol) according to Method J: ¹H NMR (300 MHz, methanol-D4) δ ppm 1.94-1.98 (m, 2H), 2.22 (br s, 1H), 2.37-2.41 (m, 2H), 2.59 (br s, 2H), 3.59 (br s, 2H), 3.66-3.75 (m, 4H), 5.56 (t, J=3.4 Hz, 1H), 7.07 (d, J=8.7 Hz, 1H), 8.12-8.17 (m, 2H), 8.56 (d, J=2.8 Hz, 1H), 9.06 (s, 2H), 9.15 (s, 1H). MS (DCI/NH$_3$) m/z=309 (M+H)$^+$.

Example 114

(4s)-4-{[5-(1H-Pyrazol-4-yl)pyridin-2-yl]oxy}-1-azatricyclo[3.3.1.1$^{3,7}$]decane hydrochloride Example 114A (4s)-4-{[5-(1-Trityl-1H-pyrazol-4-yl)pyridin-2-yl]oxy}-1-azatricyclo[3.3.1.1$^{3,7}$]decane complex Prepared from the product of Example 108A (48.5 mg, 0.15 mmol) and 4-(4,4,5,5-tetramethyl-1,3,2-dioxaborolan-2-yl)-1-trityl-1H-pyrazole (109.9 mg, 0.25 mmol) according to Method K: ¹H NMR (300 MHz, chloroform-D) δ ppm 1.76-1.81 (m, 2H), 1.99 (br s, 1H), 2.25-2.30 (m, 4H), 3.16-3.25 (m, 6H), 5.27 (t, J=3.2 Hz, 1H), 6.77 (d, J=9.2 Hz, 1H), 7.17-7.21 (m, 6H), 7.32-7.37 (m, 9H), 7.56 (s, 1H), 7.67 (dd, J=8.7, 2.5 Hz, 1H), 7.88 (s, 1H), 8.19 (d, J=2.0 Hz, 1H). MS (DCI/NH$_3$) m/z=568 (M+NH$_3$−H)$^+$.

Example 114B (4s)-4-{[5-(1H-Pyrazol-4-yl)pyridin-2-yl]oxy}-1-azatricyclo[3.3.1.1$^{3,7}$]decane hydrochloride Prepared from the product of Example 114A (44.4 mg, 0.080 mmol) according to Method J: ¹H NMR (300 MHz, methanol-D4) δ ppm 1.93-1.97 (m, 2H), 2.21 (br s, 1H), 2.36-2.41 (m, 2H), 2.57 (br s, 2H), 3.58 (br s, 2H), 3.66-3.75 (m, 4H), 5.45 (t, J=3.2 Hz, 1H), 7.12 (d, J=9.1 Hz, 1H), 8.13 (dd, J=8.6, 2.5 Hz, 1H), 8.25 (s, 2H), 8.47 (d, J=1.7 Hz, 1H). MS (DCI/NH$_3$) m/z=297 (M+H)$^+$. Anal. Calcd. for C$_{17}$H$_{20}$N$_4$O.2 HCl.1.15H$_2$O: C, 52.11; H, 6.30; N, 14.30. Found: C, 52.14; H, 6.33; N, 14.24.

Example 115

6-[(4s)-1-Azatricyclo[3.3.1.1$^{3,7}$]dec-4-yloxy]-N-pyridin-4-ylpyridine-2-carboxamide Example 115A 6-Chloro-N-(pyridin-4-yl)picolinamide 6-Chloropicolinic acid (0.50 g, 3.17 mmol) was dissolved in thionyl chloride (5.0 mL) and stirred at 25° C. for 1 hour. The thionyl chloride was evaporated, and 4-aminopyridine (0.28 g, 2.98 mmol), triethylamine (0.415 mL, 2.98 mmol) and dichloromethane (50 mL) were added. The solution was stirred at 25° C. for 18 hours. The reaction mixture was partitioned between dichloromethane (50 mL) and saturated sodium bicarbonate solution (100 mL). The organic layer was dried (sodium sulfate) and concentrated, and the residue was purified by silica gel flash column chromatography to afford the titled compound: ¹H NMR (500 MHz, methanol-D4) δ ppm 7.71 (dd, J=7.9, 0.9 Hz, 1H), 7.91-7.95 (m, 2H), 8.05 (t, J=7.8 Hz, 1H), 8.20 (dd, J=7.6, 0.6 Hz, 1H), 8.43-8.52 (m, 2H). MS (ESI) m/z=335 (M+H)$^+$.

Example 115B

6-[(4s)-1-Azatricyclo[3.3.1.1$^{3,7}$]dec-4-yloxy]-N-pyridin-4-ylpyridine-2-carboxamide fumarate Prepared from the product of Example 115A (134 mg, 0.574 mmol) and the product of Example 10B (80 mg, 0.522 mmol) according to Method B to provide the free base. It was then reacted with fumaric acid according to Method H to provide the titled compound: ¹H NMR (500 MHz, methanol-D4) δ ppm 1.91-2.01 (m, 2H), 2.20 (br s, 1H), 2.37-2.46 (m, 2H), 2.58 (br s, 2H), 3.58 (s, 2H), 3.67-3.81 (m, 4H), 5.80 (t, J=3.2 Hz, 1H), 6.69 (s, 2H, C$_4$H$_4$O$_4$), 7.18 (dd, J=8.2, 0.6 Hz, 1H), 7.86-7.90 (m, 3H), 7.97 (dd, J=8.2, 7.3 Hz, 1H), 8.48 (d, J=6.1 Hz, 2H). MS (ESI) m/z=351 (M+H)$^+$. Anal. Calcd. for C$_{20}$H$_{22}$N$_4$O$_2$.1.05C$_4$H$_4$O$_4$: C, 61.54; H, 5.59; N, 11.86. Found: C, 61.40; H, 5.76; N, 11.78.

Example 116

(4s)-4-[(2-Chloropyridin-4-yl)oxy]-1-azatricyclo[3.3.1.1$^{3,7}$]decane hydrochloride

Example 116A (4s)-4-[(2-Chloropyridin-4-yl)oxy]-1-azatricyclo[3.3.1.1$^{3,7}$]decane N-borane complex Prepared from the product of Example 10A (82.8 mg, 0.50 mmol) and 4-bromo-2-chloropyridine (85 µL, 0.77 mmol) according to Method I: $^1$H NMR (300 MHz, chloroform-D) δ ppm 1.67-1.71 (m, 2H), 2.03 (br s, 1H), 2.19-2.27 (m, 4H), 3.19-3.25 (m, 6H), 4.64 (t, J=3.4 Hz, 1H), 6.76 (dd, J=5.8, 2.4 Hz, 1H), 6.85 (d, J=2.4 Hz, 1H), 8.22 (d, J=5.8 Hz, 1H). MS (DCI/NH$_3$) m/z=279 (M+H)$^+$.

Example 116B (4s)-4-[(2-Chloropyridin-4-yl)oxy]-1-azatricyclo[3.3.1.1$^{3,7}$]decane hydrochloride Prepared from the product of Example 116A (86.6 mg, 0.31 mmol) according to Method J: $^1$H NMR (300 MHz, methanol-D4) δ ppm 1.93-1.97 (m, 2H), 2.21 (br s, 1H), 2.31-2.35 (m, 2H), 2.52 (br s, 2H), 3.59 (br s, 2H), 3.66-3.76 (m, 4H), 5.17 (t, J=3.4 Hz, 1H), 7.32 (dd, J=6.4, 2.4 Hz, 1H), 7.50 (d, J=2.4 Hz, 1H), 8.38 (d, J=6.4 Hz, 1H). MS (DCI/NH$_3$) m/z=265 (M+H)$^+$. Anal. Calcd. for C$_{14}$H$_{17}$ClN$_2$O.2 HCl.0.3H$_2$O: C, 49.01; H, 5.76; N, 8.17. Found: C, 49.18; H, 5.85; N, 7.92.

Example 117

(4s)-4-[(6-Methylpyridazin-3-yl)oxy]-1-azatricyclo[3.3.1.1$^{3,7}$]decane hydrochloride

Example 117A (4s)-4-[(6-Methylpyridazin-3-yl)oxy]-1-azatricyclo[3.3.1.1$^{3,7}$]decane N-borane complex Prepared from the product of Example 10A (83.7 mg, 0.50 mmol) and 3-chloro-6-methylpyridazine (100.6 mg, 0.78 mmol) according to Method I: $^1$H NMR (300 MHz, chloroform-D) δ ppm 1.65-1.69 (m, 2H), 2.00 (br s, 1H), 2.20-2.24 (m, 2H), 2.42 (br s, 2H), 3.18-3.30 (m, 6H), 5.50 (t, J=3.6 Hz, 1H), 6.92 (d, J=8.8 Hz, 1H), 7.25 (d, J=8.8 Hz, 1H). MS (DCI/NH$_3$) m/z=260 (M+H)$^+$.

Example 117B (4s)-4-[(6-Methylpyridazin-3-yl)oxy]-1-azatricyclo[3.3.1.1$^{3,7}$]decane hydrochloride Prepared from the product of Example 117A (28.2 mg, 0.11 mmol) according to Method J: $^1$H NMR (300 MHz, methanol-D4) δ ppm 1.97-2.01 (m, 2H), 2.23 (br s, 1H), 2.35-2.39 (m, 2H), 2.64 (br s, 2H), 2.81 (s, 3H), 3.60 (br s, 2H), 3.68-3.78 (m, 4H), 5.58 (t, J=3.4 Hz, 1H), 7.98 (d, J=9.1 Hz, 1H), 8.22 (d, J=9.1 Hz, 1H). MS (DCI/NH$_3$) m/z=246 (M+H)$^+$. Anal. Calcd. for C$_{14}$H$_{19}$N$_3$O.2.25 HCl: C, 51.37; H, 6.54; N, 12.84. Found: C, 51.37; H, 6.70; N, 12.90.

Example 118

(4s)-4-(Pyrimidin-2-yloxy)-1-azatricyclo[3.3.1.1$^{3,7}$]decane hydrochloride

Example 118A (4s)-4-(Pyrimidin-2-yloxy)-1-azatricyclo[3.3.1.1$^{3,7}$]decane N-borane complex Prepared from the product of Example 10A (86.3 mg, 0.52 mmol) and 2-chloropyrimidine (99.2 mg, 0.87 mmol) according to Method I: $^1$H NMR (300 MHz, chloroform-D) δ ppm 1.65-1.70 (m, 2H), 2.02 (br s, 1H), 2.30-2.40 (m, 4H), 3.19-3.29 (m, 6H), 5.27 (t, J=3.4 Hz, 1H), 6.96 (t, J=4.8 Hz, 1H), 8.52 (d, J=4.8 Hz, 2H). MS (DCI/NH$_3$) m/z=246 (M+H)$^+$.

Example 118B (4s)-4-(Pyrimidin-2-yloxy)-1-azatricyclo[3.3.1.1$^{3,7}$]decane hydrochloride Prepared from the product of Example 118A (61.6 mg, 0.25 mmol) according to Method J: $^1$H NMR (300 MHz, methanol-D4) δ ppm 1.92-1.97 (m, 2H); 2.21 (br s, 1H); 2.38-2.41 (m, 2H), 2.57 (br s, 2H); 3.58 (br s, 2H); 3.64-3.74 (m, 4H); 5.48 (t, J=3.2 Hz, 1H); 7.15 (t, J=4.9 Hz, 1H); 8.60 (d, J=4.8 Hz, 2H). MS (DCI/NH$_3$) m/z=232 (M+H)$^+$. Anal. Calcd. for C$_{13}$H$_{17}$N$_3$O.HCl.0.1H$_2$O: C, 57.93; H, 6.81; N, 15.59; Cl, 13.15. Found: C, 57.74; H, 6.60; N, 15.55; Cl, 13.38.

Example 119

(4s)-4-[(5-Bromopyrimidin-2-yl)oxy]-1-azatricyclo[3.3.1.1$^{3,7}$]decane hydrochloride

Example 119A (4s)-4-[(5-bromopyrimidin-2-yl)oxy]-1-azatricyclo[3.3.1.1$^{3,7}$]decane N-borane complex Prepared from the product of Example 10A (81.5 mg, 0.49 mmol) and 5-bromo-2-chloropyrimidine (135.6 mg, 0.70 mmol) according to Method I: $^1$H NMR (300 MHz, chloroform-D) δ ppm 1.66-1.70 (m, 2H), 2.02 (br s, 1H), 2.29-2.33 (m, 4H), 3.19-3.29 (m, 6H), 5.21 (t, J=3.2 Hz, 1H), 8.53 (s, 2H). MS (DCI/NH$_3$) m/z=339 (M+NH$_3$−H)$^+$.

Example 119B (4s)-4-[(5-Bromopyrimidin-2-yl)oxy]-1-azatricyclo[3.3.1.1$^{3,7}$]decane hydrochloride Prepared from the product of Example 119A (20.4 mg, 0.063 mmol) according to Method J: $^1$H NMR (300 MHz, methanol-D4) δ ppm 1.92-1.96 (m, 2H), 2.20 (br s, 1H), 2.36-2.40 (m, 2H), 2.56 (br s, 2H), 3.58-3.73 (m, 6H), 5.42 (t, J=3.4 Hz, 1H), 8.68 (s, 2H). MS (DCI/NH$_3$) m/z=310

(M+H)+. Anal. Calcd. for C₁₃H₁₆BrN₃O.HCl: C, 45.04; H, 4.94; N, 12.12. Found: C, 45.22; H, 5.24; N, 11.90.

Example 120

(4s)-4-(Pyrimidin-5-yloxy)-1-azatricyclo[3.3.1.1³,⁷] decane hydrochloride

Example 120A (4s)-4-(Pyrimidin-5-yloxy)-1-azatricyclo[3.3.1.1³,⁷] decane N-borane complex Prepared from the product of Example 10A (88.4 mg, 0.53 mmol) and 5-fluoropyrimidine (92.0 mg, 0.94 mmol) according to Method I: ¹H NMR (300 MHz, chloroform-D) δ ppm 1.68-1.73 (m, 2H), 2.05 (br s, 1H), 2.24-2.29 (m, 4H), 3.18-3.29 (m, 6H), 4.65 (t, J=3.2 Hz, 1H), 8.46 (s, 2H), 8.89 (s, 1H). MS (DCI/NH₃) m/z=261 (M+NH₃–H)+.

Example 120B (4s)-4-(Pyrimidin-5-yloxy)-1-azatricyclo[3.3.1.1³,⁷] decane hydrochloride Prepared from the product of Example 120A (91.5 mg, 0.37 mmol) according to Method J: ¹H NMR (300 MHz, methanol-D4) δ ppm 1.92-1.96 (m, 2H), 2.21 (br s, 1H), 2.36-2.41 (m, 2H), 2.53 (br s, 2H), 3.58 (s, 2H), 3.63-3.75 (m, 4H), 5.08 (t, J=3.2 Hz, 1H), 8.79 (s, 2H), 8.93 (s, 1H). MS (DCI/NH₃) m/z=232 (M+H)+. Anal. Calcd. for C₁₃H₁₇N₃O.2 HCl: C, 51.33; H, 6.30; N, 13.81. Found: C, 51.59; H, 6.70; N, 13.80.

Example 121

(4s)-4-(Pyrimidin-4-yloxy)-1-azatricyclo[3.3.1.1³,⁷] decane

Prepared from the product of Example 10B (89 mg, 0.581 mmol) and 4-chloropyrimidine hydrochloride (98 mg, 0.651 mmol) according to Method B to provide the free base. It was then reacted with fumaric acid according to Method H to provide the titled compound as a fumarate: ¹H NMR (500 MHz, methanol-D4) δ ppm 1.90-1.99 (m, 2H), 2.19 (br s, 1H), 2.30-2.38 (m, 2H), 2.55 (br s, 2H), 3.56 (br s, 2H), 3.61-3.72 (m, 4H), 5.59 (t, J=3.2 Hz, 1H), 6.69 (s, 2H, C₄H₄O₄), 7.01 (dd, J=6.0, 1.1 Hz, 1H), 8.51 (d, J=5.8 Hz, 1H), 8.74 (s, 1H). MS (ESI) m/z=232 (M+H)+.

Example 122

(4s)-4-[(6-Chloropyrimidin-4-yl)oxy]-1-azatricyclo [3.3.1.1³,⁷]decane

The product of Example 10B (73 mg, 0.437 mmol) and potassium tert-butoxide (51 mg, 0.454 mmol) were dissolved in dimethyl sulfoxide (2.5 mL) and stirred at 25° C. for 1 hour. 4,6-Dichloropyrimidine (111 mg, 0.743 mmol) was added. The reaction mixture was stirred at 25° C. for 18 hours. The mixture was dissolved in DMF (2 mL), filtered and purified by preparative HPLC [Waters® XTerra RP18 5 µm column, 30×100 mm, flow rate 40 mL/min, 5-95% gradient of acetonitrile in buffer (0.1 M aqueous ammonium bicarbonate, adjusted to pH 10 with ammonium hydroxide) over 22 min, with UV detection at 254 nm]. Fractions containing the desired product were pooled, concentrated under vacuum and then processed as described in Method C to provide the free base. It was then reacted with fumaric acid according to Method H to provide the titled compound: ¹H NMR (400 MHz, methanol-D4) δ ppm 1.89-2.01 (m, 2H), 2.18 (br s, 1H), 2.27-2.39 (m, 2H), 2.53 (br s, 2H), 3.55 (br s, 2H), 3.59-3.72 (m, 4H), 5.58 (t, J=3.1 Hz, 1H), 6.68 (s, 2H, C₄H₄O₄), 7.10 (d, J=0.9 Hz, 1H), 8.58 (s, 1H). MS (ESI) m/z=266 (M+H)+.

Example 123

(4s)-4-{[6-(1-Trityl-1H-pyrazol-4-yl)pyrimidin-4-yl] oxy}-1-azatricyclo[3.3.1.1³,⁷]decane Example 123A 4-Chloro-6-(1-trityl-1H-pyrazol-4-yl)pyrimidine In a microwave reaction tube were combined 4,6-dichloropyrimidine (480 mg, 3.22 mmol), 4-(4,4,5,5-tetramethyl-1,3,2-dioxaborolan-2-yl)-1-trityl-1H-pyrazole (1.28 g, 2.93 mmol; JP 2005232071), bis(triphenylphosphine)-palladium (II) chloride (82 mg, 0.117 mmol), sodium carbonate (776 mg, 7.32 mmol), followed by the solvents 2-propanol (9.0 mL) and water (3.0 mL). The tube was sealed, and the reaction was heated to 108° C. for 30 minutes in the microwave reactor. After cooling to room temperature, the mixture was partitioned between ethyl acetate (2×100 mL) and water (200 mL). The combined organic extracts were washed with brine, dried (sodium sulfate) and concentrated under reduced pressure, and the resulting material was purified by silica gel flash column chromatography to afford the titled compound: ¹H NMR (300 MHz, methanol-D4) δ ppm 7.11-7.22 (m, 6H), 7.28-7.41 (m, 9H), 7.81-7.83 (m, 1H), 8.23-8.26 (m, 1H), 8.30 (s, 1H), 8.75-8.78 (m, 1H). MS (DCI/NH₃) m/z=423 (M+H)+.

Example 123B (4s)-4-{[6-(1-Trityl-1H-pyrazol-4-yl)pyrimidin-4-yl] oxy}-1-azatricyclo[3.3.1.1³,⁷]decane Prepared from the product of Example 10B (80 mg, 0.522 mmol) and the product of Example 123A (243 mg, 0.574 mmol) according to Method B: ¹H NMR (500 MHz, chloroform-D) δ ppm 1.63 (br s, 1H), 1.76-1.85 (m, 2H), 2.05 (br s, 2 H), 2.23-2.32 (m, 2H), 3.11-3.21 (m, 4H), 3.24-3.34 (m, 2H), 5.41 (t, J=3.1 Hz, 1H), 6.81 (d, J=0.9 Hz, 1H), 7.14-7.21 (m, 6H), 7.29-7.36 (m, 9H), 8.05 (s, 1H), 8.15 (s, 1H), 8.62 (d, J=0.9 Hz, 1H). MS (ESI) m/z=540 (M+H)+.

Example 124

(4s)-4-{[6-(1H-Pyrazol-4-yl)pyrimidin-4-yl]oxy}-1-azatricyclo[3.3.1.1³,⁷]decane

A suspension of the product of Example 123 (76 mg, 0.141 mmol) in THF (10 mL) was treated with 3 N HCl (5 mL) and stirred at room temperature for 18 hours. The mixture was partitioned between aqueous sodium carbonate (1.0 M, 100 mL) and chloroform-isopropanol (4:1, 200 mL). The organic extract was washed with brine, dried (sodium sulfate) and concentrated under reduced pressure, and the resulting material was purified by preparative HPLC on a Waters Nova-Pak HR C18 6 µm 60 Å Prep-Pak cartridge column (40×100 mm) using a gradient of 10% to 100% acetonitrile in 10 mM aqueous ammonium acetate over 12 minutes at a flow rate of 70 mL/minute to provide the titled compound: $^1$H NMR (500 MHz, methanol-D4) δ ppm 1.70 (br s, 1H), 1.88 (m, 2H), 2.12 (br s, 2H), 2.29-2.36 (m, 2H), 3.12-3.20 (m, 4H), 3.27-3.35 (m, 2H), 5.47 (t, J=3.1 Hz, 1H), 7.17 (d, J=0.9 Hz, 1H), 8.26 (s, 2H), 8.62 (d, J=0.9 Hz, 1H). MS (APCI) m/z=298 (M+H)$^+$. Anal. Calcd. for $C_{16}H_{19}N_5O \cdot 0.5H_2O$: C, 62.73; H, 6.58; N, 22.86. Found: C, 62.66; H, 6.53; N, 22.76.

Example 125

(4s)-4-[(6-Pyridin-4-ylpyrimidin-4-yl)oxy]-1-azatricyclo[3.3.1.1$^{3,7}$]decane

Example 125A

4-Chloro-6-(pyridin-4-yl)pyrimidine

A sealed tube was charged with 4,6-dichloropyrimidine (252 mg, 1.690 mmol), trimethyl(phenyl)stannane (345 mg, 1.432 mmol), toluene (10 mL) and tetrakis(triphenylphosphine)-palladium(0) (66.2 mg, 0.057 mmol). The reaction mixture was degassed with nitrogen and then heated at 120° C. for 4 hours. After cooling to room temperature, activated carbon was added and the reaction mixture was filtered through a frit and concentrated under reduced pressure. The resulting material was purified by silica gel flash chromatography to provide the titled compound: $^1$H NMR (500 MHz, methanol-D4) δ ppm 8.16-8.21 (m, 2H), 8.27 (d, J=0.9 Hz, 1H), 8.71-8.79 (m, 2H), 9.11 (d, J=0.9 Hz, 1H). MS (ESI) m/z=192 (M+H)$^+$.

Example 125B (4s)-4-[(6-Pyridin-4-ylpyrimidin-4-yl)oxy]-1-azatricyclo[3.3.1.1$^{3,7}$]decane The borane complex of the titled compound was prepared from the product of Example 10A (48 mg, 0.287 mmol) and the product of Example 125A (55 mg, 0.287 mmol) according the Method B. It was then processed as described in Method C to provide the titled compound: $^1$H NMR (400 MHz, methanol-D4) δ ppm 1.74 (br s, 1H), 1.85-1.96 (m, 2H), 2.18 (br s, 2H), 2.29-2.44 (m, 2H), 3.15-3.24 (m, 4H), 3.32-3.37 (m, 2H), 5.55 (t, J=2.7 Hz, 1H), 7.54 (d, J=1.2 Hz, 1H), 8.09-8.13 (m, 2H), 8.68-8.72 (m, 2H), 8.83 (d, J=0.9 Hz, 1H). MS (ESI) m/z=309 (M+H)$^+$.

Example 126

(4s)-4-(Pyrazin-2-yloxy)-1-azatricyclo[3.3.1.1$^{3,7}$]decane hydrochloride

Example 126A (4s)-4-(Pyrazin-2-yloxy)-1-azatricyclo[3.3.1.1$^{3,7}$]decane N-borane complex Prepared from the product of Example 10A (82.5 mg, 0.49 mmol) and 2-chloropyrazine (80 μL, 0.91 mmol) according to Method I: MS (DCI/NH$_3$) m/z=261 (M+NH$_3$–H)$^+$.

Example 126B (4s)-4-(Pyrazin-2-yloxy)-1-azatricyclo[3.3.1.1$^{3,7}$]decane hydrochloride Prepared from the product of Example 126A (18.2 mg, 0.074 mmol) according to Method J: $^1$H NMR (300 MHz, methanol-D4) δ ppm 1.92-1.96 (m, 2H), 2.21 (br s, 1H), 2.36-2.40 (m, 2H), 2.56 (br s, 2H), 3.58 (br s, 2H), 3.64-3.74 (m, 4H), 5.49 (t, J=3.2 Hz, 1H), 8.15-8.18 (m, 2H); 8.32 (d, J=1.4 Hz, 1H). MS (DCI/NH$_3$) m/z=232 (M+H)$^+$. Anal. Calcd. for $C_{13}H_{17}N_3O \cdot 1.32HCl$: C, 55.88; H, 6.61; N, 15.04. Found: C, 56.22; H, 6.43; N, 14.68.

Example 127

4-[(6-Methylpyrazin-2-yl)oxy]-1-azatricyclo[3.3.1.1$^{3,7}$]decane hydrochloride Example 127A 4-[(6-Methylpyrazin-2-yl)oxy]-1-azatricyclo[3.3.1.1$^{3,7}$]decane N-borane complex Prepared from the product of Example 9A (101.4 mg, 0.61 mmol) and 2-chloro-6-methylpyrazine (100.7 mg, 0.78 mmol) according to Method I: MS (DCI/NH$_3$) m/z=275 (M+NH$_3$–H)$^+$.

Example 127B

4-[(6-Methylpyrazin-2-yl)oxy]-1-azatricyclo[3.3.1.1$^{3,7}$]decane hydrochloride Prepared from the product of Example 127A (18.2 mg, 0.074 mmol) according to Method J: 3.1:1.0 mixture of isomers [according to integration of $^1$H NMR (300 MHz, methanol-D4) δ ppm 5.53 (t, J=3.22, major) and 5.42 (t, J=3.39, minor)]. MS (DCI/NH$_3$) m/z=246 (M+H)$^+$. Anal. Calcd. for $C_{14}H_{18}N_2O \cdot 1.5HCl \cdot 0.65H_2O$: C, 53.94; H, 7.05; N, 13.48; Cl, 17.06. Found: C, 54.17; H, 7.26; N, 13.52; Cl, 16.80.

Example 128

(4r)-4-[(6-Phenylpyrazin-2-yl)oxy]-1-azatricyclo[3.3.1.1$^{3,7}$]decane

Example 128A

2-Chloro-6-phenylpyrazine

Prepared from 2,6-dichloropyrazine (1.01 g, 6.78 mmol) and phenylboronic acid (946.7 mg, 7.76 mmol) according to Method K, except the product was purified by silica gel chromatography (DCM, R$_f$=0.37) instead of preparative HPLC: $^1$H NMR (300 MHz, chloroform-D) δ ppm 7.46-7.53 (m, 3H), 7.94-7.98 (m, 2H), 8.22 (s, 1H), 8.63 (s, 1H). MS (DCI/NH$_3$) m/z=191 (M+H)$^+$.

Example 128B (4r)-4-[(6-Phenylpyrazin-2-yl)oxy]-1-azatricyclo[3.3.1.1$^{3,7}$]decane N-borane complex Prepared from the product of Example 9D (163.6 mg, 0.98 mmol) and the product of Example 128A (99.0 mg, 0.52 mmol) according to Method I: $^1$H NMR (300 MHz, chloroform-D) δ ppm 1.89-2.06 (m, 5H), 2.37 (br s, 1H), 2.97-3.01 (m, 2H), 3.15 (s, 2H), 3.51-3.55 (m, 2H), 5.33 (t, J=3.2 Hz, 1H), 7.50-7.56 (m, 3H), 8.00-8.05 (m, 2H), 8.53 (s, 1H), 8.94 (s, 1H). MS (DCI/NH$_3$) m/z=322 (M+H)$^+$.

Example 128C (4r)-4[(6-Phenylpyrazin-2-yl)oxy]-1-azatricyclo[3.3.1.1$^{3,7}$]decane hydrochloride Prepared from the product of Example 128B (45.1 mg, 0.14 mmol) according to Method J: $^1$H NMR (300 MHz, methanol-D4) δ ppm 2.20-2.31 (m, 5H), 2.62 (br s, 2H), 3.34-3.54 (m, 2H), 2.59 (br s, 2H), 3.86-3.91 (m, 4H), 5.56 (t, J=3.4 Hz, 1H), 7.47-4.55 (m, 3H); 8.04-8.08 (m, 2H), 8.25 (s, 1H), 8.73 (s, 1H). MS (DCI/NH$_3$) m/z=308 (M+H)$^+$. Anal. Calcd. for C$_{19}$H$_{21}$N$_3$O 1.25HCl.H$_2$O: C, 61.51; H, 6.59; N, 11.33; Cl, 11.95. Found: C, 61.36; H, 6.49; N, 11.30; Cl, 11.93.

Example 129

(4r)-4-(1,3-Thiazol-2-yloxy)-1-azatricyclo[3.3.1.1$^{3,7}$]decane hydrochloride

Example 129A (4r)-4-(1,3-Thiazol-2-yloxy)-1-azatricyclo[3.3.1.1$^{3,7}$]decane N-borane complex Prepared from the product of Example 9D (168.7 mg, 1.01 mmol) and 2-chlorothiazole (162.5 mg, 1.36 mmol) according to Method I: $^1$H NMR (300 MHz, chloroform-D) δ ppm 1.87-2.01 (m, 5H), 2.39 (br s, 1H), 2.94-2.98 (m, 2H), 3.12 (s, 2H), 3.43-3.48 (m, 2H), 5.12 (t, J=3.4 Hz, 1H), 6.70 (d, J=3.6 Hz, 1H), 7.11 (d, J=4.0 Hz, 1H). MS (DCI/NH$_3$) m/z=251 (M+H)$^+$.

Example 129B (4r)-4-(1,3-Thiazol-2-yloxy)-1-azatricyclo[3.3.1.1$^{3,7}$]decane hydrochloride Prepared from the product of Example 129A (125.7 mg, 0.50 mmol) according to Method J: $^1$H NMR (300 MHz, methanol-D4) δ ppm 2.07-2.11 (m, 2H), 2.22-2.28 (m, 3H), 2.62 (br s, 1H), 3.46-3.57 (m, 4H), 3.75-3.79 (m, 4H), 5.25 (t, J=3.4 Hz, 1H), 6.99 (d, J=3.73 Hz, 1H), 7.20 (d, J=3.73 Hz, 1H). MS (DCI/NH$_3$) m/z=237 (M+H)$^+$. Anal. Calcd. for C$_{12}$H$_{16}$N$_2$OS.1.91 HCl: C, 47.11; H, 5.90; N, 9.16. Found: C, 47.47; H, 5.51; N, 9.10.

Example 130

(4r)-4-(5-Bromo-thiazol-2-yloxy)1-aza-tricyclo[3.3.1.1$^{3,7}$]decane tosylate

Examples 130A1 and 130A2

(4r)-4-(5-Bromo-thiazol-2-yloxy)1-aza-tricyclo[3.3.1.1$^{3,7}$]decane (130A1) and (4s)-4-(5-Bromo-thiazol-2yloxy)1-aza-tricyclo[3.3.1.1$^{3,7}$]decane (130A2)

A solution of the product of Example 9A (2.4:1 diastereomer mixture; 334 mg, mmol) and 2,5-dibromothiazole following the etherification method B to provide a mixture of N-borane complex diastereomers. The diastereomers were separated by silica gel chromatography eluting with hexane/ethyl acetate to furnish the 4r-isomer as the minor product and the 4s-isomer as the major product. Then each isomer was subjected to acidic deboronation Method C to give the titled compounds 130A1 and 130A2. Minor product 130A1: $^1$H NMR (300 MHz, methanol-D4) δ ppm 1.70-1.75 (m, 1H), 1.95-2.13 (m, 4H), 2.17 (d, J=2.7 Hz, 1H), 2.21 (d, J=2.4 Hz, 1H), 2.97 (d, J=1.4 Hz, 1H), 3.01 (d, J=1.4 Hz, 1H), 3.13 (s, 2H), 3.37 (s, 1H), 3.41 (s, 1H), 5.23 (t, J=3.4 Hz, 1H), 7.11 (s, 1H). MS (DCI/NH$_3$) m/e=315, 317 (M+H)$^+$. Major product 130A2: Major product 130A2: $^1$H NMR (300 MHz, methanol-D4) δ ppm 1.67 (s, 1H), 1.85 (s, 1H), 1.89 (s, 1H), 2.13-2.30 (m, 4H), 3.05-3.16 (m, 4H), 3.26 (s, 1H), 5.22 (t, J=3.4 Hz, 1H), 7.11 (s, 1H). MS (DCI/NH$_3$) m/e=315, 317 (M+H)$^+$.

Example 130B (4r)-4-(5-Bromo-thiazol-2-yloxy)1-aza-tricyclo[3.3.1.1$^{3,7}$]decane tosylate Prepared from the product of Example 130A1 (32 mg, 0.101 mmol) following the salt formation method H to give the titled compound: $^1$H NMR (300 MHz, methanol-D4) δ ppm 2.00-2.28 (m, 5H), 2.37 (s, 3H), 2.59 (s, 2H), 3.46 (d, J=12.2 Hz, 2H), 3.55 (s, 2H), 3.73 (s, 1H), 3.77 (s, 1H), 5.28 (t, J=3.6 Hz, 1H), 7.16 (s, 1H), 7.23 (d, J=7.8 Hz, 2H), 7.70 (d, J=8.1 Hz, 2H). MS (DCI/NH$_3$) m/e=315, 317 (M+H)$^+$. Anal. calcd. for C$_{12}$H$_{15}$N$_2$BrOS.C$_7$H$_8$O$_3$S: C, 46.82; H, 4.76; N, 5.75. Found C, 46.72; H, 4.42; N, 5.68.

Example 131

(4s)-4-({5-[4-(Trifluoromethoxy)phenyl]-1,3-thiazol-2-yl}oxy)-1-azatricyclo[3.3.1.1$^{3,7}$]decane hydrochloride Example 131A (4s)-4-({5-[4-(Trifluoromethoxy)phenyl]-1,3-thiazol-2-yl}oxy)-1-azatricyclo[3.3.1.1$^{3,7}$]decane N-borane complex Prepared from the product of Example 20A (65.0 mg, 0.20 mmol) and 4-(trifluoromethoxy)phenylboronic acid (74.8 mg, 0.36 mmol) according to Method K: $^1$H NMR (300 MHz, chloroform-D) δ ppm 1.69-1.73 (m, 2H), 2.03 (br s, 1H), 2.22-2.26 (m, 2H), 2.43 (s, 2H), 3.19-3.24 (m, 6H), 5.42 (t, J=3.4 Hz, 1H), 6.81-6.84 (m, 2H), 7.27 (s, 1H), 7.43-7.47 (m, 2H). MS (DCI/NH$_3$) m/z=411 (M+H)$^+$.

Example 131B (4s)-4-({5-[4-(Trifluoromethoxy)phenyl]-1,3-thiazol-2-yl}oxy)-1-azatricyclo[3.3.1.1$^{3,7}$]decane hydrochloride Prepared from the product of Example 131A (45.7 mg, 0.11 mmol) according to Method J: $^1$H NMR (300 MHz, methanol-D4) δ ppm 1.95-1.99 (m, 2H), 2.21 (br s, 1H), 2.31-2.35 (m, 2H), 2.66 (br s, 2H), 3.58 (br s, 2H), 3.63-3.73 (m, 4H), 5.41 (t, J=3.4 Hz, 1H), 7.30-7.32 (m, 2H), 7.48 (s, 1H), 7.59-7.64 (m, 2H). MS (DCI/NH$_3$) m/z=397 (M+H)$^+$. Anal. Calcd. for C$_{19}$H$_{19}$F$_3$N$_2$O$_2$S.1.15 HCl.0.35 HCl: C, 51.32; H, 4.73; N, 6.30; Cl, 9.17. Found: C, 51.42; H, 4.77; N, 6.29; Cl, 9.05.

Example 132

(4s)-4-{[5-(4-Chlorophenyl)-1,3-thiazol-2-yl]oxy}-1-azatricyclo[3.3.1.1$^{3,7}$]decane The product of Example 20A (50 mg, 0.152 mmol) and 4-chlorophenylboronic acid (30.9 mg, 0.198 mmol) were processed as described in Example 123A to provide the N-borane complex of the titled compound. It was then processed as described in Method C. The resulting mixture in 3 N HCl was concentrated to dryness and stirred in 10:1 diethyl ether/MeOH. The precipitate was filtered and dried under vacuum to afford the titled compound as a hydrochloride salt: $^1$H NMR (500 MHz, methanol-D4) δ ppm 1.91-2.03 (m, 2H), 2.21 (br s, 1H), 2.27-2.38 (m, 2H), 2.66 (br s, 2H), 3.58 (br s, 2H), 3.62-3.76 (m, 4H), 5.40 (t, J=3.2 Hz, 1H), 7.37-7.42 (m, 2H), 7.47 (s, 1H), 7.48-7.53 (m, 2H). MS (ESI) m/z=347 (M+H)$^+$.

Example 133

4-{2-[(4s)-1-Azatricyclo[3.3.1.1$^{3,7}$]dec-4-yloxy]-1,3-thiazol-5-yl}aniline

In a sealed tube were combined the product of Example 20A (50 mg, 0.152 mmol), 4-(tert-butoxycarbonylamino)phenylboronic acid (46.8 mg, 0.198 mmol), bis(triphenylphosphine)-palladium(II) chloride (4.3 mg, 6.08 μmol), and aqueous sodium carbonate (1.0 M, 0.38 mL), followed by 2-propanol (1.2 mL). The tube was heated to 93° C. for 90 minutes. After cooling to room temperature, the mixture was partitioned between ethyl acetate (2×50 mL) and water (50 mL). The combined organic extracts were washed with brine, dried (sodium sulfate) and concentrated under reduced pressure. The resulting material was purified by preparative HPLC on a Waters Nova-Pak HR C18 6 μm 60 Å Prep-Pak cartridge column (40 mm×100 mm) using a gradient of 10% to 100% acetonitrile in 10 mM aqueous ammonium acetate over 12 minutes at a flow rate of 70 mL/minute to provide a white solid. The solid was then processed as described in Method C to provide the free base. It was then reacted with HCl-dioxane according to Method H to provide the titled compound: $^1$H NMR (500 MHz, methanol-D4) δ ppm 1.91-2.04 (m, 2H), 2.21 (br s, 1H), 2.28-2.39 (m, 2H), 2.66 (br s, 2H), 3.59 (br s, 2H), 3.62-3.75 (m, 4H), 5.40 (t, J=3.3 Hz, 1H), 7.17-7.30 (m, 2H), 7.45 (s, 1H), 7.52-7.63 (m, 2H). MS (ESI) m/z=328 (M+H)$^+$.

Example 134

(4s)-4-(5-(Pyridin-3-yl)-thiazol-2-yloxy)1-aza-tricyclo[3.3.1.1$^{3,7}$]decane tosylate Prepared from the major product of Example 130A2 (31 mg, 0.098 mmol) and pyridin-3-ylboronic acid using the microwave Suzuki coupling Method G and then the salt formation Method H to provide the titled compound: $^1$H NMR (300 MHz, methanol-D4) δ ppm 1.95 (s, 1H), 1.99 (s, 1H), 2.20 (s, 1H), 2.31 (s, 1H), 2.36 (s, 3H), 2.66 (s, 2H), 3.55-3.75 (m, 6H), 5.43 (t, J=3.4 Hz, 1H), 7.23 (d, J=7.8 Hz, 2H), 7.47 (dd, J=8.5, 5.4 Hz, 1H), 7.60 (s, 1H), 7.70 (d, J=7.8 Hz, 2H), 7.96-8.02 (m, 1H), 8.45-8.49 (m, 1H), 8.72 (d, J=2.0 Hz, 1H). MS (DCI/NH$_3$) m/e=314 (M+H)$^+$.

Example 135

(4r)-4-(5-(Pyridin-3-yl)-thiazol-2-yloxy)1-aza-tricyclo[3.3.1.1$^{3,7}$]decane tosylate Prepared from the minor product of Example 130A1 (40 mg, 0.127 mmol) and pyridin-3-ylboronic acid using the microwave Suzuki coupling Method G and then the salt formation Method H to provide the titled compound: $^1$H NMR (300 MHz, methanol-D4) δ ppm 2.04-2.30 (m, 5H), 2.36 (s, 3H), 2.65 (s, 2H), 3.43-3.84 (m, 6H), 5.35 (t, J=3.6 Hz, 1H), 7.23 (d, J=8.5 Hz, 2H), 7.47 (dd, J=8.1, 4.7 Hz, 1H), 7.61 (s, 1H), 7.70 (d, J=8.5 Hz, 2H), 7.99 (dt, J=8.1, 1.9 Hz, 1H), 8.47 (dd, J=5.1, 1.4 Hz, 1H), 8.71 (d, J=2.4 Hz, 1H). MS (DCI/NH$_3$) m/e=314 (M+H)$^+$. Anal. calcd. for C$_{17}$H$_{19}$N$_3$OS.1.05C$_7$H$_8$O$_3$S: C, 59.18; H, 5.59; N, 8.50. Found C, 59.02; H, 5.43; N, 8.55.

Example 136

(4s)-4-[(5-Pyrimidin-5-yl-1,3-thiazol-2-yl)oxy]-1-azatricyclo[3.3.1.1$^{3,7}$]decane hydrochloride Example 136A (4s)-4-[(5-Pyrimidin-5-yl-1,3-thiazol-2-yl)oxy]-1-azatricyclo[3.3.1.1$^{3,7}$]decane N-borane complex Prepared from the product of Example 20A (95.2 mg, 0.29 mmol) and pyrimidin-5-ylboronic acid (59.2 mg, 0.48 mmol) according to Method K: $^1$H NMR (300 MHz, chloroform-D) δ ppm 1.70-1.74 (m, 2H), 2.05 (br s, 1H), 2.21-2.25 (m, 2H), 2.45 (s, 2H), 3.20-3.25 (m, 6H), 5.29 (t, J=3.4 Hz, 1H), 7.41 (s, 1H), 8.81 (s, 2H), 9.13 (s, 1H). MS (DCI/NH$_3$) m/z=329 (M+H)$^+$.

Example 136B (4s)-4-[(5-Pyrimidin-5-yl-1,3-thiazol-2-yl)oxy]-1-azatricyclo[3.3.1.1$^{3,7}$]decane hydrochloride Prepared from the product of Example 136A (17.3 mg, 0.053 mmol) according to Method J: $^1$H NMR (300 MHz, methanol-D4) δ ppm 1.95-2.00 (m, 2H), 2.21 (br s, 1H), 2.31-2.36 (m, 2H), 2.68 (br s, 2H), 3.59 (s, 2H), 3.63-3.75 (m, 4H), 5.47 (t, J=3.6 Hz, 1H), 7.72 (s, 1H), 8.98 (s, 2H), 9.07 (s, 1H). MS (DCI/NH$_3$) m/z=315 (M+H)$^+$. Anal. Calcd. for C$_{16}$H$_{18}$N$_4$OS.2 HCl: C, 49.62; H, 5.20; N, 14.46. Found: C, 49.86; H, 5.23; N, 14.26.

Example 137

(4s)-4-{[5-(2-Methoxypyrimidin-5-yl)-1,3-thiazol-2-yl]oxy}-1-azatricyclo[3.3.1.1$^{3,7}$]decane To a solution of the product of Example 20A (80 mg, 0.243 mmol) in DMF (2.5 mL) was added 2-methoxypyrimidin-5-ylboronic acid (70.4 mg, 0.457 mmol), bis(triphenylphosphine)-palladium(II) chloride (8.5 mg, 0.012 mmol) and cesium carbonate (206 mg, 0.632 mmol). The reaction mixture was stirred at 65° C. for 18 hours. After cooling to room temperature, the reaction mixture was diluted with ethyl acetate (30 mL) and partitioned between ethyl acetate (2×30 mL) and water (30 mL). The organic layers were combined and washed with brine (200 mL), dried (sodium sulfate) and concentrated in vacuo. The residue was purified by silica gel flash chromatography to afford the N-borane complex, which was then processed as described in Method C. The resulting mixture in 3 N HCl was concentrated to dryness and stirred in 10:1 diethyl ether/MeOH. The precipitate was filtered and dried under vacuum to afford the titled compound as hydrochloride salt: $^1$H NMR (500 MHz, methanol-D4) δ ppm 1.94-2.02 (m, 2H), 2.22 (br s, 1H), 2.28-2.38 (m, 2H), 2.62-2.71 (m, 2H), 3.59 (br s, 2H), 3.62-3.79 (m, 4H), 4.04 (s, 3H), 5.43 (t, J=3.2 Hz, 1H), 7.51 (s, 1H), 8.71-8.75 (m, 2H). MS (ESI) m/z=345 (M+H)$^+$. Anal. Calcd. for C$_{17}$H$_{20}$N$_4$O$_2$S.1.3 HCl: C, 52.11; H, 5.48; N, 14.30. Found: C, 52.08; H, 5.52; N, 14.33.

Example 138

(4s)-4-{[5-(2-Pyrrolidin-1-ylpyrimidin-5-yl)-1,3-thiazol-2-yl]oxy}-1-azatricyclo[3.3.1.1$^{3,7}$]decane To a solution of the product of Example 20A (62 mg, 0.188 mmol) in DMF (2.0 mL) was added 2-(pyrrolidin-1-yl)-5-(4,4,5,5-tetramethyl-1,3,2-dioxaborolan-2-yl)pyrimidine (78 mg, 0.283 mmol), bis(triphenylphosphine)-palladium(II) chloride (6.6 mg, 9.42 μmol) and cesium carbonate (153 mg, 0.471 mmol), and the reaction mixture was stirred at 65° C. for 4 hours. After cooling to room temperature, the reaction mixture was diluted with methanol (4.0 mL), filtered, and purified by preparative HPLC [Waters® XTerra RP18 5 μm column, 30×100 mm, flow rate 40 mL/minute, 5-95% gradient of acetonitrile in buffer (0.1 M aqueous ammonium bicarbonate, adjusted to pH 10 with ammonium hydroxide) over 22 minutes, with UV detection at 254 nm]. Fractions containing the desired N-borane complex were pooled, concentrated under vacuum and processed as described in Method C. The resulting free base was converted to the tosylate salt by the procedure of Method H: $^1$H NMR (400 MHz, methanol-D4) δ ppm 1.93-2.01 (m, 2H), 2.11-2.17 (m, 4H), 2.18-2.23 (m, 1H), 2.27-2.34 (m, 2H), 2.36 (s, 12H), 2.65 (br s, 2H), 3.56-3.60 (m, 2H), 3.62-3.75 (m, 8H), 5.43 (t, J=3.5 Hz, 1H), 7.19-7.26 (m, 8H), 7.55 (s, 1H), 7.67-7.73 (m, 8H), 8.72 (s, 2H). MS (APCI) m/z=384 (M+H)$^+$.

Example 139

(4s)-4-{[5-(6-piperazin-1-ylpyridin-3-yl)-1,3-thiazol-2-yl]oxy}-1-azatricyclo[3.3.1.1$^{3,7}$]decane To a solution of the product of Example 20A (75 mg, 0.228 mmol) in DMF (2.0 mL) was added 1-(5-(4,4,5,5-tetramethyl-1,3,2-dioxaborolan-2-yl)pyridin-2-yl)piperazine (99 mg, 0.342 mmol), bis(triphenylphosphine)-palladium(II) chloride (8.0 mg, 0.011 mmol) and cesium carbonate (186 mg, 0.570 mmol) and the reaction mixture was stirred at 65° C. for 18 hours. After cooling to room temperature, the reaction mixture was diluted with methanol (2.0 mL), filtered, and purified by preparative HPLC [Waters® XTerra RP18 5 μm column, 30×100 mm, flow rate 40 mL/minute, 5-95% gradient of acetonitrile in buffer (0.1 M aqueous ammonium bicarbonate, adjusted to pH 10 with ammonium hydroxide) over 22 minutes, with UV detection at 254 nm]. Fractions containing the free base were pooled, concentrated under vacuum and then processed as described in Method H to provide the tosylate salt: $^1$H NMR (400 MHz, methanol-D4) δ ppm 1.92-2.00 (m, 2H), 2.14-2.23 (m, 1H), 2.27-2.34 (m, 2H), 2.36 (s, 9H), 2.65 (br s, 2H), 3.39-3.45 (m, 4H), 3.58 (s, 2H), 3.61-3.76 (m, 4H), 3.91-3.97 (m, 4H), 5.41 (t, J=3.2 Hz, 1H), 7.18-7.24 (m, 6H), 7.26 (d, J=9.2 Hz, 1H), 7.46 (s, 1H), 7.66-7.73 (m, 6H), 8.04 (dd, J=9.2, 2.5 Hz, 1H), 8.18 (d, J=2.1 Hz, 1H). MS (ESI) m/z=398 (M+H)$^+$. Anal. Calcd. for C$_{24}$H$_{27}$N$_5$OS.2.75TsOH: C, 55.50; H, 5.67; N, 8.04. Found: C, 55.31; H, 5.88; N, 7.93.

Example 140

(4s)-4-{[5-(1H-Pyrazol-1-yl)-1,3-thiazol-2-yl]oxy}-1-azatricyclo[3.3.1.1$^{3,7}$]decane The product of Example 20B (100 mg, 0.304 mmol), 1H-pyrazole (32.1 mg, 0.471 mmol), ferric acetylacetonate (32.2 mg, 0.091 mmol), copper(II) oxide (2.4 mg, 0.030 mmol) and cesium carbonate (198 mg, 0.608 mmol) were suspended in DMF (0.5 mL) and stirred at 90° C. for 60 hours. After cooling to room temperature, the reaction mixture was diluted with methanol (3.0 mL), filtered and purified by preparative HPLC [Waters® XTerra RP18 5 μm column, 30×100 mm, flow rate 40 mL/minute, 5-95% gradient of acetonitrile in buffer (0.1 M aqueous ammonium bicarbonate, adjusted to pH 10 with ammonium hydroxide) over 22 minutes, with UV detection at 254 nm]. Fractions containing the free base were pooled, concentrated under vacuum and then treated with methanol (0.3 mL) and HCl-diethyl ether (0.5 M, 3 mL). After stirring for 10 minutes at room temperature, the precipitate was filtered and dried under vacuum to afford the titled compound as the hydrochloride salt: $^1$H NMR (500 MHz, methanol-D4) δ ppm 1.90-2.01 (m, 2H), 2.21 (br s, 1H), 2.27-2.38 (m, 2H), 2.66 (br s, 2H), 3.58 (br s, 2H), 3.61-3.75 (m, 4H), 5.42 (t, J=3.3 Hz, 1H), 6.50 (t, J=2.1 Hz, 1H), 7.32 (s, 1H), 7.68 (d, J=1.5 Hz, 1H), 8.05 (d, J=2.4 Hz, 1H). MS (ESI) m/z=303 (M+H)$^+$. Anal. Calcd. for C$_{15}$H$_{18}$N$_4$OS.1.2HCl: C, 52.05; H, 5.59; N, 16.19. Found: C, 52.14; H, 5.79; N, 15.83.

Example 141

(4s)-4-{[5-(1-Trityl-1H-pyrazol-4-yl)-1,3-thiazol-2-yl]oxy}-1-azatricyclo[3.3.1.1$^{3,7}$]decane

Example 141A (4s)-4-{[5-(1-Trityl-1H-pyrazol-4-yl)-1,3-thiazol-2-yl]oxy}-1-azatricyclo[3.3.1.1$^{3,7}$]decane N-borane complex To a solution of the product of Example 20B (1.06 g, 3.23 mmol) in DMF (32 mL) was added 4-(4,4,5,5-tetramethyl-1,3,2-dioxaborolan-2-yl)-1-trityl-1H-pyrazole (1.83 g, 4.20 mmol; JP 2005232071), bis(triphenylphosphine)-palladium (II) chloride (113 mg, 0.161 mmol) and cesium carbonate (2.57 g, 7.87 mmol), and the reaction mixture was stirred at 65° C. for 6 hours. After cooling to room temperature, the reaction mixture was partitioned between water (250 mL) and ethyl acetate (3×200 mL). The combined organic extracts were washed with brine, dried (sodium sulfate) and concentrated under reduced pressure, and the resulting material was purified by silica gel flash column chromatography to afford the titled compound: $^1$H NMR (400 MHz, chloroform-D) δ ppm 1.62-1.72 (m, 2H), 1.96-2.03 (m, 1H), 2.16-2.24 (m, 2H), 2.39 (br s, 2H), 3.11-3.24 (m, 6H), 5.17 (t, J=2.9 Hz, 1H), 7.00 (s, 1H), 7.11-7.22 (m, 6H), 7.29-7.36 (m, 9H), 7.43 (d, J=0.6 Hz, 1H), 7.73 (d, J=0.6 Hz, 1H). MS (APCI) m/z=545 (M-BH$_3$+H)$^+$.

Example 141B (4s)-4-{[5-(1-Trityl-1H-pyrazol-4-yl)-1,3-thiazol-2-yl]oxy}-1-azatricyclo[3.3.1.1$^{3,7}$]decane A suspension of the product of Example 141A (60 mg, 0.107 mmol) in acetone (3.0 mL), was treated with HCl (3 N, 1.0 mL) and the reaction mixture was stirred at room temperature for 10 minutes. Sodium hydroxide (2.5 M, 2.0 mL) was added and the reaction mixture was partitioned between water (50 mL) and chloroform (3×30 mL). The combined organic extracts were dried (sodium sulfate) and concentrated under reduced pressure, and the resulting material was purified by silica gel flash column chromatography to afford the titled compound: $^1$H NMR (400 MHz, chloroform-D) δ ppm 1.79-1.88 (m, 2H), 2.21 (br s, 1H), 2.32-2.39 (m, 2H), 2.65 (br s, 2H), 3.43-3.59 (m, 6H), 5.25 (t, J=3.1 Hz, 1H), 7.00 (s, 1H), 7.12-7.20 (m, 6H), 7.29-7.36 (m, 9H), 7.45 (s, 1H), 7.73 (s, 1H). MS (APCI) m/z=545 (M+H)+.

Example 142

(4s)-4-{[5-(1-Propyl-1H-pyrazol-4-yl)-1,3-thiazol-2-yl]oxy}-1-azatricyclo[3.3.1.1³,⁷]decane A solution of the product of Example 20A (120 mg, 0.365 mmol) in 2-propanol (2.5 mL) was combined with 1-propyl-4-(4,4,5,5-tetramethyl-1,3,2-dioxaborolan-2-yl)-1H-pyrazole (103 mg, 0.438 mmol), bis(triphenylphosphine)-palladium(II) chloride (12.8 mg, 0.018 mmol) and aqueous sodium carbonate (1.0 M, 0.91 mL). The reaction mixture was degassed with nitrogen and then heated with stirring at 100° C. for 1 hour. After cooling to room temperature, the reaction mixture was passed through a glass microfiber frit, concentrated, dissolved in DMF (2 mL), and purified by preparative HPLC [Waters® XTerra RP 18 5 µm column, 30×100 mm, flow rate 40 mL/minute, 5-95% gradient of acetonitrile in buffer (0.1 M aqueous ammonium bicarbonate, adjusted to pH 10 with ammonium hydroxide) over 22 minutes, with UV detection at 254 nm]. Fractions containing both the desired free base and the N-borane complex were pooled and concentrated under vacuum. It was then processed as described in Method C. The resulting mixture in 3 N HCl was concentrated to dryness and stirred in 10:1 diethyl ether/MeOH. The precipitate was filtered and dried under vacuum to afford the titled compound as a trihydrochloride salt: $^1$H NMR (400 MHz, methanol-D4) δ ppm 0.93 (t, J=7.5 Hz, 3H), 1.91 (hex, 7.4 Hz, 2H), 1.96-2.02 (m, 2H), 2.22 (br s, 1H), 2.27-2.37 (m, 2H), 2.66 (br s, 2H), 3.59 (br s, 2H), 3.63-3.75 (m, 4H), 4.19 (t, J=7.1 Hz, 2H), 5.38 (t, J=3.2 Hz, 1H), 7.31 (s, 1H), 7.89 (s, 1H), 8.08 (s, 1H). MS (ESI) m/z=345 (M+H)+. Anal. Calcd. for $C_{18}H_{24}N_4OS.2.75HCl.0.7H_2O$: C, 47.27; H, 6.20; N, 12.25; Cl, 21.32. Found: C, 46.98; H, 6.21; N, 12.60; Cl, 21.18.

Example 143

(4s)-4-{[5-(1-Isobutyl-1H-pyrazol-4-yl)-1,3-thiazol-2-yl]oxy}-1-azatricyclo[3.3.1.1³,⁷]decane To a solution of the product of Example 20A (95 mg, 0.289 mmol) in DMF (2.5 mL) were added 1-isobutyl-4-(4,4,5,5-tetramethyl-1,3,2-dioxaborolan-2-yl)-1H-pyrazole (87 mg, 0.346 mmol), bis(triphenylphosphine)-palladium(II) chloride (10.1 mg, 0.014 mmol) and cesium carbonate (235 mg, 0.722 mmol). The reaction mixture was purged with nitrogen and then heated with stirring at 65° C. for 18 hours. After cooling to room temperature, methanol (2.0 mL) was added and the reaction mixture was passed through a glass microfiber frit and purified by preparative HPLC [Waters® XTerra RP18 5 µm column, 30×100 mm, flow rate 40 mL/minute, 5-95% gradient of acetonitrile in buffer (0.1 M aqueous ammonium bicarbonate, adjusted to pH 10 with ammonium hydroxide) over 22 minutes, with UV detection at 254 nm]. Fractions containing the N-borane complex were pooled and concentrated under vacuum. It was then processed as described in Method C. The resulting mixture in 3 N HCl was concentrated to dryness and stirred in 10:1 diethyl ether/MeOH. The precipitate was filtered and dried under vacuum to afford the titled compound as the hydrochloride salt: $^1$H NMR (400 MHz, methanol-D4) δ ppm 0.91 (d, J=6.8 Hz, 6H), 1.90-2.01 (m, 2H), 2.10-2.24 (m, 2H), 2.28-2.36 (m, 2H), 2.64 (br s, 2H), 3.58 (br s, 2H), 3.61-3.75 (m, 4H), 3.95 (d, J=7.4 Hz, 2H), 5.34 (t, J=3.4 Hz, 1H), 7.19 (s, 1H), 7.65 (d, J=0.9 Hz, 1H), 7.85 (d, J=0.9 Hz, 1H). MS (ESI) m/z=359 (M+H)+. Anal. Calcd. for $C_{19}H_{26}N_4OS.1HCl.0.25H_2O$: C, 57.13; H, 6.94; N, 14.03; Cl, 8.88. Found: C, 57.08; H, 7.07; N, 14.13; Cl, 8.92.

Example 144

(4s)-4-{[5-(1-Acetyl-1H-pyrazol-4-yl)-1,3-thiazol-2-yl]oxy}-1-azatricyclo[3.3.1.1³,⁷]decane Example 144A (4s)-4-[5-(Pyrazol-4-yl)-thiazol-2-yloxy]-1-azatricyclo[3.3.1.1³,⁷]decane bishydrochloride The product of Example 141A (128 mg, 0.229 mmol) was processed according to Method L. The resulting mixture in 3 N HCl was concentrated to dryness and stirred in 10:1 diethyl ether/MeOH. The precipitate was filtered and dried under vacuum to afford the titled compound as a bishydrochloride salt: $^1$H NMR (400 MHz, methanol-D4) δ ppm 1.93-2.01 (m, 2H), 2.22 (s, 1H), 2.27-2.37 (m, 2H), 2.66 (s, 2H), 3.59 (s, 2H), 3.62-3.75 (m, 4H), 5.40 (t, J=3.1 Hz, 1H), 7.37 (s, 1H), 8.22 (s, 2H). MS (APCI) m/z=303 (M+H)+. Anal. Calcd. for $C_{15}H_{18}N_4OS.2HCl$: C, 48.00; H, 5.37; N, 14.93; Cl, 18.89. Found: C, 47.86; H, 5.64; N, 14.57; Cl, 18.58.

Example 144B (4s)-4-{[5-(1-Acetyl-1H-pyrazol-4-yl)-1,3-thiazol-2-yl]oxy}-1-azatricyclo[3.3.1.1³,⁷]decane A suspension of the product of Example 144A (80 mg, 0.213 mmol) in acetic acid (1.0 mL) was treated with acetic anhydride (1.00 g, 9.80 mmol), and the reaction mixture was stirred at room temperature for 1 hour. The reaction mixture was concentrated to dryness and methanol (1.0 mL) was added. After stirring at room temperature for 10 minutes, the precipitate was filtered and dried under vacuum to afford the titled compound as a hydrochloride salt: $^1$H NMR (500 MHz, methanol-D4) δ ppm 1.93-2.01 (m, 2H), 2.21 (br s, 1H), 2.27-2.35 (m, 2H), 2.65 (br s, 2H), 2.67 (s, 3H), 3.58 (br s, 2H), 3.62-3.75 (m, 4H), 5.39 (t, J=3.2 Hz, 1H), 7.40 (s, 1H), 8.01 (s, 1H), 8.47 (s, 1H). MS (APCI) m/z=345 (M+H)+. Anal. Calcd. for $C_{17}H_{20}N_4O_2S.1.5HCl$: C, 51.16; H, 5.43; N, 14.04. Found: C, 51.42; H, 5.19; N, 13.81.

Example 145

(4s)-4-{[5-(5-Methyl-1-phenyl-1H-pyrazol-4-yl)-1,3-thiazol-2-yl]oxy}-1-azatricyclo[3.3.1.1³,⁷]decane To a solution of the product of Example 20A (139 mg, 0.422 mmol) in 2-propanol (2.7 mL) were added 5-methyl-1-phenyl-4-(4,4,5,5-tetramethyl-1,3,2-dioxaborolan-2-yl)-1H-pyrazole (100 mg, 0.352 mmol), bis(triphenylphosphine)-palladium(II) chloride (12.4 mg, 0.018 mmol) and aqueous sodium carbonate (1.0M, 0.88 mL). The reaction mixture was degassed with nitrogen and stirred at 100° C. for 1 hour. After cooling to room temperature, the reaction mixture was passed through a glass microfiber frit, concentrated, dissolved in MeOH (2.0 mL), and purified by preparative HPLC [Waters® XTerra RP18 5 µm column, 30×100 mm, flow rate 40 mL/minute, 5-95% gradient of acetonitrile in buffer (0.1 M aqueous ammonium bicarbonate, adjusted to pH 10 with ammonium hydroxide) over 22 minutes, with UV detection at 254 nm]. Fractions containing both the desired free base and the N-borane complex were pooled, concentrated under vacuum, and processed as described in Method C. The resulting mixture in 3 N HCl was concentrated to dryness and stirred in 10:1 diethyl ether/MeOH. The precipitate was filtered and dried under vacuum to afford the titled compound as the hydrochloride salt: $^1$H NMR (400 MHz, methanol-D4) δ ppm 1.93-2.02 (m, 2H), 2.21 (br s, 1H), 2.27-2.36 (m, 2H), 2.37-2.43 (m, 3H), 2.66 (br s, 2H), 3.58 (br s, 2H), 3.60-3.77 (m, 4H), 5.38 (br s, 1H), 7.15-7.21 (m, 1H), 7.45-7.53 (m, 3H), 7.53-7.60 (m, 2H), 7.71-7.78 (m, 1H). MS (ESI) m/z=393 (M+H)$^+$.

Example 146

(4s)-4-[(5-Isoxazol-4-yl-1,3-thiazol-2-yl)oxy]-1-azatricyclo[3.3.1.1$^{3,7}$]decane To a solution of the product of Example 20A (100 mg, 0.304 mmol) in 2-propanol (2.0 mL) were added 4-(4,4,5,5-tetramethyl-1,3,2-dioxaborolan-2-yl)isoxazole (71.1 mg, 0.365 mmol), bis(triphenylphosphine)-palladium(II) chloride (10.7 mg, 0.015 mmol) and aqueous sodium carbonate (1.0M, 0.76 mL). The reaction mixture was degassed with nitrogen and heated with stirring at 100° C. for 2 hours. After cooling to room temperature, the reaction mixture was passed through a glass microfiber frit, concentrated, dissolved in MeOH (2.0 mL), and purified by preparative HPLC [Waters® XTerra RP18 5 μm column, 30×100 mm, flow rate 40 mL/minute, 5-95% gradient of acetonitrile in buffer (0.1 M aqueous ammonium bicarbonate, adjusted to pH 10 with ammonium hydroxide) over 22 minutes, with UV detection at 254 nm]. Fractions containing both the desired free base and the N-borane complex were pooled, concentrated under vacuum, and processed as described in Method C. The resulting material was taken into 3 N HCl, was concentrated to dryness and stirred in 10:1 diethyl ether/MeOH. The precipitate was filtered and dried under vacuum to afford the titled compound as the trihydrochloride salt: $^1$H NMR (400 MHz, methanol-D4) δ ppm 1.90-2.02 (m, 2H), 2.20 (br s, 1H), 2.25-2.39 (m, 2H), 2.64 (br s, 2H), 3.58 (br s, 2H), 3.60-3.75 (m, 4H), 5.36 (t, J=3.3 Hz, 1H), 7.19 (s, 1H), 7.43 (s, 1H). MS (ESI) m/z=304 (M+H)$^+$. Anal. Calcd. for $C_{15}H_{17}N_3O_2S.2.95HCl.0.45NH_4Cl$: C, 41.42; H, 5.04; N, 11.11. Found: C, 41.35; H, 4.99; N, 11.05.

Example 147

(4s)-4-[(4-Bromo-1,3-thiazol-2-yl)oxy]-1-azatricyclo[3.3.1.1$^{3,7}$]decane

Example 147A (4s)-4-[(4-Bromo-1,3-thiazol-2-yl)oxy]-1-azatricyclo[3.3.1.1$^{3,7}$]decane N-borane complex Prepared from the product of Example 10A (600 mg, 3.59 mmol) and 2,4-dibromothiazole (1047 mg, 4.31 mmol) according to Method B: $^1$H NMR (500 MHz, methanol-D4) δ ppm 1.70-1.78 (m, 2H), 1.96 (br s, 1H), 2.11-2.19 (m, 2H), 2.36 (br s, 2H), 3.14 (br s, 2H), 3.15-3.24 (m, 4H), 5.21 (t, J=3.4 Hz, 1H), 6.88 (s, 1H). MS (APCI) m/z=329 (M+H)$^+$.

Example 147B (4s)-4-[(4-Bromo-1,3-thiazol-2-yl)oxy]-1-azatricyclo[3.3.1.1$^{3,7}$]decane Prepared from the product of Example 147A (455 mg, 1.38 mmol) according to Method C: $^1$H NMR (500 MHz, methanol-D4) δ ppm 1.68 (br s, 1H), 1.83-1.93 (m, 2H), 2.19 (br s, 2H), 2.21-2.30 (m, 2H), 3.10-3.16 (m, 4H), 3.25-3.29 (m, 2H), 5.22 (t, J=3.2 Hz, 1H), 6.86 (s, 1H). MS (ESI) m/z=315/317 (M+H)$^+$. Anal. Calcd. for $C_{12}H_{15}BrN_2OS.0.3H_2O$: C, 44.95; H, 4.90; N, 8.74. Found: C, 44.78; H, 4.62; N, 8.60.

Example 148

(4s)-4-[(4-Bromo-1,3-thiazol-2-yl)oxy]-1-azatricyclo[3.3.1.1$^{3,7}$]decane

The N-borane complex of the titled compound was prepared from the product of Example 9D (117 mg, 0.700 mmol) and 2,4-dibromothiazole (191 mg, 0.784 mmol) according to Method B. It was then processed as described in Method C to provide the free base, which was then converted to the fumarate by the procedure of Method H: $^1$H NMR (500 MHz, methanol-D4) δ ppm 2.05-2.12 (m, 2H), 2.18-2.28 (m, 3H), 2.60 (br s, 2H), 3.46 (m, 2H), 3.54 (br s, 2H), 3.70-3.80 (m, 2H), 5.28 (t, J=3.4 Hz, 1H), 6.69 (s, 2H; $C_4H_4O_4$), 6.93 (s, 1H). MS (ESI) m/z=315/317 (M+H)$^+$. Anal. Calcd. for $C_{12}H_{15}BrN_2OS.1.15C_4H_4O_4$: C, 44.43; H, 4.40; N, 6.24. Found: C, 44.62; H, 4.36; N, 6.12.

Example 149

(4s)-4-[(4-Chloro-1,3-thiazol-2-yl)oxy]-1-azatricyclo[3.3.1.1$^{3,7}$]decane

Example 149A (4s)-4-[(4-Chloro-1,3-thiazol-2-yl)oxy]-1-azatricyclo[3.3.1.1$^{3,7}$]decane N-borane complex Prepared from the product of Example 10A (66 mg, 0.395 mmol) and 2,4-dichlorothiazole (66.9 mg, 0.435 mmol) according to Method B: $^1$H NMR (500 MHz, methanol-D4) δ ppm 1.64-1.86 (m, 2H), 1.96 (br s, 1H), 2.06-2.22 (m, 2H), 2.36 (br s, 2H), 3.10-3.25 (m, 6H), 5.20 (t, J=3.4 Hz, 1H), 6.74 (s, 1H). MS (DCI/NH$_3$) m/z=300 (M+NH$_2$)$^+$.

Example 149B (4s)-4-[(4-Chloro-1,3-thiazol-2-yl)oxy]-1-azatricyclo[3.3.1.1$^{3,7}$]decane The free base was prepared from the product of Example 149A (80 mg, 0.281 mmol) according to Method C. The resulting material was taken up in 3 N HCl, was concentrated to dryness and stirred in 10:1 diethyl ether/MeOH. The precipitate was filtered and dried under vacuum to afford the titled compound as a hydrochloride salt: $^1$H NMR (500 MHz, methanol-D4) δ ppm 1.91-2.02 (m, 2H), 2.20 (br s, 1H), 2.24-2.33 (m, 2H), 2.63 (br s, 2H), 3.57 (br s, 2H), 3.61-3.81 (m, 4H), 5.37 (t, J=3.2 Hz, 1H), 6.80 (s, 1H). MS (ESI) m/z=271 (M+H)$^+$. Anal. Calcd. for $C_{12}H_{15}ClN_2OS.1.0HCl$: C, 46.91; H, 5.25; N, 9.12; Cl, 23.08. Found: C, 46.64; H, 5.01; N, 8.92; Cl, 23.06.

Example 150

(4s)-4-{[4-(1H-Pyrazol-4-yl)-1,3-thiazol-2-yl]oxy}-1-azatricyclo[3.3.1.1$^{3,7}$]decane In a sealed tube were combined the product of Example 147A (50 mg, 0.152 mmol), 4-(4,4,5,5-tetramethyl-1,3,2-dioxaborolan-2-yl)-1-trityl-1H-pyrazole (86 mg, 0.198 mmol;

JP 2005232071), bis(triphenylphosphine)-palladium(II) chloride (5.3 mg, 7.60 µmol), cesium carbonate (121 mg, 0.371 mmol), and DMF (1.5 mL). The tube was heated at 65° C. for 6 hours. After cooling to room temperature, the mixture was partitioned between ethyl acetate (3×10 mL) and water (100 mL). The combined organic extracts were washed with brine (100 mL), dried (sodium sulfate) and concentrated under reduced pressure. The residue was purified by silica gel flash chromatography to provide the trityl protected N-borane complex as a white solid. The solid was then processed as described in Method L to provide the free base. It was then reacted with p-toluenesulfonic acid monohydrate according to Method H to provide the titled compound as a bistosylate: $^1$H NMR (400 MHz, methanol-D4) δ ppm 1.91-2.01 (m, 2H), 2.20 (br s, 1H), 2.27-2.34 (m, 2H), 2.36 (s, 6H; TsOH), 2.68 (br s, 2H), 3.58 (br s, 2H), 3.63-3.77 (m, 4H), 5.46 (t, J=3.4 Hz, 1H), 7.13 (s, 1H), 7.22 (d, J=8.0 Hz, 4H; TsOH), 7.70 (d, J=8.3 Hz, 4H; TsOH), 8.35 (s, 2H). MS (ESI) m/z=303 (M+H)$^+$. Anal. Calcd. for $C_{15}H_{18}N_4OS$.2.2TsOH, 0.7; $H_2O$: C, 52.63; H, 5.37; N, 8.07. Found: C, 52.46; H, 5.19; N, 8.21.

Example 151

(4s)-4-[(4-Phenyl-1,3-thiazol-2-yl)oxy]-1-azatricyclo[3.3.1.1$^{3,7}$]decane

To a solution of the product of Example 147A (71 mg, 0.216 mmol) in 2-propanol (3.0 mL) and water (1.0 mL) were added phenylboronic acid (34.2 mg, 0.280 mmol), bis(triphenylphosphine)-palladium(II) chloride (6.1 mg, 8.6 µmol) and aqueous sodium carbonate (2.5M, 0.54 mL). The reaction mixture was degassed with nitrogen and then heated with stirring at 90° C. for 2 hours. After cooling to room temperature, the reaction mixture was diluted with ethyl acetate (5.0 mL), passed through a glass microfiber frit, concentrated and purified by silica gel flash chromatography to provide the N-borane complex. It was then processed as described in Method C. The resulting material was taken into 3 N HCl, was concentrated to dryness and stirred in 10:1 diethyl ether/MeOH. The precipitate was filtered and dried under vacuum to afford the titled compound as hydrochloride salt: $^1$H NMR (500 MHz, methanol-D4) δ ppm 1.93-2.03 (m, 2H), 2.22 (br s, 1H), 2.31-2.41 (m, 2H), 2.73 (br s, 2H), 3.59 (br s, 2H), 3.67-3.77 (m, 4H), 5.51 (t, J=3.2 Hz, 1H), 7.20 (s, 1H), 7.27-7.32 (m, 1H), 7.33-7.47 (m, 2H), 7.77-7.90 (m, 2H). MS (ESI) m/z=313 (M+H)$^+$.

Example 152

(4s)-4-[(4-Pyridin-4-yl-1,3-thiazol-2-yl)oxy]-1-azatricyclo[3.3.1.1$^{3,7}$]decane The product of Example 147A (65 mg, 0.198 mmol) was dissolved in 2-propanol (1.5 mL). Pyridine-4-boronic acid (31.6 mg, 0.257 mmol), bis(triphenylphosphine)-palladium (II) chloride (5.6 mg, 7.90 µmol) and aqueous sodium carbonate (1.0 M, 0.49 mL) were added, and the reaction mixture was degassed with nitrogen and heated with stirring at 90° C. for 1.5 hours. After cooling to room temperature, the reaction mixture was diluted with ethyl acetate (5.0 mL), passed through a glass microfiber frit, concentrated and purified by silica gel flash chromatography to provide the N-borane complex. It was then processed as described in Method C. The resulting material was taken into 3 N HCl, was concentrated to dryness and stirred in 10:1 diethyl ether/MeOH. The precipitate was filtered and dried under vacuum to afford the titled compound as the hydrochloride salt: $^1$H NMR (500 MHz, methanol-D4) δ ppm 1.92-2.08 (m, 2H), 2.23 (br s, 1H), 2.28-2.40 (m, 2H), 2.75 (br s, 2H), 3.61 (br s, 2H), 3.75 (br s, 4H), 5.62 (t, J=3.3 Hz, 1H), 8.23 (s, 1H), 8.50 (d, J=6.4 Hz, 2H), 8.80 (d, J=6.4 Hz, 2H). MS (APCI) m/z=314 (M+H)$^+$. Anal. Calcd. for $C_{17}H_{19}N_3OS$.2.15HCl.2.35$H_2O$: C, 47.03; H, 6.00; N, 9.68; Cl, 17.56. Found: C, 47.20; H, 6.25; N, 9.62; Cl, 17.56.

Example 153

(4s)-4-[(4-Pyridin-3-yl-1,3-thiazol-2-yl)oxy]-1-azatricyclo[3.3.1.1$^{3,7}$]decane In a microwave reaction tube were combined the product of Example 147A (70 mg, 0.213 mmol), pyridin-3-ylboronic acid (26.1 mg, 0.213 mmol), bis(triphenylphosphine)-palladium(II) chloride (5.2 mg, 7.45 µmol) and sodium carbonate (56.4 mg, 0.532 mmol) followed by the solvents 2-propanol (2.5 mL) and water (0.83 mL). The tube was sealed, and the reaction was heated to 105° C. for 10 minutes in the microwave reactor. After cooling to room temperature, the reaction mixture was diluted with 2-propanol (5.0 mL), passed through a glass microfiber frit, concentrated and purified by silica gel flash chromatography to provide the N-borane complex. It was then processed as described in Method C to provide the titled compound: $^1$H NMR (500 MHz, methanol-D4) δ ppm 1.71 (br s, 1H), 1.86-1.93 (m, 2H), 2.24-2.34 (m, 4H), 3.14-3.22 (m, 4H), 3.31-3.35 (m, 2H), 5.37 (t, J=2.9 Hz, 1H), 7.38 (s, 1H), 7.46 (ddd, J=8.1, 4.9, 0.8 Hz, 1H), 8.25 (ddd, J=8.2, 2.1, 1.5 Hz, 1H), 8.45 (dd, J=4.9, 1.5 Hz, 1H), 9.00 (dd, J=2.3, 0.8 Hz, 1H). MS (APCI) m/z=314 (M+H)$^+$.

Example 154

2-[(4s)-1-Azatricyclo[3.3.1.1$^{3,7}$]dec-4-yloxy]-N-pyridin-4-yl-1,3-thiazole-4-carboxamide Example 154A 2-Bromo-N-(pyridin-4-yl)thiazole-4-carboxamide Ethyl 2-bromothiazole-4-carboxylate (97 mg, 0.409 mmol) was dissolved in a solvent mixture of ethanol (15 mL) and water (7.5 mL) and treated with aqueous sodium hydroxide (2.50 M, 2.54 mL). The mixture was stirred at 35° C. for 30 minutes, and then partitioned between ethyl acetate (100 mL) and HCl (1.0 M, 100 mL). The organic phase was dried (sodium sulfate) and concentrated to afford the carboxylic acid as a white solid. To a solution of this material in pyridine (5 mL) were added 4-aminopyridine (46.1 mg, 0.490 mmol), HOBt (78 mg, 0.511 mmol), DMAP (10.0 mg, 0.082 mmol) and EDAC (117 mg, 0.613 mmol). The reaction mixture was stirred at room temperature for 18 hours then filtered through a frit. The filtrate was concentrated in vacuo and purified by preparative HPLC [Waters Nova-Pak HR C18 6 µm 60 Å Prep-Pak cartridge column (40×100 mm), 10%-100% gradient of acetonitrile in 10 mM aqueous ammonium acetate over 12 minutes at a flow rate of 70 mL/minute] to provide the titled compound: $^1$H NMR (400 MHz, methanol-D4) δ ppm 7.83-7.90 (m, 2H), 8.40 (s, 1H), 8.43-8.46 (m, 2H). MS (ESI) m/z=284/286 (M+H)$^+$.

Example 154B

2-[(4s)-1-Azatricyclo[3.3.1.1$^{3,7}$]dec-4-yloxy]-N-pyridin-4-yl-1,3-thiazole-4-carboxamide The N-borane complex of the titled compound was prepared from the product of Example 10A (32.3 mg, 0.194 mmol) and the product of Example 154A (50 mg, 0.176 mmol) according to Method B. It was then processed as described in Method C to provide the free base which was converted to the fumarate by the procedure of Method H: $^1$H NMR (500 MHz, methanol-D4) δ ppm 1.92-2.04 (m, 2H), 2.21 (br s, 1H), 2.29-2.38 (m, 2H), 2.70 (br s, 2H), 3.59 (br s, 2H), 3.64-3.82 (m, 4H), 5.62 (t, J=3.1 Hz, 1H), 6.71 (s, 2H; $C_4H_4O_4$), 7.85-7.87 (m, 2H), 7.88 (s, 1H), 8.46 (d, J=4.6 Hz, 2H). MS (ESI) m/z=357 (M+H)$^+$. Anal. Calcd. for $C_{18}H_{20}N_4O_2S.1.55C_4H_4O_4.1.65H_2O$: C, 51.35; H, 5.25; N, 9.90. Found: C, 51.52; H, 5.47; N, 9.75.

Example 155

2-[(4s)-1-azatricyclo[3.3.1.1$^{3,7}$]dec-4-yloxy]-N-(4-chlorophenyl)-1,3-oxazole-4-carboxamide Example 155A 2-chloro-N-(4-chlorophenyl)oxazole-4-carboxamide Prepared from ethyl 2-chlorooxazole-4-carboxylate (83.5 mg, 0.475 mmol) and 4-chloroaniline (60.5 mg, 0.475 mmol) as described in Example 154A: $^1$H NMR (500 MHz, DMSO-D6) δ ppm 7.37-7.45 (m, 2H), 7.81-7.89 (m, 2H), 8.91 (s, 1H), 10.45 (s, 1H). MS (DCI/NH$_3$) m/z=274 (M+NH$_4$)$^+$.

Example 155B

2-[(4s)-1-azatricyclo[3.3.1.1$^{3,7}$]dec-4-yloxy]-N-(4-chlorophenyl)-1,3-oxazole-4-carboxamide The N-borane complex of the title compound was prepared from the product of Example 10A (38.9 mg, 0.233 mmol) and the product of Example 155A (57 mg, 0.222 mmol) using methods described in Example 122. It was then converted first to the free base as described in Method C, and then to the fumarate salt according to Method H: $^1$H NMR (400 MHz, methanol-D4) δ ppm 1.93-2.05 (m, 2H), 2.20 (br s, 1H), 2.26-2.36 (m, 2H), 2.70 (br s, 2H), 3.57 (br s, 2H), 3.59-3.77 (m, 4H), 5.36 (br s, 1H), 6.66-6.75 (m, 2H), 7.31-7.40 (s, 2H; $C_4H_4O_4$), 7.64-7.72 (m, 2H), 8.05-8.15 (s, 1H). MS (APCI) m/z=374 (M+H)$^+$.

Example 156

2-[(4s)-1-azatricyclo[3.3.1.1$^{3,7}$]dec-4-yloxy]-N-phenyl-1,3-oxazole-4-carboxamide Example 156A 2-chloro-N-phenyloxazole-4-carboxamide Prepared from ethyl 2-chlorooxazole-4-carboxylate (45.4 mg, 0.258 mmol) and aniline (24 mg, 0.258 mmol) as described in Example 154A: $^1$H NMR (500 MHz, methanol-D4) δ ppm 7.13-7.18 (m, 1H), 7.32-7.38 (m, 2H), 7.65-7.71 (m, 2H), 8.53 (s, 1H). MS (APCI) m/z=223 (M+H)$^+$.

Example 156B

2-[(4s)-1-azatricyclo[3.3.1.1$^{3,7}$]dec-4-yloxy]-N-phenyl-1,3-oxazole-4-carboxamide The N-borane complex of the title compound was prepared from the product of Example 10A (33 mg, 0.198 mmol) and the product of Example 156A (42 mg, 0.189 mmol) using methods described in Example 122. It was then processed as described in Method C to provide the title compound: $^1$H NMR (500 MHz, methanol-D4) δ ppm 1.70 (br s, 1H), 1.86-1.95 (m, 2H), 2.23-2.32 (m, 4H), 3.13-3.19 (m, 4H), 3.32-3.36 (m, 2H), 5.30 (t, J=2.9 Hz, 1H), 7.12-7.17 (m, 1H), 7.32-7.38 (m, 2H), 7.65-7.69 (m, 2H), 8.04 (s, 1H). MS (ESI) m/z=340 (M+H)$^+$. Anal. Calcd. for $C_{19}H_{21}N_3O_3.0.05H_2O$: C, 67.06; H, 6.25; N, 12.35. Found: C, 66.77; H, 6.04; N, 12.73.

Example 157

(4s)-4-{[5-(3-bromophenyl)-1,3,4-thiadiazol-2-yl]oxy}-1-azatricyclo[3.3.1.1$^{3,7}$]decane Prepared from the product of Example 10B and 2-(3-bromophenyl)-5-chloro-1,3,4-thiadiazole (Zubets, I. V.; Boikov, Yu. A.; Viktorovskii, I. V.; V'yunov, K. A. Khimiya Geterotsiklicheskikh Soedinenii, 1986, 10, 1416-1419) according to Method B: $^1$H-NMR (DMSO-d6) δ 8.02 (m, 1H), 7.86 (d, J=9 Hz, 1H), 7.73 (d, J=9 Hz, 1H), 7.49 (t, J=9 Hz, 1H), 5.28 (m, 1H), 3.2-3.15 (m, 3H), 3.02-3.0 (m, 5H), 2.16-2.13 (m, 5H), 1.84-1.79 (2H), 1.56 (m, 1). MS (ESI) m/z=394, 392 (M+H)$^+$ (4%); 136 (100%).

Example 158

(4s)-4-{5-[1-azatricyclo[3.3.1.1$^{3,7}$]dec-4-yloxy]-1,3,4-thiadiazol-2-yl}phenol Example 158A 2-(4-(benzyloxy)phenyl)-5-bromo-1,3,4-thiadiazole The titled compound is prepared from 4-(benzyloxy)benzoyl chloride using the methodology described in Vachal, P.; Toth, L. M. Tetrahedron Lett. 2004, 45, 7157-7161.

Example 158B (4s)-4-({5-[4-(benzyloxy)phenyl]-1,3,4-thiadiazol-2-yl}oxy)-1-azatricyclo[3.3.1.1$^{3,7}$]decane N-borane complex Example 158A is coupled to Example 10A using the methodology described in Method A.

Example 158C (4s)-4-({5-[4-(benzyloxy)phenyl]-1,3,4-thiadiazol-2-yl}oxy)-1-azatricyclo[3.3.1.1$^{3,7}$]decane Example 158B is converted to the titled compound according to Method C.

Example 158D (4s)-4-{5-[1-azatricyclo[3.3.1.1$^{3,7}$]dec-4-yloxy]-1,3,4-thiadiazol-2-yl}phenol Example 158C is hydrogenated (~15 psi) in the presence of palladium on carbon (~10% by weight) in ethanol. Removal of the solvent by filtration and concentration in vacuo supplies the titled compound.

Example 159

(4s)-N-Pyridin-3-yl-1-azatricyclo[3.3.1.1$^{3,7}$]decan-4-amine bis(4-methylbenzenesulfonate) hemihydrate Pyridine-3-amine (143 mg, 1.52 mmol) was added to a solution of 1-azatricyclo[3.3.1.1$^{3,7}$]decan-4-one (151 mg, 1.00 mmol) in acetic acid (5 mL). Anhydrous sodium sulfate (1.82 g, 12.8 mmol) was added, and the mixture was stirred at room temperature. After 10 minutes, sodium triacetoxyborohydride (412 mg, 1.94 mmol) was added and the mixture was stirred at room temperature for 10 hours. The reaction mixture was filtered through diatomaceous earth with a chloroform (5 mL) rinse. The filtrate was concentrated under vacuum, and the residue was purified by flash chromatography on silica (eluted with chloroform-methanol-concentrated ammonium hydroxide, 90:10:1) to provide a colorless gum. This was combined with 4-methylbenzenesulfonic acid monohydrate (29 mg) in a boiling mixture of ethyl acetate (5 mL) and EtOH (0.5 mL) and cooled to room temperature. After 30 hours, the product was collected by filtration, washed with ethyl acetate (2 mL) and dried under vacuum to provide the titled compound: $^1$H NMR (300 MHz, methanol-D4) δ 1.91-2.00 (m, 3H), 2.14-2.33 (m, 5H), 2.36 (s, 6H), 3.57 (s, 2H), 3.69 (s, 4H), 4.03 (s, 1H), 7.23 (d, J=7.9 Hz, 4H), 7.70 (d, J=8.3 Hz, 4H), 7.72-7.77 (m, 1H), 7.81-7.87 (m, 1H), 8.01 (d, J=5.6 Hz, 1H), 8.18 ppm (d, J=2.8 Hz, 1H): MS (DCI/NH$_3$) m/z 230 (M+H)$^+$; Anal. Calcd for C$_{14}$H$_{19}$N$_3$.2C$_7$H$_8$O$_3$S.0.5H$_2$O: C, 57.71; H, 6.23; N, 7.21. Found: C, 57.78; H, 6.03; N, 7.19.

Example 160

(4s)-N-(5-Bromo-6-chloropyridin-3-yl)-1-azatricyclo[3.3.1.1$^{3,7}$]decan-4-amine 4-methylbenzenesulfonate Magnesium sulfate (1.80 g, 15 mmol) and 5-bromo-6-chloropyridin-3-amine (310 mg, 1.49 mmol) were added to a solution of 1-azatricyclo[3.3.1.1$^{3,7}$]decan-4-one (151 mg, 1.00 mmol) in acetic acid (5 mL). The resulting suspension was stirred for 10 minutes, then sodium triacetoxyborohydride (412 mg, 1.94 mmol) was added. The mixture was stirred at room temperature for 14 hours, then concentrated under vacuum to dryness. The white solid residue was slurried in ethyl acetate (3 mL), applied to the top of a silica column and eluted with chloroform-methanol-concentrated ammonium hydroxide (90:10:1) to provide a pink solid. This material was heated with ethyl acetate (3 mL) and a solution of 4-methylbenzenesulfonic acid monohydrate (40 mg, 1 eq.) in warm ethyl acetate (1 mL) was added. Additional ethyl acetate (3 mL) and EtOH (3 mL) were added with heating to bring the mixture to homogeneity. After cooling to room temperature and finally to −10° C., the mixture was filtered and the collected solid was washed with ethyl acetate (3 mL) and dried under vacuum to provide the titled compound: $^1$H NMR (300 MHz, methanol-D4) δ 1.91 (br d, J=13.1 Hz, 2H), 2.11-2.21 (m, 1H), 2.22-2.32 (m, 4H), 2.36 (s, 3H), 3.54 (s, 2H), 3.59-3.72 (m, 4H), 3.91 (s, 1H), 7.23 (d, J=7.9 Hz, 2H), 7.47 (d, J=2.8 Hz, 1H), 7.70 (d, J=8.3 Hz, 2H), 7.85 ppm (d, J=2.8 Hz, 1H); MS DCI/NH$_3$ m/z 342/344/346 (M+H)$^+$; Anal. Calcd for C$_{14}$H$_{17}$N$_3$ClBr. C$_7$H$_8$O$_3$S: C, 48.99; H, 4.89; N, 8.16. Found: C, 48.95; H, 4.66; N, 8.02.

Example 161

(4s)-N-[6-(1H-indol-6-yl)pyridin-3-yl]-1-azatricyclo[3.3.1.1$^{3,7}$]decan-4-amine The free base of the titled compound was prepared from the product of Example 65A (150 mg, 0.57 mmol) and indole-6-boronic acid (190 mg, 1.2 mmol; Aldrich) according to Method E: $^1$H NMR (300 MHz, methanol-D4) δ ppm 1.70 (s, 1H), 1.82-1.92 (m, 2H), 1.97 (s, 2H), 2.28 (d, J=11.2 Hz, 2H), 3.13-3.29 (m, 4H), 3.31-3.44 (m, 4H), 3.84 (s, 1H), 7.18 (dd, J=8.6, 2.9 Hz, 1H), 7.51 (d, J=8.5 Hz, 1H), 7.54-7.68 (m, 1H), 7.97 (d, J=6.8 Hz, 2H), 8.03 (d, J=9.2 Hz, 2H), 8.13 (d, J=3.1 Hz, 1H). MS (DCI/NH$_3$) m/z=345 (M+H)$^+$.

Example 162

(4s)-N-[6-(1H-indol-3-yl)pyridin-3-yl]-1-azatricyclo[3.3.1.1$^{3,7}$]decan-4-amine

Example 162A (4s)-N-[6-(1-Benzenesulfonyl-1H-indol-3-yl)pyridin-3-yl]-1-azatricyclo[3.3.1.1$^{3,7}$]decan-4-amine Prepared from the product of Example 65A (150 mg, 0.569 mmol) and 1-phenylsulfonyl-1H-indol-3-ylboronic acid (350 mg, 1.2 mmol; Aldrich) according to Method E: MS (DCI/NH$_3$) m/z=485 (M+H)$^+$.

Example 162B (4s)-N-[6-(1H-indol-3-yl)pyridin-3-yl]-1-azatricyclo[3.3.1.1$^{3,7}$]decan-4-amine A solution of the product of Example 162A (50 mg, 0.103 mmol) and potassium carbonate (34 mg, 0.25 mmol) in methanol (3 mL) was heated to reflux for 90 minutes. After cooling, the solvent was removed, the residue was dissolved in water, and the mixture was extracted with ethyl acetate (3×). The combined extracts were washed with brine, dried (Na$_2$SO$_4$), filtered and concentrated to afford the free base of the title compound: $^1$H NMR (300 MHz, methanol-D4) δ ppm 1.68 (s, 1H), 1.86 (d, J=14.9 Hz, 2H), 1.96 (s, 2H), 2.29 (d, J=12.2 Hz, 2H), 3.09-3.29 (m, 8H), 3.81 (s, 1H), 7.01-7.24 (m, 3H), 7.40 (d, J=7.1 Hz, 1H), 7.50-7.61 (m, 2H), 7.98 (d, J=7.5 Hz, 1H), 8.07 (d, J=2.4 Hz, 1H). MS (DCI/NH$_3$) m/z=345 (M+H)$^+$.

COMPOSITIONS OF THE INVENTION

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds of the invention can be used in the form of pharmaceutically acceptable salts. The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acid addition salts can be prepared using various suitable acids for example, including, but are not limited to, acetic, adipic, alginic, citric, aspartic, benzoic, benzenesulfonic, butyric, camphoric, camphorsulfonic, carbonic, digluconic, glycerophosphoric, heptanoic, hexanoic, fumaric, hydrochloric, hydrobromic, hydroiodic, 2-hydroxyethansulfonic (isethionic), lactic, maleic, methanesulfonic, nicotinic, 2-naphthalenesulfonic, oxalic, pamoic, pectinic, persulfuric, 3-phenylpropionic, picric, pivalic, propionic, succinic, sulfuric, tartaric, thiocyanic, phosphoric, glutamatic, p-toluenesulfonic, and undecanoic acids.

Particular examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, tartaric acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention also contemplates pharmaceutically acceptable compounds that when administered to a patient in need may be converted through in vivo biotransformation into compounds of formula (I).

Determination of Biological Activity

To determine the effectiveness of representative compounds of this invention as ligands for α7 nAChRs, the compounds of the invention were evaluated according to the [$^3$H]-methyllycaconitine (MLA) binding assay, or the [$^3$H]-DPPB binding assay. To determine the effectiveness of representative compounds of this invention as ligands for α4β2 nAChRs, the compounds of the invention were evaluated according to the [$^3$H]-cytisine binding assay, which were performed as described below.

[$^3$H]-Cytisine Binding

Binding to the α4β2 nAChR subtype was determined according to conditions which were modified from the procedures described in Pabreza L A, Dhawan, S, Kellar K J, [$^3$H]-Cytisine Binding to Nicotinic Cholinergic Receptors in Brain, Mol. Pharm. 39: 9-12, 1991. Membrane enriched fractions from rat brain minus cerebellum (ABS Inc., Wilmington, Del.) were slowly thawed at 4° C., washed and resuspended in 30 volumes of BSS-Tris buffer (120 mM NaCl/5 mM KCl/2 mM CaCl$_2$/2 mM MgCl$_2$/50 mM Tris-Cl, pH 7.4, 4° C.). Samples containing 100-200 μg of protein and 0.75 nM [$^3$H]-cytisine (30 C$_i$/mmol; Perkin Elmer/NEN Life Science Products, Boston, Mass.) were incubated in a final volume of 500 μL for 75 minutes at 4° C. Seven log-dilution concentrations of each compound were tested in duplicate. Non-specific binding was determined in the presence of 10 μM (−)-nicotine. Bound radioactivity was isolated by vacuum filtration onto prewetted glass fiber filter plates (Millipore, Bedford, Mass.) using a 96-well filtration apparatus (Packard Instruments, Meriden, Conn.) and were then rapidly rinsed with 2 mL of ice-cold BSS buffer (120 mM NaCl/5 mM KCl/2 mM CaCl$_2$/2 mM MgCl$_2$). Packard MicroScint-20® scintillation cocktail (40 μL) was added to each well and radioactivity determined using a Packard TopCount® instrument. The IC$_{50}$ values were determined by nonlinear regression in Microsoft Excel® software. K$_i$ values were calculated from the IC$_{50}$s using the Cheng-Prusoff equation, where K$_i$=IC$_{50}$/(1+[Ligand]/K$_D$).

[$^3$H]-Methyllycaconitine (MLA) Binding

Binding to the α7 nAChR subtype was determined according to conditions which were similar to those used for the [$^3$H]-cytisine binding assay. Membrane enriched fractions from rat brain minus cerebellum (ABS Inc., Wilmington, Del.) were slowly thawed at 4° C., washed and resuspended in 30 volumes of BSS-Tris buffer (120 mM NaCl, 5 mM KCl, 2 mM CaCl$_2$, 2 mM MgCl$_2$, and 50 mM Tris-Cl, pH 7.4, 22° C.). Samples containing 100-200 μg of protein, 5 nM [$^3$H]-MLA (25 C$_i$/mmol; Perkin Elmer/NEN Life Science Products, Boston, Mass.) and 0.1% bovine serum albumin (BSA, Millipore, Bedford, Mass.) were incubated in a final volume of 500 μL for 60 minutes at 22° C. Seven log-dilution concentrations of each compound were tested in duplicate. Non-specific binding was determined in the presence of 10 μM MLA. Bound radioactivity was isolated by vacuum filtration onto glass fiber filter plates prewetted with 2% BSA using a 96-well filtration apparatus (Packard Instruments, Meriden, Conn.) and were then rapidly rinsed with 2 mL of ice-cold BSS. Packard MicroScint-20® scintillation cocktail (40 μL) was added to each well and radioactivity was determined using a Packard TopCount® instrument. The IC$_{50}$ values were determined by nonlinear regression in Microsoft Excel® software. K$_i$ values were calculated from the IC$_{50}$s using the Cheng-Prusoff equation, where K$_i$=IC$_{50}$/(1+[Ligand]/K$_D$).

[$^3$H]-DPPB Binding

[$^3$H]-DPPB, [$^3$H]-(S,S)-2,2-dimethyl-5-(6-phenyl-pyridazin-3-yl)-5-aza-2-azonia-bicyclo[2.2.1]heptane iodide, binding to the α7 nAChR subtype was determined using membrane enriched fractions from rat brain minus cerebellum or human cortex (ABS Inc., Wilmington, Del.). Pellets were thawed at 4° C., washed and resuspended with a Polytron at a setting of 7 in 30 volumes of BSS-Tris buffer (120 mM NaCl, 5 mM KCl, 2 mM CaCl$_2$, 2 mM MgCl$_2$, and 50 mM Tris-Cl, pH 7.4, 4° C.). Seven log-dilution concentrations of test compounds containing 100-200 μg of protein, and 0.5 nM [$^3$H]-DPPB (62.8 Ci/mmol; R46V, Abbott Labs) were incubated in a final volume of 500 μl for 75 minutes at 4° C. in duplicate. Non-specific binding was determined in the presence of 10 μM methyllycaconitine. Bound radioactivity was collected on Millipore MultiScreen® harvest plates FB presoaked with 0.3% PEI using a Packard cell harvester, washed with 2.5 ml ice-cold buffer, and radioactivity was determined using a Packard TopCount Microplate beta counter. IC$_{50}$ values were determined by nonlinear regression in Microsoft® Excel or Assay Explorer. K$_i$ values were calculated from the IC$_{50}$s using the Cheng-Prusoff equation, where K$_i$=IC$_{50}$/(1+[Ligand]/K$_D$). [$^3$H]-DPPB was obtained according to the preparation procedures described below.

[Methyl-$^3$H]2,2-Dimethyl-5-(6-phenyl-pyridazin-3-yl)-5-aza-2-azonia-bicyclo[2.2.1]heptane; iodide Preparation

[Methyl-$^3$H]2,2-dimethyl-5-(6-phenyl-pyridazin-3-yl)-5-aza-2-azonia-bicyclo[2.2.1]heptane; iodide used in the [$^3$H]-DPPB binding assay above was prepared according to the following procedures.

Step 1: Preparation of t-Butyl (S,S)-5-(6-Phenyl-pyridazin-3-yl)-2,5-diazabicyclo[2.2.1]heptane-2-carboxylate Triethylamine (20 mL) was added to a suspension of t-butyl (S,S)-2,5-diazabicyclo[2.2.1]heptane-2-carboxylate (3.43 g, 17.3 mmol, Aldrich Chemical Company) and 3-chloro-6-phenylpyridazine (3.30 g, 17.3 mmol, Aldrich Chemical Company) in toluene (50 mL) and the mixture was heated under nitrogen at 100° C. for 7 days. The dark mixture was cooled to room temperature, and the resulting precipitate was isolated by filtration, washed with toluene (15 mL) and dried under vacuum to provide the title compound as an off-white solid (3.00 g). The filtrate was concentrated and the residue was purified by column chromatography on silica gel, eluting with ethyl acetate, to provide additional product (0.41 g, total yield 3.41 g, 56%): MS (DCI/NH$_3$) m/z 353 (M+H)$^+$.

Step 2: Preparation of (S,S)-2-Methyl 5-(6-phenyl-pyridazin-3-yl)-2,5-diazabicyclo[2.2.1]heptane The product obtained from Step 1 (3.41 g, 9.7 mmol) was dissolved in formic acid (20 mL) and treated with formalin (37% by weight, 1.0 g, 12.3 mmol). The mixture was heated at 100° C. for 1 hour, and the brown solution was cooled to room temperature and concentrated under vacuum. The residue was purified by column chromatography on silica gel, eluting with CH$_2$Cl$_2$—CH$_3$OH—NH$_4$OH (95:5:1) to provide the title compound as an off-white solid (2.50 g, 96%): MS (DCI/NH$_3$) m/z 267 (M+H)$^+$.

Step 3: Preparation of [$^3$H]-(S,S)-2,2-Dimethyl-5-(6-phenyl-pyridazin-3-yl)-5-aza-2-azonia-bicyclo[2.2.1] heptane iodide ([$^3$H]-DPPB)

[$^3$H]Methyl iodide in toluene (250 mCi in 0.1 mL, 85 Ci/mmol, American Radiolabeled Chemicals, Inc.) was combined with a solution of the product obtained from Step 2 in dichloromethane (0.788 mg, 2.96 μmole in 0.45 mL). The vial was capped and the mixture was allowed to react overnight at room temperature. Methanol was added and the solvents were evaporated to give 42 mCi. The product was taken up in methanol for HPLC purification.

Step 4: Purification by High Performance Liquid Chromatography (HPLC)

About 7 mCi of [$^3$H]-DPPB was evaporated to dryness and the residue was dissolved in total about 4.5 ml acetonitrile:water:TFA (15:85:0.1). Approximately 0.9 mL per injection were made onto a Phenomenex Luna C18(2) column (5 micron, 250 mm×4.6 mm ID) using an Agilent HPLC system. [$^3$H]-DPPB was eluted by a gradient mobile phase from 10% B to 20% B in 20 min where Mobile Phase A=0.1% trifluoroacetic acid in water and Mobile Phase B=0.1% trifluoroacetic acid in acetonitrile at a flow rate of approximately 1 mL/min. Peak detection and chromatograms were obtained with an Agilent variable wavelength UV detector set at 275 nm. The fractions containing [$^3$H]-DPPB were collected at approximately 14 minutes using an Agilent fraction collector. The fractions were combined and the solvents were evaporated in vacuo. The residue was dissolved in 200 proof ethanol (2 mL) to give 0.7 mCi.

Step 5: Determination of Purity and Specific Activity

[$^3$H]-DPPB was assayed using an Agilent 1100 series HPLC system consisting of a quaternary pump, an autosampler, and a photodiode array UV detector. A Packard Radiomatic A 500 radioactivity detector was connected to the HPLC system. For radiodetection, a 500 μl flow cell and a 3:1 ratio of Ultima-Flo M scintillation cocktail to HPLC mobile phase were used. The analyses were performed using a Phenomenex Luna C18(2) column (5 microns, 250 mm×4.6 mm ID). The mobile phase consisted of a gradient starting with 10% B and ramping to 20% B in 20 minutes followed by ramping to 90% B in 1 minute and hold at 90% B for 9 minutes, where Mobile Phase A=0.1% trifluoroacetic acid in water and Mobile Phase B=0.1% trifluoroacetic acid in acetonitrile. The flow rate was set at approximately 1 mL/min and the UV detection was set at 275 nm.

Preferred compounds of the invention had $K_i$ values of from about 0.1 nanomolar to about 10 micromolar when tested by the [$^3$H]-MLA assay, many having a $K_i$ of less than 1 micromolar. Other preferred compounds demonstrated [$^3$H]-Cytisine binding values of compounds of the invention ranged from about 0.1 nanomolar to at least 10 micromolar. Some preferred compounds exhibited greater potency at α7 receptors compared to α4β2 receptors. The determination of such preferred compounds typically considered the $K_i$ value as measured by MLA assay in view of the $K_1$ value as measured by [$^3$H]-cytisine binding, such that in the formula D=$K_i$ $^3$H-cytisine $K_{i\ MLA}$, D is greater than about 50. Alternatively, the $K_1$ value as measured by [$^3$H]-DPPB assay can be used in place of the $K_{i\ MLA}$ such that in the formula D'=$K_i^3$$_{H\text{-}cytisine}$/$K_i$ $_{[3H]\text{-}DPPB}$, D' is greater than about 50.

Compounds of the invention are α7 nAChRs ligands and/or α4β2 ligands that modulate function of α7 nAChRs and/or α4β2 ligands by altering the activity of the receptor or signaling. The compounds can be inverse agonists that inhibit the basal activity of the receptor or antagonists that completely block the action of receptor-activating agonists. The compounds also can be partial agonists that partially block or partially activate the α7 nAChR receptor or agonists that activate the receptor. Binding to the α7 nicotinic receptor also triggers key signaling processes involving various kinases and phosphatases and protein-protein interactions that are important to effects on memory, cytoprotection, gene transcription and disease modification.

METHODS OF THE INVENTION

Compounds and compositions of the invention are useful for modulating the effects of nAChRs, and more particularly α7 nAChRs. In particular, the compounds and compositions of the invention can be used for treating and preventing disorders modulated by α7 nAChRs. Typically, such disorders can be ameliorated by selectively modulating the α7 nAChRs in a mammal, preferably by administering a compound or composition of the invention, either alone or in combination with another active agent, for example, as part of a therapeutic regimen. Also, some compounds of the invention possess affinity at the α4β2 nAChRs in addition to α7 nAChRs, and selective compounds with dual affinities at both receptor subtypes also are expected to have beneficial effects.

The compounds of the invention, including but not limited to those specified in the examples, possess an affinity for nAChRs, and more particularly α7 nAChRs. As α7 nAChRs ligands, the compounds of the invention can be useful for the treatment and prevention of a number of α7 nAChR-mediated diseases or conditions.

For example, α7 nAChRs have been shown to play a significant role in enhancing cognitive function, including aspects of learning, memory and attention (Levin, E. D., J. Neurobiol. 53: 633-640, 2002). As such, α7 ligands are suitable for the treatment of cognitive disorders including, for example, attention deficit disorder, attention deficit hyperactivity disorder (ADHD), Alzheimer's disease (AD), mild cognitive impairment, senile dementia, AIDS dementia, Pick's disease, dementia associated with Lewy bodies, and dementia associated with Down's syndrome, as well as cognitive deficits associated with schizophrenia.

In addition, α7-containing nAChRs have been shown to be involved in the neuroprotective effects of nicotine both in vitro (Jonnala, R. B. and Buccafusco, J. J., J. Neurosci. Res. 66: 565-572, 2001) and in vivo (Shimohama, S. et al., Brain Res. 779: 359-363, 1998). More particularly, neurodegeneration underlies several progressive CNS disorders, including, but not limited to, Alzheimer's disease, Parkinson's disease, amyotrophic lateral sclerosis, Huntington's disease, dementia with Lewy bodies, as well as diminished CNS function resulting from traumatic brain injury. For example, the impaired function of α7 nAChRs by β-amyloid peptides linked to Alzheimer's disease has been implicated as a key factor in development of the cognitive deficits associated with the disease (Liu, Q.-S., Kawai, H., Berg, D. K., PNAS 98: 4734-4739, 2001). The activation of α7 nAChRs has been shown to block this neurotoxicity (Kihara, T. et al., J. Biol. Chem. 276: 13541-13546, 2001). As such, selective ligands that enhance α7 activity can counter the deficits of Alzheimer's and other neurodegenerative diseases.

Schizophrenia is a complex disease that is characterized by abnormalities in perception, cognition, and emotions. Significant evidence implicates the involvement of α7 nAChRs in this disease, including a measured deficit of these receptors in post-mortem patients (Leonard, S. Eur. J. Pharmacol. 393: 237-242, 2000). Deficits in sensory processing (gating) are one of the hallmarks of schizophrenia. These deficits can be normalized by nicotinic ligands that operate at the α7 nAChR (Adler L. E. et al., Schizophrenia Bull. 24: 189-202, 1998; Stevens, K. E. et al., Psychopharmacology 136: 320-327, 1998). Thus, α7 ligands demonstrate potential in the treatment schizophrenia.

Angiogenesis, a process involved in the growth of new blood vessels, is important in beneficial systemic functions, such as wound healing, vascularization of skin grafts, and enhancement of circulation, for example, increased circulation around a vascular occlusion. Non-selective nAChR agonists like nicotine have been shown to stimulate angiogenesis (Heeschen, C. et al., Nature Medicine 7: 833-839, 2001). Improved angiogenesis has been shown to involve activation of the α7 nAChR (Heeschen, C. et al., J. Clin. Invest. 110: 527-536, 2002). Therefore, nAChR ligands that are selective for the α7 subtype offer improved potential for stimulating angiogenesis with an improved side effect profile.

A population of α7 nAChRs in the spinal cord modulate serotonergic transmission that have been associated with the pain-relieving effects of nicotinic compounds (Cordero-Erausquin, M. and Changeux, J.-P. PNAS 98:2803-2807, 2001). The α7 nAChR ligands demonstrate therapeutic potential for the treatment of pain states, including acute pain, post-surgical pain, as well as chronic pain states including inflammatory pain and neuropathic pain. Moreover, α7 nAChRs are expressed on the surface of primary macrophages that are involved in the inflammation response, and that activation of the α7 receptor inhibits release of TNF and other cytokines that trigger the inflammation response (Wang, H. et al Nature 421: 384-388, 2003). Therefore, selective α7 ligands demonstrate potential for treating conditions involving TNF-mediated diseases, for example, rheumatoid arthritis, Crohn's disease, ulcerative colitis, inflammatory bowel disease, organ transplant rejection, acute immune disease associated with organ transplantation, chronic immune disease associated with organ transplantation, septic shock, toxic shock syndrome, sepsis syndrome, depression, and rheumatoid spondylitis.

The mammalian sperm acrosome reaction is an exocytosis process important in fertilization of the ovum by sperm. Activation of an α7 nAChR on the sperm cell has been shown to be essential for the acrosome reaction (Son, J.-H. and Meizel, S. Biol. Reproduct. 68: 1348-1353 2003). Consequently, selective α7 agents demonstrate utility for treating fertility disorders.

Compounds of the invention are particularly useful for treating and preventing a condition or disorder affecting cognition, neurodegeneration, and schizophrenia.

Cognitive impairment associated with schizophrenia often limits the ability of patients to function normally, a symptom not adequately treated by commonly available treatments, for example, treatment with an atypical antipsychotic. (Rowley, M. et al., J. Med. Chem. 44: 477-501, 2001). Such cognitive deficit has been linked to dysfunction of the nicotinic cholinergic system, in particular with decreased activity at α7 receptors. (Friedman, J. I. et al., Biol Psychiatry, 51: 349-357, 2002). Thus, activators of α7 receptors can provide useful treatment for enhancing cognitive function in schizophrenic patients who are being treated with atypical antipsychotics. Accordingly, the combination of an α7 nAChR ligand and an atypical antipsychotic would offer improved therapeutic utility. Specific examples of suitable atypical antipsychotics include, but are not limited to, clozapine, risperidone, olanzapine, quietapine, ziprasidone, zotepine, iloperidone, and the like.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.010 mg/kg body weight to about 1 g/kg body weight. More preferable doses can be in the range of from about 0.010 mg/kg body weight to about 100 mg/kg body weight. If desired, the effective daily dose can be divided into multiple doses for purposes of administration. Consequently, single dose compositions may contain such amounts or submultiples thereof to make up the daily dose.

Compounds of the invention are α7 nAChRs ligands that modulate function of α7 nAChRs by altering the activity of the receptor or signaling. The compounds can be inverse agonists that inhibit the basal activity of the receptor or antagonists that completely block the action of receptor-activating agonists. The compounds also can be partial agonists that partially block or partially activate the α7 nAChR receptor or agonists that activate the receptor. Binding to α7 receptor also trigger key signaling processes involving various kinases and phosphatases and protein-protein interactions that are important to effects on memory, cytoprotection, gene transcription and disease modification. Therefore, the administration of a therapeutically effective amount of a compound of formula (I) to a mammal provides a method of selectively modulating the effects of α4β2, α7, or both α4β2 and α7 nicotinic acetylcholine receptors.

Furthermore, the administration of a therapeutically effective amount of a compound of formula (I) to a mammal provides a method of treating or preventing a condition or disorder selected from the group consisting of attention deficit disorder, attention deficit hyperactivity disorder (ADHD), Alzheimer's disease (AD), mild cognitive impairment, senile dementia, AIDS dementia, Pick's disease, dementia associated with Lewy bodies, dementia associated with Down's syndrome, amyotrophic lateral sclerosis, Huntington's disease, smoking cessation, nicotinic withdrawal syndrome, diminished CNS function associated with traumatic brain injury, acute pain, post-surgical pain, chronic pain, inflammatory pain, neuropathic pain, infertility, need for new blood vessel growth associated with wound healing, need for new blood vessel growth associated with vascularization of skin grafts, and lack of circulation, more particularly circulation around a vascular occlusion, rheumatoid arthritis, Crohn's disease, ulcerative colitis, inflammatory bowel disease, organ transplant rejection, acute immune disease associated with organ transplantation, chronic immune disease associated with organ transplantation, septic shock, toxic shock syndrome, sepsis syndrome, depression, and rheumatoid spondylitis. More preferred, the administration of a therapeutically effective amount of a compound of formula (I) to a mammal provides a method of treating cognitive disorders, neurodegeneration, and schizophrenia. Furthermore, compounds of formula (I) may also be administered in combination with an atypical antipsychotic.

Preparation of Salts

Example A (4s)-4-(5-Phenyl-1,3,4-thiadiazol-2-yloxy)-1-azatricyclo[3.3.1.1$^{3,7}$]decane L-bitartrate anhydrate (4s)-4-(5-Phenyl-1,3,4-thiadiazol-2-yloxy)-1-azatricyclo [3.3.1.1$^{3,7}$]decane free base (21.5 mg, 0.07 mmol) was dissolved in 1.0 mL of 200 proof ethanol. Meanwhile, 11.75 mg of L-tartaric acid (0.08 mmol) was dissolved in 250 μL 200 proof ethanol. The L-tartaric acid solution was added dropwise to the (4s)-4-(5-phenyl-1,3,4-thiadiazol-2-yloxy)-1-azatricyclo[3.3.1.1$^{3,7}$]decane free base solution while stirring. The vial was removed from the stir plate after the addition. The L-bitartrate anhydrate crystallized upon standing.

Example B (4s)-4-(5-Phenyl-1,3,4-thiadiazol-2-yloxy)-1-azatricyclo[3.3.1.1$^{3,7}$]decane L-bitartrate hydrate The anhydrate of (4s)-4-(5-phenyl-1,3,4-thiadiazol-2-yloxy)-1-azatricyclo[3.3.1.1$^{3,7}$]decane L-bitartrate solid (60 mg) was suspended in water (500 μl) at ambient temperatures. The hydrate of (4s)-4-(5-phenyl-1,3,4-thiadiazol-2-yloxy)-1-azatricyclo[3.3.1.1$^{3,7}$]decane L-bitartrate crystallized over time.

Example C (4s)-4-(5-Phenyl-1,3,4-thiadiazol-2-yloxy)-1-azatricyclo[3.3.1.1$^{3,7}$]decane dihydrogen phosphate anhydrate (4s)-4-(5-Phenyl-1,3,4-thiadiazol-2-yloxy)-1-azatricyclo [3.3.1.1$^{3,7}$]decane free base (20 mg, 0.064 mmol) was dissolved in 1.0 mL of methanol. Meanwhile, 5 μl of 85% phosphoric acid (0.073 mmol) was diluted with 245 μl methanol. The phosphoric acid solution was then added dropwise to the (4s)-4-(5-phenyl-1,3,4-thiadiazol-2-yloxy)-1-azatricyclo [3.3.1.1$^{3,7}$]decane free base solution while stirring. The vial was removed from the stir plate after the addition. The dihydrogen phosphate anhydrate crystallized upon standing.

Example D (4s)-4-(5-Phenyl-1,3,4-thiadiazol-2-yloxy)-1-azatricyclo[3.3.1.1$^{3,7}$]decane dihydrogen phosphate hydrate The anhydrous (4s)-4-(5-phenyl-1,3,4-thiadiazol-2-yloxy)-1-azatricyclo[3.3.1.1$^{3,7}$]decane dihydrogen phosphate solid was exposed to high humidity. The hydrate of (4s)-4-(5-phenyl-1,3,4-thiadiazol-2-yloxy)-1-azatricyclo [3.3.1.1$^{3,7}$]decane dihydrogen phosphate crystallized over time.

Example E (4s)-4-(5-Phenyl-1,3,4-thiadiazol-2-yloxy)-1-azatricyclo[3.3.1.1$^{3,7}$]decane bisuccinate anhydrate (4s)-4-(5-Phenyl-1,3,4-thiadiazol-2-yloxy)-1-azatricyclo [3.3.1.1$^{3,7}$]decane free base (20 mg, 0.064 mmol) was dissolved in 1.0 mL of 2-propanol (or tetrahydrofuran). Meanwhile, succinic acid (8.25 mg, 0.07 mmol) was dissolved in 500 μl of 2-propanol (or tetrahydrofuran). Both solutions were heated to 50° C. The succinic acid solution was then added dropwise to the (4s)-4-(5-phenyl-1,3,4-thiadiazol-2-yloxy)-1-azatricyclo[3.3.1.1$^{3,7}$]decane free base solution while stirring at 50° C. The vial was removed from the hot/stir plate afterwards. The bisuccinate anhydrate crystallized upon standing and natural cooling to ambient temperatures.

Example F (4s)-4-(5-Phenyl-1,3,4-thiadiazol-2-yloxy)-1-azatricyclo[3.3.1.1$^{3,7}$]decane bisuccinate hydrate The anhydrate of (4s)-4-(5-phenyl-1,3,4-thiadiazol-2-yloxy)-1-azatricyclo[3.3.1.1$^{3,7}$]decane bisuccinate solid (25 mg) was suspended in 100 μL of water at ambient temperatures. The hydrate of (4s)-4-(5-phenyl-1,3,4-thiadiazol-2-yloxy)-1-azatricyclo[3.3.1.1$^{3,7}$]decane bisuccinate crystallized over time.

Example G (4s)-4-(5-Phenyl-1,3,4-thiadiazol-2-yloxy)-1-azatricyclo[3.3.1.1$^{3,7}$]decane hydrochloride quarterhydrate (1 salt:0.25 water)

(4s)-4-(5-Phenyl-1,3,4-thiadiazol-2-yloxy)-1-azatricyclo [3.3.1.1$^{3,7}$]decane free base (40 mg, 0.13 mmol) was dissolved in 2.0 mL of 200 proof ethanol. Concentrated HCl solution (5N, 30 μL, 0.15 mmol) was diluted with 220 μl of 200 proof ethanol. The diluted HCl solution was added to the (4s)-4-(5-phenyl-1,3,4-thiadiazol-2-yloxy)-1-azatricyclo [3.3.1.1$^{3,7}$]decane free base solution while stirring. The vial was removed from the stir plate, and the solvent was allowed to evaporate. The hydrochloride quarterhydrate crystallized over time To prepare a (4s)-4-(5-phenyl-1,3,4-thiadiazol-2-yloxy)-1-azatricyclo[3.3.1.1$^{3,7}$]decane hydrochloride quarterhydrate single crystal, the supernatant obtained from the above experiment was used for this experiment. Solvent was allowed to evaporate slowly. Single crystals of the hydrochloride quarterhydrate formed over time.

Example H (4s)-4-(5-Phenyl-1,3,4-thiadiazol-2-yloxy)-1-azatricyclo[3.3.1.1³,⁷]decane hydrochloride sesquihydrate (1 salt: 1.5 water)

(4s)-4-(5-Phenyl-1,3,4-thiadiazol-2-yloxy)-1-azatricyclo[3.3.1.1³,⁷]decane hydrochloride quarterhydrate solid, 50 mg, was suspended of in 200 μL of water. (4s)-4-(5-Phenyl-1,3,4-thiadiazol-2-yloxy)-1-azatricyclo[3.3.1.1³,⁷]decane hydrochloride sesquihydrate crystallized over time.

Example I (4s)-4-(5-Phenyl-1,3,4-thiadiazol-2-yloxy)-1-azatricyclo[3.3.1.1³,⁷]decane dihydrogen citrate (4s)-4-(5-Phenyl-1,3,4-thiadiazol-2-yloxy)-1-azatricyclo[3.3.1.1³,⁷]decane free base (63 mg, 0.2 mmol) was dissolved in 1.0 mL of methanol. Citric acid (41 mg, 0.21 mmol) was dissolved in 0.5 mL of methanol. The citric acid solution was added to the (4s)-4-(5-phenyl-1,3,4-thiadiazol-2-yloxy)-1-azatricyclo[3.3.1.1³,⁷]decane freebase solution while stirring. The vial was removed from the stir plate after the addition, and the solvent allowed to evaporate slowly. (4s)-4-(5-Phenyl-1,3,4-thiadiazol-2-yloxy)-1-azatricyclo[3.3.1.1³,⁷]decane dihydrogen citrate crystallized over time.

To prepare a (4s)-4-(5-phenyl-1,3,4-thiadiazol-2-yloxy)-1-azatricyclo[3.3.1.1³,⁷]decane dihydrogen citrate single crystal, (4s)-4-(5-phenyl-1,3,4-thiadiazol-2-yloxy)-1-azatricyclo[3.3.1.1³,⁷]decane dihydrogen citrate (20 mg) was dissolved in 0.8 mL water/2-propanol (1:6, V/V) at 50° C. The solution was seeded with (4s)-4-(5-phenyl-1,3,4-thiadiazol-2-yloxy)-1-azatricyclo[3.3.1.1³,⁷]decane dihydrogen citrate solid and allowed to cool to ambient temperatures in a sealed vial. Single crystals formed over time.

Example J (4s)-4-(5-Phenyl-1,3,4-thiadiazol-2-yloxy)-1-azatricyclo[3.3.1.1³,⁷]decane monohydrogen citrate (4s)-4-(5-Phenyl-1,3,4-thiadiazol-2-yloxy)-1-azatricyclo[3.3.1.1³,⁷]decane free base (62 mg, 0.2 mmol) was dissolved in 1.5 mL of methanol. Citric acid (19 mg, 0.1 mmol) was dissolved in 0.5 mL of methanol. The citric acid solution was added to the (4s)-4-(5-phenyl-1,3,4-thiadiazol-2-yloxy)-1-azatricyclo[3.3.1.1³,⁷]decane free base solution while stirring. (4s)-4-(5-Phenyl-1,3,4-thiadiazol-2-yloxy)-1-azatricyclo[3.3.1.1³,⁷]decane monohydrogen citrate crystallized over time while stirring.

Example K (4s)-4-(5-Phenyl-1,3,4-thiadiazol-2-yloxy)-1-azatricyclo[3.3.1.1³,⁷]decane free base To prepare a (4s)-4-(5-phenyl-1,3,4-thiadiazol-2-yloxy)-1-azatricyclo[3.3.1.1³,⁷]decane free base single crystal, (4s)-4-(5-phenyl-1,3,4-thiadiazol-2-yloxy)-1-azatricyclo[3.3.1.1³,⁷]decane free base (13 mg) was dissolved in 1.0 mL of 2-propanol. The solvent was allowed evaporate slowly. Single crystals of (4s)-4-(5-phenyl-1,3,4-thiadiazol-2-yloxy)-1-azatricyclo[3.3.1.1³,⁷]decane free base formed over time.

A process for preparing a citric acid salt of (4s)-4-(5-phenyl-1,3,4-thiadiazol-2-yloxy)-1-azatricyclo[3.3.1.1³,⁷]decane by recrystallizing (4s)-4-(5-phenyl-1,3,4-thiadiazol-2-yloxy)-1-azatricyclo[3.3.1.1³,⁷]decane in citric acid and methanol also is contemplated.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of formula (I)

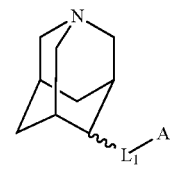

or a pharmaceutically acceptable salt thereof, wherein
L₁ is —O— or —NR_a—;
A is —Ar₂-L₂-Ar₃;
Ar₂ is an optionally substituted 5- or 6-membered monocyclic heteroaryl;
Ar₃ is an optionally substituted heteroaryl;
L₂ is a bond; and
R_a is hydrogen or alkyl.

2. The compound according to claim 1, wherein Ar₂ is a group selected from

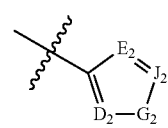

(i)

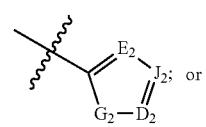

(ii) or

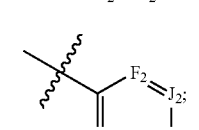

(iii)

D₂, E₂, F₂, J₂, and K₂ are each independently —CT₂ or —N, wherein at least one of D₂, E₂, F₂, J₂, and K₂ is —N;
G₂ is O, —NR_{2a}, or S;
in each group of (i), (ii), and (iii), one substituent represented by T₂, or R_{2a} wherein R_{2a} is T₂, is L₂-Ar₃ and the other substituents represented by T$_2$ are hydrogen, alkyl, alkoxy, alkoxycarbonyl, cyano, halo, nitro, or NR$_b$R$_c$;

R$_{2a}$ is hydrogen, alkyl, or T$_2$; and

R$_b$ and R$_c$ are each independently hydrogen, alkyl, alkoxycarbonyl or alkylcarbonyl.

3. The compound according to claim 1, wherein Ar$_3$ is a group selected from

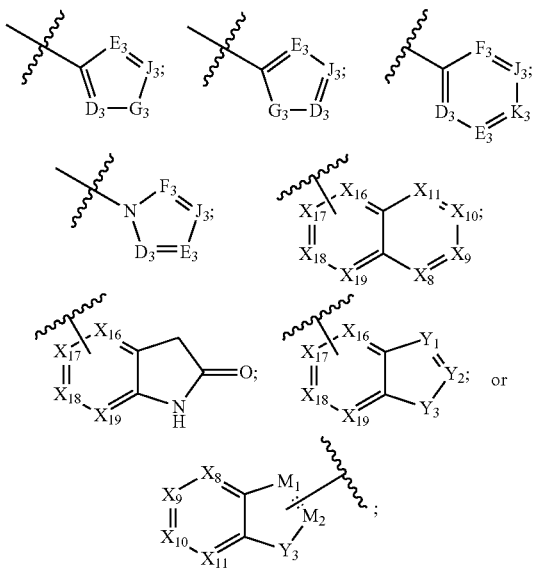

wherein D$_3$, E$_3$, F$_3$, J$_3$, K$_3$, X$_8$, X$_9$, X$_{10}$, and X$_{11}$ are each independently —CR$_3$ or N, wherein at least one of D$_2$, E$_2$, F$_2$, J$_2$, and K$_2$ is —N;

X$_{16}$, X$_{17}$, X$_{18}$, X$_{19}$, M$_1$, and M$_2$ are each independently —CR$_3$, N, or C;

G$_3$ is O, —NR$_{3a}$, or S;

Y$_1$ is —CR$_3$ or N;

Y$_2$ is —CR$_3$ or N;

Y$_3$ is NH, O, or S;

R$_3$ is hydrogen, alkyl, alkoxy, alkoxylalkyl, alkoxycarbonyl, alkylcarbonyl, cyano, halo, haloalkoxy, haloalkyl, hydroxy, nitro, R$_e$R$_f$N—, or aryl, wherein aryl is a phenyl optionally substituted with halo, alkyl or cyano;

R$_{3a}$ is hydrogen, alkyl, alkylcarbonyl, or tritylaryl, wherein aryl is phenyl;

R$_e$ and R$_f$ are each independently hydrogen, alkyl, alkoxycarbonyl, or alkylcarbonyl, or R$_e$ and R$_f$ are each taken together with the nitrogen atom to which they are attached to form a heterocyclic ring, wherein the heterocyclic ring is pyrrolidinyl, piperidinyl or piperazinyl;

one of X$_{16}$, X$_{17}$, X$_{18}$, and X$_{19}$, is C; and

M$_1$ or M$_2$ is C.

4. The compound according to claim 1, wherein L$_1$ is —NR$_a$—.

5. The compound according to claim 1, wherein L$_1$ is —O—.

6. A compound of claim 1, wherein the compound is (4s)-4-[6-(1H-indol-5-yl)pyridazin-3-yloxy]-1-azatricyclo[3.3.1.1$^{3,7}$]decane;

(4r)-4-[6-(1H-indol-5-yl)pyridazin-3-yloxy]-1-azatricyclo[3.3.1.1$^{3,7}$]decane;

(4s)-4-[6-(1-benzothien-5-yl)pyridazin-3-yloxy]-1-azatricyclo[3.3.1.1$^{3,7}$]decane;

(4r)-4-[6-(1-benzothien-5-yl)pyridazin-3-yloxy]-1-azatricyclo[3.3.1.1$^{3,7}$]decane;

(4s)-4-[5-(1H-indol-5-yl)pyridin-2-yloxy]-1-azatricyclo[3.3.1.1$^{3,7}$]decane;

(4r)-4-[5-(1H-indol-5-yl)pyridin-2-yloxy]-1-azatricyclo[3.3.1.1$^{3,7}$]decane;

(4r)-4-[5-(benzothien-5-yl)pyridin-2-yloxy]-1-azatricyclo[3.3.1.1$^{3,7}$]decane;

(4s)-4-[5-(1H-indol-5-yl)-thiazol-2-yloxy]-1-azatricyclo[3.3.1.1$^{3,7}$]decane;

(4s)-4-[5-(1H-indol-5-yl)-thiazol-2-yloxy]-1-azatricyclo[3.3.1.1$^{3,7}$]decane-1-oxide;

(4s)-4-[5-(2-trifluoromethyl-1H-indol-5-yl)-thiazol-2-yloxy]-1-azatricyclo[3.3.1.1$^{3,7}$]decane;

(4s)-4-[5-(1H-indol-4-yl)-thiazol-2-yloxy]-1-azatricyclo[3.3.1.1$^{3,7}$]decane;

(4s)-4-[5-(1H-indol-6-yl)-thiazol-2-yloxy]-1-azatricyclo[3.3.1.1$^{3,7}$]decane;

(4s)-4-[5-(1H-indol-3-yl)-thiazol-2-yloxy]-1-azatricyclo[3.3.1.1$^{3,7}$]decane;

(4s)-4-[5-(pyridin-4-yl)-thiazol-2-yloxy]-1-azatricyclo[3.3.1.1$^{3,7}$]decane;

(4s)-4-[5-(furan-2-yl)-thiazol-2-yloxy]-1-azatricyclo[3.3.1.1$^{3,7}$]decane;

(4s)-4-[5-(furan-3-yl)-thiazol-2-yloxy]-1-azatricyclo[3.3.1.1$^{3,7}$]decane;

(4s)-4-[5-(thien-3-yl)-thiazol-2-yloxy]-1-azatricyclo[3.3.1.1$^{3,7}$]decane;

(4s)-4-[5-(pyrazol-4-yl)-thiazol-2-yloxy]-1-azatricyclo[3.3.1.1$^{3,7}$]decane;

(4s)-4-[5-(1H-indol-5-yl)-1,3,4-thiadiazol-2-yloxy]-1-azatricyclo[3.3.1.1$^{3,7}$]decane;

(4s)-4-[5-(1H-indol-6-yl)-1,3,4-thiadiazol-2-yloxy]-1-azatricyclo[3.3.1.1$^{3,7}$]decane;

(4s)-4-[5-(1H-indol-4-yl)-1,3,4-thiadiazol-2-yloxy]-1-azatricyclo[3.3.1.1$^{3,7}$]decane;

(4s)-4-[5-(benzothien-5-yl)-1,3,4-thiadiazol-2-yloxy]-1-azatricyclo[3.3.1.1$^{3,7}$]decane;

(4s)-4-[5-(pyrazol-4-yl)-1,3,4-thiadiazol-2-yloxy]-1-azatricyclo[3.3.1.1$^{3,7}$]decane;

(4s)-N-[6-(indol-5-yl)-pyridin-3-yl]-1-azatricyclo[3.3.1.1$^{3,7}$]decan-4-amine;

(4s)-N-[5-(indol-5-yl)-pyridin-3-yl]-1-azatricyclo[3.3.1.1$^{3,7}$]decan-4-amine;

(4s)-N-[5-(indol-6-yl)-pyridin-3-yl]-1-azatricyclo[3.3.1.1$^{3,7}$]decan-4-amine;

(4s)-N-[5-(indol-4-yl)-pyridin-3-yl]-1-azatricyclo[3.3.1.1$^{3,7}$]decan-4-amine;

(4s)-4-{[5-(1H-pyrazol-4-yl)pyridin-3-yl]oxy}-1-azatricyclo[3.3.1.1$^{3,7}$]decane;

(4s)-4-{[5-(1-methyl-1H-pyrazol-4-yl)pyridin-3-yl]oxy}-1-azatricyclo[3.3.1.1$^{3,7}$]decane;

(4s)-4-{[5-(1H-pyrazol-1-yl)pyridin-3-yl]oxy}-1-azatricyclo[3.3.1.1$^{3,7}$]decane;

(4s)-4-(3,4'-bipyridin-5-yloxy)-1-azatricyclo[3.3.1.1$^{3,7}$]decane;

(4s)-4-[(5-pyrimidin-5-ylpyridin-3-yl)oxy]-1-azatricyclo[3.3.1.1$^{3,7}$]decane;

(4s)-4-[(5-thien-2-ylpyridin-2-yl)oxy]-1-azatricyclo[3.3.1.1$^{3,7}$]decane;

(4s)-4-{[6-(1H-indol-5-yl)pyridin-3-yl]oxy}-1-azatricyclo[3.3.1.1$^{3,7}$]decane;

(4r)-4-{[6-(1H-indol-5-yl)pyridin-3-yl]oxy}-1-azatricyclo[3.3.1.1$^{3,7}$]decane;

(4s)-4-{[6-(1H-indol-6-yl)pyridin-3-yl]oxy}-1-azatricyclo[3.3.1.1$^{3,7}$]decane;

(4r)-4-{[6-(1H-indol-6-yl)pyridin-3-yl]oxy}-1-azatricyclo[3.3.1.1$^{3,7}$]decane;

(4r)-4-{[6-(1-benzofuran-5-yl)pyridin-3-yl]oxy}-1-azatricyclo[3.3.1.1$^{3,7}$]decane;
(4s)-4-(3,3'-bipyridin-6-yloxy)-1-azatricyclo[3.3.1.1$^{3,7}$]decane;
(4s)-4-(3,4'-bipyridin-6-yloxy)-1-azatricyclo[3.3.1.1$^{3,7}$]decane;
(4r)-4-(3,4'-bipyridin-6-yloxy)-1-azatricyclo[3.3.1.1$^{3,7}$]decane;
(4s)-4-[(5-pyrimidin-5-ylpyridin-2-yl)oxy]-1-azatricyclo[3.3.1.1$^{3,7}$]decane;
(4s)-4-{[5-(1H-pyrazol-4-yl)pyridin-2-yl]oxy}-1-azatricyclo[3.3.1.1$^{3,7}$]decane;
(4s)-4-{[6-(1-trityl-1H-pyrazol-4-yl)pyrimidin-4-yl]oxy}-1-azatricyclo[3.3.1.1$^{3,7}$]decane;
(4s)-4-{[6-(1H-pyrazol-4-yl)pyrimidin-4-yl]oxy}-1-azatricyclo[3.3.1.1$^{3,7}$]decane;
(4s)-4-[(6-pyridin-4-ylpyrimidin-4-yl)oxy]-1-azatricyclo[3.3.1.1$^{3,7}$]decane;
(4s)-4-[(5-pyridin-3-yl-1,3-thiazol-2-yl)oxy]-1-azatricyclo[3.3.1.1$^{3,7}$]decane;
(4r)-4-[(5-pyridin-3-yl-1,3-thiazol-2-yl)oxy]-1-azatricyclo[3.3.1.1$^{3,7}$]decane;
(4s)-4-[(5-pyrimidin-5-yl-1,3-thiazol-2-yl)oxy]-1-azatricyclo[3.3.1.1$^{3,7}$]decane;
(4s)-4-{[5-(2-methoxypyrimidin-5-yl)-1,3-thiazol-2-yl]oxy}-1-azatricyclo[3.3.1.1$^{3,7}$]decane;
(4s)-4-{[5-(2-pyrrolidin-1-ylpyrimidin-5-yl)-1,3-thiazol-2-yl]oxy}-1-azatricyclo[3.3.1.1$^{3,7}$]decane;
(4s)-4-{[5-(6-piperazin-1-ylpyridin-3-yl)-1,3-thiazol-2-yl]oxy}-1-azatricyclo[3.3.1.1$^{3,7}$]decane;
(4s)-4-{[5-(1H-pyrazol-1-yl)-1,3-thiazol-2-yl]oxy}-1-azatricyclo[3.3.1.1$^{3,7}$]decane;
(4s)-4-{[5-(1-trityl-1H-pyrazol-4-yl)-1,3-thiazol-2-yl]oxy}-1-azatricyclo[3.3.1.1$^{3,7}$]decane;
(4s)-4-{[5-(1-propyl-1H-pyrazol-4-yl)-1,3-thiazol-2-yl]oxy}-1-azatricyclo[3.3.1.1$^{3,7}$]decane;
(4s)-4-{[5-(1-isobutyl-1H-pyrazol-4-yl)-1,3-thiazol-2-yl]oxy}-1-azatricyclo[3.3.1.1$^{3,7}$]decane;
(4s)-4-{[5-(1-acetyl-1H-pyrazol-4-yl)-1,3-thiazol-2-yl]oxy}-1-azatricyclo[3.3.1.1$^{3,7}$]decane;
(4s)-4-{[5-(5-methyl-1-phenyl-1H-pyrazol-4-yl)-1,3-thiazol-2-yl]oxy}-1-azatricyclo[3.3.1.1$^{3,7}$]decane;
(4s)-4-[(5-isoxazol-4-yl-1,3-thiazol-2-yl)oxy]-1-azatricyclo[3.3.1.1$^{3,7}$]decane;
(4s)-4-{[4-(1H-pyrazol-4-yl)-1,3-thiazol-2-yl]oxy}-1-azatricyclo[3.3.1.1$^{3,7}$]decane;
(4s)-4-[(4-pyridin-4-yl-1,3-thiazol-2-yl)oxy]-1-azatricyclo[3.3.1.1$^{3,7}$]decane;
(4s)-4-[(4-pyridin-3-yl-1,3-thiazol-2-yl)oxy]-1-azatricyclo[3.3.1.1$^{3,7}$]decane;
(4s)-N-[6-(1H-indol-6-yl)pyridin-3-yl]-1-azatricyclo[3.3.1.1$^{3,7}$]decan-4-amine;
(4s)-N-[6-(1H-indol-3-yl)pyridin-3-yl]-1-azatricyclo[3.3.1.1$^{3,7}$]decan-4-amine;
(4s)-4-[5-(1H-indol-5-yl)pyridin-3-yloxy]-1-azatricyclo[3.3.1.1$^{3,7}$]decane;
(4s)-4-[5-(1H-indol-6-yl)pyridin-3-yloxy]-1-azatricyclo[3.3.1.1$^{3,7}$]decane;
(4r)-4-[5-(1H-indol-5-yl)pyridin-3-yloxy]-1-azatricyclo[3.3.1.1$^{3,7}$]decane;
(4r)-4-[5-(1H-indol-6-yl)pyridin-3-yloxy]-1-azatricyclo[3.3.1.1$^{3,7}$]decane; or
(4r)-4-[5-(1-benzofuran-5-yl)pyridin-3-yloxy]-1-azatricyclo[3.3.1.1$^{3,7}$]decane.

\* \* \* \* \*